(12) United States Patent
Wang et al.

(10) Patent No.: US 8,933,075 B2
(45) Date of Patent: Jan. 13, 2015

(54) COMPOUNDS USEFUL AS ANTIVIRAL AGENTS, COMPOSITIONS, AND METHODS OF USE

(75) Inventors: Guoxin Wang, Shenzhen (CN); Ming Luo, Vestavia Hills, AL (US); Zhen Yang, Shenzhen (CN)

(73) Assignees: FUZIANS BIOMEDICALS, Inc., George Town, Grand Cayman (KY); The UAB Research Foundation, Birmingham, AL (US)

( * ) Notice: Subject to any disclaimer, the term of this patent is extended or adjusted under 35 U.S.C. 154(b) by 0 days.

(21) Appl. No.: 13/703,383

(22) PCT Filed: Jun. 17, 2011

(86) PCT No.: PCT/US2011/040888
§ 371 (c)(1),
(2), (4) Date: Dec. 11, 2012

(87) PCT Pub. No.: WO2011/160024
PCT Pub. Date: Dec. 22, 2011

(65) Prior Publication Data
US 2013/0090339 A1    Apr. 11, 2013

Related U.S. Application Data

(60) Provisional application No. 61/355,808, filed on Jun. 17, 2010.

(51) Int. Cl.
| | |
|---|---|
| *C07D 417/14* | (2006.01) |
| *C07D 417/06* | (2006.01) |
| *A61K 31/44* | (2006.01) |
| *A61K 31/415* | (2006.01) |
| *A61K 31/425* | (2006.01) |
| *C07D 233/38* | (2006.01) |
| *C07D 277/00* | (2006.01) |
| *A01N 43/50* | (2006.01) |

(52) U.S. Cl.
CPC ............ *C07D 417/14* (2013.01); *C07D 417/06* (2013.01)
USPC ............ 514/236.8; 435/5; 435/375; 546/209; 544/133; 544/310; 544/369; 514/254.02; 514/274; 514/342; 514/369

(58) Field of Classification Search
USPC ............ 548/146, 183, 333.5, 334.1, 334.5, 548/314.7
See application file for complete search history.

(56) References Cited

U.S. PATENT DOCUMENTS

| | | | |
|---|---|---|---|
| 6,809,101 B2 | 10/2004 | Fujishita et al. | |
| 2007/0179137 A1 | 8/2007 | Gregor et al. | |
| 2010/0286212 A1* | 11/2010 | Luo et al. | 514/341 |

FOREIGN PATENT DOCUMENTS

| | | | |
|---|---|---|---|
| EP | 1834642 | A2 | 9/2007 |
| WO | 0076987 | A1 | 12/2000 |
| WO | 0220497 | A1 | 3/2002 |
| WO | 2005089067 | A2 | 9/2005 |
| WO | 2006047269 | A2 | 5/2006 |
| WO | WO 2007062568 | A1 * | 6/2007 |
| WO | 2007081091 | A1 | 7/2007 |
| WO | WO 2008005651 | A2 * | 1/2008 |
| WO | 2008043733 | A1 | 4/2008 |
| WO | 2009059243 | A1 | 5/2009 |
| WO | 2010044924 | A1 | 4/2010 |
| WO | 2011130419 | A2 | 10/2011 |
| WO | 2012177924 | A2 | 12/2012 |

OTHER PUBLICATIONS

Nan et al. WO 2007/062568 A1, publ. Jun. 7, 2007, Machine Translation (English).*
Cram et al. "The Taming of Cyclobutadiene" Angew. Chem. Int. Ed. Engl. 1991, 30 (8), 1024-1027.*
Emerson et al. "Cyclobutadiene- and Benzocyclobutadiene-Iron Tricarbonyl Complexes." J. Am. Chem. Soc. 1965, 87, 131-133.*
Bally, T. "Cyclobutadiene: The Antiaromatic Paradigm?" Angew. Chem. Int. Ed. 2006, 45, 6616-6619.*
Efraty, A. "Cyclobutadienemetal Complexes." Chem. Rev. 1977, 77, 691-744.*
Tallarico et al. "Intramolecular Cycloadditions Between Cyclobutadiene and Alkenes." J. Am. Chem. Soc. 1996, 118, 9196-9197.*
Int'l Search Report, Written Opinion issued Feb. 14, 2012 in Int'l Application No. PCT/US11/40888.
Miao et al, "Synthesis and potential antibacterial activity of new rhodanine-3-acetic acid derivatives", Medicinal Chemistry Research, 8 pages, published online Dec. 21, 2012.
Wolf et al, "A broad-spectrum antiviral targeting entry of enveloped viruses", Proceedings of the National Academy of Sciences, vol. 107, No. 7, pp. 3157-3162 (Feb. 16, 2010).
Luo, "Chapter 9—Influenza Virus Entry", Viral Molecular Machines, Eds. Rossman and Rao, Advances in Experimental Medicine and Biology vol. 726, pp. 201-221 (2012).
Magano, "Synthetic Approaches to the Neuraminidase Inhibitors Zanamivir (Relenza) and Oseltamivir Phosphate (Tamiflu) for the Treatment of Influenza", Chemical Reviews, vol. 109, pp. 4398-4438 (2009).
Skehel et al, "Receptor Binding and Membrane Fusion in Virus Entry: The Influenza Hemagglutinin", Annual Review of Biochemistry, vol. 69, pp. 531-569 (2000).
Shors, "Chapter 3—Virus Replication Cycles", Understanding Viruses, First Ed., pp. 46-69 (2008).

* cited by examiner

*Primary Examiner* — Samantha Shterengarts
*Assistant Examiner* — Amanda L Aguirre
(74) *Attorney, Agent, or Firm* — Panitch Schwarze Belisario & Nadel LLP

(57) ABSTRACT

Novel 3-N-cycloalkyl-5-substituted-2-thioxothiazolidin-4-one derivatives that are effective for use in treating viral infections are described. Also described are pharmaceutical compositions comprising the 3-N-cycloalkyl-5-substituted-2-thioxothiazolidin-4-one derivatives and methods for using the compounds or compositions.

16 Claims, No Drawings

COMPOUNDS USEFUL AS ANTIVIRAL AGENTS, COMPOSITIONS, AND METHODS OF USE

STATEMENT OF GOVERNMENT LICENSE RIGHTS

This invention was made in part with government support under Grant Nos. 5U54AI057157-04 and RO1AI080669 awarded by the National Institutes of Health. The U.S. government has certain rights in this invention.

CROSS-REFERENCE TO RELATED APPLICATIONS

This application is a Section 371 of International Application No. PCT/US2011/040888, filed Jun. 17, 2011, which was published in the English language on Dec. 22, 2011, under International Publication No. WO 2011/160024 A2 and the disclosure of which is incorporated herein by reference.

FIELD OF THE INVENTION

Embodiments of the current invention relate to novel 3-N-cycloalkyl-5-substituted-2-thioxothiazolidin-4-one derivatives and the use of such compounds to treat disorders related to pathogens that enter the host cell through a pathogen protein mediated membrane fusion. More particularly, the compounds are inhibitors of the influenza virus hemagglutinin (HA) or human immunodeficiency virus (HIV) glycoprotein mediated fusion process.

BACKGROUND OF THE INVENTION

Infection by an enveloped virus begins with recognition by the virus of certain receptors on the host cell's membrane. Enveloped viruses enter the host cell by a common mechanism, i.e., fusion of the viral membrane with the host cell membrane, often mediated by a surface protein or surface proteins on the virion. The membrane fusion allows the viral genome segments to be released as ribonucleoproteins (RNP). For example, influenza virus gains entry into the host cell through membrane fusion mediated by hemagglutinin (HA), a glycoprotein found on the surface of the influenza viruses. HA contains a protein motif known as the "jelly roll motif," or the "Swiss roll motif," which is frequently found in a variety of different structures including the coating proteins of most spherical viruses examined thus far by x-ray crystallography. Typically, jelly roll motifs comprise eight antiparallel β-strands, although any even number of β-strands greater than four can form a jelly roll motif. The jelly roll motif is at least one structural aspect that is thought to be important for the activity of HA.

Once HA is synthesized on membrane bound ribosomes, its polypeptide chain is eventually cleaved into two chains of amino acids, known as $HA_1$ and $HA_2$, which can be held together by disulfide bonds. Three HA monomers (each with one $HA_1$ and $HA_2$) can trimerize and be transported to the plasma membrane, where the $HA_2$ tails anchor the monomers to the membrane, with the large part of the monomers protruding outside of the membrane. It is believed that about 20 residues at the N-terminal end of $HA_2$ are associated with the mechanism by which virus particles penetrate a host cell. This portion on $HA_2$ is known as the fusion peptide.

HA functions in at least two known roles during viral infection. First, HA binds to the cell, and second, HA acts as a membrane fusogen. HA protein binds to sialic acid residues of glycosylated receptor molecules on target cell surfaces. Once bound, the virus can then enter the cell through endocytosis. The sialic acid binding site has been shown by X-ray crystallography to be located at the tip of an HA subunit within the jelly roll motif.

HA also functions as a membrane fusogen. Once viruses bind to and then enter the cell through endocytosis, proton pumps in the endocytic vesicles (that now contain bound viruses) produce an accumulation of protons and thus a drop of the pH inside the vesicles. If the pH drops below about 6, HA can function as a membrane fusogen. Specifically, a pH drop can induce a conformational change in HA. At a pH of above about 6, the fusion peptide attached to the N-terminus is about 100 Å away from the receptor binding site. At a pH of lower than about 6, the N-terminus moves about 100 Å toward the region of the receptor binding site. It is believed that this structural change enables a fusion mechanism whereby HA brings viral and cellular membranes close together and thus allows the release of viral nucleotides into the cell. This structural change is irreversible, since the low pH conformation is more thermostable than the high pH form. It is also believed that the energy gain during this conformational shift is used by HA as fusion energy.

Vaccinations, a common form of influenza prevention, allow for the production of antibodies that may bind near the receptor binding site on a target cell, and thereby limit the ability of the virus to enter the cell. The virus, however, can evade such inhibitory mechanisms through mutations in residues that form the binding site. Typically, however, such mutations are only found at the rim of the sialic acid binding pocket. It is believed that drastic mutations in this binding pocket could prevent the virus from binding to the cell surface receptor protein. This property of HA makes the binding site one of the ideal targets for inhibitory actors. Compounds inhibiting the fusion process mediated by a viral protein have been tested against viral infections.

For example, Triperiden was shown to inhibit influenza virus replication at a concentration of 20 µg/ml (Heider et al., The influence of Norakin on the reproduction of influenza A and B viruses. *Arch Virol.* 1985; 86(3-4):283-90. PMID: 2415085). This compound was later shown to inhibit hemolysis of red blood cells and the sensitivity of HA1 to trypsin after low pH treatment of HA (Ghendon et al., Haemagglutinin of influenza A virus is a target for the antiviral effect of Norakin. *J Gen Virol.* 1986 June; 67 (Pt 6):1115-22. PMID: 3711865). Reassortment of the drug sensitive strain with a strain that was not sensitive confirmed that the target sensitive to triperiden was HA. Triperiden-resistant mutations were mapped to HA as well (Prosch et al., Mutations in the hemagglutinin gene associated with influenza virus resistance to norakin. *Arch Virol.* 1988; 102(1-2):125-9. PMID: 3196166). In a more recent report, it was shown that inhibition of influenza virus replication by triperiden may be due to its ability to lower the internal pH in the prelysosomal compartment (Ott S et al., Effect of the virostatic Norakin (triperiden) on influenza virus activities. *Antiviral Res.* 1994 May; 24(1):37-42. PMID: 7944312).

An HA inhibitor (BMY-27709) was shown to have an $EC_{50}$ of 6-8 µM against influenza viruses that have HA subtypes H1 and H2, but not H3 (Luo et al., Characterization of a hemagglutinin-specific inhibitor of influenza A virus. *Virology.* 1996 Dec. 1; 226(1):66-76. PMID: 8941323). The compound was shown to inhibit virus replication at an early stage and the inhibition was reversible Inhibitor-resistant mutations were found in HA, and the compound inhibited hemolysis (Luo et al., Molecular mechanism underlying the action of a novel fusion inhibitor of influenza A virus. *J. Virol.* 1997 May; 71(5):4062-70. PMID: 9094684).

A podocarpic acid derivative (180299) was found as an inhibitor of HA from a chemical library screening (Staschke et al, Inhibition of influenza virus hemagglutinin-mediated membrane fusion by a compound related to podocarpic acid. *Virology.* 1998 Sep. 1; 248(2):264-74. PMID: 9721235). The $EC_{50}$ of 180299 is 0.01 μg/ml against influenza A/Kawasaki/86, but ≥10 μg/ml against other trains of virus. The target of action was also confirmed to be HA by inhibition of cell fusion and positions of inhibitor-resistant mutation analyses.

Stachyflin, having an $EC_{50}$ in the μM range against H1 and H2 viruses, but not H3 viruses, was also identified from a screening (Yoshimoto et al., Identification of amino acids of influenza virus HA responsible for resistance to a fusion inhibitor, Stachyflin. *Microbiol. Immunol.* 2000; 44(8):677-85. PMID: 11021398). HA as the target for Stachyflin was confirmed by time of addition, inhibition of hemolysis and reassortment between subtype H1 and H3.

Inhibitors of HA fusion were identified from a structure-aided approach (Bodian et al., Inhibition of the fusion-inducing conformational change of influenza hemagglutinin by benzoquinones and hydroquinones. *Biochemistry.* 1993 Mar. 30; 32(12):2967-78. PMID: 8457561; Hoffman et al., Structure-based identification of an inducer of the low-pH conformational change in the influenza virus hemagglutinin: irreversible inhibition of infectivity. *J. Virol.* 1997 November; 71(11):8808-20. PMID: 9343241). The most effective compound identified (S19) was shown to have an $EC_{50}$ of 0.8 μM against influenza virus X-31, while its activities on other strains were not reported. Interestingly, a moderate inhibitor (C22), unlike the other inhibitors that prevented the conformational change of HA, facilitated the conformational change at fusion pH and its effect was irreversible. C22 destabilized HA and also inhibited hemolysis, fusion, and viral infectivity. The authors concluded that because C22 does not induce the conformational change at neutral pH, it was conceivable that it might facilitate fusion by destabilizing HA as an effector.

Small molecular compounds targeted fusion proteins of other enveloped viruses have also been shown to be effective antivirals. For instance, BMS-433771 has an $EC_{50}$ of 0.02 μM against respiratory syncytial virus (RSV), a negative strand RNA virus (Clanci et al., Orally active fusion inhibitor of respiratory syncytial virus. *Antimicrob Agents Chemother.* 2004 February; 48(2):413-22. PMID: 14742189). BMS-433771 was shown to inhibit virus replication only when added early, and the compound could inhibit syncythium formation of cells induced by RSV. Drug-resistant mutations were mapped only in the F1 subunit of the fusion protein, suggesting that BMS-433771 inhibits the fusion step in RSV replication cycle. It was later shown that BMS-433771 binds near the N-terminal heptad repeat domain, destabilizes the trimer-of-hairpins structure required for fusion, and is effective to inhibit virus infection in rodent models (Clanci et al., Antiviral activity and molecular mechanism of an orally active respiratory syncytial virus fusion inhibitor. *J Antimicrob Chemother.* 2005 March; 55(3):289-92. PMID: 15681582).

T-20 is a peptide inhibitor of gp41-mediated virus entry that has been approved by FDA for the treatment of HIV infection [Manfredi et al., A novel antiretroviral class (fusion inhibitors) in the management of HIV infection. Present features and future perspectives of enfuvirtide (T-20). *Curr Med. Chem.* 2006; 13(20):2369-84. PMID: 16918361). T-20 associates with the gp41 helix bundle present in the fusion intermediate.

Small molecular inhibitors that interact with the glycoprotein of HIV have also been developed (Jiang et al., N-substituted pyrrole derivatives as novel human immunodeficiency virus type 1 entry inhibitors that interfere with the gp41 six-helix bundle formation and block virus fusion. *Antimicrob Agents Chemother.* 2004 November; 48(11):4349-59. PMID: 15504864; Frey et al., Small molecules that bind the inner core of gp41 and inhibit HIV envelope-mediated fusion. *Proc Natl Acad Sci USA.* 2006 Sep. 19; 103(38):13938-43. PMID: 16963566). In the first case, two N-substituted pyrroles were identified from a syncythium formation screen. They inhibit HIV-1 fusion and entry by interfering with the gp41 six-helix bundle formation. The mechanism of action of these compounds were confirmed by time-of-addition experiments that use a HIV entry assay based on a luciferase cell line and cell-cell fusion based on dye transfer. The binding site for these compounds was modeled on the surface of the six-helix bundle, suggesting that they may behave against the HIV glycoprotein similarly as BMS-433771 against the RSV glycoprotein. The second group designed a binding assay in which a five-helix bundle of gp41 may associate with a fluorescently labeled sixth helix. By this assay, a class of compounds was found to block the association of the sixth helix at 5 μM. This action was more dramatic than only interfering with the fusion activity of the viral glycoprotein. These compounds were shown to inhibit fusion as well as HIV replication. Nevertheless, the data further support that inhibition of fusion is a realistic mechanism to inhibit virus replication by small molecular antivirals.

Viral infection is a major threat to human health and results in significant morbidity and mortality worldwide. For example, according to World Health Organization estimates, seasonal influenza epidemics influence 5~15% of the global populations annually and are responsible for more than 3-5 million hospitalizations and about 250,000 to 500,000 deaths per year (www.who.int/mediacentre/factsheets/fs211/en/index.html). There is a need for novel therapies for treating viral infections.

Novel compounds that inhibit the fusion process mediated by a viral protein represent an important new class of antiviral agents. Such compounds and methods of using the compounds for treating viral infections are described in the present invention.

BRIEF SUMMARY OF THE INVENTION

Embodiments of the present invention relate to novel 3-N-cycloalkyl-5-substituted-2-thioxothiazolidin-4-one derivatives as inhibitors of the influenza virus hemagglutinin (HA) or human immunodeficiency virus (HIV) glycoprotein mediated fusion process and the use of such compounds to treat or prevent a viral infection, and the like.

In one general aspect, embodiments of the present invention relate to a compound, having the formula of:

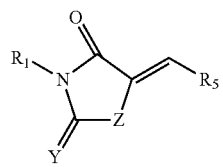

Formula (I)

or an optical isomer, enantiomer, diastereomer, racemate, or pharmaceutically acceptable salt thereof, wherein $R_1$ is an optionally substituted cycloalkyl having from 3 to 20 carbon atoms;

Z is S or NH;

Y is O or S;

$R_5$ is selected from the group consisting of
(1) phenyl optionally substituted with a substituent other than an optionally substituted aryl or heteroaryl;
(2) a 6-member heteroaryl optionally substituted with a substituent other than an optionally substituted aryl or heteroaryl;
(3) an optionally substituted heterocyclic ring; and
(4) a moiety having the formula of:

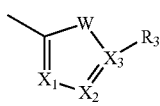

Formula 1a wherein

W is selected from the group consisting of a direct bond, O, S, NH, $CH_2$, and a linking unit having 1 to 4 carbon atoms and up to 2 heteroatoms selected from the group consisting of O, N and S, and each of the NH, $CH_2$ and the linking unit is optionally substituted with an alkyl or aryl;

one of $X_1$ and $X_2$ is unsubstituted and is selected from the group consisting of CH, O, S and N, the other one of $X_1$ and $X_2$ is C linked to a substituent $R_2$, and $R_2$ is H or A-B, wherein A is an optionally substituted aryl, or an optionally substituted alkyl, alkenyl or alkynyl having 1 to 10 carbon atoms; and B is selected from the group consisting of an alkoxy, a hydrogen, a hydroxyl, an acid ester, a carboxyl, an amine, an amide, an ether, an amino acid derivative, an alpha-hydroxy acid, a guanidino, an optionally substituted aryl, an optionally substituted heteroaryl, an optionally substituted cycloalkyl, and an optionally substituted heterocyclic ring;

$X_3$ is selected from the group consisting of C and N; and $R_3$ is selected from the group consisting of H, a halogen, an amino acid derivative, an acid ester, an optionally substituted aryl, an optionally substituted heteroaryl and an optionally substituted heterocyclic ring, provided that when $R_5$ has Formula 1a, W is O, both $X_1$ and $X_2$ are CH, $X_3$ is C, and $R_3$ is a halogen, then $R_1$ is an optionally substituted fused or bicyclic cycloalkyl ring; and when $R_5$ has Formula 1a, W is S or O, both $X_1$ and $X_2$ are CH, $X_3$ is C, and $R_3$ is a substituted aryl, then $R_3$ is substituted with at least one selected from the group consisting of an amino acid derivative, an optionally substituted aryl, an optionally substituted heteroaryl, an optionally substituted cycloalkyl, and an optionally substituted heterocyclic ring.

In a preferred embodiment, $R_1$ is an optionally substituted fused or bicyclic cycloalkyl ring.

In another preferred embodiment, $R_5$ is a moiety having Formula 1a, wherein one of $X_1$ and $X_2$ is substituted with A-B.

Other aspects of the present invention relate to pharmaceutical compositions comprising a compound according to an embodiment of the present invention, and methods of using the composition for the treatment or prevention of a viral infection.

Yet another aspect of the present invention relates to a method for identifying novel antiviral agents. According to an embodiment of the present invention, the method comprises:
(a) synthesizing a compound of Formula (I);
(b) testing the compound by one or a number of antiviral assays;
(c) designing a second compound that modifies the structure of the compound in order to incorporate one or more new functional chemical groups;
(d) synthesizing the second compound;
(e) determining the ability of the second compound to inhibit the HA or HIV glycoprotein mediated membrane fusion, and
(f) identifying the second compound as the inhibitor for the HA or HIV grlycoprotein mediated membrane fusion based on the result of step (e).

These steps can be repeated to obtain the optimal compounds by fine tuning the interaction features between the compounds and virus particles bearing the HA or HIV glycoprotein.

Other aspects, features and advantages of the invention will be apparent from the following disclosure, including the detailed description of the invention and its preferred embodiments and the appended claims.

DETAILED DESCRIPTION OF THE INVENTION

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the present invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

DEFINITIONS

As used herein, the term "composition" is intended to encompass a product comprising the specified ingredients in the specified amounts, as well as any product which results, directly or indirectly, from combinations of the specified ingredients in the specified amounts.

As used herein, the term "subject" means any animal, preferably a mammal, most preferably a human, to whom will be or has been administered compounds or compositions according to embodiments of the invention. The term "mammal" as used herein, encompasses any mammal. Examples of mammals include, but are not limited to, cows, horses, sheep, pigs, cats, dogs, mice, rats, rabbits, guinea pigs, monkeys, humans etc., more preferably, a human. Preferably, a subject is in need of, or has been the object of observation or experiment of, treatment or prevention of a disorder related to pathogen, such as a viral infection.

In one embodiment, "treatment" or "treating" refers to an amelioration, prophylaxis, or reversal of a disease or disorder, or at least one discernible symptom thereof, for example, treating a disorder related to pathogen by reducing or stabilizing a symptom of the disorder, such as by reducing fever or other flu symptoms in an influenza virus infection. In another embodiment, "treatment" or "treating" refers to an amelioration, prophylaxis, or reversal of at least one measurable physical parameter related to the disease or disorder being treated, not necessarily discernible in or by the mammal, for example, treating a disorder related to pathogen by blocking the entry of the pathogen into the host cell, thus reducing the number of pathogen in the host cell. In yet another embodiment, "treatment" or "treating" refers to inhibiting or slowing the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder.

In certain embodiments, compounds of interest are administered as a preventative measure. As used herein, "prevention" or "preventing" refers to a reduction of the risk of acquiring a given disease or disorder. In a preferred mode of the embodiment, the specified compounds are administered as a preventative measure to a subject having a predisposition to a disorder related to pathogen, such as subjects of young or advanced age or subjects with otherwise compromised immune systems.

As used herein, a "therapeutically effective amount" means the amount of a compound that elicits the biological or medicinal response in a tissue system, animal or human that is being sought by a researcher, veterinarian, medical doctor or other clinician, which can include alleviation of the symptoms of the disease or disorder being treated. In a preferred embodiment, the therapeutically effective amount is effective to treat, improve the treatment of, or prophylactically prevent a disorder related to pathogen, such as a viral infection.

The term "prophylactically effective amount" refers to amount of active compound or pharmaceutical agent that inhibits in a subject the onset of a disorder as being sought by a researcher, veterinarian, medical doctor or other clinician, the delaying of which disorder is mediated by the inhibition of a viral protein mediated fusion process.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The term "organic unit" as described herein refers to groups or moieties that comprise one or more carbon atoms and which form a portion of one of the compounds or pharmaceutically acceptable salts thereof. For example, many of the substituent units referred to elsewhere herein are organic units. In order to effectively function in the context of their presence in the compounds and/or salts disclosed herein, the organic units should often have variable ranges of restricted size and/or molecular weight, so as to provide desired binding to the target enzymes, solubility, bioabsorption characteristics. For example, organic unit can have, for example, 1-26 carbon atoms, 1-18 carbon atoms, 1-12 carbon atoms, 1-8 carbon atoms, or 1-4 carbon atoms. Organic units often have hydrogen bound to at least some of the carbon atoms of the organic units, and can optionally contain the common heteroatoms found in substituted organic compounds, such as oxygen, nitrogen, sulfur, and the like, or inorganic atoms such as halogens, phosphorus, and the like. One example, of an organic radical that comprises no inorganic atoms is a 5,6,7,8-tetrahydro-2-naphthyl radical.

In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamido, substituted alkylcarboxamido, dialkylcarboxamido, substituted dialkylcarboxamido, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

Unless otherwise noted, the term "alkyl" as used herein means a saturated, monovalent, unbranched or branched hydrocarbon chain. An alkyl group can be unsubstituted or substituted with one or more suitable substituents.

Substituted and unsubstituted "haloalkyl" are used herein denotes an alkyl unit having a hydrogen atom substituted by one or more halogen atoms, for example, trifluoromethyl, 1,2-dichloroethyl, and 3,3,3-trifluoropropyl.

Unless otherwise noted, the term "cycloalkyl" as used herein, whether used alone or as part of a substituent group, shall mean any saturated ring system, for example cyclopropyl, cyclobutyl, cyclopentyl, cyclohexyl, cycloheptyl and cyclooctyl. The cycloalkyl can be a single ring, a fused ring, or a bicyclic ring, such as decalin, norbornane, adamantane, etc.

Unless otherwise noted, the term "partially unsaturated carbocycle" as used herein, whether used alone or as part of a substituent group, shall mean any partially unsaturated ring system, wherein the carbocycle contains, at least one unsaturated bond, for example cyclopentenyl, cyclohexenyl, cycloheptenyl, and the like.

Optionally substituted, i.e., substituted and unsubstituted, linear, branched, or cyclic alkyl units include the following non-limiting examples: methyl ($C_1$), ethyl ($C_2$), n-propyl ($C_3$), iso-propyl ($C_3$), cyclopropyl ($C_3$), n-butyl ($C_4$), sec-butyl ($C_4$), iso-butyl ($C_4$), tert-butyl ($C_4$), cyclobutyl ($C_4$), cyclopentyl ($C_5$), cyclohexyl ($C_6$), and the like; whereas substituted linear, branched, or cyclic alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl ($C_2$), 1,2-difluoroethyl ($C_2$), 2,2,2-trifluoroethyl ($C_3$), 3-carboxypropyl ($C_3$), 2,3-dihydroxycyclobutyl ($C_4$), and the like.

Substituted and unsubstituted linear, branched, or cyclic alkenyl include, ethenyl ($C_2$), 3-propenyl ($C_3$), 1-propenyl (also 2-methylethenyl) ($C_3$), isopropenyl (also 2-methylethen-2-yl) ($C_3$), buten-4-yl ($C_4$), and the like; substituted linear or branched alkenyl, non-limiting examples of which include, 2-chloroethenyl (also 2-chlorovinyl) ($C_2$), 4-hydroxybuten-1-yl ($C_4$), 7-hydroxy-7-methyloct-4-en-2-yl ($C_9$), 7-hydroxy-7-methyloct-3,5-dien-2-yl ($C_9$), and the like.

Substituted and unsubstituted linear or branched alkynyl include, ethynyl ($C_2$), prop-2-ynyl (also propargyl) ($C_3$), propyn-1-yl ($C_3$), and 2-methyl-hex-4-yn-1-yl ($C_7$); substituted linear or branched alkynyl, non-limiting examples of which include, 5-hydroxy-5-methylhex-3-ynyl ($C_7$), 6-hydroxy-6-methylhept-3-yn-2-yl ($C_8$), 5-hydroxy-5-ethylhept-3-ynyl ($C_9$), and the like.

As used herein, the term "heterocyclic ring" shall denote any saturated or partially unsaturated ring structure containing C atoms and at least one heteroatom selected from the group consisting of O, N and S, optionally containing one or more additional heteroatoms independently selected from the group consisting of O, N and S. The rings can be single rings, fused rings, or bicyclic rings. The monocyclic or bicyclic heterocyclic ring may be attached at any heteroatom or carbon atom of the ring such that the result is a stable structure. Examples of suitable monocyclic or bicyclic heterocyclic rings include, but are not limited to, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, and the like.

Unless otherwise noted, the term "alkoxy" as used herein, denotes a unit having the general formula —$OR^{100}$ wherein $R^{100}$ is an alkyl, alkylenyl, or alkynyl unit as defined herein above, for example, methoxy, methoxymethyl, methoxymethyl. Other examples of alkoxy include, but are not limited to, ethoxy, n-propoxy, sec-butoxy, t-butoxy, n-hexyloxy and the like. An alkoxy group can be unsubstituted or substituted with one or more suitable substituents.

Unless otherwise stated, the term "aryl" as used herein, employed alone or in combination with other terms (e.g., aryloxy, arylthioxy, arylalkyl), denotes cyclic organic units that comprise at least one benzene ring having a conjugated and aromatic six-membered ring, non-limiting examples of which include phenyl ($C_6$), naphthylen-1-yl ($C_{10}$), naphthylen-2-yl ($C_{10}$). Aryl rings can have one or more hydrogen atoms substituted by another organic or inorganic radical. Non-limiting examples of substituted aryl rings include: 4-fluorophenyl ($C_6$), 2-hydroxyphenyl ($C_6$), 3-methylphenyl ($C_6$), 2-amino-4-fluorophenyl ($C_6$), 2-(N,N-diethylamino) phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), and 6-cyanonaphthylen-1-yl ($C_{10}$).

As used herein, unless otherwise noted, "aralkyl" shall mean any lower alkyl group substituted with an aryl group such as phenyl, naphthyl and the like, for example, benzyl, phenylethyl, phenylpropyl, naphthylmethyl, and the like.

Throughout the description of the present disclosure the terms having the spelling "thiophene-2-yl and thiophene-3-yl" are used to describe the heteroaryl units having the respective formulae:

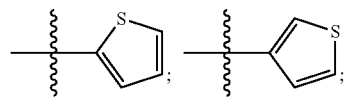 [SMILES: *c1cccs1 ; *c1ccsc1]

whereas in naming the compounds of the present disclosure, the chemical nomenclature for these moieties are typically spelled "thiophen-2-yl and thiophen-3-yl" respectively. Herein the terms "thiophene-2-yl and thiophene-3-yl" are used when describing these rings as units or moieties which make up the compounds of the present disclosure solely to make it unambiguous to the artisan of ordinary skill which rings are referred to herein.

Unless otherwise noted, the term "heteroaryl group" as used herein, whether used alone or as part of a substituent group, shall denote any five to ten membered monocyclic or bicyclic aromatic ring structure which containing carbon atoms and at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure. Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

The following are non-limiting examples of heteroaryl rings according to the present disclosure:

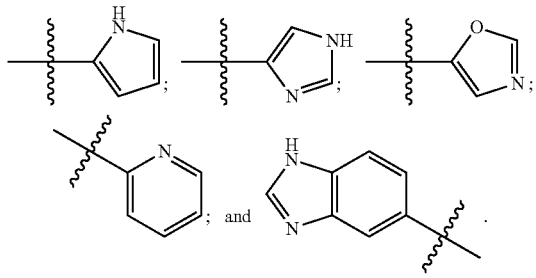

As used herein, unless otherwise noted, the term "benzofused heteroaryl" shall mean a bicyclic ring structure wherein one of the rings is phenyl and the other is a five to six membered heteroaryl. The benzo-fused heteroaryls are a subset of heteroaryls. Suitable example include, but are not limited to, indolyl, isoindolyl, benzofuryl, benzothienyl, benzopyranyl, indazolyl, benzthiazolyl, quinolinyl, isoquinolinyl, cinnolinyl, phthalazinyl, quinazolinyl, pteridinyl, and the like.

As used herein, unless otherwise noted, the term "benzo-fused cycloalkyl" shall mean a bicyclic ring structure wherein one of the rings is phenyl and the other is a three to eight membered cycloalkyl. The benzo-fused cycloalkyls are a subset of the cycloalkyl groups, wherein the cycloalkyl also encompass hetero cycloalkyl. Suitable examples include, but are not limited to, 1,2,3,4-tetrahydronaphthyl, 6,7,8,9,-tetrahydro-5H-benzocycloheptenyl, 5,6,7,8,9,10-hexahydrobenzocyclooctenyl, 1,3-benzodioxolyl (also known as 3,4-methylenedioxyphenyl), indolinyl, 3,4-ethylenedioxyphenyl, benzodihydrofuranyl, benzotetrahydropyranyl, benzodihydrothiophene and the like.

All of the aforementioned aryl, heteroaryl, cycloalkyl or heterocyclic rings can be optionally substituted with one or more substitutes for hydrogen as described herein further.

When a particular group is "substituted", that group can have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the term "halogen" means fluorine, chlorine, bromine, or iodine. Correspondingly, the term "halo" means fluoro, chloro, bromo, and iodo.

As used herein, the name of a compound is intended to encompass all possible existing isomeric forms (e.g., optical isomer, enantiomer, diastereomer, racemate or racemic mixture), esters, prodrugs, metabolite forms, or pharmaceutically acceptable salts, of the compound.

One skilled in the art will recognize that the compounds according to embodiment of the present invention may have one or more asymmetric carbon atoms in their structure. It is intended that the present invention includes within its scope the stereochemically pure isomeric forms of the compounds as well as their racemates. Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereoselective reactions.

Some of the compounds of the present invention may have trans and cis isomers. In addition, where the processes for the preparation of the compounds according to the invention give rise to mixture of stereoisomers, these isomers may be separated by conventional techniques such as preparative chromatography. The compounds may be prepared as a single stereoisomer or in racemic form as a mixture of some possible stereoisomers. The non-racemic forms may be obtained by either synthesis or resolution. The compounds may, for example, be resolved into their component enantiomers by standard techniques, such as the formation of diastereomeric pairs by salt formation. The compounds may also be resolved by covalent linkage to a chiral auxiliary, followed by chromatographic separation and/or crystallographic separation, and removal of the chiral auxiliary. Alternatively, the compounds may be resolved using chiral chromatography. The scope of the present invention is intended to cover all such isomers or stereoisomers per se, as well as mixtures of cis and trans isomers, mixtures of diastereomers and racemic mixtures of enantiomers (optical isomers) as well.

The phrase "pharmaceutically acceptable salt(s)", as used herein, means those salts of a compound of interest that are safe and effective for topical use in mammals and that possess the desired biological activity. Pharmaceutically acceptable salts include salts of acidic or basic groups present in the specified compounds. Pharmaceutically acceptable acid addition salts include, but are not limited to, hydrochloride, hydrobromide, hydroiodide, nitrate, sulfate, bisulfate, phosphate, acid phosphate, isonicotinate, carbonate, bicarbonate, acetate, lactate, salicylate, citrate, tartrate, propionate, butyrate, pyruvate, oxalate, malonate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds used in the present invention can form pharmaceutically acceptable salts with various amino acids. Suitable base salts include, but are not limited to, aluminum, calcium, lithium, magnesium, potassium, sodium, zinc, bismuth, and diethanolamine salts. For a review on pharmaceutically acceptable salts see BERGE ET AL., 66 *J. PHARM. SCI.* 1-19 (1977), incorporated herein by reference.

As used herein, the term "protective group" refers to means that are necessary and/or desirable to protect sensitive or reactive groups on any of the molecules concerned (for example hydroxy, amino, thio, oxo or carboxy groups) during any of the processes for preparation of a compound. Conventional protecting groups are known to those skilled in the art, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art in view of the present disclosure.

As used herein, the term "a side chain of an amino acid" refers to any of a group of linked atoms attached to an alpha carbon atom of an amino acid. The side chain can be apolar, uncharged polar or charged polar. Examples of the side chains that can be used in the present invention include those associated with the 20 commonly occurring α-amino acids, such as the side chains for alanine, valine, leucine, isoleucine, proline, phenylalanine, typtophan, methionine, glycine, serine, theonine, cysteine, tyrosine, asparagine, glutamine, aspartic acid, glutamic acid, lysine, arginine and histidine, which are known to those skilled in the art and can be found from biochemistry texbooks. The side chains that can be used in the present invention include those associated other amino acids, such as those found in minor amounts in proteins and in nonprotein compounds. These other amino acids can result from modification of the common amino acids using methods known in the art. The side chains that can be used in the present invention also include those associated with amino acid analogs.

Several advantages can be realized from the practice of the present invention, a few of which are disclosed herein as non-limiting advantages. First, the compounds disclosed herein can be administered to a subject before or after pathogen, such as a virus, has taken place. It has been found the disclosed compounds can both at least partially inhibit the binding of virions to target cells as well as at least partially inhibit viral replication after infection has occurred. Second, the effect of the disclosed compounds on virions appears to be irreversible, and thus dilution of the disclosed compounds bound to virions is not likely to lower the compounds efficacy against the flu or HIV infection. Third, the compounds disclosed herein can be administered in low concentrations (e.g., as low as 0.4 nM). Fourth, the compounds disclosed herein can be readily synthesized, and would thus be amenable to widespread distribution. It is believed that additional advantages will be realized through the practice of the present disclosure.

Compounds

In one general aspect, the present application relates to a compound having the formula of:

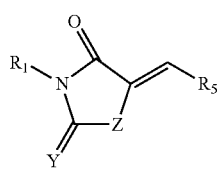

Formula (I)

or an optical isomer, enantiomer, diastereomer, racemate, or pharmaceutically acceptable salt thereof, wherein,
  $R_1$ is an optionally substituted cycloalkyl having from 3 to 20 carbon atoms;
  Z is S or NH;
  Y is O or S;
  $R_5$ is selected from the group consisting of
  (1) phenyl optionally substituted with a substituent other than an optionally substituted aryl or heteroaryl;
  (2) a 6-member heteroaryl optionally substituted with a substituent other than an optionally substituted aryl or heteroaryl;
  (3) an optionally substituted heterocyclic ring; and
  (4) a moiety having the formula of:

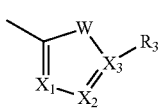

Formula 1a wherein
  W is selected from the group consisting of a direct bond, O, S, NH, $CH_2$, and a linking unit having 1 to 4 carbon atoms and up to 2 heteroatoms selected from the group consisting of O, N and S, and each of the NH, $CH_2$ and the linking unit is optionally substituted with an alkyl or aryl;
  one of $X_1$ and $X_2$ is unsubstituted and is selected from the group consisting of CH, O, S and N,
  the other one of $X_1$ and $X_2$ is C linked to a substituent $R_2$, and $R_2$ is H or A-B,
  wherein,
    A is an optionally substituted aryl, or an optionally substituted alkyl, alkenyl or alkynyl having 1 to 10 carbon atoms; and
    B is selected from the group consisting of an alkoxy, a hydrogen, a hydroxyl, an acid ester, a carboxyl, an amine, an amide, an ether, an amino acid derivative, an alpha-hydroxy acid, a guanidino, an optionally substituted aryl, an optionally substituted heteroaryl, an optionally substituted cycloalkyl, and an optionally substituted heterocyclic ring;
  $X_3$ is selected from the group consisting of C and N; and $R_3$ is selected from the group consisting of H, a halogen, an amino acid derivative, an acid ester, an optionally substituted aryl, an optionally substituted heteroaryl and an optionally substituted heterocyclic ring,
  provided that
    when $R_5$ has Formula 1a, W is O, both $X_1$ and $X_2$ are CH, $X_3$ is C, and $R_3$ is a halogen, then $R_1$ is an optionally substituted fused or bicyclic cycloalkyl ring; and
    when $R_5$ has Formula 1a, W is S or O, both $X_1$ and $X_2$ are CH, $X_3$ is C, and $R_3$ is a substituted aryl, then $R_3$ is substituted with at least one selected from the group consisting of an amino acid derivative, an optionally substituted aryl, an optionally substituted heteroaryl, an optionally substituted cycloalkyl, and an optionally substituted heterocyclic ring.

In one embodiment of the present invention, a compound of Formula (I) has $R_5$ of Formula 1a, wherein one of $X_1$ and $X_2$ is substituted with A-B.

In another embodiment of the present invention, a compound of Formula (I) has the formula of:

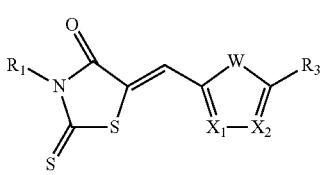

Formula (II)

wherein:
  W is $CH_2$, S, NH or O, each of the $CH_2$ and NH is optionally substituted with an alkyl or aryl;
  $R_3$ is selected from the group consisting of an optionally substituted aryl, an optionally substituted heteroaryl, and an optionally substituted heterocyclic ring, and
  each of $R_1$, $X_1$ and $X_2$ has the same meaning as that in Formula (I), and one of $X_1$ and $X_2$ is substituted with A-B.

In a particular embodiment of the present invention, in a compound of Formula (II), one of $X_1$ and $X_2$ is CH, O, S or N, the other one of $X_1$ and $X_2$ is C linked to a substituent $R_2$, and $R_2$ has the formula of:

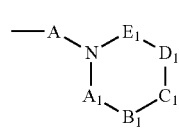

Formula 2a wherein each of $A_1$, $B_1$, $C_1$, $D_1$, $E_1$ is independently selected from the group consisting of N, NH, S, O, CH and CH2, each of NH, CH and $CH_2$ is optionally independently substituted, and the $A_1B_1C_1D_1E_1N$ ring optionally contains one or more double bonds.

According to an embodiment of the present invention, in a compound of Formula (II) having $R_2$ of Formula 2a described above:
  W is O, S or an optionally substituted NH;
  one of $X_1$ and $X_2$ is CH, and the other one of $X_1$ and $X_2$ is C—$R_2$;
  A is an optionally substituted alkyl having 1 to 10 carbon atoms;
  $X_3$ is C;
  $R_1$ is an optionally substituted fused or bicyclic cycloalkyl ring; and
  $R_3$ is an optionally substituted aryl or heteroaryl.

Other exemplary compounds of Formula (II) having $R_2$ of Formula 2a, include, but are not limited to:

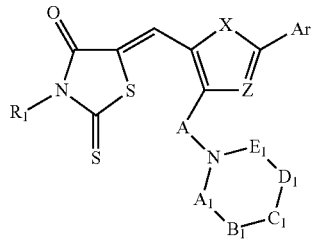
Formula 2(a)

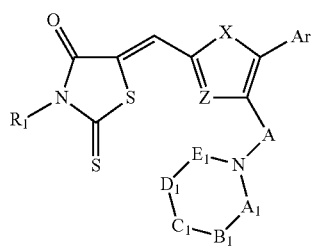
Formula 2(a)

wherein each of X and Z is independently selected from the group consisting of CH, O, S, N and N(R) (R is alkyl or aryl), A is selected from an unsubstituted or substituted aryl or alkyl chain from $C_1$-$C_{10}$, each of $A_1$, $B_1$, $C_1$, $D_1$, $E_1$ is independently selected from the group consisting of N, N(R), S, O, CH and $CH_2$, Ar is selected from the group consisting of a substituted or unsubstituted aryl or heteroaryl ring.

In another embodiment of the present invention, in a compound of Formula (I), $R_5$ has Formula 1a, and $R_3$ is a benzopyranyl or quinolinyl, which includes, but is not limited to, a moiety having the formula of:

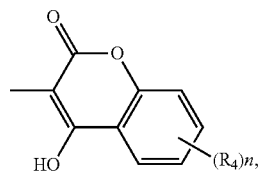
Formula 2b(1)

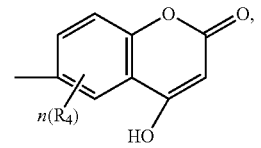
Formula 2b(2)

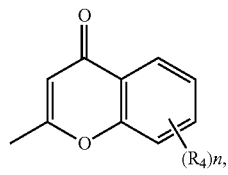
Formula 2b(3)

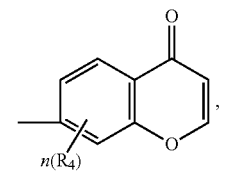
Formula 2b(4)

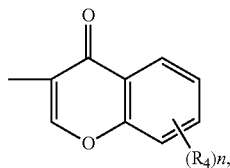
Formula 2b(5)

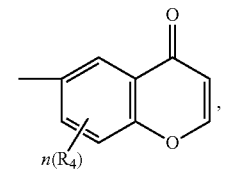
Formula 2b(6)

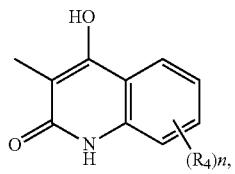
Formula 2b(7)

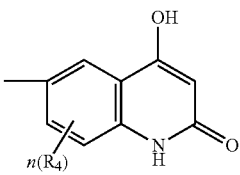
Formula 2b(8)

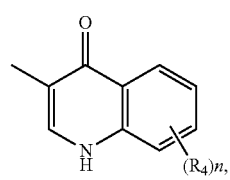
Formula 2b(9)

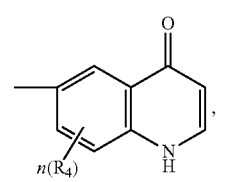
Formula 2b(10)

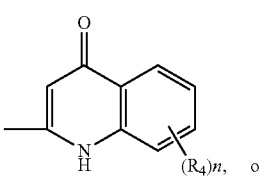
Formula 2b(11)

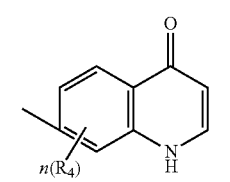
Formula 2b(12)

wherein
n is an integer of 0 to 3, and
$R_4$ is independently selected from the group consisting of an alkoxy, a halogen, a hydroxy, an amide, a thio, a nitro, a cyano, an alkyl, an alcohol, an amine, an amino acid derivative, a carboxyl, an acid ester, an alpha-hydroxy acid, an ether, a guanidino, an optionally substituted aryl, an optionally substituted heteroaryl, an optionally substituted cycloalkyl, and an optionally substituted heterocyclic ring.

According to an embodiment of the present invention, in a compound of Formula (I) having $R_5$ of Formula 1a, and $R_3$ of a benzopyranyl or quinolinyl, such as those described herein:
W is O, S or an optionally substituted NH;
both of $X_1$ and $X_2$ are CH;
$X_3$ is C;
Y is S;
Z is S; and
$R_1$ is an optionally substituted fused or bicyclic cycloalkyl ring.

Other exemplary compounds of Formula (I) having $R_3$ of a benzopyranyl or quinolinyl include, but are not limited to, a compound having the formula of:

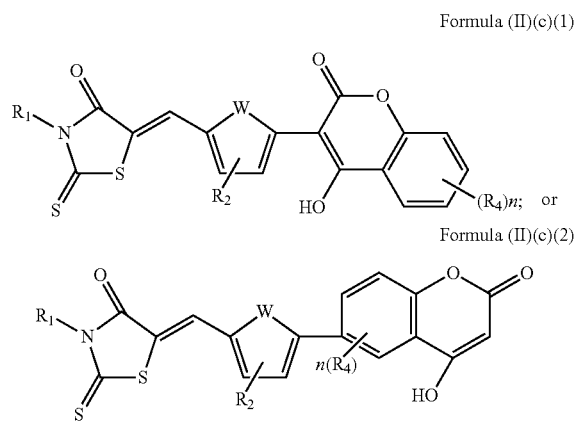

Formula (II)(c)(1)

or

Formula (II)(c)(2)

wherein each of $R_1$, $R_2$ and W has the same meaning as that in Formula (I), preferably W is $CH_2$, S, NH or O, and each of the $CH_2$ and NH is optionally substituted with an alkyl or aryl,
n is an integer of 0 to 3, and
$R_4$ is independently selected from the group consisting of an alkoxy, a halogen, a hydroxy, an amide, a thio, a nitro, a cyano, an alkyl, an alcohol, an amine, an amino acid derivative, a carboxyl, an acid ester, an alpha-hydroxy acid, an ether, a guanidino, an optionally substituted aryl, an optionally substituted heteroaryl, an optionally substituted cycloalkyl, and an optionally substituted heterocyclic ring.

In a particular embodiment of the present invention, an illustrative compound of Formula (II)(c)(1) has the formula of:

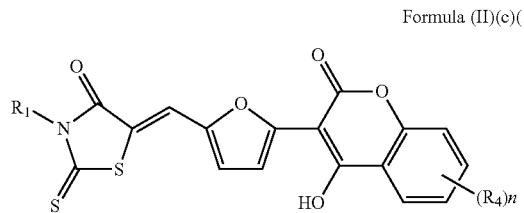

Formula (II)(c)(1)(i)

wherein each of $R_1$, $R_4$ and n has the same meaning as that in Formula (II)(c)(1).

Exemplary compounds of Formula (II)(c)(1) include, but are not limited to, compounds listed under Type-3a in Table 1 and additional compounds in Table 3.

In another particular embodiment of the present invention, an illustrative compound of Formula (II)(c)(2) has the formula of:

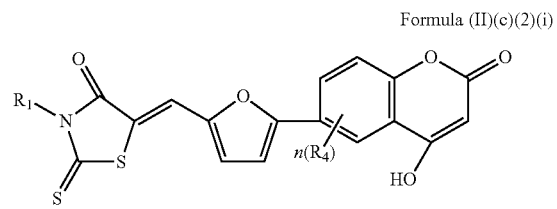

Formula (II)(c)(2)(i)

Exemplary compounds of Formula (II)(c)(2) include, but are not limited to, compounds listed under Type-3b in Table 1 and additional compounds in Table 3.

In another embodiment of the present invention, a compound of Formula (I) has the formula of:

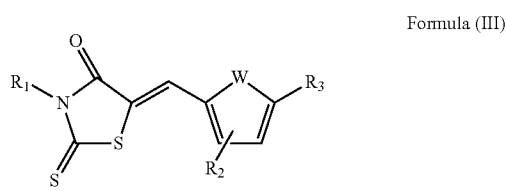

Formula (III)

wherein each of $R_1$, $R_2$, $R_3$ has the same meaning as that in Formula (I), W is O, S or an optionally substituted NH.

According to an embodiment of the present invention, $R_2$ in Formula (III) is H.

Exemplary compound of Formula (III) includes, but is not limited to, a compound having the formula of:

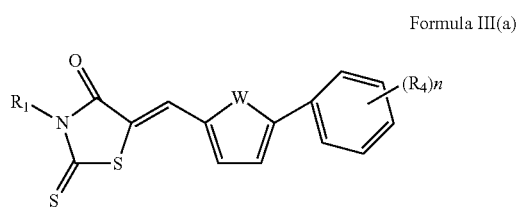

Formula III(a)

wherein
n is an integer of 1 to 3; and
$R_4$ is independently selected from the group consisting of an alkoxy, a halogen, a hydroxy, an amide, a thio, a nitro, a cyano, an alkyl, an alcohol, an amine, an amino acid derivative, a carboxyl, an acid ester, an alpha-hydroxy acid, an ether, a guanidino, an optionally substituted aryl, an optionally substituted heteroaryl, an optionally substituted cycloalkyl, and an optionally substituted heterocyclic ring,
preferably, when n is 1 and W is O or S, then $R_4$ is selected from the group consisting of an amino acid derivative, an optionally substituted aryl, an optionally substituted heteroaryl, an optionally substituted cycloalkyl, and an optionally substituted heterocyclic ring.

In a particular embodiment of the present invention, an illustrative compound of Formula III(a) has the formula of:

Formula III(a)(i)

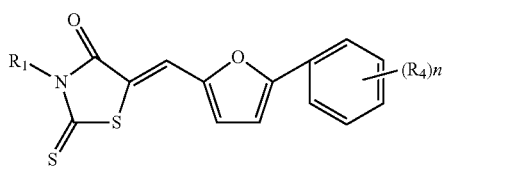

wherein each of $R_1$, $R_4$ and n has the meaning as that in Formula III(a).

Some of the exemplary compounds of Formula III(a) are listed under Type-1 in Table 1

In an embodiment of the present invention, a compound of Formula III(a) has the formula of:

Formula III(a)(1)

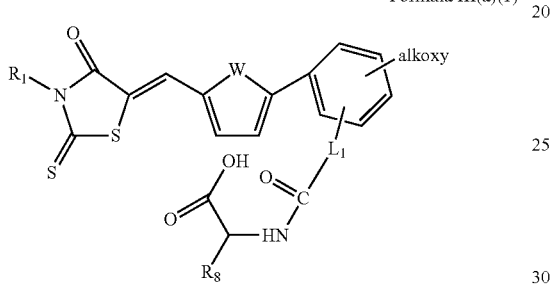

wherein $R_1$ and W each has the same meaning as that in Formula III(a), $L_1$ is a direct bond or an optionally substituted linking unit having 1 to 4 carbon atoms and up to 2 heteroatoms selected from the group consisting of O, N and S; and $R_8$ is a side chain of an amino acid or a derivative thereof.

In a particular embodiment of the present invention, an illustrative compound of Formula (III)(a)(1) has the formula of:

Formula III(a)(1)(i)

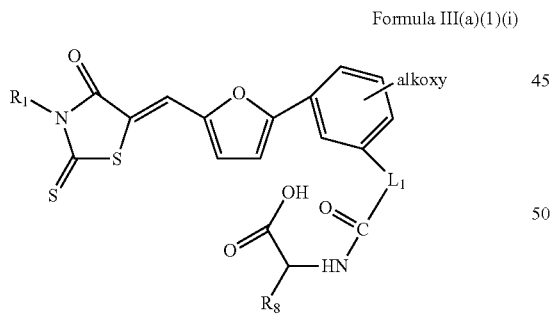

wherein each of $R_1$ and $R_8$ has the same meaning as that in Formula (III)(a)(1).

Exemplary compounds of Formula (III)(a)(1) include, but are not limited to, compounds listed under Type-4 in Table 1.

According to an embodiment of the present invention, $R_2$ in Formula (III) is A-B, wherein A is an optionally substituted aryl, or an optionally substituted alkyl, alkenyl or alkynyl having 1 to 10 carbon atoms, and B is hydrogen.

According to yet another embodiment of the present invention, $R_2$ in Formula (III) is A-B, wherein A is an optionally substituted aryl, or an optionally substituted alkyl, alkenyl or alkynyl having 1 to 10 carbon atoms, and B is selected from the group consisting of an alkoxy, a hydroxyl, an acid ester, a carboxyl, an amine, an amide, an ether, an amino acid derivative, an alpha-hydroxy acid, a guanidino, an optionally substituted aryl, an optionally substituted heteroaryl, an optionally substituted cycloalkyl, and an optionally substituted heterocyclic ring.

Compounds of Formula (III) according to embodiments of the present invention include, but are not limited to, a compound having the formula of:

Formula (III)(b)(1)

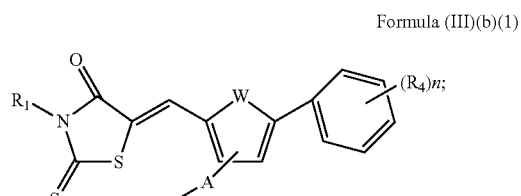

Formula (III)(b)(2)

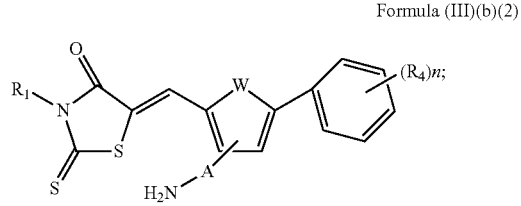

Formula (III)(b)(3)

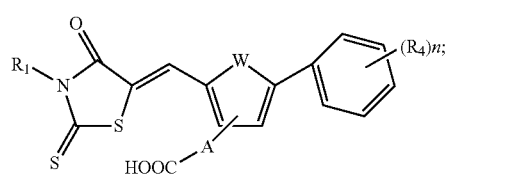

Formula (III)(b)(4)

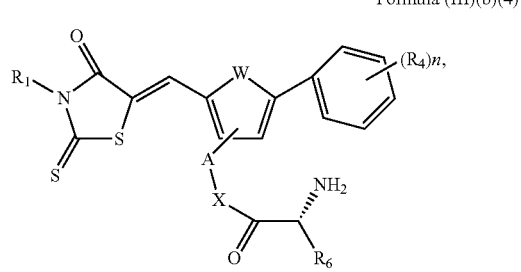

wherein X is O, N or S, and $R_6$ is a side chain of an amino acid or a derivative thereof;

Formula (III)(b)(5)

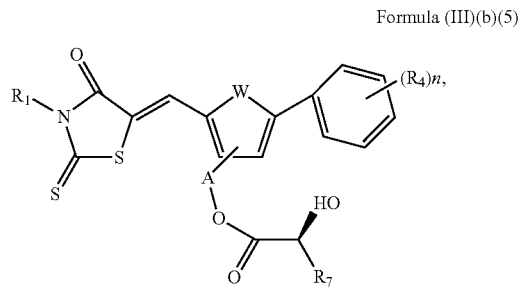

wherein $R_7$ is a side chain of an amino acid or a derivative thereof;

Formula (III)(b)(6)

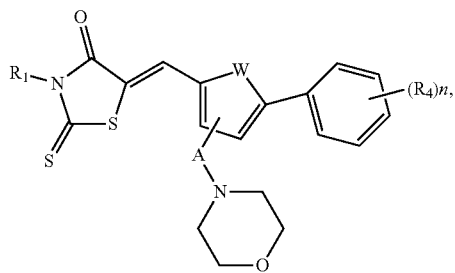

wherein the morpholine is optionally substituted;

Formula (III)(b)(7)

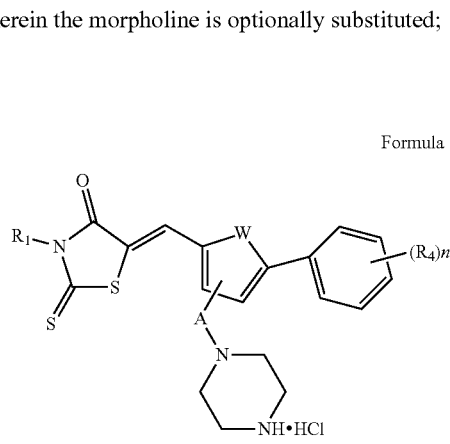

wherein the piperazine is optionally substituted;

Formula (III)(b)(8)

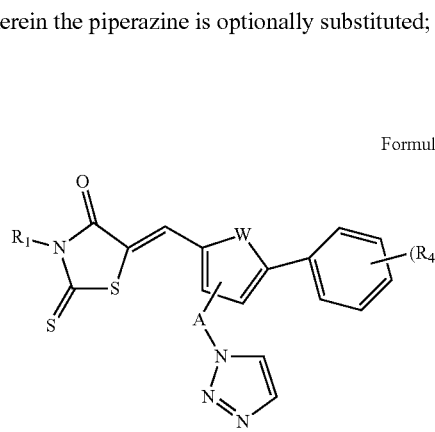

wherein the triazole is optionally substituted;

Formula (III)(b)(9)

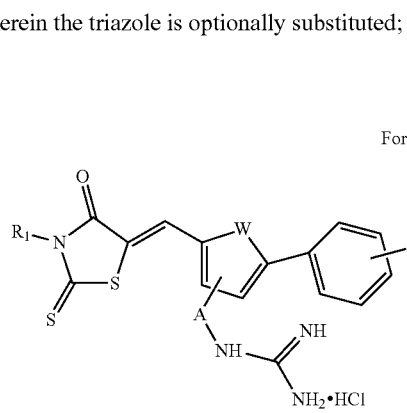

Formula (III)(b)(10)

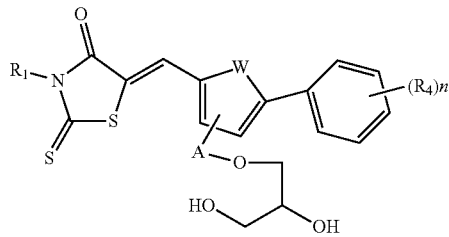

Formula (III)(b)(11)

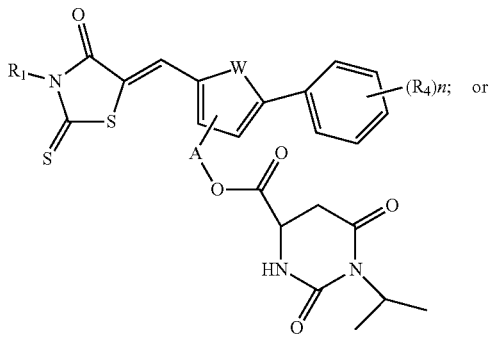

Formula (III)(b)(12)

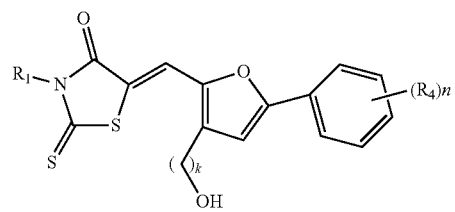

wherein the Ar is an optionally substituted aryl.

In each of Formula (III)(b)(1) to Formula (III)(b)(12), each of $R_1$ and W has the same meaning as that in Formula (III); n is an integer of 0 to 3; and $R_4$ is independently selected from the group consisting of an alkoxy, a halogen, a hydroxy, an amide, a thio, a nitro, a cyano, an alkyl, an alcohol, an amine, an amino acid derivative, a carboxyl, an acid ester, an alpha-hydroxy acid, an ether, a guanidino, an optionally substituted aryl, an optionally substituted heteroaryl, an optionally substituted cycloalkyl, and an optionally substituted heterocyclic ring.

In a particular embodiment of the present invention, an illustrative compound of Formula (III)(b)(1) has the formula of:

Formula (III)(b)(1)(i)

wherein k is an integer of 1 to 10, and each of n, $R_1$ and $R_4$ has the same meaning as that in Formula (III)(b)(1).

Exemplary compounds of Formula (III)(b)(1) include, but are not limited to, compounds listed under Type-5 in Table 1.

In another particular embodiment of the present invention, a compound of Formula (III)(b)(2) has the formula of:

Formula (III)(b)(2)(i)

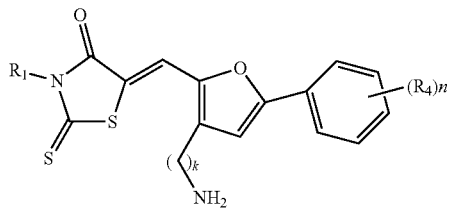

wherein k is an integer of 1 to 10, and each of n, $R_1$ and $R_4$ has the same meaning as that in Formula (III)(b)(2).

Exemplary compounds of Formula (III)(b)(2) include, but are not limited to, compounds listed under Type-6 in Table 1.

In another particular embodiment of the present invention, a compound of Formula (III)(b)(3) has the formula of:

Formula (III)(b)(3)(i)

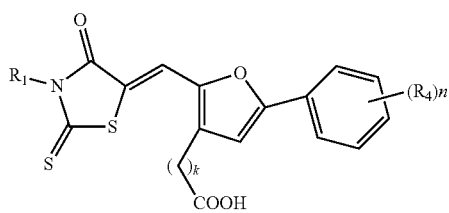

wherein k is an integer of 1 to 10, and each of n, $R_1$ and $R_4$ has the same meaning as that in Formula (III)(b)(3).

Exemplary compounds of Formula (III)(b)(3) include, but are not limited to, compounds listed under Type-7 in Table 1.

In another particular embodiment of the present invention, a compound of Formula (III)(b)(4) has the formula of:

Formula (III)(b)(4)(i)

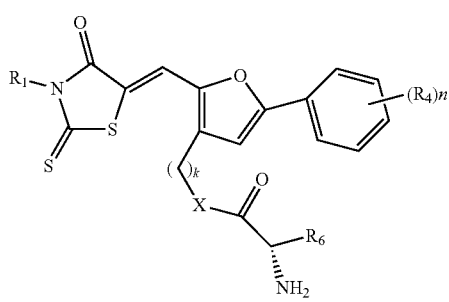

wherein k is an integer of 1 to 10, each of X, n, $R_1$, $R_4$ and $R_6$ has the same meaning as that in Formula (III)(b)(4).

Exemplary compounds of Formula (III)(b)(4) include, but are not limited to, compounds listed under Type-8 in Table 1.

In another particular embodiment of the present invention, a compound of Formula (III)(b)(5) has the formula of:

Formula (III)(b)(5)(i)

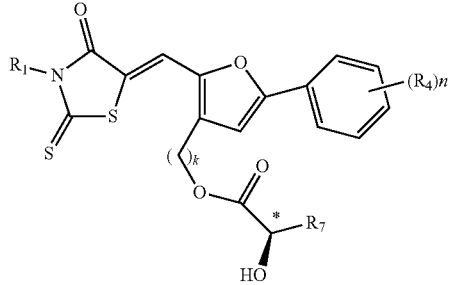

wherein k is an integer of 1 to 10, each of n, $R_1$, $R_4$ and $R_7$ has the same meaning as that in Formula (III)(b)(5).

Exemplary compounds of Formula (III)(b)(5) include, but are not limited to, compounds listed under Type-9 in Table 1.

In another particular embodiment of the present invention, a compound of Formula (III)(b)(6) has the formula of:

Formula (III)(b)(6)(i)

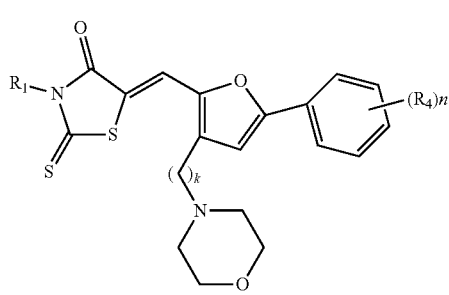

wherein k is an integer of 1 to 10, each of n, $R_1$ and $R_4$ has the same meaning as that in Formula (III)(b)(6).

Exemplary compounds of Formula (III)(b)(6) include, but are not limited to, compounds listed under Type-10 in Table 1.

In another particular embodiment of the present invention, a compound of Formula (III)(b)(7) has the formula of:

Formula (III)(b)(7)(i)

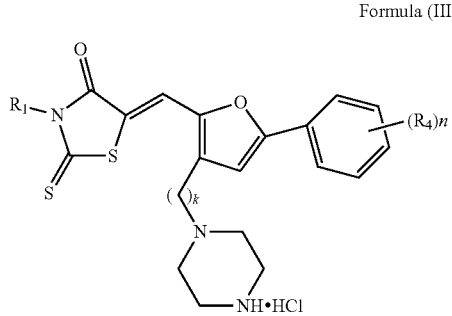

wherein k is an integer of 1 to 10, each of n, $R_1$ and $R_4$ has the same meaning as that for Formula (III)(b)(7).

Exemplary compounds of Formula (III)(b)(7) include, but are not limited to, compounds listed under Type-11 in Table 1.

In another particular embodiment of the present invention, a compound of Formula (III)(b)(8) has the formula of:

Formula (III)(b)(8)(i)

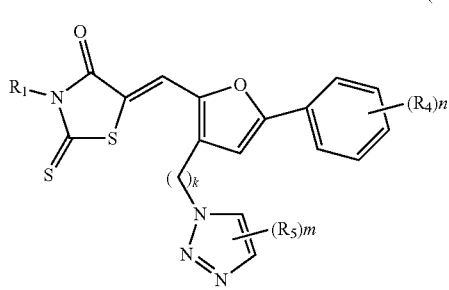

Formula (IV)(1)

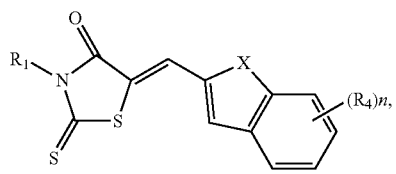

wherein X is O, S or an optionally substituted NH;

wherein k is an integer of 1 to 10, m is an integer of 0 to 2, $R_5$ is a substituent, such as one independently selected from the group of substituents described herein for $R_4$; each of n, $R_1$ and $R_4$ has the same meaning as that for Formula (III)(b)(8).

Exemplary compounds of Formula (III)(b)(8) include, but are not limited to, compounds listed under Type-13 in Table 1.

In another particular embodiment of the present invention, a compound of Formula (III)(b)(9) has the formula of:

Formula (III)(b)(9)(i)

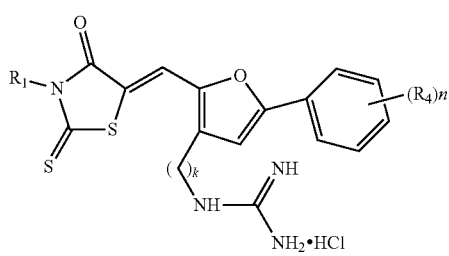

(ii)

Formula (IV)(2)

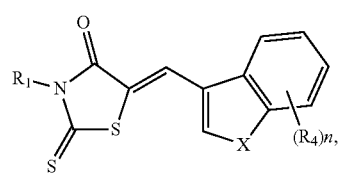

wherein X is O, S or an optionally substituted NH;

Formula (IV)(3)

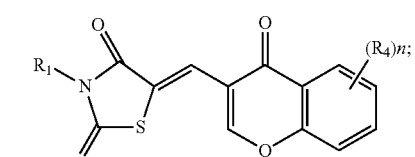

(iii)

Formula (IV)(4)

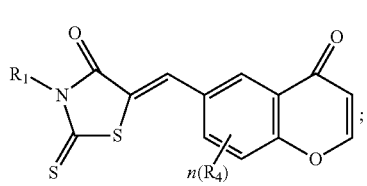

(iv)

wherein k is an integer of 1 to 10, each of n, $R_1$ and $R_4$ has the same meaning as that for Formula (III)(b)(9).

Exemplary compounds of Formula (III)(b)(9) include, but are not limited to, compounds listed under Type-12 in Table 1.

In another particular embodiment of the present invention, a compound of Formula (III)(b)(10) has the formula of:

Formula (III)(b)(10)(i)

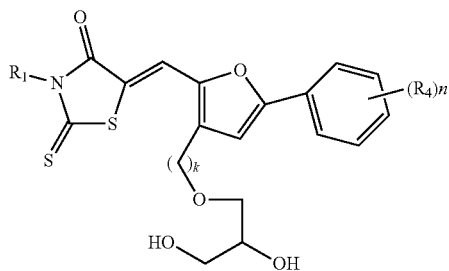

Formula (IV)(5)

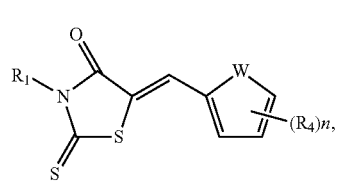

(v)

wherein W is O, S or an optionally substituted NH; or wherein k is an integer of 1 to 10, each of n, $R_1$ and $R_4$ has the same meaning as that for Formula (III)(b)(10).

Exemplary compounds of Formula (III)(b)(10) include, but are not limited to, compounds listed under Type-14 in Table 1.

Exemplary compounds of Formula (III)(b)(11) and Formula (III)(b)(12) include, but are not limited to, compounds listed in Table 3.

According to another embodiments of the present invention, a compound of Formula (I) has a formula of:

Formula (IV)(6)

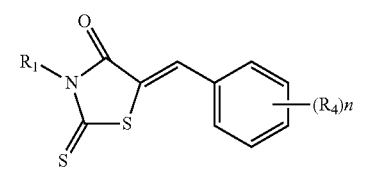

(vi)

in each of Formula (IV)(1) to Formula (IV)(6), wherein
R$_1$ is an optionally substituted fused or bicyclic cycloalkyl ring,
n is an integer of 0 to 3; and
R$_4$ is independently selected from the group consisting of an alkoxy, a halogen, a hydroxy, an amide, a thio, a nitro, a cyano, an alkyl, an alcohol, an amine, an amino acid derivative, a carboxyl, an acid ester, an alpha-hydroxy acid, an ether, a guanidino, an optionally substituted aryl, an optionally substituted heteroaryl, an optionally substituted cycloalkyl, and an optionally substituted heterocyclic ring,
provided that
in Formula (IV)(5) and Formula (IV)(6), R$_4$ is not an optionally substituted aryl or an optionally substituted heteroaryl.

described generally below and more specifically illustrated by the exemplary compounds which follow herein.

Synthesis of the Type-1 Compounds: Basic Scheme

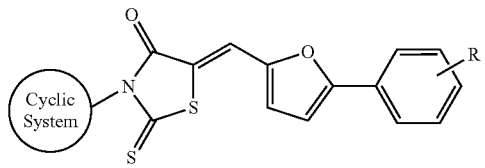

Type I

This type of compound was prepared according to the synthetic route below.

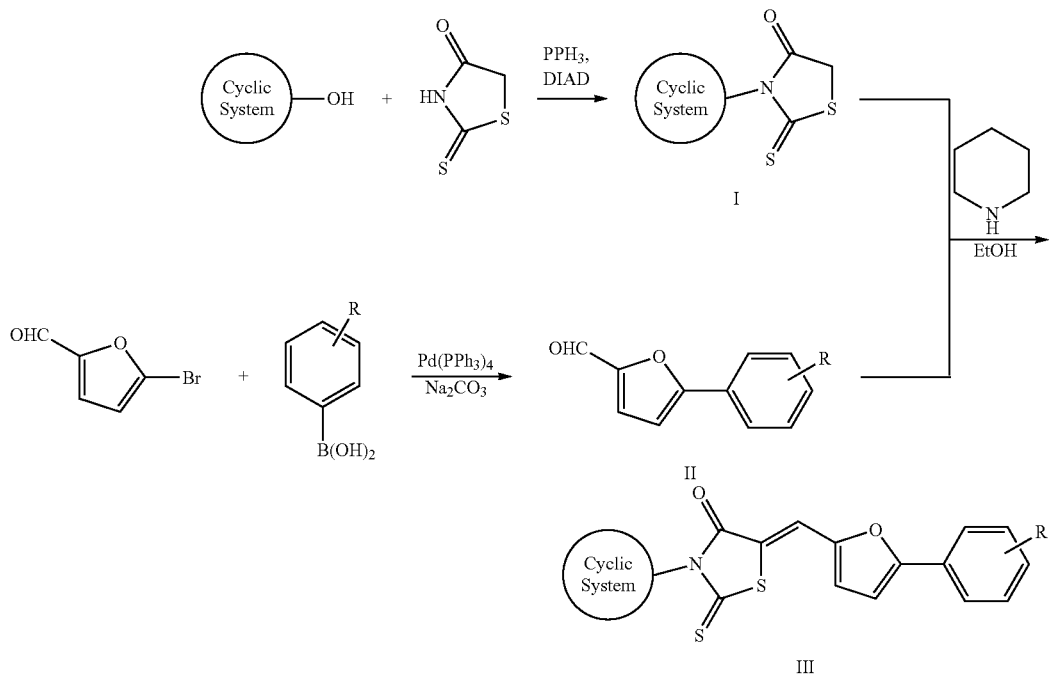

In a particular embodiment of the present invention, a compound of Formula (IV)(5) has the formula of:

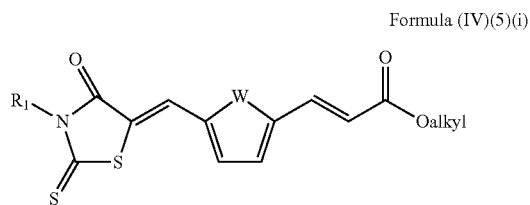

Formula (IV)(5)(i)

Exemplary compounds of Formula (IV)(1) to Formula (IV)(6) include, but are not limited to, compounds listed under Type-15 and 16 in Table 1.

Additional exemplary compounds of the present invention are also provided in Table 3.

Methods of Synthesis

The compounds according to embodiments of the present invention can be prepared by any number of processes as Compounds of 3-N-cycloalkyl-2-thioxothiazolidin-4-one (I) can be synthesized by the following general procedure. To a solution of PPh$_3$ (6.3 g, 24 mmol) in THF (150 mL) was added DIAD (5.2 g, 24 mmol) at −78° C. within 2 min, and the formed mixture was stirred at the same temperature for 10 min. after addition of cycloalkyl alcohol (30 mmol) at −78° C., the mixture was stirred for 10 min. To this solution was added rhodanine (2.7 g, 20 mmol) at −78° C., and the formed mixture was first stirred at −78° C. for 10 min. then allowed to warm to room temperature and stirred overnight. The reaction was worked up by addition of water (30 mL) and the formed solid is filtered off. The aqueous phase was extracted with ethyl acetate (3×30 mL), and the combined organic phase was washed with brine (20 mL) and dried over anhydrous Na$_2$SO$_4$. After removal of the solvent under vacuum, the crude product was purified by a flash column chromatography on silica gel (ethyl acetate-hexane) to afford the desired products.

Compounds of 5-substituted aryl furan-2-yl carboxaldehyde (II) can be synthesized by the following general procedure. To a solution of 5-bromofuran-2-carbaldehyde (1.5 g, 8.6 mmol), aryl boronic acid (9.0 mmol) in a mixed solvent of toluene (30 mL), ethanol (15 mL) and saturated aqueous Na$_2$CO$_3$ (30 mL) was added Pd(PPh$_3$)$_4$ (104 mg, 0.09 mmol) at room temperature, and the reaction mixture was stirred under refluxing conditions for 10 h. After cooling to room temperature, the reaction mixture was concentrated, and the residue was extracted with CH$_2$Cl$_2$ (3×50 mL). The combined organic phase was first washed with brine (2×10 mL), and then dried over anhydrous Na$_2$SO$_4$. After removing the solvent, the residue was purified by a flash chromatography (CH$_2$Cl$_2$) on silica gel to afford the desired products.

(Z)-3-cycloalkyl-5-((5-arylfuran-2-yl)methylene)-2-thioxothiazolidin-4-one (III) can be synthesized by the following general procedure. To a solution of 3-N-cycloalkyl-2-thioxothiazolidin-4-one (I) (0.5 mmol) and 5-substituted aryl furan-2-yl carboxaldehyde (II) (0.5 mmol) in EtOH (5 mL) was added anhydrous piperidine (43 mg, 0.5 mmol) at room temperature, and the mixture was refluxed for 16 h. After cooling to room temperature, the mixture was diluted with ethyl acetate (50 mL), and the organic phase was washed with water (3×10 mL), and then dried over anhydrous Na$_2$SO$_4$. The solvent was removed under vacuum, and the residue was recrystallized from ethyl acetate-hexane or a flash chromatography (CH$_2$Cl$_2$) on silica gel to afford the desired products as illustrated below.

(Z)-3-(adamantan-2-yl)-5-[(3',4',5'-trimethoxyphenyl)furan-2-yl)methylene]-2-thioxothiazolidin-4-one

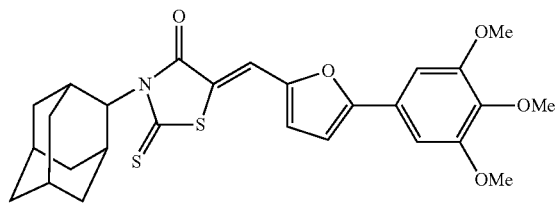 [SMILES: COc1cc(-c2ccc(/C=C3\SC(=S)N(C4C5CC6CC(C5)CC4C6)C3=O)o2)cc(OC)c1OC]

$^1$H-NMR (300 MHz, CDCl$_3$): 7.38 (s, 1H), 7.03 (s, 1H), 6.90 (d, J=3.6, 1H), 6.78 (d, J=3.6, 1H), 5.15 (s, 1H), 3.99 (s, 6H), 3.92 (s, 3H), 2.52-2.51 (m, 2H), 2.44 (s, 1H), 2.01-1.89 (m, 6H), 1.81 (s, 1H), 1.73 (d, J=12.6, 1H), 1.57 (s, 2H). HRMS (ESI): 512.1558 (M+H).

(Z)-3-(bicyclo[2.2.1]heptan-2-yl)-5-[(3',4',5'-trimethoxyphenyl)furan-2-yl)methylene]-2-thioxothiazolidin-4-one

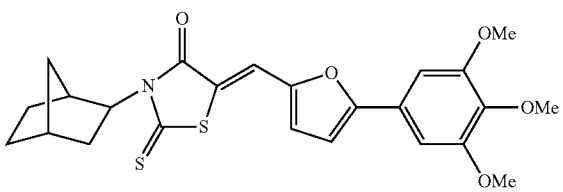 [SMILES: COc1cc(-c2ccc(/C=C3\SC(=S)N(C4CC5CCC4C5)C3=O)o2)cc(OC)c1OC]

$^1$H-NMR (300 MHz, CDCl$_3$): 7.36 (s, 1H), 7.03 (m, 1H), 6.91 (d, J=3.9, 1H), 6.79 (d, J=3.6, 1H), 4.96 (dd, J=6.0, 3.6, 1H), 3.99 (s, 6H), 3.91 (s, 3H), 2.57 (s, 1H), 2.47 (s, 1H), 2.25-2.24 (m, 2H), 1.83-1.81 (m, 1H), 1.62-1.61 (m, 5H), 1.28-1.27 (m, 4H). HRMS (ESI): 472.1243 (M+H).

(Z)-3-(adamantan-2-yl)-5-[(4'-carboxyphenyl)furan-2-yl)methylene]-2-thioxothiazolidin-4-one

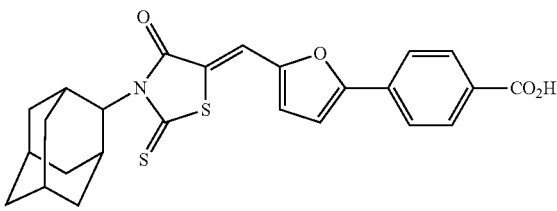 [SMILES: O=C(O)c1ccc(-c2ccc(/C=C3\SC(=S)N(C4C5CC6CC(C5)CC4C6)C3=O)o2)cc1]

$^1$H-NMR (300 MHz, DMSO-d6): 8.06 (d, J=8.1, 2H), 7.89 (d, J=8.1, 2H), 7.57 (s, 1H), 7.43 (d, J=3.6, 1H), 7.34 (d, J=3.9, 1H), 5.04 (s, 1H), 2.98 (s, 6H), 2.94-2.48 (s, 3H), 2.38 (s, 2H), 1.74 (s, 2H). HRMS (ESI): 466.1145 (M+H).

(Z)-3-(bicyclo[2.2.1]heptan-2-yl)-5-[(4'-carboxyphenyl)furan-2-yl)methylene]-2-thioxothiazolidin-4-one

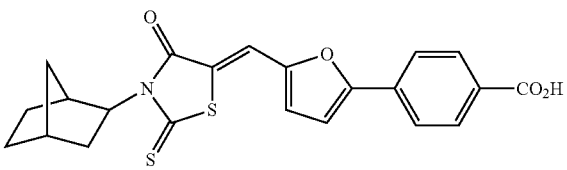 [SMILES: O=C(O)c1ccc(-c2ccc(/C=C3\SC(=S)N(C4CC5CCC4C5)C3=O)o2)cc1]

$^1$H-NMR (300 MHz, DMSO-d6): 8.04 (d, J=5.4, 2H), 7.87-7.85 (m, 3H), 7.56 (s, 1H), 7.41 (d, J=3.9, 1H), 7.36 (d, J=3.6, 1H), 4.86 (t, J=6.0, 1H), 2.57 (s, 1H), 2.47 (s, 1H), 2.25-2.24 (m, 2H), 1.83-1.81 (m, 1H), 1.62-1.61 (m, 5H), 1.28-1.27 (m, 4H). HRMS (ESI): 426.081 (M+H).

(Z)-3-(adamantan-2-yl)-5-[(3',5'-dihydroxyphenyl)furan-2-yl)methylene]-2-thioxothiazolidin-4-one

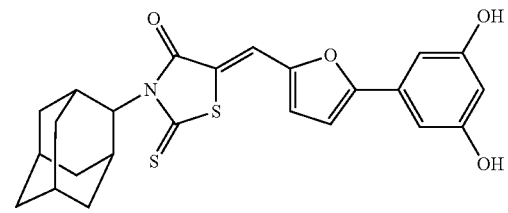 [SMILES: O=C1/C(=C/c2ccc(-c3cc(O)cc(O)c3)o2)SC(=S)N1C1C2CC3CC(C2)CC1C3]

$^1$H-NMR (300 MHz, CDCl$_3$): 9.66 (s, 1H), 7.54 (s, 1H), 7.29 (d, J=3.9, 1H), 7.14 (d, J=3.9, 1H), 6.71 (d, J=2.1, 2H), 6.29 (d, J=2.1, 1H), 5.06 (s, 1H), 2.44 (s, 2H), 1.89 (s, 5H), 1.75 (s, 2H), 1.65 (d, J=12.0, 2H).

(Z)-3-(bicyclo[2.2.1]heptan-2-yl)-5-[(4'-hydroxy-3', 5'-dimethoxyphenyl)furan-2-yl)methylene]-2-thioxo-thiazolidin-4-one

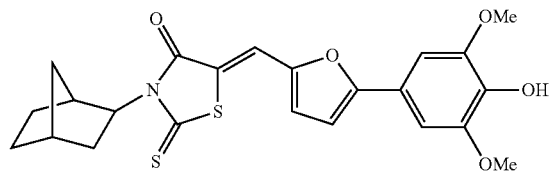 [SMILES: COc1cc(-c2ccc(/C=C3\SC(=S)N(C4CC5CCC4C5)C3=O)o2)cc(OC)c1O]

¹H-NMR (300 MHz, CDCl₃): 9.05 (s, 1H), 7.51 (d, J=1.8, 1H), 7.30 (s, 1H), 7.22 (s, 1H), 7.13 (s, 2H), 4.85 (t, J=7.2, 1H), 3.87 (s, 6H), 2.38 (s, 1H), 2.30 (m, 1H), 2.22 (d, J=8.4, 1H), 1.69 (t, J=10.8, 1H), 1.53 (d, J=5.4, 2H), 1.23 (m, 4H). HRMS (ESI): 458.1084 (M+H).

(Z)-3-(adamantan-2-yl)-5-[(4'-hydroxy-3',5'-dimethoxyphenyl)furan-2-yl)methylene]-2-thioxothiazolidin-4-one

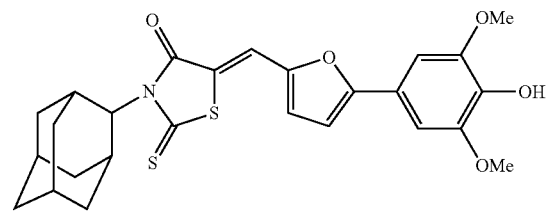 [SMILES: COc1cc(-c2ccc(/C=C3\SC(=S)N(C4C5CC6CC(C5)CC4C6)C3=O)o2)cc(OC)c1O]

¹H-NMR (300 MHz, CDCl₃): 7.51 (s, 1H), 7.28 (d, J=3.6, 1H), 7.18 (d, J=3.6, 1H), 7.11 (s, 2H), 5.03 (s, 1H), 3.86 (s, 6H), 2.63 (t, J=4.5, 4H), 2.43 (s, 3H), 2.38 (s, 1H), 1.88 (s, 5H), 1.74 (s, 2H), 1.64 (d, J=12.9, 2H), 1.39 (m, 6H).

(Z)-3-(bicyclo[2.2.1]heptan-2-yl)-5-[(4'-methoxyphenyl)furan-2-yl)methylene]-2-thioxothiazolidin-4-one

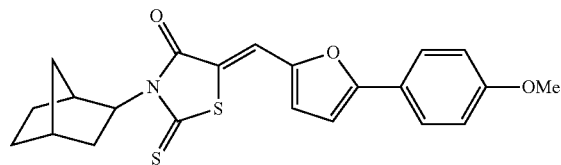 [SMILES: COc1ccc(-c2ccc(/C=C3\SC(=S)N(C4CC5CCC4C5)C3=O)o2)cc1]

¹H-NMR (300 MHz, CDCl₃): 7.73 (m, 2H), 7.34 (s, 1H), 7.01 (m, 2H), 6.90 (d, J=3.6, 1H), 6.72 (d, J=3.6, 1H), 4.97 (dd, J=6.0, 3.6, 1H), 3.88 (s, 3H), 2.56 (s, 1H), 2.47 (s, 1H), 2.36 (m, 2H), 1.80 (m, 1H), 1.36 (t, J=10.8, 1H), 1.24 (t, J=6.9, 2H). HRMS (ESI): 412.1028 (M+H).

(Z)-3-(adamantan-2-yl)-5-[(4'-methoxyphenyl)furan-2-yl)methylene]-2-thioxothiazolidin-4-one

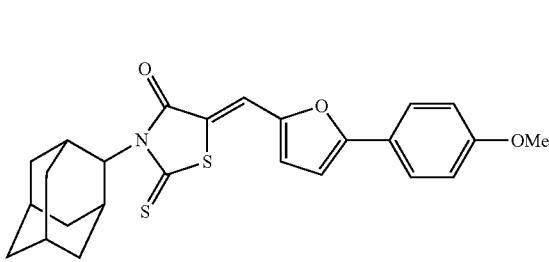 [SMILES: COc1ccc(-c2ccc(/C=C3\SC(=S)N(C4C5CC6CC(C5)CC4C6)C3=O)o2)cc1]

¹H-NMR (300 MHz, CDCl₃): 7.74 (m, 2H), 7.37 (s, 1H), 7.02 (m, 2H), 6.89 (d, J=2.7, 1H), 6.72 (d, J=3.6, 1H), 5.17 (s, 1H), 3.89 (s, 3H), 2.51 (s, 2H), 2.45 (s, 1H), 1.96 (m, 6H), 1.81 (s, 2H), 1.73 (d, J=12.3, 2H). HRMS (ESI): 452.1345 (M+H).

(Z)-3-(bicyclo[2.2.1]heptan-2-yl)-5-[(3'-hydroxy-4'-methoxyphenyl)furan-2-yl)methylene]-2-thioxothiazoli-din-4-one

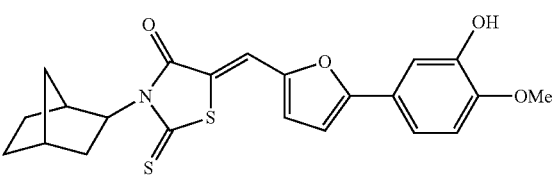 [SMILES: COc1ccc(-c2ccc(/C=C3\SC(=S)N(C4CC5CCC4C5)C3=O)o2)cc1O]

¹H-NMR (300 MHz, CDCl₃): 7.39 (d, J=2.1, 1H), 7.36 (m, 1H), 7.30 (d, J=2.1, 1H), 6.97 (d, J=8.4, 2H), 6.90 (d, J=3.6, 1H), 6.72 (d, J=3.6, 1H), 5.73 (s, 1H), 4.98 (dd, J=6.0, 3.6, 1H), 3.97 (s, 3H), 2.56 (s, 1H), 2.47 (s, 1H), 2.36 (m, 2H), 1.78 (m, 1H), 1.37 (m, 1H), 1.26 (m, 2H).

(Z)-3-(bicyclo[2.2.1]heptan-2-yl)-5-[(4'-aminophenyl)furan-2-yl)methylene]-2-thioxothiazolidin-4-one

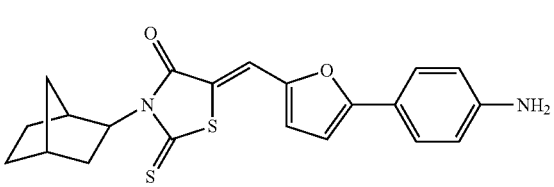 [SMILES: Nc1ccc(-c2ccc(/C=C3\SC(=S)N(C4CC5CCC4C5)C3=O)o2)cc1]

¹H-NMR (300 MHz, CDCl₃): 7.52 (d, J=8.7, 2H), 7.45 (s, 1H), 7.28 (d, J=3.6, 1H), 6.95 (d, J=3.6, 1H), 6.67 (d, J=8.7,

2H), 5.80 (s, 2H), 4.86 (dd, J=6.0, 3.6, 1H), 2.50 (s, 1H), 2.48 (m, 2H), 1.68 (t, J=10.5, 1H), 1.52 (m, 2H), 1.22 (m, 3H).

(Z)-3-(adamantan-2-yl)-5-[(4'-aminophenyl)furan-2-yl)methylene]-2-thioxothiazolidin-4-one

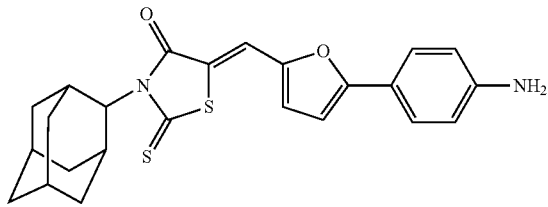 [SMILES: Nc1ccc(-c2ccc(/C=C3\SC(=S)N(C4C5CC6CC(C5)CC4C6)C3=O)o2)cc1]

$^1$H-NMR (300 MHz, CDCl$_3$): 7.53 (d, J=8.7, 2H), 7.48 (s, 1H), 7.28 (d, J=3.9, 1H), 6.95 (d, J=3.9, 1H), 6.66 (d, J=8.4, 2H), 5.79 (s, 2H), 5.06 (s, 1H), 2.43 (s, 4H), 2.43 (s, 4H), 1.89 (s, 6H), 1.74 (s, 2H), 1.64 (d, J=9.3, 2H), 1.21 (m, 2H).

Methyl 5-(5-((Z)-(3-adamantan-2-yl)-4-oxo-2-thioxothiazolidin-5-ylidene)methyl)furan-2-yl)-2-methoxy-benzoate

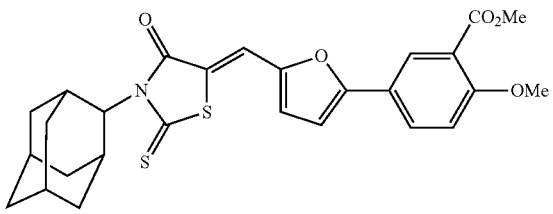 [SMILES: COC(=O)c1cc(-c2ccc(/C=C3\SC(=S)N(C4C5CC6CC(C5)CC4C6)C3=O)o2)ccc1OC]

$^1$H-NMR (300 MHz, CDCl$_3$): 8.19 (d, J=2.1, 1H), 7.94 (m, 1H), 7.38 (s, 1H), 7.13 (d, J=8.7, 1H), 6.90 (d, J=3.9, 1H), 6.79 (d, J=3.6, 1H), 5.16 (s, 1H), 3.99 (s, 3H), 3.97 (s, 3H), 2.52 (s, 3H), 2.45 (s, 1H), 1.99 (m, 6H), 1.81 (s, 2H), 1.73 (d, J=9.3, 2H).

Methyl 5-(5-((Z)-(3-(bicyclo[2.2.1]heptan-2-yl)-4-oxo-2-thioxothiazolidin-5-ylidene)-methyl)furan-2-yl)-2-methoxybenzoate

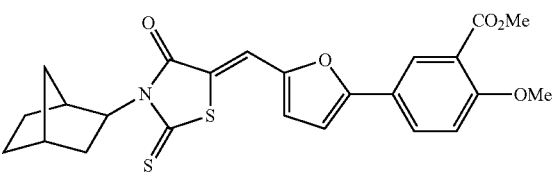

$^1$H-NMR (300 MHz, CDCl$_3$): 8.19 (d, J=2.4, 1H), 7.95 (m, 1H), 7.35 (s, 1H), 7.12 (d, J=9.0, 1H), 6.90 (d, J=3.6, 1H), 6.79 (d, J=3.6, 1H), 4.96 (dd, J=6.0, 3.6, 1H), 3.99 (s, 3H), 2.56 (s, 1H), 2.47 (s, 1H), 2.38 (m, 2H), 1.80 (m, 1H), 1.38 (m, 1H), 1.26 (m, 3H).

(Z)-3-(adamantan-2-yl)-5-[(4'-hydroxyphenyl)furan-2-yl)methylene]-2-thioxothiazolidin-4-one

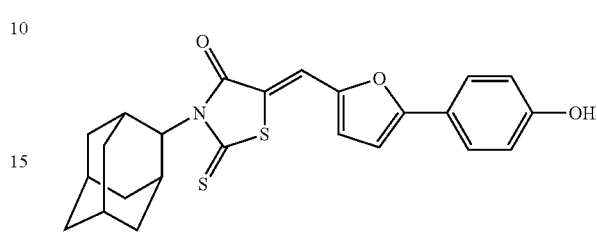

$^1$H-NMR (300 MHz, DMSO-d6): 10.06 (s, 1H), 7.69 (d, J=8.1, 2H), 7.54 (d, J=5.4, 1H), 7.31 (d, J=3.7, 1H), 6.94 (d, J=8.4, 2H), 5.06 (s, 1H), 2.50-2.40 (m, 4H), 1.99 (s, 1H), 1.93-1.90 (m, 6H), 1.67-1.62 (m, 2H). HRMS (ESI): 438.1173 (M+H).

(Z)-3-(bicyclo[2.2.1]heptan-2-yl)-5-[(4'-trimethoxyphenyl)furan-2-yl)methylene]-2-thioxothiazolidin-4-one

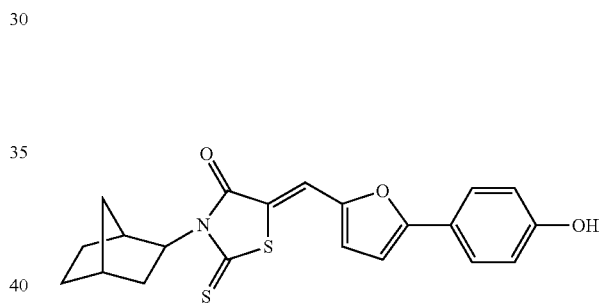

$^1$H-NMR (300 MHz, CDCl$_3$): 7.61 (d, J=8.4, 2H), 7.30 (s, 1H), 7.03 (d, J=8.7, 2H), 6.86 (d, J=3.9, 1H), 6.63 (d, J=3.6, 1H), 4.95 (dd, J=6.3, 3.6, 1H), 3.14 (s, 5H), 2.54 (s, 1H), 2.46 (s, 1H), 2.37 (m, 3H), 1.79 (m, 6H), 1.28 (m, 6H).

(Z)-3-(bicyclo[2.2.1]heptan-2-yl)-5-[(3'-hydroxy-5'-methoxyphenyl)furan-2-yl)methylene]-2-thioxothia-zoli-din-4-one

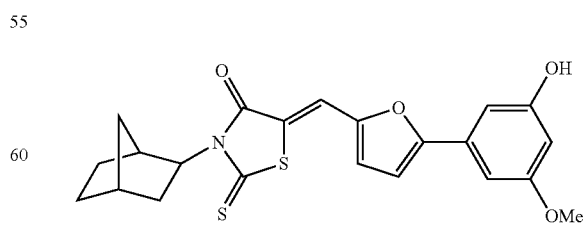

$^1$H-NMR (300 MHz, CDCl$_3$): 9.92 (s, 1H), 7.54 (s, 1H), 7.29 (dd, J=6.0, 2.4, 2H), 6.87 (s, 2H), 6.40 (d, J=2.1, 1H), 4.86 (dd, J=5.8, 2.4, 1H), 3.78 (s, 3H), 2.38 (s, 1H), 2.29-2.23

(m, 3H), 2.01-1.97 (m, 2H), 1.70-1.64 (m, 2H), 1.56-1.52 (m, 2H), 1.33-1.28 (m, 6H). HRMS (ESI): 429.0999 (M+H).

(Z)-3-(adamantan-2-yl)-5-[(3'-hydroxy-5'-methoxyphenyl)furan-2-yl)methylene]-2-thioxothiazolidin-4-one

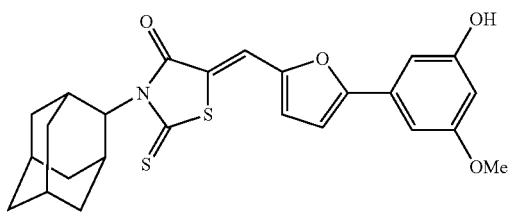 [SMILES: COc1cc(O)cc(-c2ccc(/C=C3\SC(=S)N(C4C5CC6CC(C5)CC4C6)C3=O)o2)c1]

¹H-NMR (300 MHz, CDCl₃): 9.91 (s, 1H), 7.55 (s, 1H), 7.28 (dd, J=6.3, 3.9, 2H), 6.86 (d, J=1.5, 2H), 6.40 (t, J=2.1, 1H), 5.05 (s, 1H), 3.78 (s, 3H), 2.44 (s, 2H), 2.36 (s, 1H), 1.89-1.81 (m, 5H), 1.76 (s, 2H), 1.78-1.76 (m, 2H).

(Z)-3-(bicyclo[2.2.1]heptan-2-yl)-5-[(3',5'-dimethoxyphenyl)furan-2-yl)methylene]-2-thioxothiazolidin-4-one

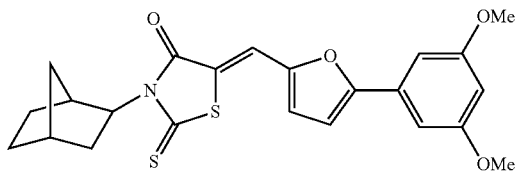 [SMILES: COc1cc(OC)cc(-c2ccc(/C=C3\SC(=S)N(C4CC5CCC4C5)C3=O)o2)c1]

¹H-NMR (500 MHz, CDCl₃): 7.36 (s, 1H), 6.94 (d, J=2.2, 2H), 6.89 (d, J=3.6, 1H), 6.83 (d, J=3.6, 1H), 6.50 (t, J=2.1, 1H), 4.96 (dd, J=8.4, 6.2, 1H), 3.89 (s, 6H), 2.56 (s, 1H), 2.46 (s, 1H), 2.40-2.32 (m, 1H), 2.30 (d, J=9.7, 1H), 1.79 (t, J=11.0, 1H), 1.66-1.50 (m, 2H), 1.42-1.20 (m, 3H).

(Z)-3-(adamantan-2-yl)-5-((5-(3,5-dimethoxyphenyl)furan-2-yl)methylene)-2-thioxothiazolidin-4-one

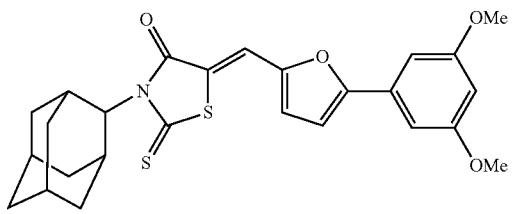 [SMILES: COc1cc(OC)cc(-c2ccc(/C=C3\SC(=S)N(C4C5CC6CC(C5)CC4C6)C3=O)o2)c1]

¹H-NMR (300 MHz, CDCl₃): 7.38 (s, 1H), 6.94 (s, 2H), 6.88 (d, J=1.8, 1H), 6.82 (d, J=3.6, 1H), 6.49 (s, 1H), 5.15 (s, 1H), 3.89 (s, 6H), 2.47 (d, J=22, 4H), 1.99 (s, 8H), 1.75 (m, 7H), 1.26 (s, 6H).

Ethyl 2-(5-(5-((Z)-(3-adamantan-2-yl)-4-oxo-2-thioxothiazolidin-5-ylidene)methyl)furan-2-yl)-2-methoxy-phenoxy)acetate

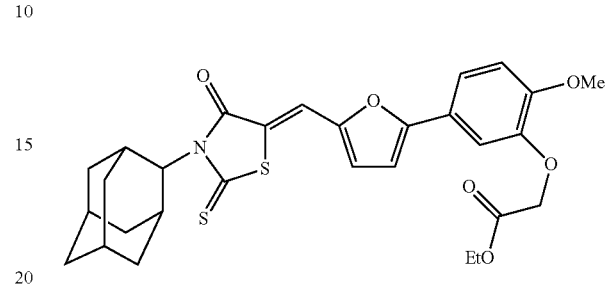

¹H-NMR (300 MHz, CDCl₃): 7.42 (m, 1H), 7.36 (s, 1H), 7.24 (d, J=1.8, 1H), 7.02 (d, J=8.7, 1H), 6.88 (d, J=2.1, 1H), 6.70 (d, J=3.6, 1H), 5.16 (s, 1H), 4.80 (s, 2H), 4.31 (m, 2H), 3.96 (s, 3H), 2.51 (s, 3H), 2.44 (s, 1H), 1.99 (m, 7H), 1.81 (s, 2H), 1.73 (d, J=12.6, 2H), 1.31 (t, J=7.2, 3H). HRMS (ESI): 554.1672 (M+H).

Ethyl 2-(5-(5-((Z)-(3-(bicyclo[2.2.1]heptan-2-yl)-4-oxo-2-thioxothiazolidin-5-ylidene)methyl)furan-2-yl)-2-methoxyphenoxy)acetate

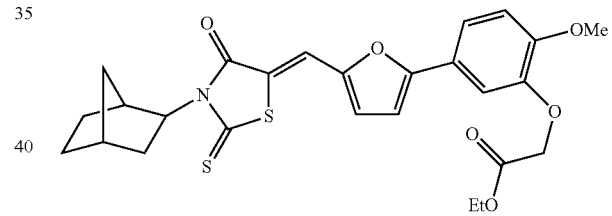

¹H-NMR (300 MHz, CDCl₃): 7.45 (m, 1H), 7.32 (s, 1H), 7.22 (d, J=2.1, 1H), 7.00 (d, J=8.4, 1H), 6.88 (d, J=3.6, 1H), 6.69 (d, J=3.6, 1H), 4.96 (dd, J=6.0, 2.1, 1H), 4.79 (s, 2H), 4.31 (m, 2H), 3.95 (s, 3H), 2.55 (s, 1H), 2.46 (s, 1H), 2.36 (m, 2H), 1.78 (t, J=10.2, 1H), 1.67 (s, 1H), 1.59 (d, J=6.0, 2H), 1.38 (m, 2H), 1.28 (m, 3H). HRMS (ESI): 514.1352 (M+H).

(Z)-3-(adamantan-2-yl)-5-[(3'-hydroxy-4'-methoxyphenyl)furan-2-yl)methylene]-2-thioxothiazolidin-4-one

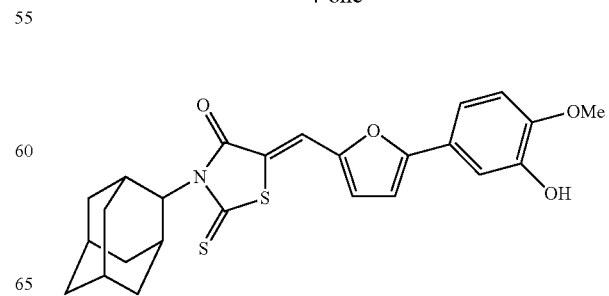

¹H-NMR (300 MHz, CDCl₃): 7.36 (m, 2H), 7.30 (s, 1H), 6.96 (d, J=8.4, 1H), 6.89 (s, 1H), 6.71 (s, 1H), 5.16 (s, 1H), 3.97 (s, 3H), 2.48 (m, 6H), 1.99 (s, 8H), 1.81 (s, 2H), 1.73 (d, J=12.6, 4H).

(Z)-3-(bicyclo[2.2.1]heptan-2-yl)-5-[(4'-hydroxy-3'-methoxyphenyl)furan-2-yl)methylene]-2-thioxothiazoli-din-4-one

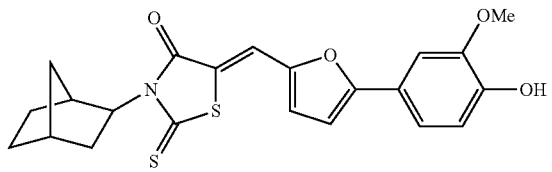 [SMILES: COc1cc(-c2ccc(/C=C3\SC(=S)N(C4CC5CCC4C5)C3=O)o2)ccc1O]

¹H-NMR (300 MHz, CDCl₃): 7.36 (d, J=8.4, 1H), 7.35 (s, 1H), 7.30 (d, J=2.0, 1H), 6.97 (d, J=8.4, 1H), 6.89 (d, J=3.5, 1H), 6.71 (d, J=3.5, 1H), 5.75 (s, 1H), 4.98 (t, J=7.5, 1H), 3.97 (s, 3H), 2.56 (s, 1H), 2.46 (s, 1H), 2.37 (m, 1H), 2.31 (d, J=4.5, 2H), 1.79 (t, J=10.4, 1H), 1.39 (t, J=9.0, 1H), 1.32 (m, 4H). HRMS (ESI): 428.0982 (M+H).

(Z)-3-(adamantan-2-yl)-5-[(3',4'-dimethoxy-5'-(methoxymethoxy)phenyl)furan-2-yl)methylene]-2-thioxo-thiazolidin-4-one

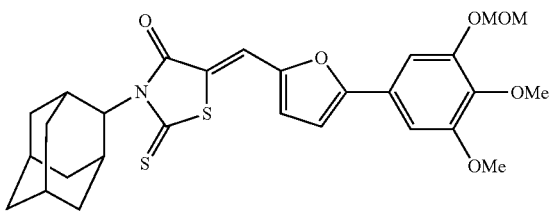

¹H-NMR (300 MHz, CDCl₃): 7.35 (s, 1H), 7.28 (d, J=1.8, 1H), 7.07 (d, J=2.1, 1H), 6.89 (d, J=3.3, 1H), 6.78 (d, J=3.6, 1H), 5.30 (s, 2H), 4.96 (dd, J=6.0, 3.6, 1H), 4.00 (s, 3H), 3.93 (s, 3H), 3.60 (s, 3H), 2.55 (s, 1H), 2.46 (s, 1H), 1.81 (t, J=1.5, 1H), 1.35 (m, 1H), 1.28 (m, 2H). HRMS (ESI): 542.1669 (M+H).

(Z)-3-(bicyclo[2.2.1]heptan-2-yl)-5-[(3'-methoxy-4',5'-bis(methoxymethoxy)phenyl)furan-2-yl)methylene]-2-thioxothiazolidin-4-one (1000051778)

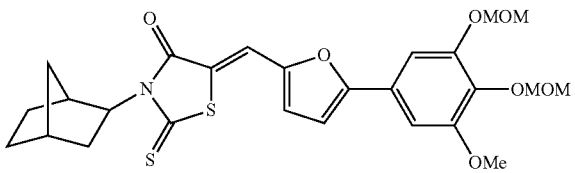

¹H-NMR (300 MHz, CDCl₃): 7.53 (s, 1H), 7.29 (d, J=1.5, 1H), 7.08 (d, J=2.1, 1H), 6.89 (d, J=3.9, 1H), 6.78 (d, J=3.6, 1H), 5.29 (s, 2H), 5.20 (s, 2H), 4.96 (dd, J=6.3, 3.6, 1H), 3.98 (s, 3H), 3.63 (s, 3H), 3.59 (s, 3H), 2.55 (s, 1H), 2.49 (s, 1H), 2.32 (m, 3H), 1.78 (t, J=11.2, 1H), 1.32 (m, 5H).

(Z)-3-(bicyclo[2.2.1]heptan-2-yl)-5-[(3',4'-dimethoxy-5'-(methoxymethoxy)phenyl)furan-2-yl)methylene]-2-thioxothiazolidin-4-one

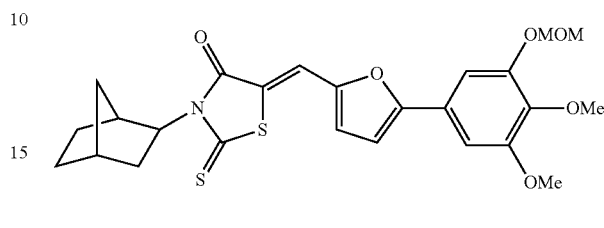

¹H-NMR (300 MHz, CDCl₃): 7.38 (s, 1H), 7.29 (d, J=2.1, 1H), 7.07 (d, J=1.8, 1H), 6.88 (d, J=3.6, 1H), 6.78 (d, J=3.9, 1H), 5.31 (s, 2H), 4.83 (s, 1H), 4.00 (s, 3H), 3.93 (s, 3H), 3.60 (s, 3H), 2.48 (m, 3H), 1.98 (m, 6H), 1.80 (s, 2H), 1.73 (d, J=12.6, 2H). HRMS (ESI): 502.1776 (M+H).

(Z)-3-(adamantan-2-yl)-5-[(3'-methoxy-4',5'-bis(methoxymethoxy)phenyl)furan-2-yl)methylene]-2-thioxo-thiazolidin-4-one

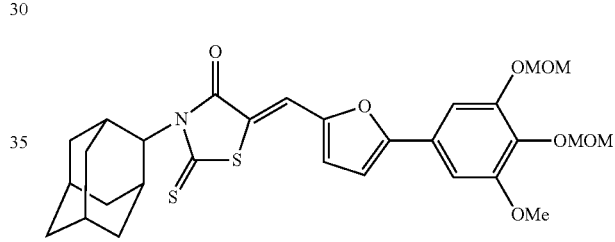

¹H-NMR (300 MHz, CDCl₃): 7.37 (s, 1H), 7.29 (d, J=1.8, 1H), 7.07 (d, J=1.8, 1H), 6.88 (d, J=3.6, 1H), 6.78 (d, J=3.9, 1H), 5.29 (s, 2H), 5.20 (s, 2H), 5.15 (s, 1H), 3.99 (s, 3H), 3.64 (s, 3H), 3.60 (s, 3H), 2.51 (m, 3H), 2.44 (s, 1H), 1.96 (m, 6H), 1.80 (s, 2H), 1.73 (d, J=12.3, 2H), 1.63 (s, 2H).

Ethyl 2-(5-(5-((Z)-(3-(bicyclo[2.2.1]heptan-2-yl)-4-oxo-2-thioxothiazolidin-5-ylidene)methyl)furan-2-yl)-2,3-dimethoxyphenoxy)acetate

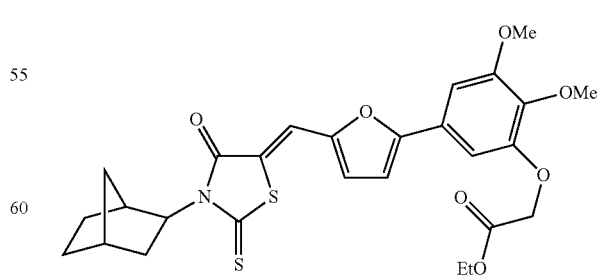

¹H-NMR (300 MHz, CDCl₃): 7.35 (s, 1H), 7.07 (d, J=1.8, 1H), 6.94 (d, J=1.8, 1H), 6.90 (d, J=3.6, 1H), 6.94 (d, J=3.9, 1H), 4.96 (dd, J=6.3, 3.6, 1H), 4.30 (m, 3H), 4.00 (s, 3H), 3.96

(s, 3H), 2.55 (s, 1H), 2.33 (m, 2H), 1.80 (m, 1H), 1.39 (m, 3H), 1.31 (t, J=7.2, 3H). HRMS (ESI): 544.1452 (M+H).

Ethyl 2-(5-(5-((Z)-(3-(adamantan-2-yl)-4-oxo-2-thioxothiazolidin-5-ylidene)methyl)furan-2-yl)-2,3-dimeth-oxyphenoxy)acetate

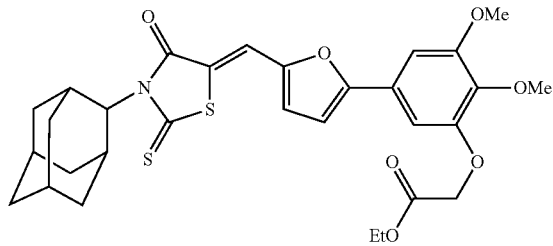 [SMILES: CCOC(=O)COc1cc(-c2ccc(/C=C3\SC(=S)N(C4C5CC6CC(C5)CC4C6)C3=O)o2)cc(OC)c1OC]

¹H-NMR (300 MHz, CDCl₃): 7.36 (s, 1H), 7.06 (s, 1H), 6.93 (s, 1H), 6.87 (d, J=3.6, 1H), 6.73 (d, J=3.6, 1H), 5.14 (s, 1H), 4.80 (s, 2H), 4.30 (q, J=7.2, 2H), 3.99 (s, 3H), 3.96 (s, 3H), 2.48 (m, 4H), 1.95 (m, 6H), 1.80 (s, 1H), 1.74 (s, 1H), 1.68 (d, J=10.5, 2H), 1.31 (m, 3H).

Methyl 5-(5-((Z)-(3-(bicyclo[2.2.1]heptan-2-yl)-4-oxo-2-thioxothiazolidin-5-ylidene)methyl)furan-2-yl)-2,3-dimethoxybenzoate

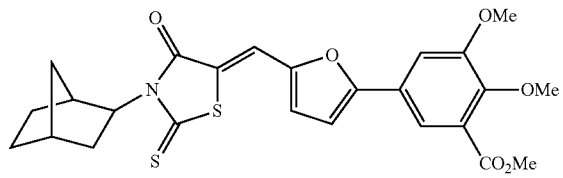

¹H-NMR (300 MHz, CDCl₃): 7.71 (d, J=2.1, 1H), 7.51 (d, J=1.8, 1H), 7.36 (s, 1H), 6.91 (d, J=3.6, 1H), 6.83 (d, J=3.6, 1H), 4.96 (dd, J=6.0, 3.6, 1H), 4.04 (s, 3H), 3.97 (s, 3H), 3.95 (s, 3H), 2.55 (s, 1H), 2.46 (s, 1H), 2.31 (m, 2H), 1.78 (m, 1H), 1.28 (m, 3H).

Methyl 5-(5-((Z)-(3-(adamantan-2-yl)-4-oxo-2-thioxothiazolidin-5-ylidene)methyl)furan-2-yl)-2,3-dimethoxybenzoate

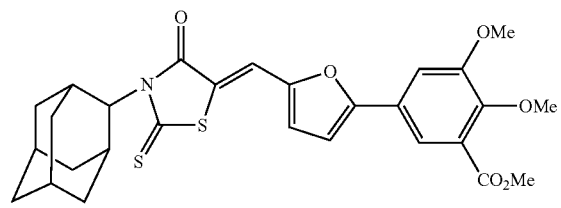 [SMILES: COC(=O)c1cc(-c2ccc(/C=C3\SC(=S)N(C4C5CC6CC(C5)CC4C6)C3=O)o2)cc(OC)c1OC]

¹H-NMR (300 MHz, CDCl₃): 7.71 (d, J=2.1, 1H), 7.52 (d, J=1.8, 1H), 7.38 (s, 2H), 6.87 (s, 1H), 6.89 (d, J=3.6, 1H), 6.83 (d, J=3.6, 1H), 5.14 (s, 1H), 4.04 (s, 3H), 3.97 (s, 2H), 3.96 (s,

3H), 2.51 (m, 4H), 1.98 (m, 6H), 1.80 (s, 1H), 1.73 (d, J=12.3, 2H). HRMS (ESI): 540.1501 (M+H).

2-(5-(5-((Z)-(3-(adamantan-2-yl)-4-oxo-2-thioxothiazolidin-5-ylidene)methyl)furan-2-yl)-2-methoxyphen-oxy)acetic acid

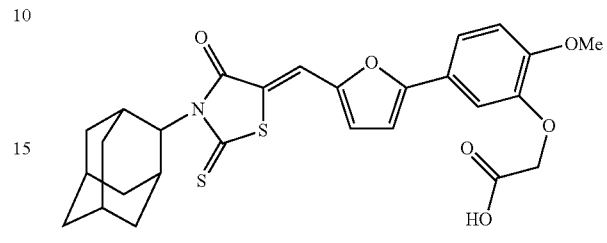

¹H-NMR (300 MHz, CDCl₃): 7.46 (m, 1H), 7.36 (s, 1H), 7.24 (d, J=2.1, 1H), 7.01 (d, J=8.7, 1H), 6.88 (d, J=3.9, 1H), 6.70 (d, J=3.6, 1H), 5.15 (s, 1H), 4.80 (s, 2H), 3.95 (s, 3H), 2.50 (s, 2H), 2.44 (s, 1H), 1.95 (m, 6H), 1.80 (s, 2H), 1.72 (d, J=12.3, 2H).

5-(5-((Z)-(3-(adamantan-2-yl)-4-oxo-2-thioxothiazolidin-5-ylidene)methyl)furan-2-yl)-2-methoxy-benzoic acid

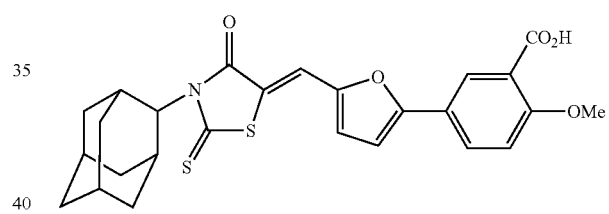

¹H-NMR (300 MHz, DMSO-d6): 8.09 (d, J=2.1, 1H), 7.95 (dd, J=9.0, 2.1, 2.4, 1H), 7.55 (s, 1H), 7.36 (d, J=9.0, 1H), 7.30 (dd, J=9.0, 3.6, 2H), 6.68 (dd, J=4.2, 3.8, 1H), 5.04 (s, 1H), 4.25 (dd, J=3.8, 2H), 3.88 (s, 3H), 2.99-2.97 (m, 2H), 2.38-2.30 (m, 2H), 2.04 (s, 1H), 1.96-1.92 (m, 4H). HRMS (ESI): 496.1248 (M+H).

2-(5-(5-((Z)-(3-(bicyclo[2.2.1]heptan-2-yl)-4-oxo-2-thioxothiazolidin-5-ylidene)methyl)furan-2-yl)-2-meth-oxyphenoxy)acetic acid

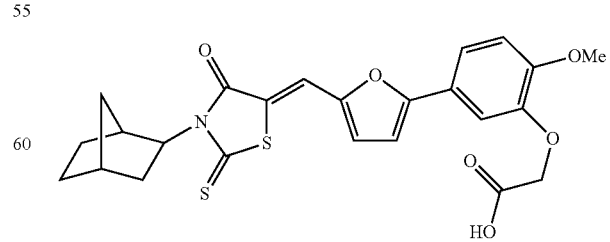

¹H-NMR (300 MHz, CDCl₃): 7.48-7.44 (m, 1H), 7.39 (s, 1H), 7.27 (d, J=2.7, 1H), 7.01 (d, J=8.7, 1H), 6.88 (d, J=3.9,

1H), 6.70 (d, J=3.6, 1H), 5.15 (s, 1H), 4.80 (s, 2H), 3.95 (s, 3H), 2.55 (s, 1H), 2.46 (s, 1H), 2.31 (m, 2H), 1.78 (m, 1H), 1.28 (m, 3H).

5-(5-((Z)-(3-(bicyclo[2.2.1]heptan-2-yl)-4-oxo-2-thioxothiazolidin-5-ylidene)methyl)furan-2-yl)-2-methoxy-benzoic acid

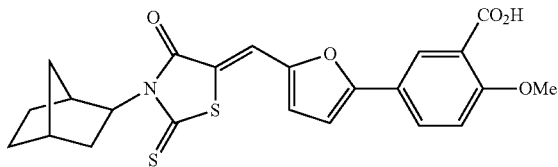 [SMILES: COc1ccc(-c2ccc(/C=C3\SC(=S)N(C4CC5CCC4C5)C3=O)o2)cc1C(=O)O]

¹H-NMR (300 MHz, DMSO-d6): 8.15-8.09 (m, 1H), 7.95 (dd, J=8.1, 3.9, 1H), 7.58 (s, 1H), 7.40 (d, J=8.1, 1H), 7.34 (dd, J=8.0, 3.9, 2H), 6.69 (dd, J=6.0, 3.9, 1H), 5.04 (s, 1H), 4.25 (dd, J=6.0, 3.8, 2H), 3.90 (s, 3H), 2.55 (s, 1H), 2.46 (s, 1H), 2.31 (m, 2H), 1.78 (m, 1H), 1.28 (m, 3H).

2-(5-(5-((Z)-(3-(bicyclo[2.2.1]heptan-2-yl)-4-oxo-2-thioxothiazolidin-5-ylidene)methyl)furan-2-yl)-3-meth-oxyphenoxy)acetic acid

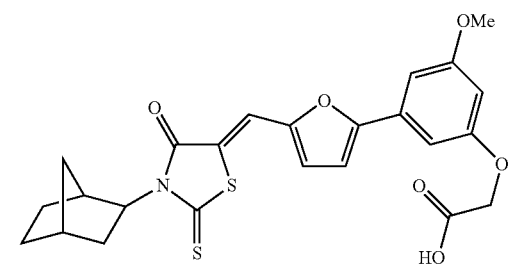 [SMILES: COc1cc(OCC(=O)O)cc(-c2ccc(/C=C3\SC(=S)N(C4CC5CCC4C5)C3=O)o2)c1]

¹H-NMR (300 MHz, DMSO-d6): 7.54 (s, 1H), 7.38 (d, J=3.6 1H), 7.32 (d, J=3.6, 2H), 6.99 (d, 2H), 6.56 (t, 1H), 4.87 (t, J=14.4, 1H), 4.75 (s, 2H), 3.82 (s, 3H), 2.37 (m, 4H), 1.71 (s, 1H), 1.54 (m, 2H), 1.21 (m, 4H). HRMS (ESI): 486.1035 (M+H).

2-(5-(5-((Z)-(3-(adamantan-2-yl))-4-oxo-2-thioxothiazolidin-5-ylidene)methyl)furan-2-yl)-3-methoxyphen-oxy)acetic acid

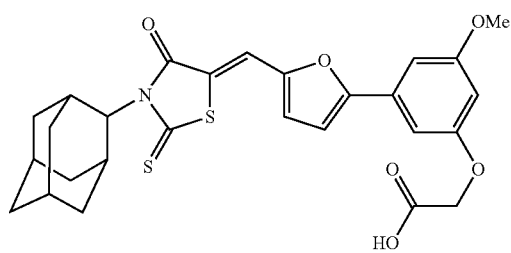 [SMILES: COc1cc(OCC(=O)O)cc(-c2ccc(/C=C3\SC(=S)N(C4C5CC6CC(C5)CC4C6)C3=O)o2)c1]

¹H-NMR (300 MHz, CDCl₃): 13.1 (s, 1H), 7.54 (s, 1H), 7.37 (d, J=3.6 1H), 7.29 (d, J=3.6, 2H), 6.99 (d, 2H), 6.56 (t, 1H), 5.03 (s, 1H), 4.76 (s, 2H), 3.82 (s, 3H), 2.43 (m, 4H), 1.88 (s, 5H), 1.62 (m, 4H). HRMS (ESI): 526.1352 (M+H).

tert-butyl 2-(3-(5-((Z)-(3-(bicyclo[2.2.1]heptan-2-yl)-4-oxo-2-thioxothiazolidin-5-ylidene)methyl)furan-2-yl)-5-methoxyphenoxy)acetate

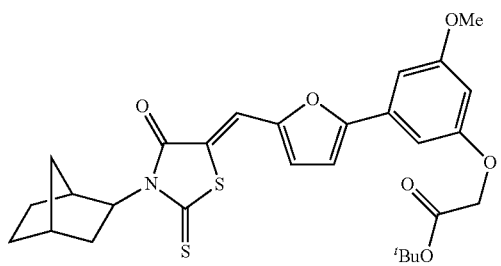 [SMILES: COc1cc(OCC(=O)OC(C)(C)C)cc(-c2ccc(/C=C3\SC(=S)N(C4CC5CCC4C5)C3=O)o2)c1]

¹H-NMR (300 MHz, CDCl₃): 7.35 (s, 1H), 6.98 (s, 1H), 6.90 (d, J=3.9, 2H), 6.81 (d, J=3.6, 2H), 6.50 (t, J=4.2, 1H), 4.98 (m, 1H), 4.61 (s, 2H), 3.88 (s, 3H), 2.55 (s, 1H), 2.46 (s, 1H), 2.35 (m, 2H), 1.83 (m, 1H), 1.41 (s, 1H), 1.29 (m, 5H). HRMS (ESI): 542.1664 (M+H).

tert-butyl 2-(3-(5-((Z)-(3-(adamantan-2-yl)-4-oxo-2-thioxothiazolidin-5-ylidene)methyl)furan-2-yl)-5-methoxyphenoxy)acetate

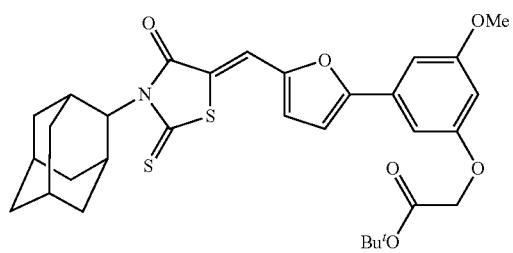

¹H-NMR (300 MHz, CDCl₃): 7.37 (s, 1H), 6.98 (s, 1H), 6.90 (d, J=3.9, 2H), 6.81 (d, J=3.6, 2H), 6.50 (t, J=4.2, 1H), 5.14 (s, 1H), 4.61 (s, 2H), 3.88 (s, 3H), 2.51 (m, 4H), 1.98 (m, 7H), 1.81 (m, 5H), 1.41 (s, 1H), 1.26 (m, 4H).

(Z)-3-(bicyclo[2.2.1]heptan-2-yl)-5-((5-(4'-methoxy-2',5'-dimethylphenyl))furan-2-yl)methylene)-2-thioxothiazolidin-4-one

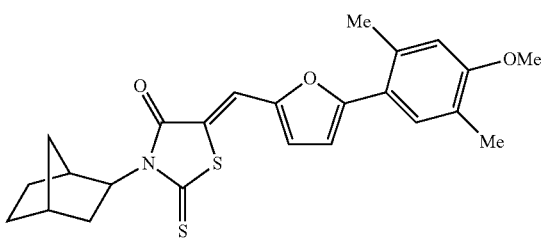 [SMILES: COc1cc(C)c(-c2ccc(/C=C3\SC(=S)N(C4CC5CCC4C5)C3=O)o2)cc1C]

¹H-NMR (300 MHz, CDCl₃): 7.56 (s, 1H), 7.37 (s, 1H), 6.93 (d, J=3.6, 1H), 6.72 (s, 1H), 6.63 (d, J=3.6, 1H), 5.0-4.95

(m, 1H), 3.89 (s, 3H), 2.54 (s, 3H), 2.46 (s, 1H), 2.33 (s, 1H), 2.28 (s, 3H), 1.81-1.75 (m, 2H), 1.39-1.26 (m, 6H).

(Z)-3-(bicyclo[2.2.1]heptan-2-yl)-5-((5-(4'-chlorophenyl)furan-2-yl)methylene)-2-thioxothiazolidin-4-one

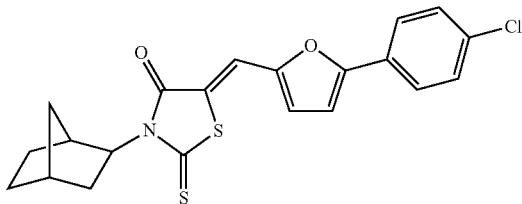 [SMILES: O=C1/C(=C/c2ccc(-c3ccc(Cl)cc3)o2)SC(=S)N1C1CC2CCC1C2]

¹H-NMR (300 MHz, CDCl₃): 7.76 (d, J=8.0, 2H), 7.50 (d, J=9.0, 2H), 7.42 (s, 1H), 6.93 (s, 1H), 6.90 (s, 1H), 5.17 (s, 1H), 2.50 (d, J=18.0, 4H), 2.15 (m, 4H), 1.79-1.72 (m, 4H), 1.29-1.26 (m, 3H).

(Z)-3-(adamantan-2-yl)-5-((5-(4'-chlorophenyl)furan-2-yl)methylene)-2-thioxothiazolidin-4-one

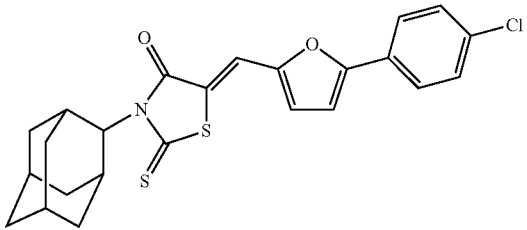 [SMILES: O=C1/C(=C/c2ccc(-c3ccc(Cl)cc3)o2)SC(=S)N1C1C2CC3CC(C2)CC1C3]

¹H-NMR (300 MHz, CDCl₃): 7.72 (d, J=7.8, 2H), 7.46 (d, J=9.0, 2H), 7.38 (s, 1H), 6.89 (s, 1H), 6.85 (s, 1H), 5.16 (s, 1H), 2.47 (d, J=18.0, 4H), 1.99 (s, 6H), 1.76 (m, 4H), 1.27 (s, 3H).

(Z)-3-(adamantan-2-yl)-5-((5-(4-bromophenyl)furan-2-yl)methylene)-2-thioxothiazolidin-4-one

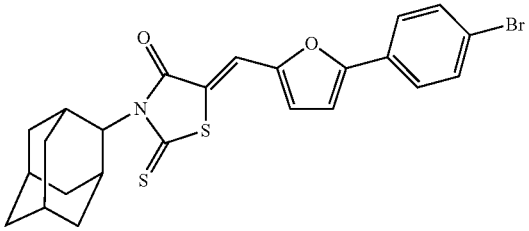 [SMILES: O=C1/C(=C/c2ccc(-c3ccc(Br)cc3)o2)SC(=S)N1C1C2CC3CC(C2)CC1C3]

¹H-NMR (300 MHz, CDCl₃): 7.64-7.62 (m, 4H), 7.38 (s, 1H), 6.88 (d, J=10.0, 2H), 5.16 (s, 1H), 2.48 (m, 4H), 1.99 (s, 6H), 1.79-1.74 (m, 4H).

(Z)-ethyl 3-(5-((3-cyclopentyl-4-oxo-2-thioxothiazolidin-5-ylidene)methyl)furan-2-yl)-2,6-difluorobenzoate

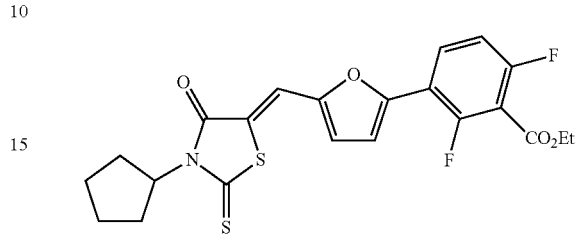

¹H-NMR (300 MHz, CDCl₃): 8.10 (d, J=6.6, 1H), 7.29 (s, 1H), 6.81 (d, J=3.6, 1H), 6.20 (d, J=63.6, 1H), 6.15-6.10 (m, 1H), 5.71-5.66 (m, 1H), 4.25 (q, J=6.9, 2H), 2.34-2.30 (m, 2H), 1.97-1.93 (m, 2H), 1.80-1.77 (m, 2H), 1.43-1.41 (m, 2H), 1.10-1.06 (m, 3H).

(Z)-ethyl 3-(5-((3-cyclooctyl-4-oxo-2-thioxothiazolidin-5-ylidene)methyl)furan-2-yl)-2,6-difluorobenzoate

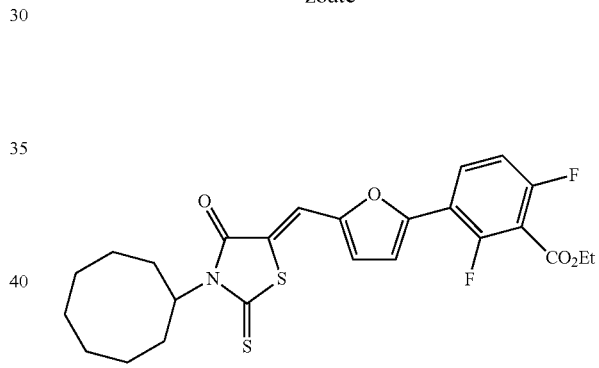

¹H-NMR (300 MHz, CDCl₃): 8.13 (d, J=6.6, 1H), 7.38 (s, 1H), 7.16 (m, 2H), 6.94 (d, J=3.6, 1H), 5.37 (m, 1H), 4.43 (q, J=6.9, 2H), 2.39 (m, 2H), 1.81 (m, 2H), 1.75-1.73 (m, 3H), 1.67-1.53 (m, 14H).

(Z)-5-((5-(4'-chlorophenyl)furan-2-yl)methylene)-3-cyclohexyl-2-thioxothiazolidin-4-one

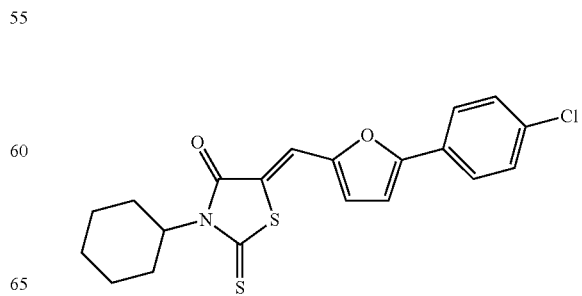

¹H-NMR (300 MHz, CDCl₃): 7.34-7.29 (m, 3H), 7.07 (d, J=1.8, 1H), 7.04 (d, J=1.5, 2H), 6.15 (d, J=1.8, 1H), 5.38-5.31 (m, 1H), 2.71-2.68 (m, 2H), 1.75-1.72 (m, 4H), 1.53-1.52 (m, 1H), 1.32-1.12 (m, 3H).

(Z)-5-((5-(4'-chlorophenyl)furan-2-yl)methylene)-3-cyclopentyl-2-thioxothiazolidin-4-one

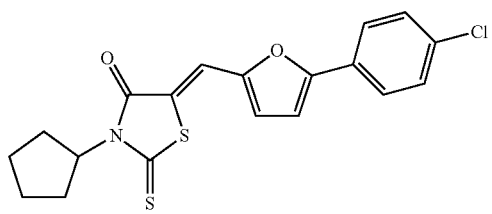 [SMILES: O=C1/C(=C/c2ccc(-c3ccc(Cl)cc3)o2)SC(=S)N1C1CCCC1]

¹H-NMR (300 MHz, CDCl₃): 7.34-7.29 (m, 3H), 7.07 (d, J=1.8, 1H), 7.04 (d, J=1.5, 2H), 6.15 (d, J=1.8, 1H), 5.79-5.67 (m, 1H), 2.41-2.32 (m, 2H), 1.99-1.98 (m, 2H), 1.84-1.81 (m, 2H), 1.48-1.43 (m, 2H).

(Z)-3-cyclooctyl-5-((5-(4'-methoxy-2,5-dimethylphenyl)furan-2-yl)methylene)-2-thioxothiazolidin-4-one

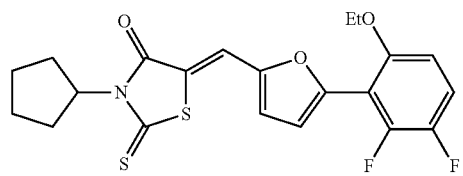 [SMILES: CCOc1ccc(F)c(F)c1-c1ccc(/C=C2\SC(=S)N(C3CCCC3)C2=O)o1]

¹H-NMR (500 MHz, CDCl₃): 7.54 (s, 1H), 7.38 (s, 1H), 6.92 (d, J=3.4, 1H), 6.72 (s, 1H), 6.63-6.62 (d, J=3.4, 1H), 5.38 (board, 1H), 3.87 (s, 3H), 2.53 (s, 3H), 2.40 (s, 2H), 2.27 (s, 3H), 1.81-1.78 (m, 2H), 1.75-1.65 (m, 8H).

(Z)-3-cyclopentyl-5-((5-(6-ethoxy-2,3-difluorophenyl)furan-2-yl)methylene)-2-thioxothiazolidin-4-one ¹H-NMR (300 MHz, CDCl₃): 7.40 (s, 1H), 7.13 (d, J=3.4, 1H), 6.93 (d, J=3.7, 1H), 5.50 (m, 1H), 4.15 (q, J=7.0, 2H), 2.24 (m, 2H), 2.01 (m, 2H), 1.93 (m, 2H), 1.66 (m, 2H), 1.49 (t, J=7.0, 3H).

(Z)-3-cyclopentyl-5-((5-(4-methoxy-2,5-dimethylphenyl)furan-2-yl)methylene)-2

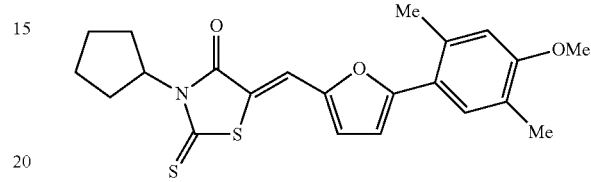

¹H-NMR (300 MHz, CDCl₃): 7.55 (s, 1H), 7.41 (d, J=5.1, 1H), 6.95 (m, 1H), 6.74 (m, 1H), 6.64 (m, 1H), 5.51 (m, 1H), 3.89 (s, 3H), 2.54 (s, 3H), 2.41-2.27 (m, 3H), 2.05-1.788 (m, 5H), 1.64-1.53 (m, 3H).

(Z)-3-cyclohexyl-5-((5-(2,3-difluoro-4-methoxyphenyl)furan-2-yl)methylene)-2-thioxothiazolidin-4-one

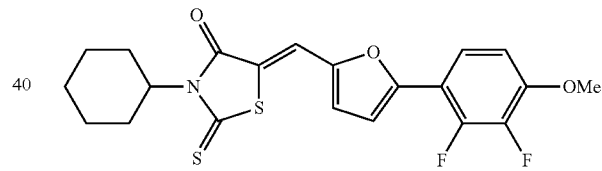

¹H-NMR (500 MHz, C₆D₆): 7.52 (m, 1H), 6.62 (t, J=3.7, 1H), 6.20 (d, J=3.7, 1H), 6.05 (d, J=4.5, 1H), 5.35 (t, J=12.3, 1H), 3.27 (s, 1H), 2.70 (q, J=11, 2H), 1.74 (t, J=4.9, 4H), 1.52 (d, J=10.6, 2H), 1.23 (m, 3H).

(Z)-3-(decahydronaphthalen-2-yl)-5-((5-(2,3-difluoro-4-methoxyphenyl)furan-2-yl)methylene)-2-thioxothi-azolidin-4-one

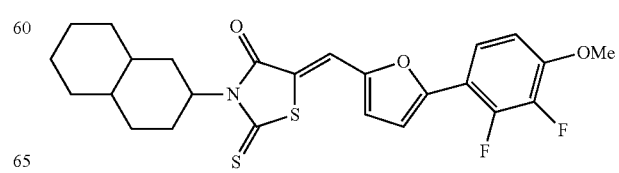

¹H-NMR (300 MHz, CDCl₃): 7.65 (t, J=12.0, 1H), 7.38 (s, H), 6.95 (m, 3H), 5.18-4.96 (m, 1H), 3.98 (s, 3H), 2.93 and 2.62 (m, total 2H), 1.95-1.18 (m, 14H).

(Z)-3-(decahydronaphthalen-2-yl)-5-((5-(2,3-difluoro-4-ethoxyphenyl)furan-2-yl)methylene)-2-thioxothiaz-olidin-4-one

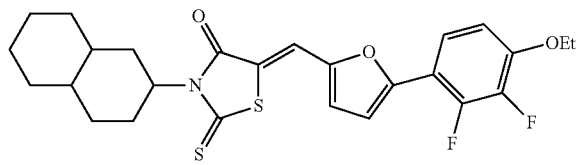 [SMILES: CCOc1ccc(-c2ccc(/C=C3\SC(=S)N(C4CCC5CCCCC5C4)C3=O)o2)c(F)c1F]

¹H-NMR (300 MHz, CDCl₃): 7.62 (t, J=12.0, 1H), 7.38 (s, H), 6.93 (m, 3H), 5.30 (m, 1H), 4.21 (q, J=7.0, 2H), 2.90 and 2.45 (m, total 2H), 1.95-1.18 (m, 17H).

(Z)-5-((5-(4-chlorophenyl)furan-2-yl)methylene)-3-(decahydronaphthalen-2-yl)-2-thioxothiazolidin-4-one

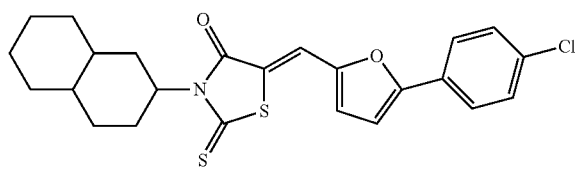 [SMILES: O=C1/C(=C/c2ccc(-c3ccc(Cl)cc3)o2)SC(=S)N1C1CCC2CCCCC2C1]

¹H-NMR (300 MHz, CDCl₃): 7.72-7.69 (m, 2H), 7.46-7.44 (m, 2H), 7.37-7.35 (d, J=2.2, 1H), 6.91 (t, J=2.4, 1H), 6.85-6.83 (m, 1H), 5.31-5.08 (m, 1H), 2.83 and 2.60 (m, total 2H), 1.95-1.18 (m, 14H).

(Z)-3-(decahydronaphthalen-2-yl)-5-((5-(3,5-dimethoxyphenyl)furan-2-yl)methylene)-2-thioxothiazolidin-4-one

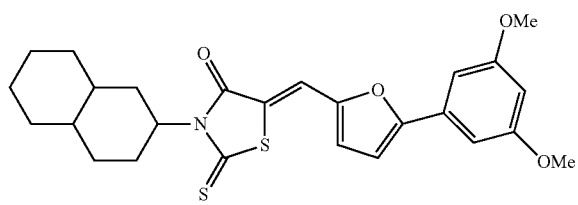 [SMILES: COc1cc(OC)cc(-c2ccc(/C=C3\SC(=S)N(C4CCC5CCCCC5C4)C3=O)o2)c1]

¹H-NMR (300 MHz, CDCl₃): 7.38 (s, 1H), 6.94 (d, J=2.2, 2H), 6.91 (d, J=3.2, 1H), 6.83 (d, J=3.2, 1H), 6.50 (t, J=2.0, 1H), 5.08 (br, 1H), 3.90 (s, 6H), 2.83 (br, 1H), 2.60 (br, 1H), 1.92-1.84 (m, 1H), 1.83-1.81 (m, 2H), 1.70-1.65 (m, 2H), 1.44 (s, 3H), 1.32-1.27 (m, 6H).

Synthesis of Type-2 Compound: Modification of C-Ring

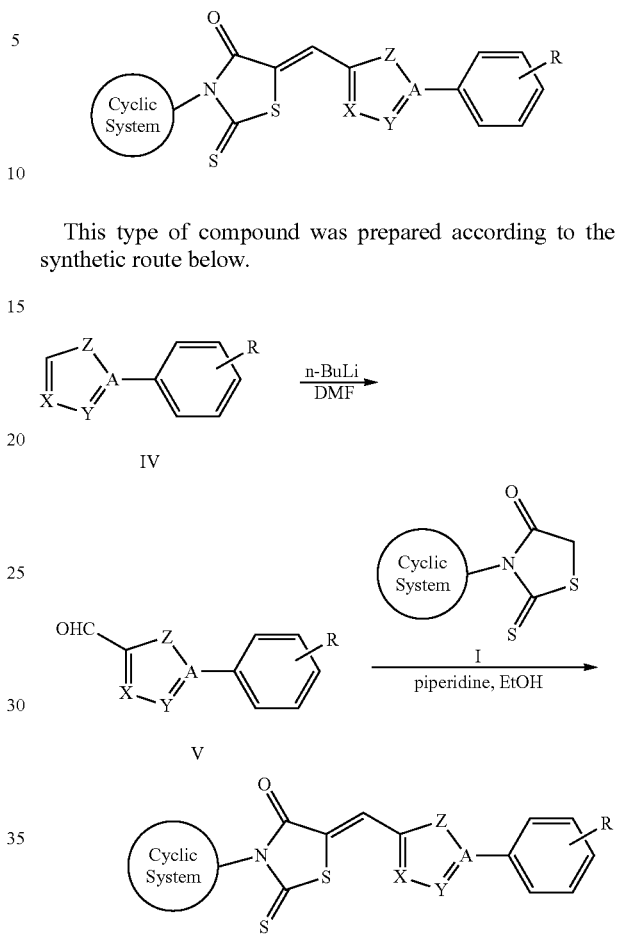

This type of compound was prepared according to the synthetic route below.

General Procedure for the Synthesis of Aldehyde V:

The starting material IV (1.30 mmol) was placed in a 50 mL two-necked flask in THF, and cool to −78° C., then n-BuLi (0.53 ml, 2.5 M in hexane) was added to the mixture slowly, and the mixture was allowed to stir for 0.5 h at −78° C. DMF (0.12 g, 1.66 mmol) was added to the mixture, and the reaction was keep at −78° C. for 1 h. The mixture was poured into saturated NH₄Cl solution and extracted with EA. The combined organic layers were washed with brine and dried over Na₂SO₄. After removal of the solvent under vacuum, the crude product was purified by a flash column chromatography on silica gel (ethyl acetate-hexane) to afford the desired aldehyde products. General procedure for the synthesis of (Z)-3-cycloalkyl-5-((5-heterocycles-2-yl)methylene)-2-thioxothiazo-lidin-4-one VI:

To a solution of 3-N-cycloalkyl-2-thioxothiazolidin-4-one I (0.5 mmol) and 5-substituted aryl furan-2-yl carboxaldehyde V (0.5 mmol) in EtOH (5 mL) was added anhydrous piperidine (43 mg, 0.5 mmol) at room temperature, and the mixture was refluxed for 16 h. After cooling to room temperature, the mixture was diluted with ethyl acetate (50 mL), and the organic phase was washed with water (3×10 mL), and then dried over anhydrous Na₂SO₄. The solvent was removed under vacuum, and the residue was recrystallized from ethyl acetate-hexane or a flash chromatography (CH$_2$Cl$_2$) on silica gel to afford the desired products as illustrated below.

(Z)-3-(bicyclo[2.2.1]heptan-2-yl)-5-((5-(3',5'-dimethoxyphenyl)-1H-pyrrol-2-yl)methylene)-2-thioxothiazoli-din-4-one

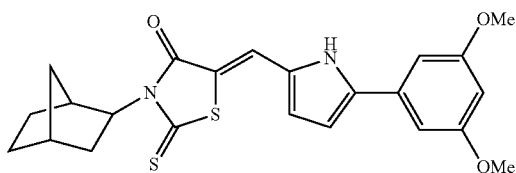 [SMILES: COc1cc(OC)cc(-c2ccc(/C=C3\SC(=S)N(C4CC5CCC4C5)C3=O)[nH]2)c1]

$^1$H-NMR (300 MHz, CDCl$_3$): 13.31 (s, 1H), 6.86 (s, 3H), 6.74 (s, 2H), 6.48 (s, 1H), 5.08 (t, J=6.9, 1H), 3.89 (s, 6H), 2.57 (s, 1H), 2.49-2.48 (m, 2H), 2.47-2.45 (m, 1H), 1.83 (t, J=10.2, 1H), 1.41-1.40 (m, 1H), 1.30 (d, J=9.6, 2H). HRMS (ESI): 441.1300 (M+H).

(Z)-3-(adamantan-2-yl)-5-((5-(3',5'-dimethoxyphenyl)-1H-pyrrol-2-yl)methylene)-2-thioxothiazolidin-4-one

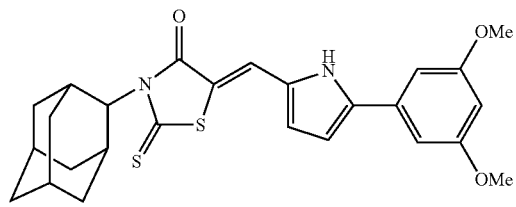 [SMILES: COc1cc(OC)cc(-c2ccc(/C=C3\SC(=S)N(C4C5CC6CC(C5)CC4C6)C3=O)[nH]2)c1]

$^1$H-NMR (300 MHz, CDCl$_3$): 13.27 (s, 1H), 6.85 (t, J=2.1, 3H), 6.74 (t, J=2.1, 2H), 6.47 (t, J=2.4, 1H), 5.28 (s, 1H), 3.88 (s, 6H), 2.63 (d, J=13.2, 2H), 2.48 (s, 2H), 2.02 (m, 6H), 1.82 (s, 2H), 1.78 (d, J=22.0, 2H). HRMS (ESI): 481.1631 (M+H).

(Z)-3-(bicyclo[2.2.1]heptan-2-yl)-5-((4-(6'-ethoxy-2',3'-difluorophenyl)thiophen-2-yl)methylene)-2-thioxothi-azolidin-4-one

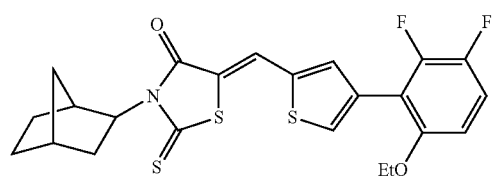 [SMILES: CCOc1ccc(F)c(F)c1-c1csc(/C=C2\SC(=S)N(C3CC4CCC3C4)C2=O)c1]

$^1$H-NMR (300 MHz, CDCl$_3$): 7.92 (s, 1H), 7.78 (s, 1H), 7.67 (s, 1H), 7.09 (m, 1H), 6.84 (m, 1H), 4.96 (m, 1H), 4.04 (q, J=14.1, 2H), 2.56 (s, 1H), 2.46 (s, 1H), 2.36-2.10 (m, 4H), 1.81 (m, 2H), 1.44-1.22 (m, 14H).

(Z)-3-(bicyclo[2.2.1]heptan-2-yl)-5-((4-(3'-methoxy-2',5'-dimethylphenyl)thiophen-2-yl)methylene)-2-thioxo-thiazolidin-4-one

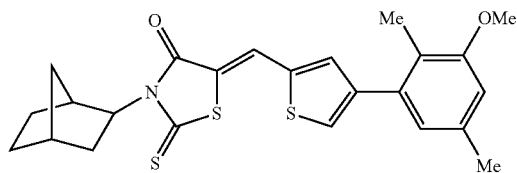 [SMILES: COc1cc(C)cc(-c2csc(/C=C3\SC(=S)N(C4CC5CCC4C5)C3=O)c2)c1C]

$^1$H-NMR (300 MHz, CDCl$_3$): 7.82 (s, 1H), 7.75 (s, 1H), 7.60 (s, 1H), 7.09 (s, 1H), 6.75 (m, 1H), 5.00 (m, 1H), 2.53 (s, 3H), 2.50 (s, 1H), 2.46 (s, 1H), 2.27 (s, 3H), 1.81 (m, 2H), 1.44-1.22 (m, 6H).

(Z)-3-cyclooctyl-5-((1-(4'-nitrophenyl)-1H-imidazol-4-yl)methylene)-2-thioxothiazolidin-4-one

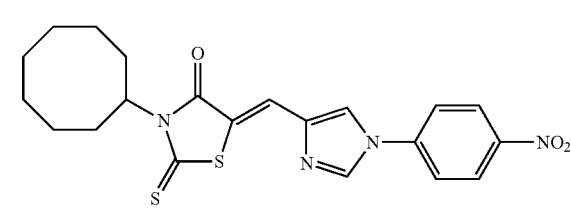 [SMILES: O=C1/C(=C/c2cn(-c3ccc([N+](=O)[O-])cc3)cn2)SC(=S)N1C1CCCCCCC1]

$^1$H-NMR (300 MHz, CDCl$_3$): 8.78 (s, 1H), 8.42 (d, J=7.9, 2H), 7.66 (d, J=7.9, 2H), 7.43 (s, 1H), 7.18 (s, 1H), 5.39 (br, 1H), 1.85-1.46 (m, 14H).

(Z)-3-cyclooctyl-5-((1-(4'-nitrophenyl)-1H-imidazol-4-yl)methylene)-2-thioxothiazolidin-4-one

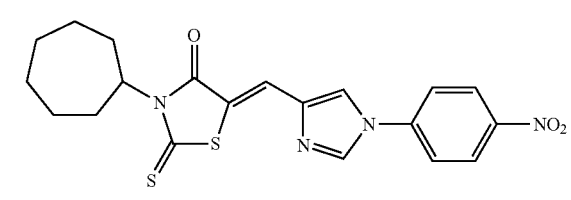 [SMILES: O=C1/C(=C/c2cn(-c3ccc([N+](=O)[O-])cc3)cn2)SC(=S)N1C1CCCCCC1]

$^1$H-NMR (300 MHz, CDCl$_3$): 8.80 (s, 1H), 8.43 (d, J=7.9, 2H), 7.67 (d, J=7.9, 2H), 7.40 (s, 1H), 7.18 (s, 1H), 5.38 (br, 1H), 1.85-1.43 (m, 12H).

(Z)-3-cyclooctyl-5-((1-(4'-nitrophenyl)-1H-imidazol-4-yl)methylene)-2-thioxothiazolidin-4-one

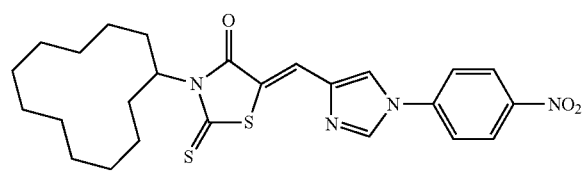 [SMILES: O=C1/C(=C/c2cn(-c3ccc([N+](=O)[O-])cc3)cn2)SC(=S)N1C1CCCCCCCCCCC1]

¹H-NMR (300 MHz, CDCl₃): 8.76 (s, 1H), 8.42 (d, J=7.9, 2H), 7.66 (d, J=7.9, 2H), 7.43 (s, 1H), 7.18 (s, 1H), 5.35 (br, 1H), 2.09 (br, 2H), 1.91 (br, 2H), 1.73 (br, 2H), 1.43 (br, 16H).

(Z)-3-cycloheptyl-5-((5-phenyloxazol-2-yl)methylene)-2-thioxothiazolidin-4-one

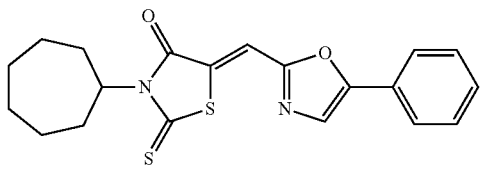 [SMILES: O=C1/C(=C/c2ncc(-c3ccccc3)o2)SC(=S)N1C1CCCCCC1]

¹H-NMR (300 MHz, CDCl₃): 7.70 (m, 2H), 7.56 (s, 1H), 7.39 (s, 1H), 7.17 (m, 2H), 7.12 (m, 1H), 4.60 (br, 1H), 1.85-1.43 (m, 12H).

(Z)-3-cycloheptyl-5 #5-phenyloxazol-2-yl)methylene)-2-thioxothiazolidin-4-one

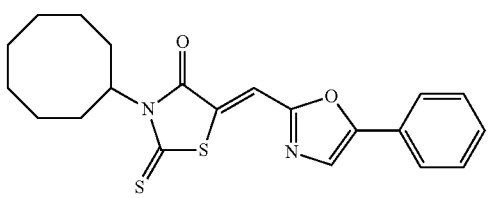 [SMILES: O=C1/C(=C/c2ncc(-c3ccccc3)o2)SC(=S)N1C1CCCCCCC1]

¹H-NMR (300 MHz, CDCl₃): 7.68 (m, 2H), 7.52 (s, 1H), 7.40 (s, 1H), 7.18 (m, 2H), 7.10 (m, 1H), 4.54 (br, 1H), 1.85-1.46 (m, 14H

Synthesis of Type-3: Coumarin as D-Ring

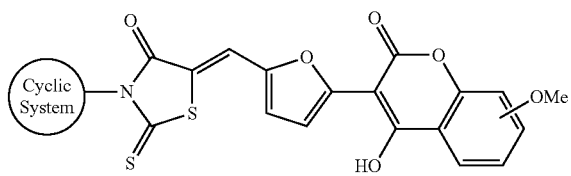

This type of compound was prepared according to the synthetic route below.

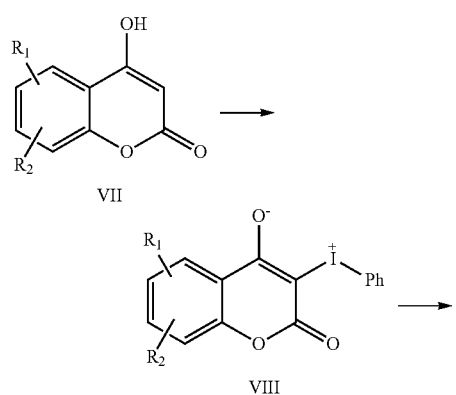

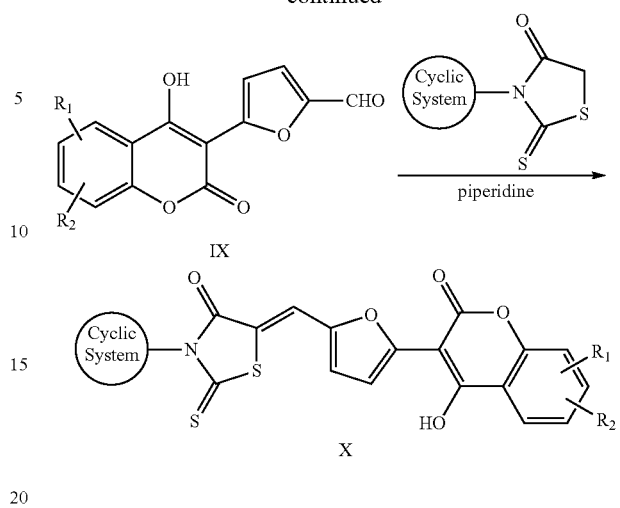

General Procedure for the Synthesis of Aldehyde VIII

Iodobenzene diacetate (10.0 mmol) was suspended in a solution of Na₂CO₃ (10.0 mmol) in water (100 mL) and the formed mixture was stirred at room temperature for 30 min. To this solution was added a mixture of 4-hydroxycoumarin derivative VII (10.0 mmol) and Na₂CO₃ (10.0 mmol) in water (100 mL), and the mixture was stirred at room temperature for 2 h. After removal of the precipitate by filtration, the remained organic phase was washed with water, and then dried over anhydrous Na₂SO₄. After removal of the solvent, the formed white solid was used in the next step without further purification.

General Procedure for the Synthesis of 5-(4-hydroxy-2-oxo-2H-chromen-3-yl)furan-2-carbaldehyde derivatives IX To a degassed solution of 5-carbaldehyde furan-2-boronic (1.53 g, 11.0 mmol), and P(t-Bu)₃ (10.0 equiv) in DME (40 mL) and water (10 mL) was added to a mixture of iodonium ylide (5.0 mmol), LiOH.H₂O (0.63 g, 15.0 mmol), and Pd(OAc)₂ (0.06 g, 0.25 mmol) under nitrogen at room temperature. After being stirred at the same temperature for 14 h, the mixture was extracted with CH₂Cl₂. The organic phase was washed with brine, and then dried over anhydrous Na₂SO₄. After removal of the solvent, the residue was purified by a flash chromatography (CH₂Cl₂) on silica gel to give the corresponding products General Procedure for the Synthesis of X To a solution of 3-N-cycloalkyl-2-thioxothiazolidin-4-one I (0.5 mmol) and 5-substituted aryl furan-2-yl carboxaldehyde IX (0.5 mmol) in EtOH (5 mL) was added anhydrous piperidine (43 mg, 0.5 mmol) at room temperature, and the mixture was refluxed for 16 h. After cooling to room temperature, the mixture was diluted with ethyl acetate (50 mL), and the organic phase was washed with water (3×10 mL), and then dried over anhydrous Na₂SO₄. The solvent was removed under vacuum, and the residue was recrystallized from ethyl acetate-hexane or a flash chromatography (CH$_2$Cl$_2$) on silica gel to afford the desired products as illustrated below.

(Z)-3-(adamantan-2-yl)-5-((5-(4-hydroxy-2-oxo-2H-chromen-3-yl)furan-2-yl)methylene)-2-thioxothiazolidin-4-one

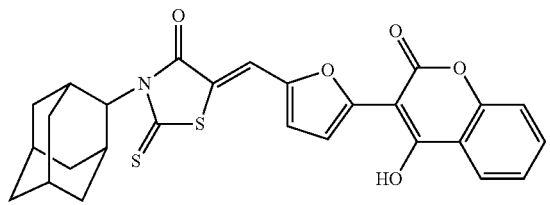 [SMILES: O=C1/C(=C/c2ccc(-c3c(O)c4ccccc4oc3=O)o2)SC(=S)N1C1C2CC3CC(C2)CC1C3]

$^1$H-NMR (300 MHz, DMSO-d6): 8.08 (dd, J=3.6, 1.5, 1H), 7.62 (m, 1H), 7.34 (dd, J=3.6, 1.2, 1H), 7.28 (d, J=3.6, 4H), 7.18 (d, J=3.6, 1H), 5.06 (s, 1H), 2.49 (t, J=3.6, 5H), 1.90-1.88 (m, 5H), 1.72 (t, J=11.7, 4H). HRMS (ESI): 505.1023 (M).

(Z)-3-(bicyclo[2.2.1]heptan-2-yl)-5-((5-(4-hydroxy-2-oxo-2H-chromen-3-yl)furan-2-yl)methylene)-2-thioxoth-iazolidin-4-one

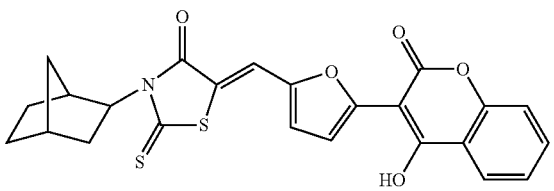 [SMILES: O=C1/C(=C/c2ccc(-c3c(O)c4ccccc4oc3=O)o2)SC(=S)N1C1CC2CCC1C2]

$^1$H-NMR (300 MHz, DMSO-d6): 8.01 (d, J=7.8, 1H), 7.54 (dd, J=7.8, 7.5, 1H), 7.42 (s, 2H), 7.26 (m, 4H), 4.91 (t, J=15.0, 1H), 2.49 (t, J=3.6, 1H), 1.68 (t, J=20.4, 1H), 1.54 (t, J=6.3, 4H), 1.30-1.10 (m, 4H). HRMS (ESI): 465.0711 (M).

(Z)-3-(bicyclo[2.2.1]heptan-2-yl)-5-((5-(4-hydroxy-6-methoxy-2-oxo-2H-chromen-3-yl)furan-2-yl)methylene)-2-thioxothiazolidin-4-one

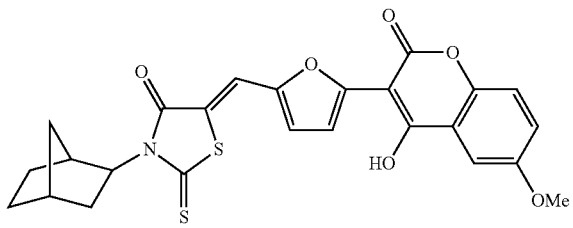 [SMILES: COc1ccc2oc(=O)c(-c3ccc(/C=C4\SC(=S)N(C5CC6CCC5C6)C4=O)o3)c(O)c2c1]

Dark-brown fluorescence solid in 41% yield. $^1$H-NMR (300 MHz, DMSO-d6): 7.36 (d, J=3.0, 1H), 7.31 (s, 1H), 7.26 (d, J=3.9, 1H), 7.22 (d, J=3.9, 1H), 7.03 (s, 1H), 7.01 (d, J=3.0, 1H), 4.89 (m, 1H), 3.76 (s, 3H), 2.35-2.33 (m, 2H), 1.72-1.70 (m, 2H), 1.51-1.49 (m, 2H), 1.25-1.19 (m, 5H). HRMS (ESI): 518.0706 (M+Na).

(Z)-3-(adamantan-2-yl)-5-((5-(4-hydroxy-6-methoxy-2-oxo-2H-chromen-3-yl)furan-2-yl)methylene)-2-thioxo-thiazolidin-4-one

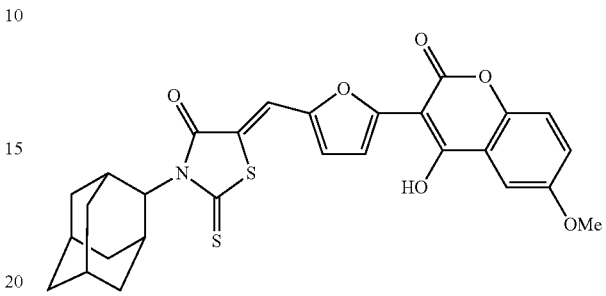

$^1$H-NMR (300 MHz, DMSO-d6): 7.50 (d, J=2.7, 1H), 7.43 (s, 1H), 7.21 (m, 3H), 7.14 (t, J=1.2, 1H), 5.05 (s, 1H), 3.80 (s, 3H), 2.69 (t, J=1.8, 1H), 2.39 (s, 3H), 1.89 (m, 2H), 1.74-1.71 (m, 2H), 1.65-1.62 (m, 2H), 1.22-1.20 (m, 3H).

(Z)-3-(bicyclo[2.2.1]heptan-2-yl)-5-((5-(4-hydroxy-7,8-dimethoxy-2-oxo-2H-chromen-3-yl)furan-2-yl)methyl-ene)-2-thioxothiazolidin-4-one

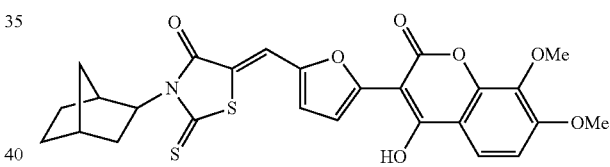

$^1$H-NMR (300 MHz, DMSO-d6): 7.62 (d, J=9.0, 1H), 7.31 (s, 1H), 7.23 (t, J=3.6, 2H), 6.90 (d, J=9.0, 1H), 5.37 (m, 1H), 4.91 (d, J=6.0, 1H), 3.83 (s, 3H), 3.77 (s, 3H), 2.30 (m, 2H), 1.65-1.63 (m, 1H), 1.52-1.50 (m, 2H), 1.22-1.20 (m, 5H). HRMS (ESI): 526.1003 (M+H).

(Z)-3-(adamantan-2-yl)-5-((5-(4-hydroxy-7,8-dimethoxy-2-oxo-2H-chromen-3-yl)furan-2-yl)meth-ylene)-2-thioxothiazolidin-4-one

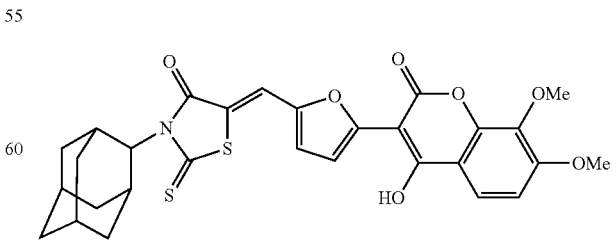

$^1$H-NMR (300 MHz, DMSO-d6): 7.67 (d, J=9.0, 1H), 7.37 (s, 1H), 7.21 (t, J=2.4, 2H), 6.95 (d, J=9.0, 1H), 5.06 (s, 1H), 3.85 (s, 3H), 3.77 (s, 3H), 2.38 (s, 3H), 1.87 (s, 5H), 1.71 (d, J=0.6, 2H), 1.61 (d, J=12.0, 2H), 1.20 (d, J=1.8, 2H), 0.80 (m, 2H).

(Z)-3-(bicyclo[2.2.1]heptan-2-yl)-5-((5-(4-hydroxy-7-methoxy-2-oxo-2H-chromen-3-yl)furan-2-yl)-methylene)-2-thioxothiazolidin-4-one

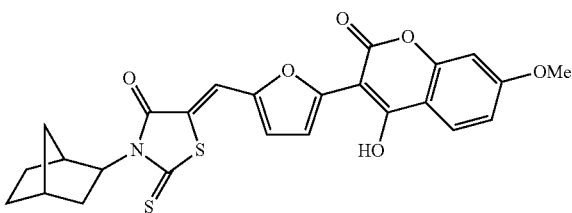 [SMILES: COc1ccc2c(O)c(-c3ccc(/C=C4\SC(=S)N(C5CC6CCC5C6)C4=O)o3)c(=O)oc2c1]

¹H-NMR (300 MHz, DMSO-d6): 7.78 (d, J=8.7, 1H), 7.29 (s, 1H), 7.23 (dd, J=9.6, 2.4, 2H), 6.72 (dd, J=8.7, 2.4, 1H), 6.64 (d, J=2.4, 1H), 4.88 (m, 1H), 3.78 (s, 3H), 2.35 (m, 2H), 1.64 (m, 1H), 1.50 (m, 2H), 1.22 (m, 5H). HRMS (ESI): 496.0882 (M+H).

(Z)-3-(adamantan-2-yl)-5-((5-(4-hydroxy-7-methoxy-2-oxo-2H-chromen-3-yl)furan-2-yl)methylene)-2-thioxothiazolidin-4-one

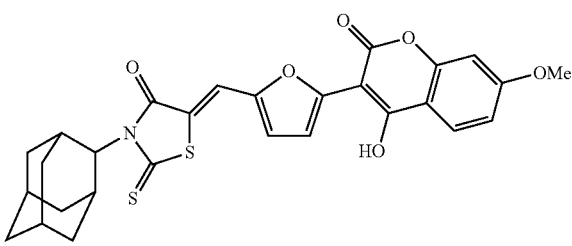 [SMILES: COc1ccc2c(O)c(-c3ccc(/C=C4\SC(=S)N(C5C6CC7CC(C6)CC5C7)C4=O)o3)c(=O)oc2c1]

¹H-NMR (300 MHz, DMSO-d6): 7.78 (d, J=8.4, 1H), 7.31 (s, 1H), 7.21 (dd, J=12.0, 2.4, 2H), 6.72 (dd, J=8.7, 2.4, 1H), 6.64 (d, J=2.4, 1H), 5.08 (s, 1H), 3.78 (s, 3H), 2.48 (m, 2H), 1.89 (m, 1H), 1.71 (s, 2H), 1.60 (m, 2H), 1.20 (m, 3H).

(Z)-3-(adamantan-2-yl)-5-((5-(4-(methoxymethoxy)-2-oxo-2H-chromen-6-yl)furan-2-yl)methylene)-2-thioxothiazolidin-4-one

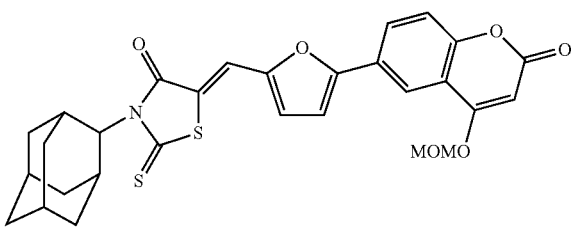

¹H-NMR (300 MHz, CDCl₃): 8.27 (d, J=2.1 1H), 7.91 (dd, J=8.7, 2.1, 1H), 7.41 (d, J=8.7, 2H), 6.89 (dd, J=8.7, 2.1, 2H), 5.97 (s, 1H), 5.45 (s, 2H), 5.13 (s, 1H), 3.62 (s, 3H), 2.54 (m, 4H), 1.97 (m, 6H), 1.74 (m, 5H), 1.23 (m, 8H). HRMS (ESI): 550.1350 (M+H).

(Z)-3-(bicyclo[2.2.1]heptan-2-yl)-5-((5-(4-(methoxymethoxy)-2-oxo-2H-chromen-6-yl)furan-2-yl)-methylene)-2-thioxothiazolidin-4-one

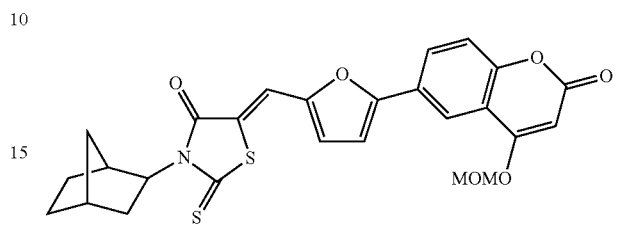

¹H-NMR (300 MHz, CDCl₃): 8.27 (d, J=2.1 1H), 7.91 (dd, J=8.7, 2.1, 1H), 7.43 (d, J=8.1, 2H), 6.89 (d, J=8.1, 2H), 5.97 (s, 1H), 5.45 (s, 2H), 4.94 (t, J=2.1, 1H), 3.62 (s, 3H), 2.53 (m, 2H), 2.36 (m, 4H), 1.73 (m, 4H), 1.33 (m, 8H).

(Z)-3-(bicyclo[2.2.1]heptan-2-yl)-5-((5-(4-hydroxy-2-oxo-6-pentyl-2H-chromen-3-yl)furan-2-yl)methylene)-2-thioxothiazolidin-4-one

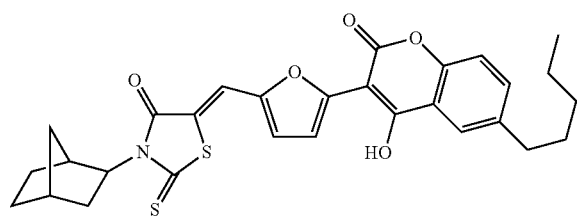 [SMILES: CCCCCc1ccc2oc(=O)c(-c3ccc(/C=C4\SC(=S)N(C5CC6CCC5C6)C4=O)o3)c(O)c2c1]

¹H-NMR (300 MHz, DMSO-d₆): 7.89 (d, J=1.5 Hz, 1H), 7.53 (d, J=4.0 Hz, 1H), 7.45 (dd, J=1.8 Hz, 1H), 7.40 (s, 1H), 7.01 (d, J=4.0 Hz, 1H), 4.95 (t, J=7.5 Hz, 1H), 2.73 (t, J=7.8 Hz, 2H), 2.48 (s, 1H), 2.32 (m=2.38-2.32, 1H), 2.23 (m=2.28-2.23, 1H), 1.76 (m=1.83-1.76, 2H), 1.54 (m=1.61-1.54, 2H), 1.57 (m=1.62-1.57, 4H), 1.33 (m=1.41-1.33, 4H), 1.26 (m=1.31-1.26, 4H), 0.97 (t, J=6.0 Hz, 3H). HRMS (ESI): 536.1573 (M+H).

(Z)-3-(bicyclo[2.2.1]heptan-2-yl)-5-((5-(7-(cyclohexyloxy)-4-hydroxy-2-oxo-2H-chromen-3-yl)furan-2-yl)methylene)-2-thioxothiazolidin-4-one

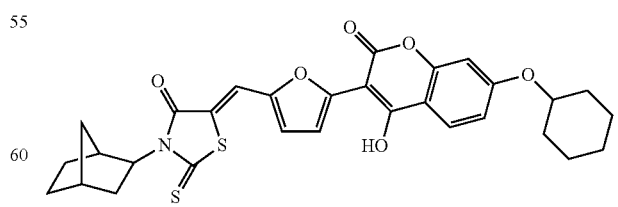

¹H-NMR (300 MHz, DMSO-d₆): 7.97 (d, J=6.0 Hz, 1H), 7.40 (s, 1H), 6.99 (d, J=3.0 Hz, 1H), 6.93 (dd, J=2.1 Hz, 1H), 6.81 (d, J=3.0 Hz, 1H), 4.95 (t, J=7.5 Hz, 1H), 4.33 (m=4.37-4.33, 1H), 2.56 (s, 1H), 2.48 (s, 1H), 2.23 (m=2.27-2.23, 1H), 2.14 (m=2.20-2.14, 1H), 1.94 (m=2.03-1.94, 2H), 1.79 (m=1.82-1.79, 4H), 1.42 (m=1.51-1.43, 4H), 1.32 (m=1.39-1.32, 2H), 1.26 (m=1.30-1.26, 3H). HRMS (ESI): 564.1521 (M+H).

(Z)-3-(bicyclo[2.2.1]heptan-2-yl)-5-((5-(7-cyclohexyl-4-hydroxy-2-oxo-2H-chromen-3-yl)thiophen-2-yl)methylene)-2-thioxothiazolidin-4-one

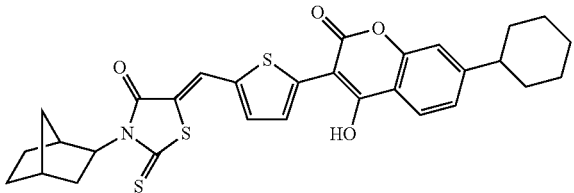 [SMILES: O=C1/C(=C/c2ccc(-c3c(O)c4ccc(C5CCCCC5)cc4oc3=O)s2)SC(=S)N1C1CC2CCC1C2]

$^1$H-NMR (300 MHz, DMSO-d$_6$): 7.90 (d, J=1.8 Hz, 1H), 7.44 (m=7.47-7.44, 2H), 7.55 (d, J=4.2 Hz, 1H), 7.09 (d, J=8.1 Hz, 1H), 7.01 (d, J=1.2 Hz, 1H), 4.84 (t, J=6.0 Hz, 1H), 3.96 (m=4.08-3.96, 1H), 2.66 (t, J=7.2 Hz, 1H), 2.38 (s, 1H), 2.29 (m=2.33-2.29, 2H), 1.60 (m=1.71-1.60, 4H), 1.52 (m=1.58-1.52, 2H), 1.28 (m=1.36-1.286, 4H), 1.19 (m=1.23-1.19, 4H). HRMS (ESI): 564.1360 (M+H).

Synthesis of Type-4: Modification of D-Ring with Amino Acid

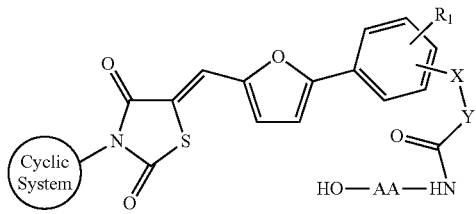

This type of compound was prepared according to the synthetic route below.

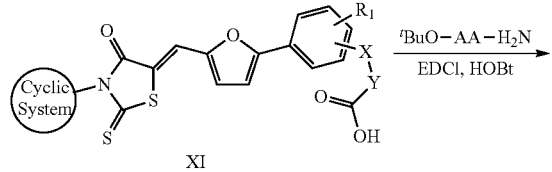

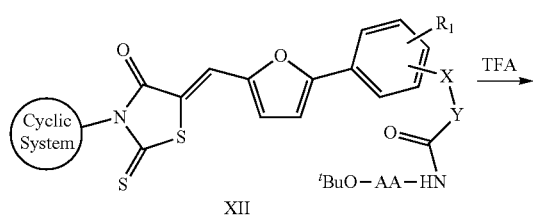

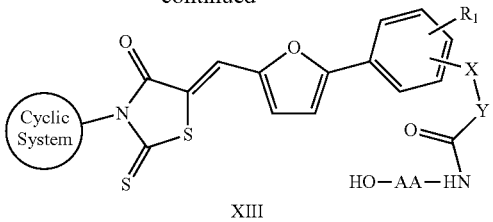

General Procedure for the Synthesis of XII by Coupling Reaction

To a solution of the carboxylic-containing VEIs XI (10.0 mmol) in dry CH$_2$Cl$_2$ (50 mL) was added HOBt (1.62 g, 12.0 mmol), Boc- or Fmoc-amino acid (12.0 mmol) and EDCI (2.87 g, 15.0 mmol) at 0° C., and the formed mixture was stirred at room temperature for 24 h. The reaction was worked up addition of water, and the formed organic phase was washed sequentially with 5% diluted HCl, brine, saturated NaHCO$_3$ and brine, and then dried over anhydrous Na$_2$SO$_4$. After removal of the solvent, the residue was purified by a flash chromatography (PE/EA) to give the corresponding products.

General Procedure for the Synthesis of XIII by Deprotection Reaction

To a solution of the compound XII made above in CH$_2$Cl$_2$ (30 mL) was added TFA (10.0 equiv) at 0° C., and then formed mixture was stirred at room temperature until the starting material was fully consumed. The reaction mixture was concentrated, and the residue was purified by a recrystallization from diethyl ether or a flash chromatography (CH$_2$Cl$_2$/HOAc) on silica gel to give the corresponding product.

(2S)-2-(2-(5-(5-((Z)-(3-(bicyclo[2.2.1]heptan-2-yl)-4-oxo-2-thioxothiazolidin-5-ylidene)methyl)furan-2-yl)-2-methoxyphenoxy)acetamido)-3-(4-hydroxyphenyl)propanoic acid

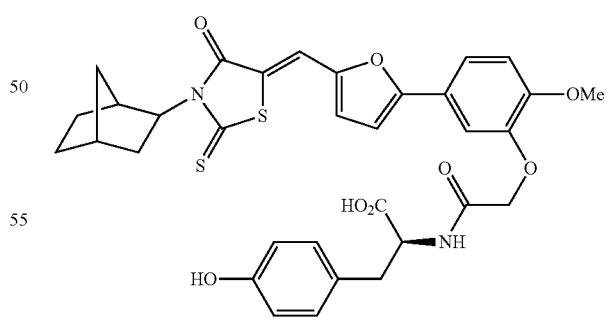

$^1$H-NMR (300 MHz, DMSO-d6): 9.24 (s, 1H), 8.01 (d, J=7.8, 1H), 7.51 (s, 1H), 7.48-7.44 (m, 2H), 7.31-7.29 (m, 3H), 6.97 (d, J=8.4, 1H), 6.61 (d, J=8.4, 1H), 5.32 (t, J=9.6, 1H), 4.90-4.86 (m, 1H), 4.60-4.56 (s, 2H), 4.50-4.46 (m, 1H), 3.81 (s, 3H), 3.04-3.00 (m, 3H), 2.39-2.35 (m, 5H), 2.04-2.00 (m, H), 1.74-1.71 (m, 1H), 1.22 (m, 4H). HRMS (ESI): 649.1692 (M+H).

(2S)-2-(2-(5-(5-((Z)-(3-(bicyclo[2.2.1]heptan-2-yl)-4-oxo-2-thioxothiazolidin-5-ylidene)methyl)furan-2-yl)-2-methoxyphenoxy)acetamido)-4-methylpentanoic acid

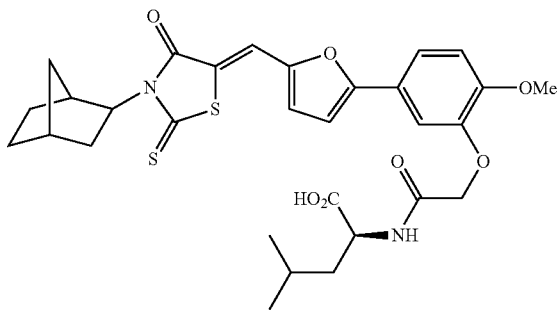 [SMILES: COc1ccc(-c2ccc(/C=C3\SC(=S)N(C4CC5CCC4C5)C3=O)o2)cc1OCC(=O)N[C@@H](CC(C)C)C(=O)O]

¹H-NMR (300 MHz, CDCl₃): 7.57 (d, J=2.1, 1H), 7.34 (m, 2H), 7.06 (d, J=8.7, 1H), 6.90 (d, J=3.6, 1H), 6.74 (d, J=3.6, 1H), 4.99 (t, J=14.4, 1H), 4.69 (m, 3H), 3.96 (s, 3H), 2.55 (m, 7H), 1.82 (m, 2H), 1.22 (m, 6H).

(2S)-2-(2-(5-(5-((Z)-(3-(bicyclo[2.2.1]heptan-2-yl)-4-oxo-2-thioxothiazolidin-5-ylidene)methyl)furan-2-yl)-2-methoxyphenoxy)acetamido)-3-phenylpropanoic acid

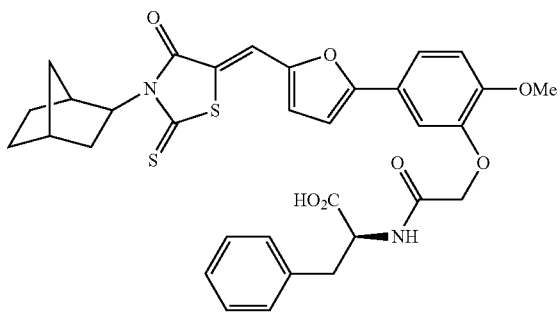 [SMILES: COc1ccc(-c2ccc(/C=C3\SC(=S)N(C4CC5CCC4C5)C3=O)o2)cc1OCC(=O)N[C@@H](Cc1ccccc1)C(=O)O]

Red solid in 90% yield. ¹H-NMR (300 MHz, CDCl₃): 7.59 (s, 1H), 7.42 (d, J=8.4, 2H), 7.27 (m, 1H), 6.90 (d, J=7.2, 1H), 6.79 (s, 1H), 6.63 (s, 1H), 4.95 (t, J=14.1, 2H), 4.56 (s, 2H), 3.72 (s, 3H), 3.23 (m, 2H), 2.55 (m, 4H), 1.81 (m, 1H), 1.22 (m, 6H).

(2S)-1-(2-(5-(5-((Z)-(3-(bicyclo[2.2.1]heptan-2-yl)-4-oxo-2-thioxothiazolidin-5-ylidene)methyl)furan-2-yl)-2-methoxyphenoxy)acetyl)pyrrolidine-2-carboxylic acid

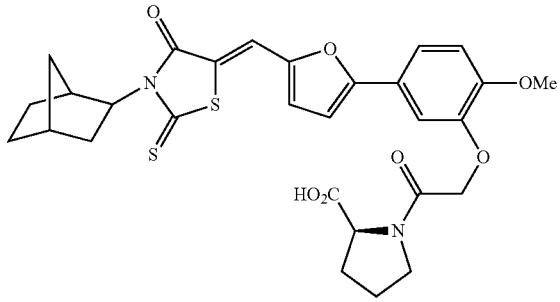 [SMILES: COc1ccc(-c2ccc(/C=C3\SC(=S)N(C4CC5CCC4C5)C3=O)o2)cc1OCC(=O)N1CCC[C@H]1C(=O)O]

¹H-NMR (300 MHz, DMSO-d6): 7.51 (s, 1H), 7.40 (s, 1H), 7.31 (d, J=3.3, 1H), 7.17 (m, 3H), 4.86 (m, 3H), 4.28 (m, 1H), 3.835 (S, 1H), 2.37 (m, 5H), 1.99 (m, 3H), 1.72 (m, 4H), 7.17 (m, 3H).

(2S)-5-(benzyloxy)-2-(2-(5-(5-((Z)-(3-(bicyclo[2.2.1]heptan-2-yl)-4-oxo-2-thioxothiazolidin-5-ylidene)methyl)-furan-2-yl)-2-methoxyphenoxy)acetamido)-5-oxopentanoic acid

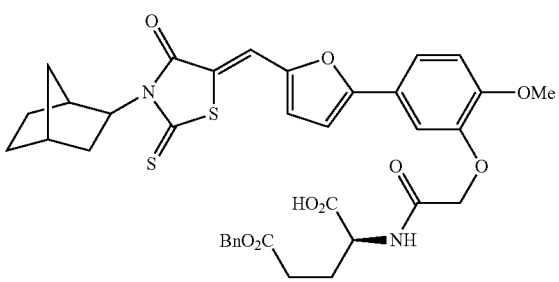

¹H-NMR (300 MHz, CDCl₃): 7.75 (s, 1H), 7.51 (d, J=8.1, 1H), 7.35 (m, 7H), 7.01 (d, J=8.4, 2H), 6.87 (d, J=3.3, 1H), 6.72 (d, J=3.6, 2H), 5.09 (s, 2H), 4.96 (m, 1H), 4.66 (m, 3H), 3.89 (s, 3H), 2.55 (m, 10H), 1.78 (m, 5H), 1.61 (m, 3H), 1.32 (m, 6H). HRMS (ESI): 705.1912 (M+H).

(2S)-2-(2-(5-(5-((Z)-(3-(bicyclo[2.2.1]heptan-2-yl)-4-oxo-2-thioxothiazolidin-5-ylidene)methyl)furan-2-yl)-2-methoxyphenoxy)acetamido)-3-(1H-imidazol-5-yl)propanoic acid TFA salt

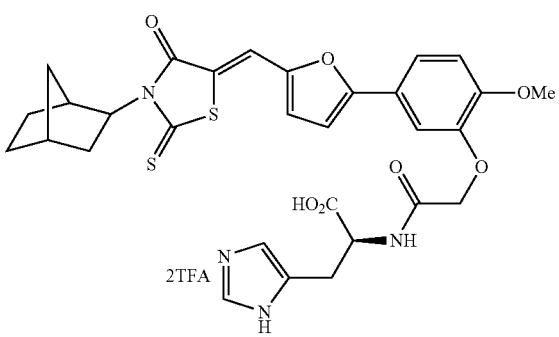 [SMILES: COc1ccc(-c2ccc(/C=C3\SC(=S)N(C4CC5CCC4C5)C3=O)o2)cc1OCC(=O)N[C@@H](Cc1cnc[nH]1)C(=O)O]

¹H-NMR (300 MHz, DMSO-d₆): 8.76 (d, J=6.9, 1H), 8.50 (t, J=1.8, 1H), 8.23 (d, J=2.4, 1H), 7.95 (dd, J=8.7, 3.6, 1H), 7.53 (s, 1H), 7.39 (d, J=8.7, 1H), 7.32 (d, J=3.6, 1H), 7.25 (d, J=4.2, 1H), 4.85 (t, J=1.2, 1H), 4.76 (d, J=6.0, 1H), 3.94 (s, 3H), 3.36 (d, J=7.2, 3H), 2.37 (m, 4H), 1.69 (d, J=0.9, 1H), 1.54 (t, J=2.4, 2H), 1.21 (d, J=2.1, 4H).

(2S)-2-(2-(5-(5-((Z)-(3-(bicyclo[2.2.1]heptan-2-yl)-4-oxo-2-thioxothiazolidin-5-ylidene)methyl)furan-2-yl)-2-methoxyphenoxy)acetamido)-3-phenylpropanoic acid

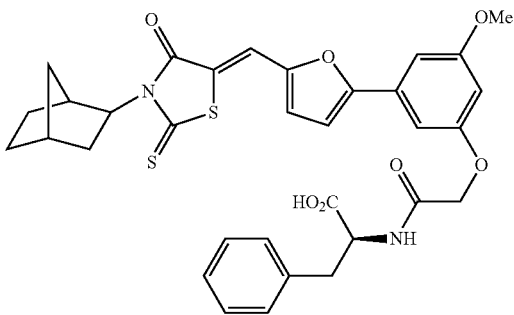 [SMILES: COc1cc(OCC(=O)N[C@@H](Cc2ccccc2)C(=O)O)cc(-c2ccc(/C=C3\SC(=S)N(C4CC5CCC4C5)C3=O)o2)c1]

¹H-NMR (CDCl₃, 300 MHz): 7.59 (s, 1H), 7.42 (d, J=8.4, 2H), 7.29-7.25 (m, 1H), 6.90 (d, J=7.2, 1H), 6.79 (s, 1H), 6.63 (s, 1H), 4.95 (t, J=14.1, 2H), 4.56 (s, 2H), 3.72 (s, 3H), 3.25-3.20 (m, 2H), 2.57-2.53 (m, 4H), 1.84-1.80 (m, 1H), 1.24-1.20 (m, 6H). HRMS (ESI): 633.1744 (M+H).

(2S)-1-(2-(3-(5-((Z)-(3-(bicyclo[2.2.1]heptan-2-yl)-4-oxo-2-thioxothiazolidin-5-ylidene)methyl)furan-2-yl)-5-methoxyphenoxy)acetyl)pyrrolidine-2-carboxylic acid

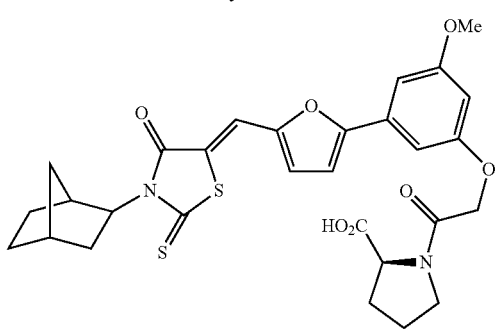

Red solid. ¹H-NMR (300 MHz, DMSO-d₆): 7.52 (s, 1H), 7.32 (m, 2H), 6.98 (, 2H), 6.55 (s 1H), 4.87-4.85 (m, 2H), 4.28 (m, 1H), 3.82 (s, 3H), 3.64 (m, 2H), 2.39-2.35 (m, 5H), 1.99-1.96 (m, 3H), 1.69 (m, 4H), 1.27-1.23 (m, 5H) HRMS (ESI): 583.1571 (M+H).

(2S)-2-(5-(5-((Z)-(3-(bicyclo[2.2.1]heptan-2-yl)-4-oxo-2-thioxothiazolidin-5-ylidene)methyl)furan-2-yl)-2-methoxybenzamido)-3-phenylpropanoic acid

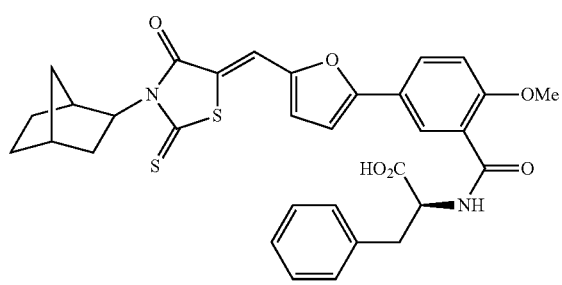 [SMILES: COc1ccc(-c2ccc(/C=C3\SC(=S)N(C4CC5CCC4C5)C3=O)o2)cc1C(=O)N[C@@H](Cc1ccccc1)C(=O)O]

Red-brown solid. ¹H-NMR (300 MHz, DMSO-d₆): 8.39 (d, J=1.5, 1H), 8.24 (d, J=2.1, 1H), 7.95-7.93 (m, 1H), 7.52 (s, 1H), 7.26 (m, 7H), 4.87-4.85 (m, 1H), 4.65 (t, J=2.1, 1H), 3.86 (s, 3H), 3.17-3.14 (m, 2H), 2.34-2.32 (m, 2H), 1.71-1.68 (m, 1H), 1.55-1.52 (m, 3H), 1.23-1.20 (m, 4H). HRMS (ESI): 603.1612 (M+H).

(2S)-2-(5-(5-((Z)-(3-(bicyclo[2.2.1]heptan-2-yl)-4-oxo-2-thioxothiazolidin-5-ylidene)methyl)furan-2-yl)-2-methoxybenzamido)-3-(4-hydroxyphenyl)propanoic acid

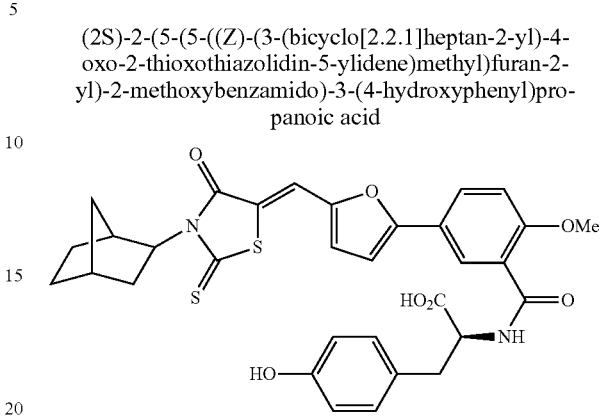

Red-brown solid. ¹H-NMR (300 MHz, DMSO-d₆): 8.45 (t, J=4.8, 1H), 7.38 (m, 9H), 6.93 (d, J=2.1, 2H), 6.56 (s, 1H), 4.84 (m, 1H), 3.80 (s, 6H), 3.04 (d, J=7.5, 5H), 2.38 (m, 4H), 1.68 (m, 3H), 1.51 (m, 3H), 1.13 (m, 4H).

(2S)-2-(5-(5-((Z)-(3-(bicyclo[2.2.1]heptan-2-yl)-4-oxo-2-thioxothiazolidin-5-ylidene)methyl)furan-2-yl)-2-methoxybenzamido)-4-methylpentanoic acid

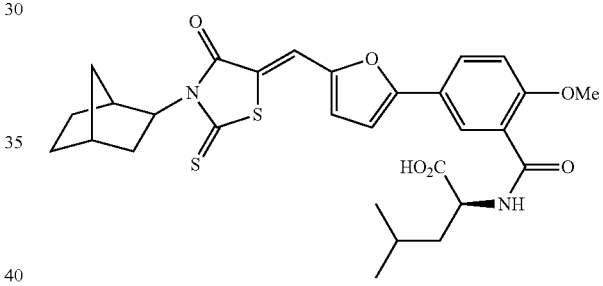

¹H-NMR (CDCl₃, 300 MHz): 7.57 (d, J=2.1, 1H), 7.34 (m, 2H), 7.06 (d, J=8.7, 1H), 6.90 (d, J=3.6, 1H), 6.74 (d, J=3.6, 1H), 4.99 (t, J=14.4, 1H), 4.69 (m, 3H), 3.96 (s, 3H), 2.55 (m, 7H), 1.82 (m, 2H), 1.22 (m, 6H).

(2S)-2-(5-(5-((Z)-(3-(bicyclo[2.2.1]heptan-2-yl)-4-oxo-2-thioxothiazolidin-5-ylidene)methyl)furan-2-yl)-2-methoxybenzamido)-3-(1H-imidazol-5-yl)propanoic acid TFA salt

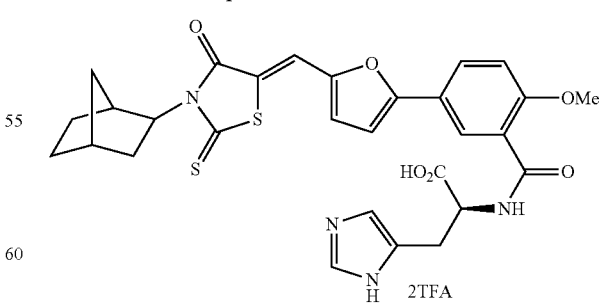

Yellow-brown solid in 39% yield. ¹H-NMR (300 MHz, DMSO-d₆): 8.76 (d, J=6.9, 1H), 8.50 (t, J=1.8, 1H), 8.23 (d, J=2.4, 1H), 7.95 (dd, J=8.7, 2.4, 1H), 7.53 (s, 1H), 7.39 (d, J=8.7, 1H), 7.32 (d, J=3.6, 1H), 7.25 (d, J=4.2, 1H), 4.85 (t, J=1.2, 1H), 4.76 (d, J=6.0, 1H), 3.94 (s, 3H), 3.36 (d, J=7.2, 3H), 2.37 (m, 4H), 1.69 (d, J=0.9, 1H), 1.54 (t, J=2.4, 2H), 1.21 (d, J=2.1, 4H).

(2S)-1-(5-(5-((Z)-(3-(bicyclo[2.2.1]heptan-2-yl)-4-oxo-2-thioxothiazolidin-5-ylidene)methyl)furan-2-yl)-2-methoxybenzoyl)pyrrolidine-2-carboxylic acid

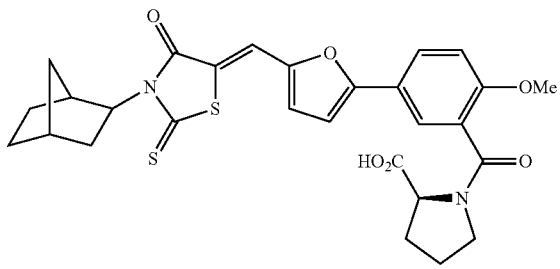 [SMILES: COc1ccc(-c2ccc(/C=C3\SC(=S)N(C4CC5CCC4C5)C3=O)o2)cc1C(=O)N1CCC[C@H]1C(=O)O]

Yellow-brown solid in 45% yield. $^1$H-NMR (300 MHz, DMSO-d$_6$): 7.84 (m, 1H), 7.63 (m, 2H), 7.27 (m, 3H), 4.85 (m, 1H), 4.36 (m, 1H), 4.00 (m, 1H), 3.86 (s, 3H), 3.56 (d, J=0.6, 1H), 2.23 (m, 4H), 1.88 (m, 3H), 1.70 (m, 1H), 1.53 (m, 2H), 1.20 (m, 4H).

(2S)-2-(5-(5-((Z)-(3-(bicyclo[2.2.1]heptan-2-yl)-4-oxo-2-thioxothiazolidin-5-ylidene)methyl)furan-2-yl)-2-methoxybenzamido)-4-methoxy-4-oxobutanoic acid

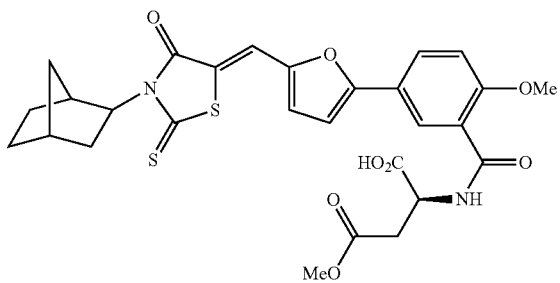 [SMILES: COC(=O)C[C@H](NC(=O)c1cc(-c2ccc(/C=C3\SC(=S)N(C4CC5CCC4C5)C3=O)o2)ccc1OC)C(=O)O]

Yellow-brown solid in 55% yield. $^1$H-NMR (300 MHz, DMSO-d$_6$): 8.93 (d, J=6.3, 1H), 8.36 (s, 1H), 7.93 (d, J=8.4, 1H), 7.52 (s, 1H), 7.38 (d, J=9.0, 1H), 7.32 (d, J=3.6, 1H), 7.23 (d, J=3.3, 1H), 5.43 (s, 1H), 4.86 (t, J=6.0, 1H), 4.42-4.41 (m, 1H), 3.98 (s, 1H), 3.57 (s, 3H), 2.77-2.75 (m, 2H), 2.37-2.23 (m, 6H), 1.74-1.68 (m, 1H), 1.53-1.40 (m, 4H).

(2S)-ethyl 1-(5-(5-((Z)-(3-((1S,4R)-bicyclo[2.2.1]heptan-2-yl)-4-oxo-2-thioxothiazolidin-5-ylidene)methyl)furan-2-yl)-2-methoxybenzoyl)piperidine-2-carboxylate

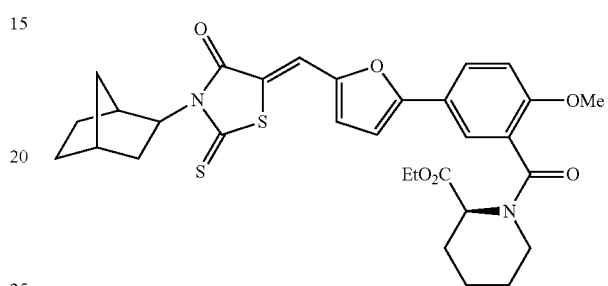

$^1$H-NMR (300 MHz, CDCl$_3$): 7.85 (s, 1H), 7.62 (s, 1H), 7.34 (s, 1H), 7.08 (m, 1H), 6.89 (m, 1H), 6.70 (m, 1H), 5.57 (m, 1H), 5.34 (m, 1H), 4.96 (m, 1H), 4.24 (m, 2H), 3.92 (s, 3H), 2.54 (s, 1H), 2.45 (s, 1H), 2.31 (m, 4H), 2.02 (m, 1H), 1.78 (m, 3H), 1.28 (m, 7H), 0.89 (m, 3H).

Synthesis of Type-5: Modification of Side Chain in C-Ring with Alcohol Moiety

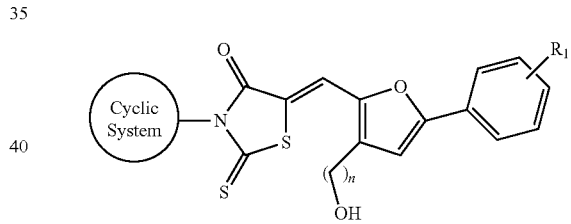

This type of compound was prepared according to the synthetic route below.

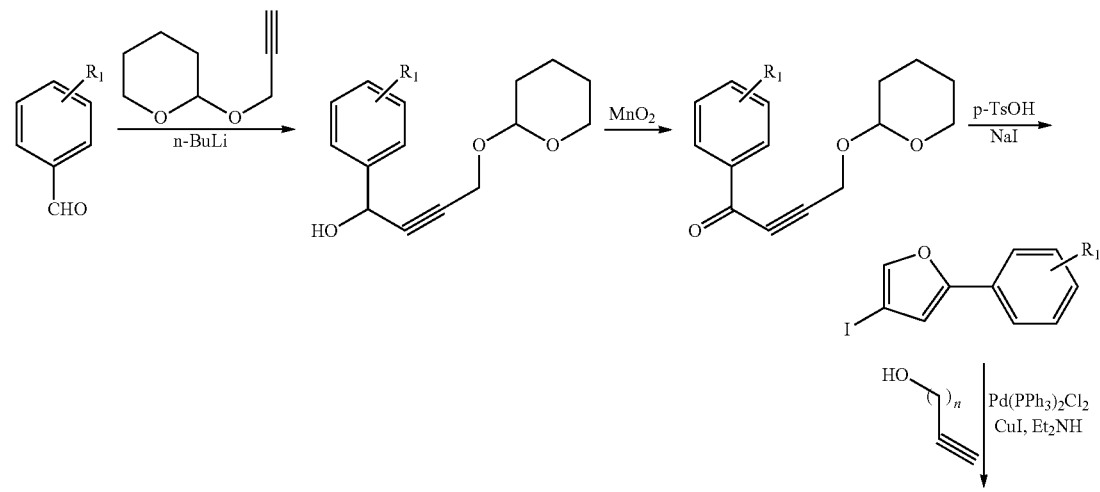

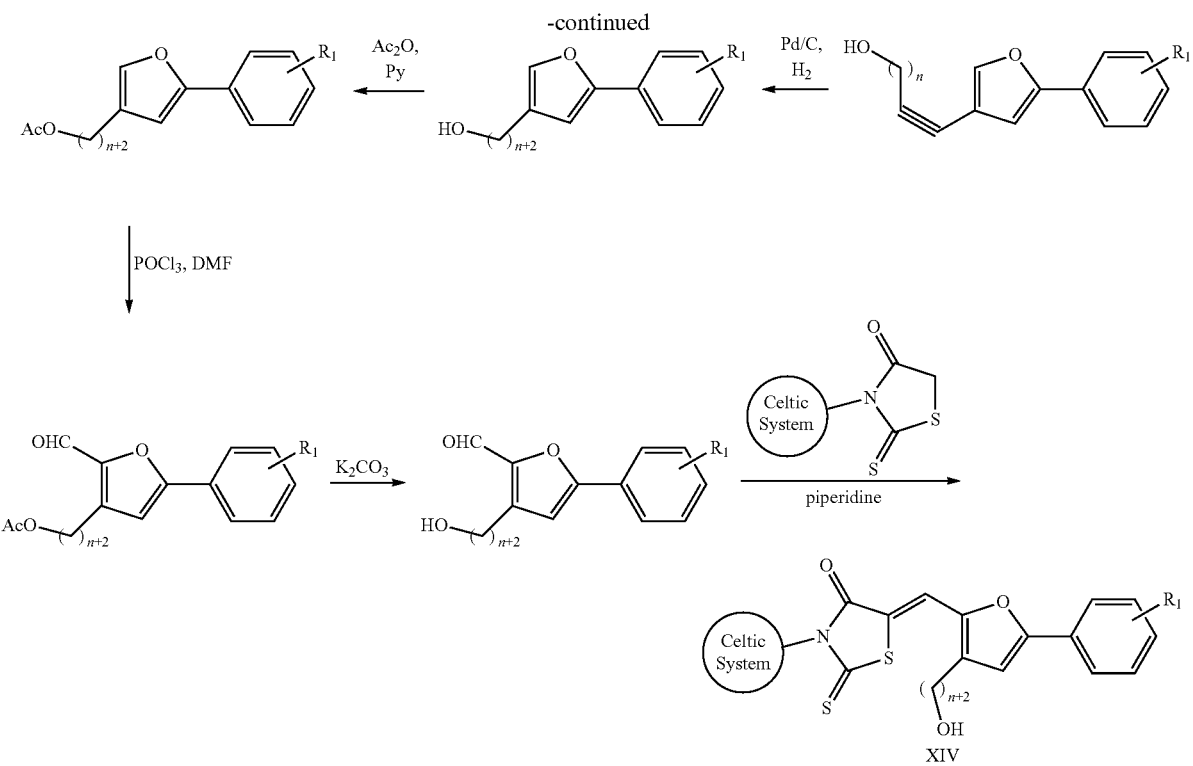

General Procedure for the Synthesis of 4-iodo-2-(substituted phenyl)furan

To a stirred solution of THP-protected propargylic alcohol (16.8 g, 0.12 mol) in dry THF (100 mL) was added n-BuLi (0.12 mol, 2.5 M in hexane) at −78° C. The mixture was stirred for 30 min at −30° C., followed by addition of the aldehyde (0.10 mol) in THF (50 mL) at −78° C. The mixture was stirred for 30 min at −78° C., allowed to slowly warm up to 0° C., and stirred for 30 min at 0° C., and poured into Et$_2$O/saturated NH$_4$Cl solution and ice. The aqueous layer was extracted with AcOEt, the combined organic phase were washed with saturated brine, and then dried with MgSO$_4$. After the solvents removed, the residue was dissolved in CH$_2$Cl$_2$ (50 mL) and was added to a mechanically stirred suspension of active MnO$_2$ (3.0 mol) in CH$_2$Cl$_2$ (100 mL) at room temperature. The mixture was stirred until the starting material was fully consumed. Filtering to remove the solid and the organic phase was dried with MgSO$_4$ and the solvents were removed. The residue was redissolved in methanol (100 mL), and then sodium iodide (75.0 g, 0.50 mol), p-toluene-sulfonic acid monohydrate (19.0 g, 0.10 mol) were added, and the reaction mixture was stirred at room temperature for 2 h. After complete conversion of ynone to furan (TLC), the reaction mixture was diluted with a saturated solution of NaHCO$_3$ and Na$_2$SO$_3$, and extracted with dichloromethane. The combined organic layers were dried with MgSO$_4$, and the solvents evaporated in vacuo. The residue was chromatographed on the neutral aluminium oxide (hexane/ethyl acetate) to give the analytically pure 4-iodo-2-(substituted phenyl)furan as solid.

General Procedure of Sonogashira Coupling

To a solution of 4-iodo-2-(substituted phenyl)furan (10.0 mmol) and homo propargylic alcohol (20.0 mmol) in degassed THF (80 mL) was added Pd(PPh$_3$)$_2$Cl$_2$ (0.702 g, 1.0 mmol), CuI (0.382, 2.0 mmol) and Et$_3$N (5.05 g, 50.0 mmol) successively. The reaction mixture was heated to reflux for 10 h. After removal of solvents, the residue was purified by a flash chromatography (PE/EA) on silica gel to give the corresponding products.

General Procedure of Hydrogenation Reaction

To a solution of Sonogashira coupling product (1.00 g) in methanol (20 mL) was added 10% Pd/C (0.10 g) at hydrogen balloon, and the mixture was stirred for 10 h. After removal of the solvent, the residue was purified by a flash chromatography (PE/EA) on silica gel to give the corresponding product.

General Procedure of Acylation Reaction

To a solution of alcohol compound (10.0 mmol) in dry CH$_2$Cl$_2$ (50 mL) was added Et$_3$N (5.05 g, 50.0 mmol) and acryl chloride (0.94 g, 12.0 mmol) at 0° C., and the mixture was then stirred until the starting material disappeared. The reaction was quenched by addition of water, and then washed with saturated NaHCO$_3$, dried with MgSO$_4$. The solvent was removed under vacuum, and the residue was purified by a flash chromatography (PE/EA) on silica gel to give the corresponding acetate products.

General Procedure of Formylation Reaction

To a solution of the above product (10.0 mmol) in N,N-dimethyl formamide (50 mL) was added a solution made by mixing of N,N-dimethylformamide (20 mL) and phosphorus oxychloride (1.53 g, 10.0 mmol) at 0° C. under nitrogen, and the formed reaction mixture was allowed to warm to room temperature, and then stirred for 30 min before the mixture was heated at 80° C. for 2 h. After the reaction mixture was cooled to 0° C., saturated Na₂CO₃ solution was added slowly and pH 6 was set. The mixture was extracted with diethyl ether twice, the organic layer was washed with saturated NaHCO₃, dried with MgSO₄, the solvent was removed under vacuum, and the residue was purified by a flash chromatography (PE/EA) on silica gel to give the corresponding aldehyde products.

General Procedure of Deprotection Reaction

To a solution of acetate aldehyde compound (10.0 mmol) in dry MeOH (50 mL) was added K₂CO₃ (6.90 g, 50.0 mmol) at 0° C., and the mixture was then stirred until the starting material disappeared. The reaction was filtered to remove the solid. Removing the solvent, the residue was dissolved in EA, washed with saturated NaCl, dried with MgSO₄. The solvent was removed under vacuum, and the residue was purified by a flash chromatography (PE/EA) on silica gel to give the corresponding acetate products.

General Procedure of Condensation Reaction

To a solution of 3-N-cycloalkyl-2-thioxothiazolidin-4-one I (0.5 mmol) and 3-(n-hydroxyalkyl)-5-phenylfuran-2-carbaldehyde (0.5 mmol) in EtOH (5 mL) was added anhydrous piperidine (43 mg, 0.5 mmol) at room temperature, and the mixture was refluxed for 16 h. After cooling to room temperature, the mixture was diluted with ethyl acetate (50 mL), and the organic phase was washed with water (3×10 mL), and then dried over anhydrous Na₂SO₄. The solvent was removed under vacuum, and the residue was recrystallized from ethyl acetate-hexane or a flash chromatography (CH₂Cl₂) on silica gel to afford the desired products as illustrated below.

(Z)-3-(adamantan-2-yl)-5-((3-(hydroxymethyl)-5-phenylfuran-2-yl)methylene)-2-thioxothiazolidin-4-one

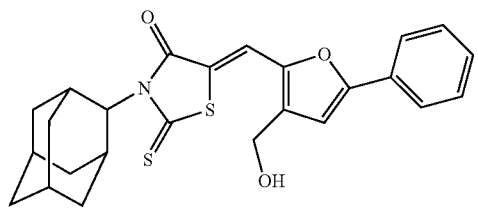 [SMILES: O=C1/C(=C/c2oc(-c3ccccc3)cc2CO)SC(=S)N1C1C2CC3CC(C2)CC1C3]

¹H NMR (300 MHz, CDCl₃): 7.76 (d, J=7.5, 2H), 7.49 (m, 4H), 6.88 (s, 1H), 4.97 (m, 1H), 4.75 (s, 2H), 2.50 (m, 4H), 1.89 (m, 6H), 1.71 (m, 8H).

(Z)-3-(bicyclo[2.2.1]heptan-2-yl)-5-(hydroxymethyl)-5-phenylfuran-2-yl)methylene)-2-thioxothiazolidin-4-one

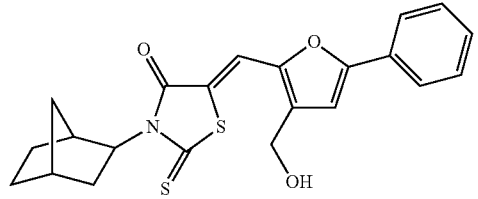 [SMILES: O=C1/C(=C/c2oc(-c3ccccc3)cc2CO)SC(=S)N1C1CC2CCC1C2]

¹H NMR (300 MHz, CDCl₃): 7.76 (d, J=7.5, 2H), 7.49 (m, 4H), 6.88 (s, 1H), 4.97 (m, 1H), 4.75 (s, 2H), 2.55 (s, 1H), 2.45 (s, 1H), 2.35 (m, 2H), 2.26 (s, 1H), 1.82 (m, 1H), 1.65 (m, 3H), 1.32 (m, 3H).

(Z)-3-(bicyclo[2.2.1]heptan-2-yl)-5-((5-(4'-chlorophenyl)-3-(hydroxymethyl)furan-2-yl)methylene)-2-thioxothiazolidin-4-one

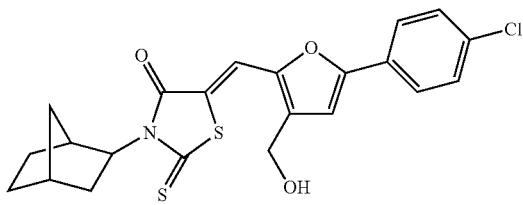 [SMILES: O=C1/C(=C/c2oc(-c3ccc(Cl)cc3)cc2CO)SC(=S)N1C1CC2CCC1C2]

¹H NMR (300 MHz, CDCl₃): 7.63 (d, J=8.7, 2H), 7.40 (m, 3H), 6.83 (m, 1H), 4.91 (q, J=6.0, 1H), 4.71 (s, 2H), 2.50 (s, 1H), 2.41 (m, 1H), 2.24 (m, 2H), 1.74 (m, 2H), 1.20-1.27 (m, 4H)

(Z)-3-(adamantan-2-yl)-5-((5-(3',5'-dimethoxyphenyl)-3-(3-hydroxypropyl)furan-2-yl)methylene)-2-thioxo-thiazolidin-4-one

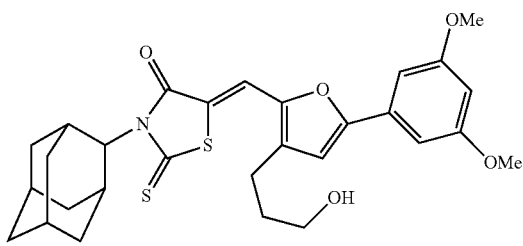

¹H-NMR (300 MHz, CDCl₃): 7.46 (s, 1H), 6.92 (d, J=2.4, 2H), 6.75 (s, 1H), 6.49 (t, J=2.1, 1H), 5.17 (s, 1H), 3.89 (s, 6H), 3.71 (d, J=6.0, 2H), 2.74 (d, J=7.8, 2H), 2.50 (s, 3H), 2.46 (s, 1H), 1.96 (m, 5H), 1.88 (m, 2H), 1.81 (s, 2H), 1.73 (d, J=12.3, 2H), 1.42 (t, J=5.1, 1H). HRMS (ESI): 540.1889 (M+H).

(Z)-3-(bicyclo[2.2.1]heptan-2-yl)-5-((5-(3',5'-dimethoxyphenyl)-3-(3-hydroxypropyl)furan-2-yl)methylene)-2-thioxothiazolidin-4-one

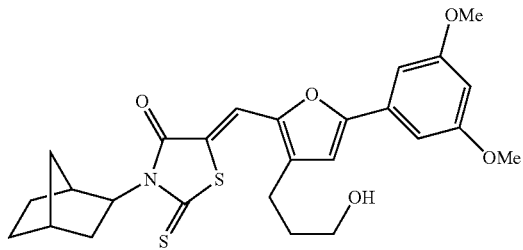 [SMILES: COc1cc(OC)cc(-c2cc(CCCO)c(/C=C3\SC(=S)N(C4CC5CCC4C5)C3=O)o2)c1]

¹H-NMR (300 MHz, CDCl₃): 7.43 (s, 1H), 6.91 (d, J=2.1, 2H), 6.74 (s, 1H), 6.49 (t, J=2.4, 1H), 4.97 (m, 1H), 3.88 (s,

6H), 3.70 (t, J=6.3, 2H), 2.73 (t, J=7.2, 2H), 2.54 (s, 1H), 2.46 (s, 1H), 2.33 (m, 2H), 1.89 (m, 2H), 1.78 (m, 1H), 1.56 (m, 2H), 1.46-1.25 (m, 4H). HRMS (ESI): 500.1565 (M+H).

3-(2-((Z)-(3-(bicyclo[2.2.1]heptan-2-yl)-4-oxo-2-thioxothiazolidin-5-ylidene)methyl)-5-(3',5'-dimethoxy-phenyl)furan-3-yl)propyl acetate

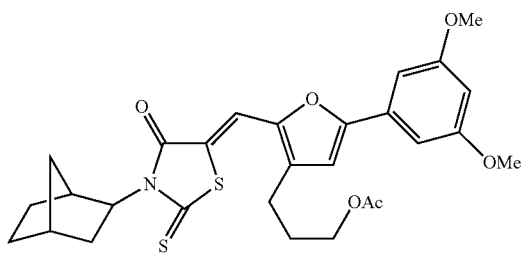 [SMILES: COc1cc(OC)cc(-c2cc(CCCOC(C)=O)c(/C=C3\SC(=S)N(C4CC5CCC4C5)C3=O)o2)c1]

$^1$H-NMR (300 MHz, CDCl$_3$): 7.39 (s, 1H), 6.92 (d, J=2.1, 2H), 6.74 (s, 1H), 6.50 (t, J=2.1, 1H), 4.98 (d, J=4.0, 1H), 4.12 (t, J=4.5, 2H), 3.89 (s, 6H), 2.71 (t, J=7.2, 2H), 2.56 (s, 1H), 2.46 (s, 1H), 2.34 (m, 2H), 2.11 (s, 3H), 1.97 (t, J=6.9, 2H), 1.80 (t, J=7.5, 2H), 1.39 (t, J=9.9, 1H), 1.27 (m, 2H). HRMS (ESI): 542.1657 (M+H).

3-(2-((Z)-(3-(adamantan-2-yl)-4-oxo-2-thioxothiazolidin-5-ylidene)methyl)-5-(3',5'-dimethoxyphenyl)furan-3-yl)propyl acetate

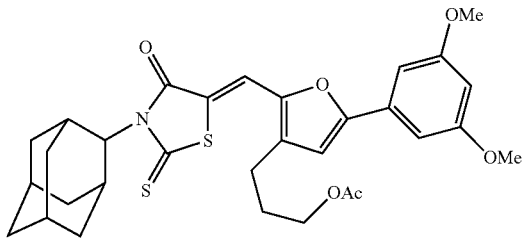

$^1$H-NMR (300 MHz, CDCl$_3$): 7.41 (s, 1H), 6.91 (d, J=2.1, 2H), 6.73 (s, 1H), 6.50 (s, 1H), 5.17 (s, 1H), 4.11 (t, J=6.3, 2H), 3.91 (s, 6H), 2.71 (t, J=7.8, 2H), 2.50 (s, 3H), 2.46 (s, 1H), 2.11 (s, 3H), 2.02 (m, 8H), 1.81 (s, 2H), 1.73 (d, J=12.9, 2H). HRMS (ESI): 582.1956 (M+H).

(Z)-3-(bicyclo[2.2.1]heptan-2-yl)-5-((5-(4'-chlorophenyl)-3-(3-hydroxypropyl)furan-2-yl)methylene)-2-thioxothiazolidin-4-one

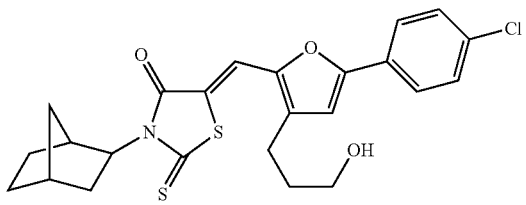 [SMILES: O=C1/C(=C/c2oc(-c3ccc(Cl)cc3)cc2CCCO)SC(=S)N1C1CC2CCC1C2]

$^1$H-NMR (300 MHz, CDCl$_3$): 7.68 (d, J=8.4, 2H), 7.44 (d, J=7.5, 2H), 7.41 (s, 1H), 6.75 (s, 1H), 4.97 (dd, J=6.0, 2.5, 1H), 3.70 (t, J=6.0, 2H), 2.73 (t, J=7.5, 2H), 2.55 (s, 1H), 2.46 (s, 1H), 2.34-2.28 (m, 2H), 1.90-1.79 (m, 3H), 1.42-1.23 (m, 5H). HRMS (ESI): 474.0954 (M+H).

(Z)-3-(adamantan-2-yl)-5-((5-(4'-chlorophenyl)-3-(3-hydroxypropyl)furan-2-yl)methylene)-2-thioxothiazo-lidin-4-one

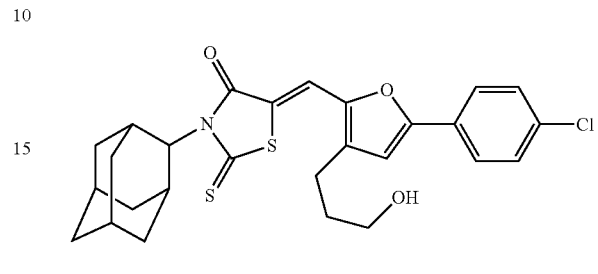

$^1$H-NMR (300 MHz, CDCl$_3$): 7.71-7.68 (m, 2H), 7.46-7.63 (m, 2H), 7.41 (s, 1H), 6.76 (s, 1H), 5.18 (s, 1H), 3.72 (t, J=6.0, 2H), 2.74 (t, J=7.5, 2H), 2.55 (s, 2H), 2.46 (s, 1H), 2.05-1.98 (m, 5H), 1.81 (s, 2H), 1.72-1.68 (m, 2H). HRMS (ESI): 514.1257 (M+H).

(Z)-3-(bicyclo[2.2.1]heptan-2-yl)-5-((5-(3'-hydroxy-5'-methoxyphenyl)-3-(3-hydroxypropyl)furan-2-yl)-methylene)-2-thioxothiazolidin-4-one

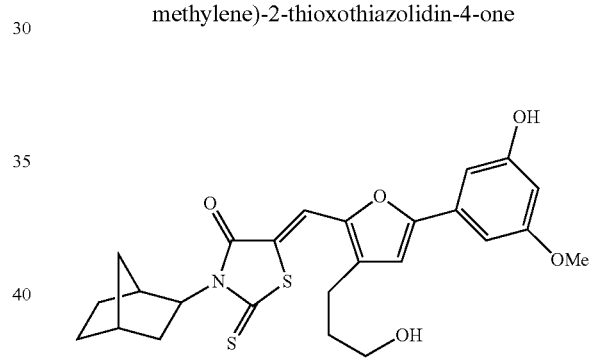

$^1$H-NMR (300 MHz, CDCl$_3$): 7.44 (s, 1H), 7.22 (s, 1H), 6.84 (s, 2H), 6.40 (s, 1H), 5.72 (s, 1H), 4.85 (t, J=6.6, 1H), 4.67 (t, J=6.6, 1H), 3.54 (s, 3H), 3.48-3.40 (m, 4H), 2.66 (t, J=7.5, 2H), 2.39 (s, 1H), 2.37-2.21 (m, 2H), 1.70-1.62 (m, 2H), 1.52-1.48 (m, 1H).

(Z)-3-(adamantan-2-yl)-5-((5-(3'-hydroxy-5'-methoxyphenyl)-3-(3-hydroxypropyl)furan-2-yl)methylene)-2-thioxothiazolidin-4-one

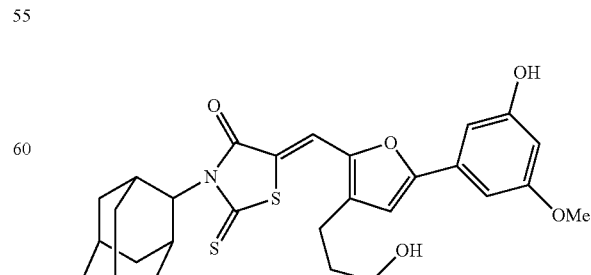

¹H-NMR (300 MHz, CDCl₃): 7.46 (s, 1H), 7.21 (s, 1H), 6.82 (s, 3H), 6.40 (s, 1H), 5.04 (s, 1H), 4.68 (t, J=5.1, 1H), 2.66 (t, J=7.5, 2H), 2.41 (s, 6H), 1.87 (s, 7H), 1.72 (s, 7H), 1.63 (d, J=12.3, 1H).

(Z)-3-(adamantan-2-yl)-5-((5-(4'-fluorophenyl)-3-(3-hydroxypropyl)furan-2-yl)methylene)-2-thioxothiazo-lidin-4-one

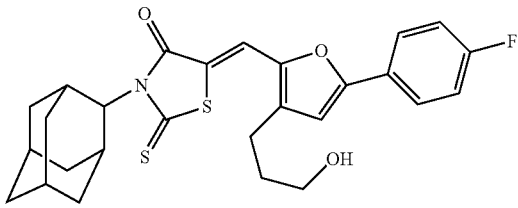 [SMILES: O=C1/C(=C/c2oc(-c3ccc(F)cc3)cc2CCCO)SC(=S)N1C1C2CC3CC(C2)CC1C3]

¹H-NMR (300 MHz, CDCl₃): 7.30 (dd, J=8.7, 5.1, 2H), 7.44 (s, 1H), 7.16 (t, J=8.7, 2H), 6.69 (s, 1H), 5.16 (s, 1H), 3.68 (d, J=6, 1H), 2.73 (t, J=7.2, 2H), 2.48 (m, 4H), 2.02-1.83 (m, 8H), 1.79-1.73 (m, 4H), 1.27 (m, 1H).

(Z)-3-(bicyclo[2.2.1]heptan-2-yl)-5-((5-(4'-fluorophenyl)-3-(3-hydroxypropyl)furan-2-yl)methylene)-2-thio-xothiazolidin-4-one

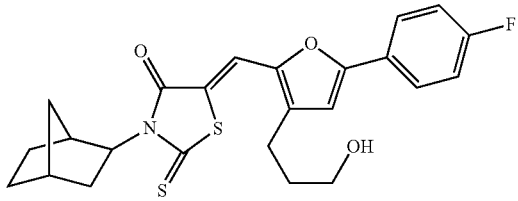 [SMILES: O=C1/C(=C/c2oc(-c3ccc(F)cc3)cc2CCCO)SC(=S)N1C1CC2CCC1C2]

¹H-NMR (300 MHz, CDCl₃): 7.74 (m, 2H), 7.27 (s, 1H), 7.20 (t, J=1.8, 2H), 6.71 (s, 1H), 4.98 (dd, J=6.3, 1.8, 1H), 3.71 (t, J=6.3, 2H), 2.74 (t, J=7.5, 2H), 2.56 (s, 1H), 2.47 (s, 1H), 2.36-2.3 (m, 2H), 1.92-1.90 (m, 2H), 1.94-1.79 (m, 3H), 1.55 (m, 2H), 1.33-1.27 (m, 4H).

(Z)-3-(bicyclo[2.2.1]heptan-2-yl)-5-((5-(4'-fluorophenyl)-3-(5-hydroxypentyl)furan-2-yl)methylene)-2-thio-xothiazolidin-4-one

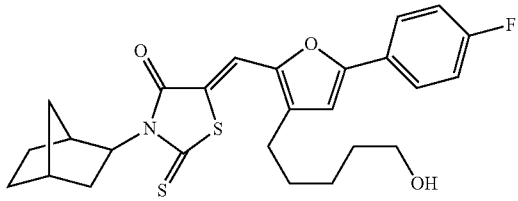 [SMILES: O=C1/C(=C/c2oc(-c3ccc(F)cc3)cc2CCCCCO)SC(=S)N1C1CC2CCC1C2]

¹H-NMR (300 MHz, CDCl₃): 7.75 (m, 2H), 7.40 (s, 1H), 7.27 (s, 1H), 7.18 (t, J=17.4, 2H), 6.69 (s, 1H), 4.99 (m, 1H), 3.67 (m, 2H), 2.63 (t, J=15.0, 2H), 2.56 (s, 1H), 2.47 (s, 1H), 2.38-2.3 (m, 2H), 1.62 (m, 4H), 1.45-1.24 (m, 6H). HRMS (ESI): 486.1581 (M+H).

(Z)-3-(adamantan-2-yl)-5-((5-(4'-fluorophenyl)-3-(5-hydroxypentyl)furan-2-yl)methylene)-2-thioxothiazo-lidin-4-one

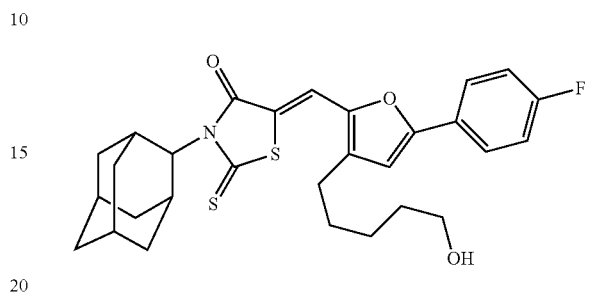

¹H-NMR (300 MHz, CDCl₃): 7.75 (m, 2H), 7.42 (s, 1H), 7.18 (t, J=17.1, 2H), 6.69 (s, 1H), 5.19 (s, 1H), 3.67 (m, 2H), 2.63 (t, J=15.0, 2H), 2.56 (m, 6H), 1.93-1.69 (m, 7H), 1.42-1.22 (m, 9H). HRMS (ESI): 526.1897 (M+H).

(Z)-3-(bicyclo[2.2.1]heptan-2-yl)-5-((5-(4'-fluorophenyl)-3-(6-hydroxyhexyl)furan-2-yl)methylene)-2-thio-xothiazolidin-4-one

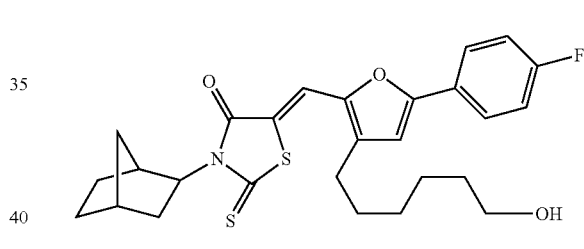

¹H-NMR (300 MHz, CDCl₃): 7.77 (dd, J=6.3, 3.2, 2H), 7.40 (s, 1H), 7.21 (dd, J=4.8, 3.2, 2H), 6.69 (s, 1H), 4.99 (dd, J=6.3, 2.4, 1H), 3.67 (dd, J=6.3, 3.2, 2H), 2.64-2.56 (m, 3H), 2.40-2.30 (m, 3H), 2.05-1.77 (m, 8H), 1.70-1.24 (m, 7H).

(Z)-3-(adamantan-2-yl)-5-((5-(4'-fluorophenyl)-3-(6-hydroxyhexyl)furan-2-yl)methylene)-2-thioxothiazo-lidin-4-one

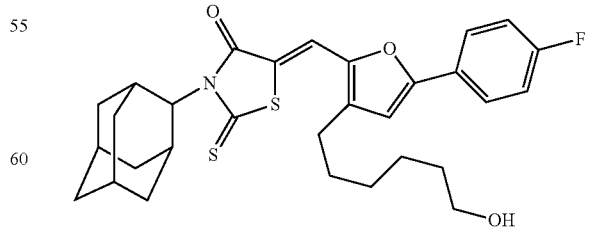

¹H-NMR (300 MHz, CDCl₃): 7.77 (dd, J=8.7, 3.3, 2H), 7.62 (s, 1H), 7.16 (t, J=8.7, 2H), 6.87 (s, 1H), 5.19 (s, 1H), 3.65 (t, J=3.9, 2H), 2.62 (t, J=15.3, 2H), 2.51-2.46 (m, 4H), 2.04-1.97 (m, 6H), 1.82-17.4 (m, 6H), 1.42-1.40 (m, 7H). HRMS (ESI): 540.2037 (M+H).

(Z)-3-(bicyclo[2.2.1]heptan-2-yl)-5-((5-(3',5'-dimethoxyphenyl)-3-(5-hydroxypentyl)furan-2-yl)methylene)-2-thioxothiazolidin-4-one

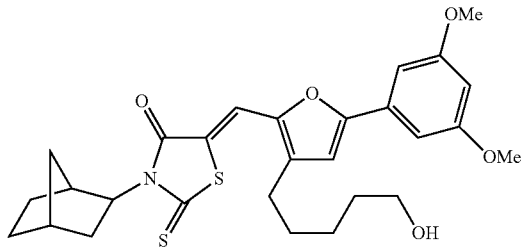 [SMILES: COc1cc(OC)cc(-c2cc(CCCCCO)c(/C=C3\SC(=S)N(C4CC5CCC4C5)C3=O)o2)c1]

¹H-NMR (300 MHz, CDCl₃): 7.38 (s, 1H), 6.91 (d, J=2.4, 2H), 6.72 (s, 1H), 6.48 (s, 1H), 4.97 (m, 1H), 3.88 (s, 6H), 3.66 (t, J=12.6, 2H), 3.10 (t, J=1.2, 1H), 2.61 (t, J=15.2, 2H), 2.45-2.32 (m, 4H), 1.62-1.43 (m, 9H).

(Z)-3-(adamantan-2-yl)-5-((5-(3',5'-dimethoxyphenyl)-3-(5-hydroxypentyl)furan-2-yl)methylene)-2-thioxo-thiazolidin-4-one

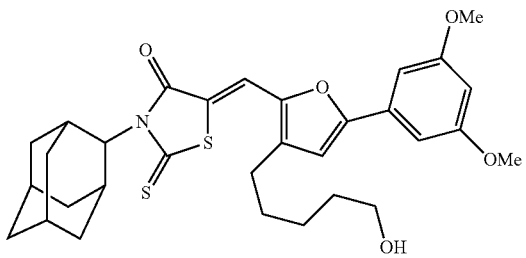 [SMILES: COc1cc(OC)cc(-c2cc(CCCCCO)c(/C=C3\SC(=S)N(C4C5CC6CC(C5)CC4C6)C3=O)o2)c1]

¹H-NMR (300 MHz, CDCl₃): 7.42 (s, 1H), 6.30 (d, J=2.1, 2H), 6.72 (s, 1H), 6.49 (t, J=4.5, 1H), 5.18 (s, 1H), 3.89 (s, 6H), 2.70 (m, 3H), 2.63 (t, J=15.2, 2H), 2.49 (d, J=10.5, 4H), 1.98 (m, 6H), 1.75-1.63 (m, 4H), 1.47 (m, 5H). HRMS (ESI): 568.2192 (M+H).

(Z)-3-(bicyclo[2.2.1]heptan-2-yl)-5-((5-(3',5'-dimethoxyphenyl)-3-(6-hydroxyhexyl)furan-2-yl)methylene)-2-thioxothiazolidin-4-one

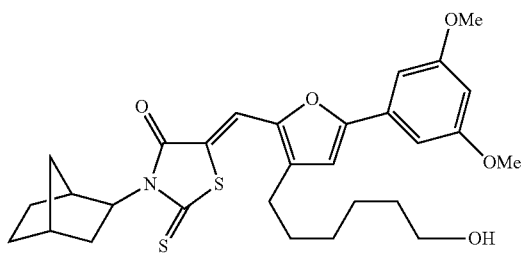 [SMILES: COc1cc(OC)cc(-c2cc(CCCCCCO)c(/C=C3\SC(=S)N(C4CC5CCC4C5)C3=O)o2)c1]

¹H-NMR (300 MHz, CDCl₃): 7.37 (s, 1H), 6.93 (d, J=5.4, 2H), 6.72 (s, 1H), 6.50 (s, 1H), 4.98 (dd, J=5.4, 3.3, 1H), 3.89 (s, 6H), 3.66 (dd, J=5.7, 2.6, 2H), 2.64-2.55 (m, 2H), 2.48-2.33 (m, 3H), 2.32-2.20 (m, 3H), 2.05-2.01 (m, 2H), 1.68-1.60 (m, 2H), 1.52-1.32 (m, 8H). HRMS (ESI): 542.2021 (M+H).

(Z)-3-(adamantan-2-yl)-5-((5-(3',5'-dimethoxyphenyl)-3-(6-hydroxyhexyl)furan-2-yl)methylene)-2-thioxo-thiazolidin-4-one

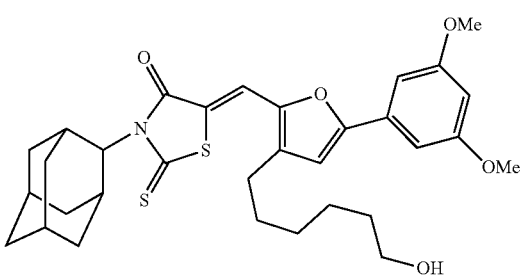 [SMILES: COc1cc(OC)cc(-c2cc(CCCCCCO)c(/C=C3\SC(=S)N(C4C5CC6CC(C5)CC4C6)C3=O)o2)c1]

¹H-NMR (300 MHz, CDCl₃): 7.42 (s, 1H), 6.93 (d, J=2.4, 2H), 6.72 (s, 1H), 6.49 (t, J=4.5, 1H), 5.18 (s, 1H), 3.89 (s, 6H), 3.66 (dd, J=5.4, 2.4, 2H), 2.61 (m, 2H), 2.51 (m, 4H), 2.00-1.96 (m, 6H), 1.42-1.40 (m, 2H), 1.32-1.26 (m, 10H).

(Z)-3-(bicyclo[2.2.1]heptan-2-yl)-5-((5-(3',5'-dimethoxyphenyl)-3-(4-hydroxybutyl)furan-2-yl)methylene)-2-thioxothiazolidin-4-one

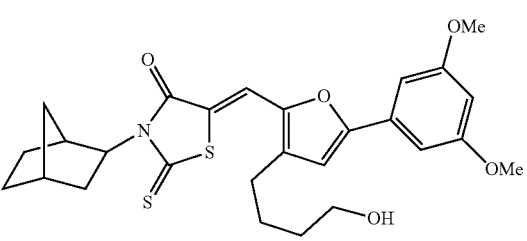 [SMILES: COc1cc(OC)cc(-c2cc(CCCCO)c(/C=C3\SC(=S)N(C4CC5CCC4C5)C3=O)o2)c1]

¹H-NMR (300 MHz, CDCl₃): 7.40 (s, 1H), 6.93 (d, J=2.1, 2H), 6.74 (s, 1H), 6.50 (t, J=4.5, 1H), 4.98 (m, 6H), 3.90 (s, 6H), 3.71 (t, J=6.0, 2H), 2.66 (t, J=14.4, 2H), 2.56 (s, 1H), 2.46 (d, J=2.4, 1H), 2.32 (d, J=7.8, 2H), 1.72-1.45 (m, 8H).

(Z)-3-(adamantan-2-yl)-5-((5-(3',5'-dimethoxyphenyl)-3-(4-hydroxybutyl)furan-2-yl)methylene)-2-thioxo-thiazolidin-4-one

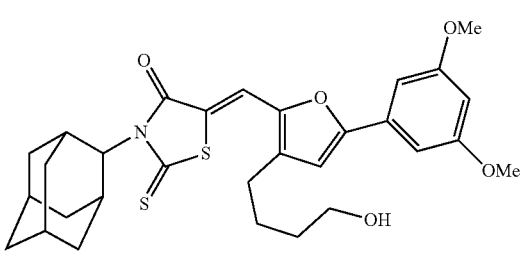 [SMILES: COc1cc(OC)cc(-c2cc(CCCCO)c(/C=C3\SC(=S)N(C4C5CC6CC(C5)CC4C6)C3=O)o2)c1]

¹H-NMR (300 MHz, CDCl₃): 7.42 (s, 1H), 6.93 (d, J=2.1, 2H), 6.74 (s, 1H), 6.49 (t, J=4.5, 1H), 5.18 (s, 1H), 3.89 (s,

6H), 3.70 (m, 2H), 2.66 (t, J=14.4, 2H), 2.47 (t, J=13.2, 4H), 2.04-1.91 (m, 9H), 1.75-1.61 (m, 5H). HRMS (ESI): 554.2042 (M+H).

(Z)-3-(bicyclo[2.2.1]heptan-2-yl)-5-((5-(4'-fluorophenyl)-3-(4-hydroxybutyl)furan-2-yl)methylene)-2-thio-xothiazolidin-4-one

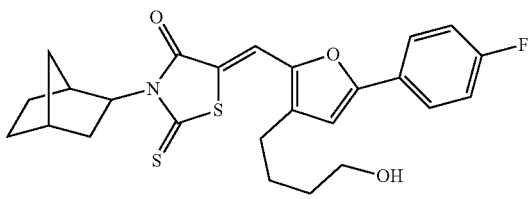 [SMILES: O=C1/C(=C/c2oc(-c3ccc(F)cc3)cc2CCCCO)SC(=S)N1C1CC2CCC1C2]

¹H-NMR (300 MHz, CDCl₃): 7.69 (m, 2H), 7.12 (t, J=17.1, 2H), 6.64 (d, J=3.9, 1H), 4.92 (t, J=14.7, 1H), 3.62 (m, 2H), 2.60 (t, J=14.4, 2H), 2.50 (s, 1H), 2.41 (s, 1H), 2.26 (m, 2H), 1.27-1.21 (m, 11H).

(Z)-3-(adamantan-2-yl)-5-((5-(4'-fluorophenyl)-3-(4-hydroxybutyl)furan-2-yl)methylene)-2-thioxothiazolidin-4-one

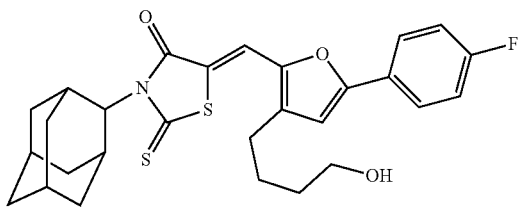 [SMILES: O=C1/C(=C/c2oc(-c3ccc(F)cc3)cc2CCCCO)SC(=S)N1C1C2CC3CC(C2)CC1C3]

¹H-NMR (300 MHz, CDCl₃): 7.74 (m, 2H), 7.17 (t, J=17.4, 2H), 6.72 (s, 1H), 5.18 (s, 1H), 3.70 (t, J=12.3, 2H), 2.65 (t, J=14.4, 2H), 2.48 (d, J=12.6, 2H), 1.98 (d, J=10.2, 4H), 1.74 (m, 6H), 1.27-1.25 (m, 6H).

(Z)-3-cyclohexyl-5-((5-(3',5'-dimethoxyphenyl)-3-(3-hydroxypropyl)furan-2-yl)methylene)-2-thioxothiazo-lidin-4-one

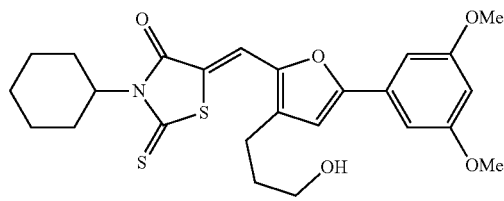 [SMILES: COc1cc(OC)cc(-c2cc(CCCO)c(/C=C3\SC(=S)N(C4CCCCC4)C3=O)o2)c1]

¹H-NMR (300 MHz, CDCl₃): 7.43 (s, 1H), 6.92 (d, J=2.4, 2H), 6.74 (s, 1H), 6.49 (d, J=2.4, 1H), 5.03 (m, 1H), 3.88 (s, 6H), 3.71 (t, J=6.0, 2H), 2.74 (t, J=7.5, 2H), 2.52-2.34 (m, 2H), 1.84-1.87 (m, 4H), 1.47-1.19 (m, 6H).

(Z)-3-cyclooctyl-5-((5-(3',5'-dimethoxyphenyl)-3-(3-hydroxypropyl)furan-2-yl)methylene)-2-thioxothiazo-lidin-4-one

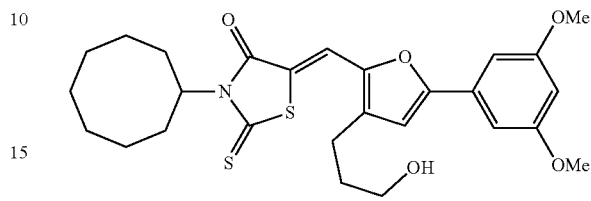

¹H-NMR (300 MHz, CDCl₃): 7.43 (s, 1H), 6.92 (d, J=2.4, 2H), 6.74 (s, 1H), 6.49 (d, J=2.4, 1H), 5.03 (m, 1H), 3.88 (s, 6H), 3.71 (t, J=6.0, 2H), 2.74 (t, J=7.5, 2H), 2.52-2.34 (m, 2H), 1.84-1.87 (m, 4H), 1.47-1.19 (m, 6H).

(Z)-3-cyclododecyl-5-((5-(3',5'-dimethoxyphenyl)-3-(3-hydroxypropyl)furan-2-yl)methylene)-2-thioxothi-azolidin-4-one

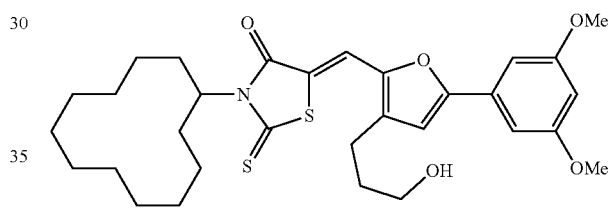

¹H-NMR (300 MHz, CDCl₃): 7.44 (s, 1H), 6.92 (d, J=2.1, 2H), 6.74 (s, 1H), 6.49 (t, J=2.1, 1H), 5.44-5.40 (m, 1H), 3.88 (s, 6H), 3.71 (t, J=6.0, 2H), 2.74 (t, J=7.5, 2H), 2.23-2.15 (m, 2H), 1.92-1.76 (m, 4H), 1.72-1.18 (m, 18H).

In view of the present disclosure, C-ring containing N or S can also be modified to contain an alcohol side chain.

(Z)-3-(bicyclo[2.2.1]heptan-2-yl)-5-((3-(5-hydroxypentyl)-5-(3-methoxyphenyl)-thiophen-2-yl)methylene)-2-thioxothiazolidin-4-one

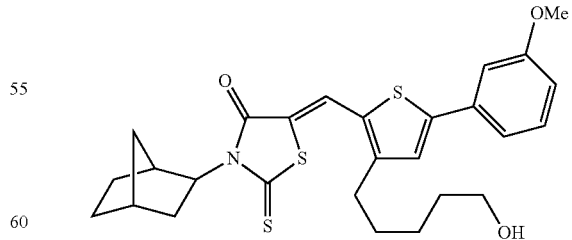

¹H-NMR (300 MHz, DMSO-d₆): 7.85 (s, 1H), 7.34 (t, J=7.8 Hz, 1H), 7.23 (m=7.27-7.23, 3H), 7.16 (t, J=1.8 Hz, 1H), 6.92 (dd, J=1.8 Hz, 1H), 4.95 (dd, J=6.6 Hz, 1H), 3.89 (s, 3H), 3.67 (t, J=6.0 Hz, 2H), 2.81 (t, J=7.8 Hz, 2H), 2.56 (s, 1H), 2.47 (s, 1H), 2.30 (m=2.32-2.30, 2H), 1.75 (t, J=7.5 Hz,

1H), 1.69 (m=1.73-1.69, 3H), 1.60 (m=1.65-1.60, 5H), 1.46 (m=1.49-1.45, 2H), 1.26 (m=1.38-1.26, 5H). HRMS (ESI): 514.1547 (M+H)

Synthesis of Type-6: Modification of Side Chain in C-Ring with Amine Moiety

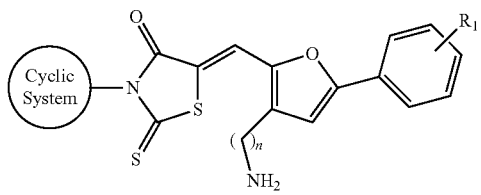

This type of compound was prepared according to the synthetic route below.

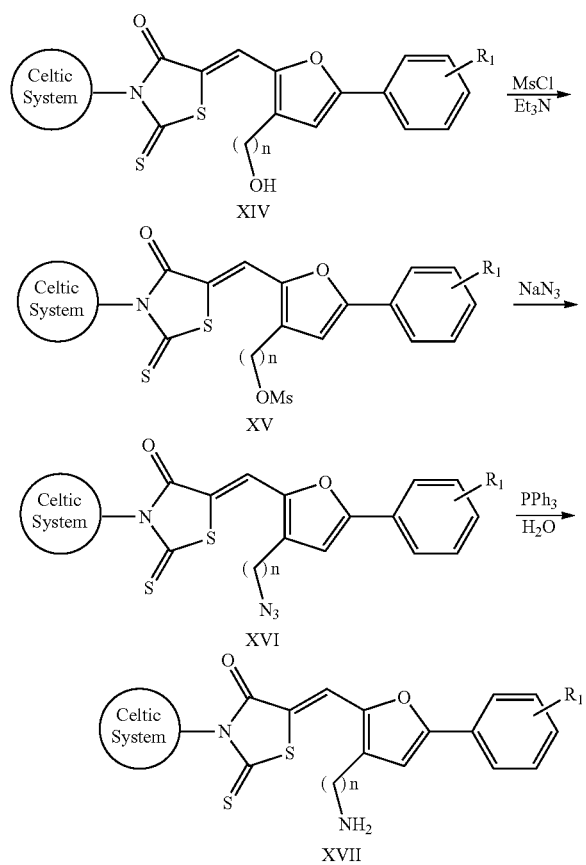

General Procedure of Mesylation Reaction

To a solution of the alcohol XIV (10.0 mmol) made above in dry $CH_2Cl_2$ (50 mL) was added $Et_3N$ (5.05 g, 50.0 mmol) and methanesulfonyl chloride (1.37 g, 12.0 mmol) at 0° C., and the mixture was then stirred until the starting material disappeared. The reaction was quenched by addition of water, and then washed with saturated $NaHCO_3$, dried with $MgSO_4$. The solvent was removed under vacuum, and the residue was purified by a flash chromatography (PE/EA) on silica gel to give the corresponding mesylate products.

General Procedure of the Synthesis of Azide Compound XVI

To a solution of mesylate XV (10.0 mmol) in DMF (20 mL) was added sodium azide (0.65 g, 100 mmol), and the mixture was stirred at 90° C. until the starting material disappeared. The reaction was quenched by addition of water, and then extracted with saturated diethyl ether, dried with $MgSO_4$. The solvent was removed under vacuum, and the residue was purified by a flash chromatography (PE/EA) on silica gel to afford the corresponding azide products.

General Procedure of the Synthesis of Amine Compound XVII

A solution of azide (10.0 mmol) in THF (50 mL) was added $PPh_3$ (3.93 g, 15.0 mmol), and the mixture was stirred at room temperature until the starting material was fully consumed. The reaction was quenched by addition of water and stirred another 2 h. After removal of the solvent, the residue was redissolved in EA and washed with 10% HCl. The aqueous phased was extracted with EA twice. The combined aqueous phase was then neutralized to pH 9 by addition of 10% NaOH, and the formed mixture was extracted with saturated $CH_2Cl_2$, dried with $MgSO_4$. After removal of the solvent, the residue was purified by recrystallion from diethyl ether/PE to afford the corresponding amine products.

(Z)-3-(bicyclo[2.2.1]heptan-2-yl)-5-((3-(3-aminopropyl)-5-(3',5'-dimethoxyphenyl)furan-2-yl)methylene)-2-thioxothiazolidin-4-one

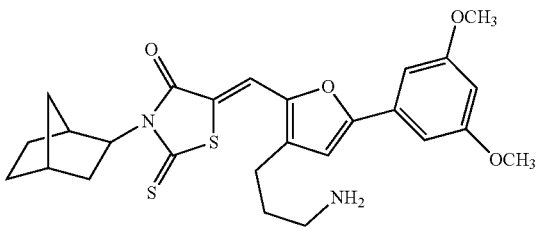 [SMILES: COc1cc(OC)cc(-c2cc(CCCN)c(/C=C3\SC(=S)N(C4CC5CCC4C5)C3=O)o2)c1]

$^1$H-NMR (300 MHz, $CDCl_3$): 7.55 (s, 1H), 7.38 (s, 1H), 6.97 (d, J=2.1, 2H), 6.59 (t, J=2.1, 1H), 4.86 (t, J=6.0, 1H), 3.83 (s, 6H), 2.83 (t, J=7.5, 2H), 2.75 (t, J=7.5, 2H), 2.38 (s, 1H), 2.29 (m, 1H), 1.89 (m, 2H), 1.75 (m, 1H), 1.54 (m, 2H), 1.25 (m, 4H). HRMS (ESI): 499.1736 (M+H).

(Z)-3-(adamantan-2-yl)-5-((3-(3-aminopropyl)-5-(3', 5'-dimethoxyphenyl)furan-2-yl)methylene)-2-thioxothiazolidin-4-one

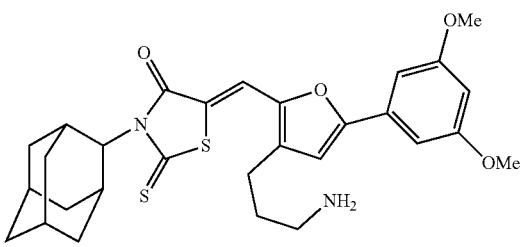 [SMILES: COc1cc(OC)cc(-c2cc(CCCN)c(/C=C3\SC(=S)N(C4C5CC6CC(C5)CC4C6)C3=O)o2)c1]

¹H-NMR (300 MHz, CDCl₃): 7.81 (s, 2H), 7.59 (s, 1H), 7.37 (s, 1H), 6.98 (d, J=2.1, 2H), 6.60 (d, J=2.1, 1H), 5.05 (s, 1H), 3.83 (s, 6H), 2.85 (m, 2H), 2.76 (t, J=7.5, 2H), 2.44 (s, 2H), 2.39 (s, 1H), 1.86 (m, 1H), 1.75 (s, 2H), 1.65 (d, J=10.8, 2H). HRMS (ESI): 539.2031 (M+H).

(Z)-3-(bicyclo[2.2.1]heptan-2-yl)-5-((3-(3-aminopropyl)-5-(3'-hydroxy-5'-methoxyphenyl)furan-2-yl)-methylene)-2-thioxothiazolidin-4-one

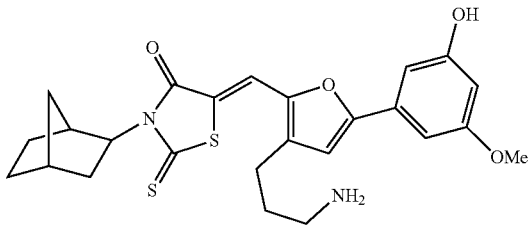 [SMILES: COc1cc(O)cc(-c2cc(CCCN)c(/C=C3\SC(=S)N(C4CC5CCC4C5)C3=O)o2)c1]

¹H-NMR (300 MHz, DMSO-d6): 7.50 (s, 1H), 7.25 (s, 1H), 6.85 (s, 2H), 6.40 (s, 1H), 4.88 (dd, J=6.0, 3.9, 1H), 3.78 (s, 3H), 3.34-3.44 (m, 5H), 2.68 (s, 2H), 2.27-2.40 (m, 4H), 1.42-1.74 (m, 6H), 1.22 (s, 3H).

(Z)-3-(adamantan-2-yl)-5-((3-(3-aminopropyl)-5-(3'-hydroxy-5'-methoxyphenyl)furan-2-yl)methylene)-2-thioxothiazolidin-4-one

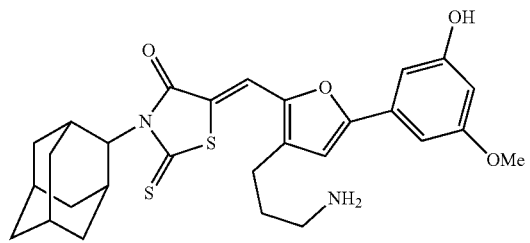

¹H-NMR (300 MHz, DMSO-d6): 7.51 (s, 1H), 7.23 (s, 1H), 6.84 (s, 2H), 6.39 (s, 1H), 5.06 (s, 1H), 3.78 (s, 3H); 3.47-3.40 (m, H); 2.67 (t, J=7.8, 2H); 2.65-2.58 (m, 2H); 2.48-2.39 (m, 5H); 1.70 (s, 2H); 1.68-1.60 (m, 5H). HRMS (ESI): 525.1871 (M+H).

(Z)-3-(bicyclo[2.2.1]heptan-2-yl)-5-((3-(3-aminopropyl)-5-(4'-chlorophenyl)furan-2-yl)methylene)-2-thioxo-thiazolidin-4-one hydrochloride

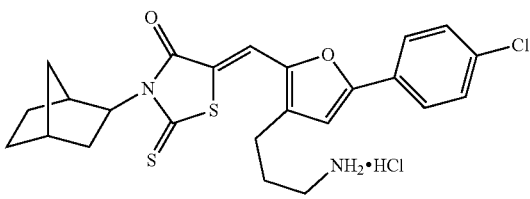

¹H-NMR (300 MHz, DMSO-d6): 7.84-7.81 (m, 4H), 7.65 (d, J=8.4, 2H), 7.55 (s, 1H), 7.35 (s, 1H), 4.90-4.85 (m, 1H), 3.46-3.35 (m, 2H), 2.88-2.84 (m, 1H), 2.76 (t, J=7.5, 1H), 2.50 (m, 2H), 2.38 (s, 1H), 2.26-2.22 (m, 1H), 1.90-1.86 (m, 1H), 1.72 (t, J=11.1, 1H), 1.53 (m, 2H), 1.06 (m, 4H).

(Z)-3-(adamantan-2-yl)-5-((3-(3-aminopropyl)-5-(4'-chlorophenyl)furan-2-yl)methylene)-2-thioxothiazolidin-4-one hydrochloride

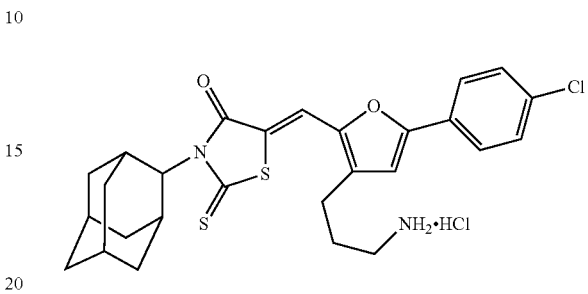

¹H-NMR (300 MHz, DMSO-d6): 7.95 (s, 2H), 7.79 (d, J=8.7, 2H), 7.65 (d, J=8.7, 2H), 7.57 (s, 1H), 7.31 (s, 1H), 5.07 (s, 1H), 3.50 (m, 4H), 2.73-2.64 (m, 3H), 2.55-2.37 (m, 5H), 2.01-2.37 (m, 5H), 2.01-1.82 (m, 5H), 1.80-1.57 (m, 3H).

(Z)-3-(adamantan-2-yl)-5-((3-(3-aminopropyl)-5-(4'-chlorophenyl)furan-2-yl)methylene)-2-thioxo-thiazolidin-4-one hydrochloride

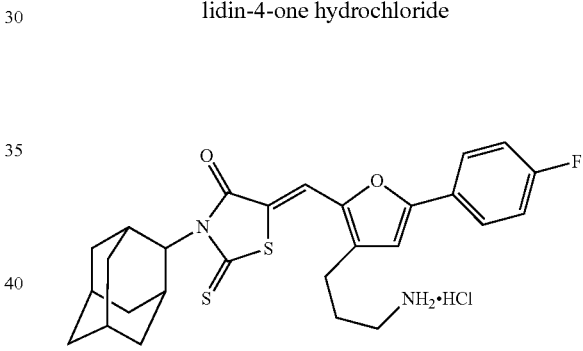

¹H-NMR (300 MHz, DMSO-d6): 7.92-7.83 (m, 4H), 7.61 (s, 1H), 7.41 (t, J=4.5, 2H), 7.28 (s, 1H), 5.05 (s, 1H), 3.46-3.35 (m, 4H), 2.86-2.84 (m, 2H), 2.75-2.73 (m, 1H), 2.50 (s, 1H), 2.43 (m, 3H), 1.89-1.80 (m, 5H), 1.67-1.63 (m, 4H). HRMS (ESI): 497.1573 (M−HCl+H).

(Z)-3-(bicyclo[2.2.1]heptan-2-yl)-5-((3-(3-aminopropyl)-5-(4'-fluorophenyl)furan-2-yl)methylene)-2-thioxo-thiazolidin-4-one hydrochloride

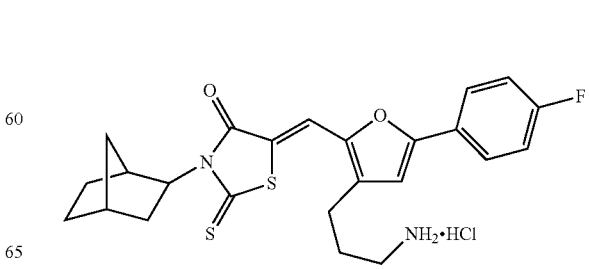

¹H-NMR (300 MHz, DMSO-d6): 7.88-7.84 (m, 4H), 7.66 (d, J=9.0, 2H), 7.54 (s, 1H), 7.37 (s, 1H), 4.92-4.84 (m, 1H), 3.46-3.35 (m, 2H), 2.88-2.84 (m, 1H), 2.76 (t, J=7.5, 1H), 2.50 (m, 2H), 2.38 (s, 1H), 2.26-2.22 (m, 1H), 1.90-1.86 (m, 1H), 1.72 (t, J=11.1, 1H), 1.53 (m, 2H), 1.06 (m, 4H).

(Z)-3-(bicyclo[2.2.1]heptan-2-yl)-5-((3-(3-amino-pentyl)-5-(4'-chlorophenyl)furan-2-yl)methylene)-2-thioxo-thiazolidin-4-one hydrochloride

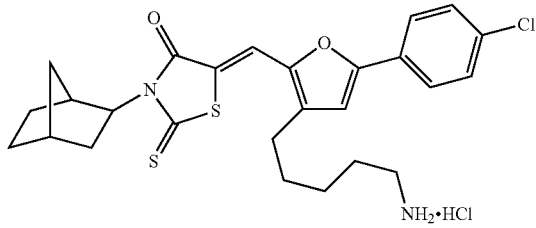

¹H-NMR (300 MHz, DMSO-d6): 7.84-7.81 (m, 4H), 7.65 (d, J=8.4, 2H), 7.55 (s, 1H), 7.35 (s, 1H), 4.90-4.85 (m, 1H), 3.46-3.35 (m, 2H), 2.88-2.84 (m, 1H), 2.76 (t, J=7.5, 2H), 2.50 (m, 3H), 2.38 (s, 2H), 2.26-2.22 (m, 4H), 1.90-1.86 (m, 4H), 1.72 (t, J=11.1, 2H), 1.53 (m, 2H), 1.06 (m, 4H). HRMS (ESI): 501.1444 (M−HCl+H).

In view of the present disclosure, C-ring containing N or S can also be modified to contain an amine side chain.

(Z)-5-((3-(5-aminopentyl)-5-(3-methoxyphenyl)thiophen-2-yl)methylene)-3-(bicyclo[2.2.1]heptan-2-yl)-2-thioxothiazolidin-4-one hydrochloride

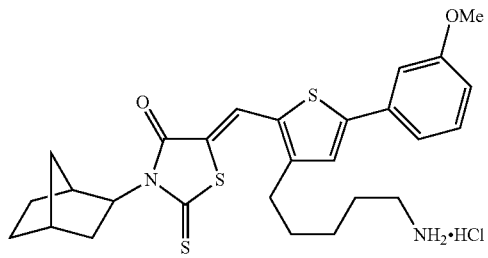

¹H-NMR (300 MHz, DMSO-d₆): 7.85 (s, 1H), 7.34 (t, J=7.8 Hz, 1H), 7.2 (m=7.27-7.23, 3H), 7.16 (t, J=1.8 Hz, 1H), 6.92 (dd, J=1.8 Hz, 1H), 4.95 (dd, J=6.6 Hz, 1H), 3.89 (s, 3H), 3.67 (t, J=6.0 Hz, 2H), 2.81 (t, J=7.8 Hz, 2H), 2.56 (s, 1H), 2.47 (s, 1H), 2.30 (m=2.32-2.30, 2H), 1.75 (t, J=7.5 Hz, 1H), 1.69 (m=1.73-1.69, 3H), 1.60 (m=1.65-1.60, 5H), 1.46 (m=1.49-1.45, 2H), 1.26 (m=1.38-1.26, 5H). HRMS (ESI): 513.1709 (M+H−HCl)

Synthesis of Type-7: Modification of Side Chain in C-Ring with Acid Moiety

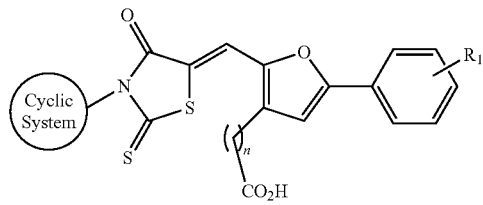

This type of compound was prepared according to the synthetic route below.

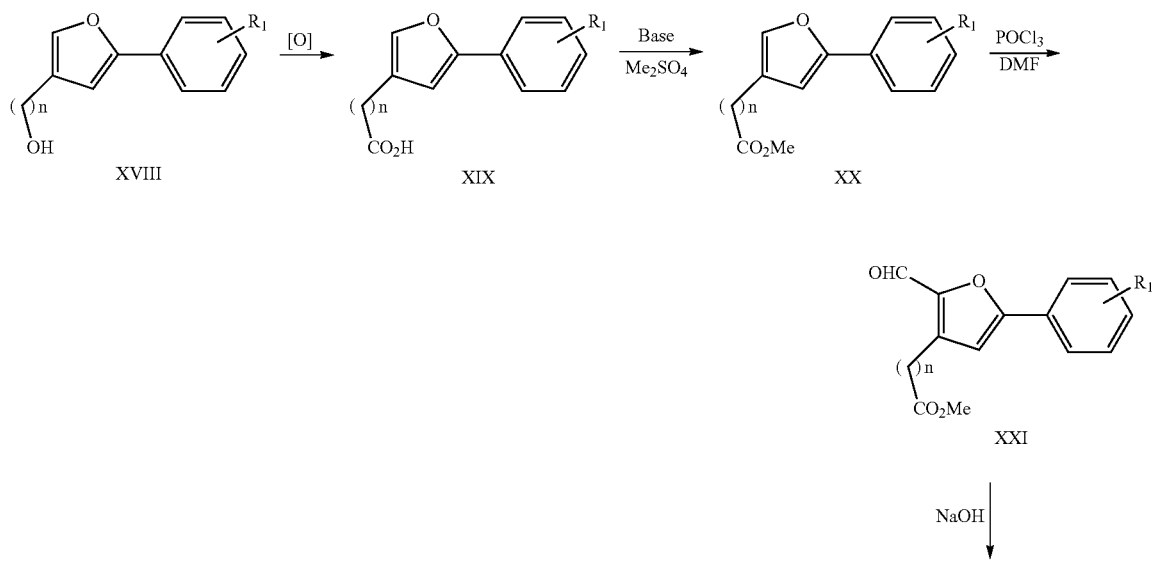

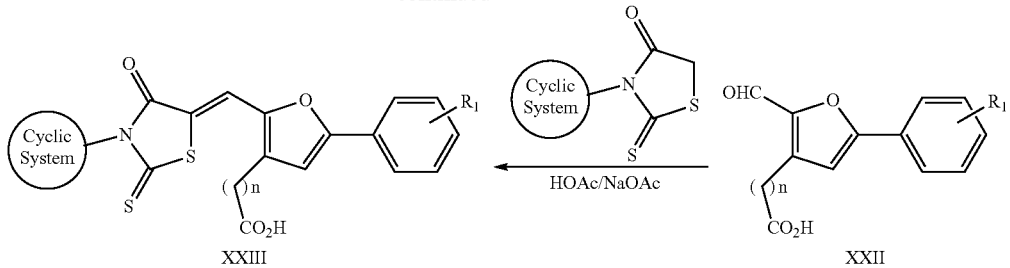

General Procedure of Oxidation Reaction

To a solution of 4-hydroxyalkyl-2-(substituted phenyl)furan XVIII (10.0 mmol) in acetone (50 mL) was added Jone's reagent at 0° C., then the mixture was stirred until the starting material fully consumed. After removal of the solvent, the residue was extracted with EA, and the organic layer was washed with saturated NaCl, dried with $MgSO_4$, the solvent was removed under vacuum, and the residue was purified by a flash chromatography (PE/EA) on silica gel to give the corresponding monoacid products.

General Procedure of Esterification Reaction

To a solution of mono acid compound XIX (10.0 mmol) in acetone (50 mL) was added MeI (2.13 g, 15.0 mmol) and $K_2CO_3$ (8.3 g, 60.0 mmol) was refluxed until the starting material fully consumed. After removal of the solvent, the residue was extracted with EA, and the organic layer was washed with saturated NaCl, dried with $MgSO_4$, the solvent was removed under vacuum, and the residue was purified by a flash chromatography (PE/EA) on silica gel to give the corresponding ester products.

General Procedure of Formylation Reaction

To a solution of ester compound XX (10.0 mmol) in N,N-dimethyl formamide (50 mL) was added a solution made by mixing of N,N-dimethylformamide (20 mL) and phosphorus oxychloride (1.53 g, 10.0 mmol) at 0° C. under nitrogen, and the formed reaction mixture was allowed to warm to room temperature, and then stirred for 30 min before the mixture was heated at 80° C. for 2 h. After the reaction mixture was cooled to 0° C., saturated $Na_2CO_3$ solution was added slowly and pH 6 was set. The mixture was extracted with diethyl ether twice, the organic layer was washed with saturated $NaHCO_3$, dried with $MgSO_4$, the solvent was removed under vacuum, and the residue was purified by a flash chromatography (PE/EA) on silica gel to give the corresponding aldehyde products.

General Procedure of Hydrolysis of Ester

A solution of ester aldehyde compound XXI (10.0 mmol) in ethanol (50 mL) was added 100 mL of 1 N NaOH solution, and the mixture was stirred at room temperature until the starting material was fully consumed. Removing the ethanol and the residue was diluted by addition of water. The aqueous phased was extracted with EA twice, dried with $MgSO_4$. After removal of the solvent, the residue was purified by recrystallion from diethyl ether/PE to afford the corresponding products.

General Procedure of Condensation Reaction

To a solution of 3-N-cycloalkyl-2-thioxothiazolidin-4-one I (0.5 mmol) and acid aldehyde XXII (0.5 mmol) in EtOH (5 mL) was added anhydrous piperidine (43 mg, 0.5 mmol) at room temperature, and the mixture was refluxed for 16 h. After cooling to room temperature, the mixture was diluted with ethyl acetate (50 mL), and the organic phase was washed with water (3×10 mL), and then dried over anhydrous $Na_2SO_4$. The solvent was removed under vacuum, and the residue was recrystallized from ethyl acetate-hexane or a flash chromatography ($CH_2Cl_2$) on silica gel to afford the desired products as illustrated below.

3-(2-((Z)-(3-(adamantan-2-yl)-4-oxo-2-thioxothiazolidin-5-ylidene)methyl)-5-(3',5'-dimethoxyphenyl)furan-3-yl)propanoic acid

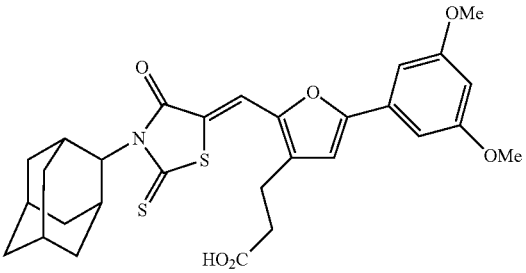 [SMILES: COc1cc(OC)cc(-c2cc(CCC(=O)O)c(/C=C3\SC(=S)N(C4C5CC6CC(C5)CC4C6)C3=O)o2)c1]

$^1$H-NMR (300 MHz, $CDCl_3$): 12.25 (s, 1H), 7.51 (s, 1H), 7.34 (s, 1H), 6.93 (d, J=2.1, 2H), 6.56 (s, 1H), 5.04 (s, 1H), 3.82 (s, 6H), 2.86 (t, J=7.5, 2H), 2.59 (d, J=7.5, 2H), 2.44 (s, 3H), 1.89 (s, 6H), 1.74 (s, 2H), 1.64 (d, J=11.1, 2H). HRMS (ESI): 554.1653 (M+H).

(E)-3-(2-((Z)-(3-(bicyclo[2.2.1]heptan-2-yl)-4-oxo-2-thioxothiazolidin-5-ylidene)methyl)-5-(3',5'-dimethoxy-phenyl)furan-3-yl)acrylic acid

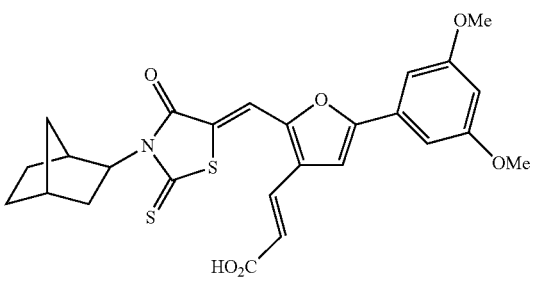 [SMILES: COc1cc(OC)cc(-c2cc(/C=C/C(=O)O)c(/C=C3\SC(=S)N(C4CC5CCC4C5)C3=O)o2)c1]

$^1$H-NMR (300 MHz, $CDCl_3$): 7.77 (s, 1H), 7.68 (d, J=15.6, 1H), 7.61 (s, 1H), 6.90 (d, J=2.1, 2H), 6.54 (t, J=2.1, 1H), 6.45

(d, J=8.1, 1H), 3.81 (s, 6H), 2.53 (s, 2H), 2.38 (s, 1H), 2.26-2.25 (m, 2H), 1.72 (t, J=10.8, 1H), 1.25-1.24 (m, 2H). HRMS (ESI): 512.1192 (M+H).

(E)-3-(2-((Z)-(3-(adamantan-2-yl)-4-oxo-2-thioxothiazolidin-5-ylidene)methyl)-5-(3',5'-dimethoxyphenyl)-furan-3-yl)acrylic acid

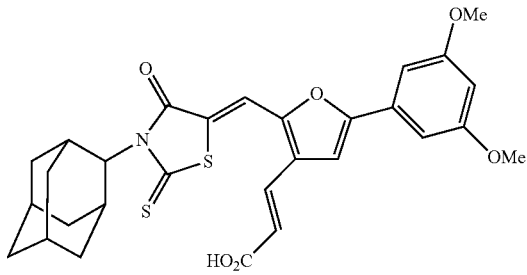 [SMILES: COc1cc(OC)cc(-c2cc(/C=C/C(=O)O)c(/C=C3\SC(=S)N(C4C5CC6CC(C5)CC4C6)C3=O)o2)c1]

¹H-NMR (300 MHz, CDCl₃): 12.52 (s, 1H), 7.75 (s, 1H), 7.66 (d, J=15.6, 1H), 7.61 (s, 1H), 6.88 (t, J=1.8, 2H), 6.53 (s, 1H), 6.43 (d, J=15.6, 1H), 4.98 (s, 1H), 3.80 (s, 6H), 2.99 (s, 1H), 2.45 (s, 2H), 2.38 (s, 1H), 1.87-1.86 (m, 6H), 1.74 (s, 3H), 1.65 (d, J=12.6, 3H). HRMS (ESI): 552.1525 (M+H).

3-(2-((Z)-(3-(bicyclo[2.2.1]heptan-2-yl)-4-oxo-2-thioxothiazolidin-5-ylidene)methyl)-5-(3',5'-dimethoxy-phenyl)furan-3-yl)propanoic acid

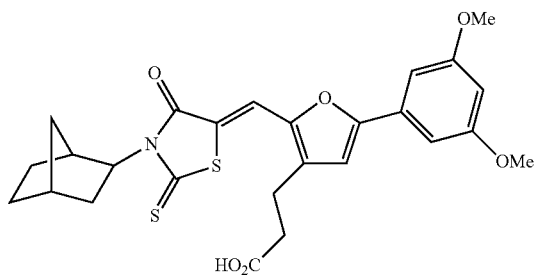 [SMILES: COc1cc(OC)cc(-c2cc(CCC(=O)O)c(/C=C3\SC(=S)N(C4CC5CCC4C5)C3=O)o2)c1]

¹H-NMR (300 MHz, CDCl₃): 12.15 (s, 1H), 7.48 (s, 1H), 7.32 (s, 1H), 6.91 (d, J=2.1, 2H), 6.54 (s, 1H), 5.00 (s, 1H), 3.80 (s, 6H), 2.53 (s, 2H), 2.59 (d, J=7.5, 2H), 2.44 (s, 3H), 1.89 (s, 6H), 1.74 (s, 2H), 1.64 (d, J=11.1, 2H).

5-(2-((Z)-(3-(bicyclo[2.2.1]heptan-2-yl)-4-oxo-2-thioxothiazolidin-5-ylidene)methyl)-5-(4'-chlorophenyl)-furan-3-yl)pentanoic acid

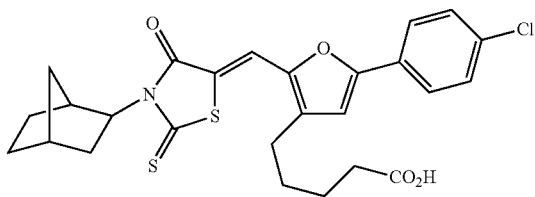 [SMILES: O=C(O)CCCCc1cc(-c2ccc(Cl)cc2)oc1/C=C1\SC(=S)N(C2CC3CCC2C3)C1=O]

¹H NMR (300 MHz, CDCl₃): 7.67 (d, J=8.4, 2H), 7.43 (d, J=8.4, 2H), 7.35 (s, 1H), 6.71 (s, 1H), 4.98 (m, 1H), 2.64 (t, J=15, 2H), 2.45 (m, 6H), 2.02 (m, 8H), 1.65 (m, 6H). HRMS (ESI): (M+H).

This type of compound was prepared according to the synthetic route below.

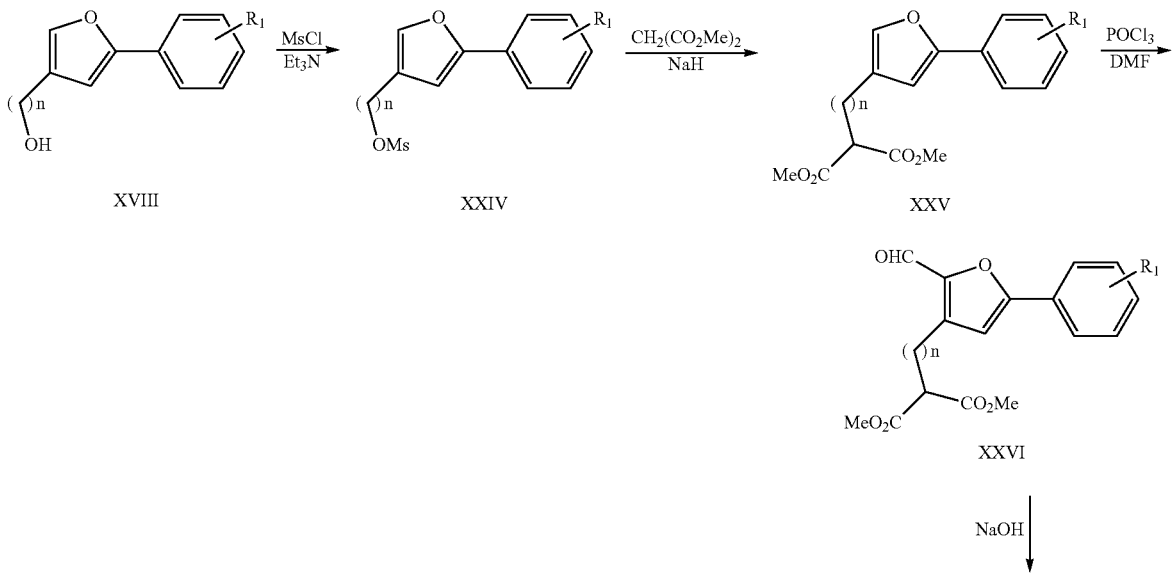

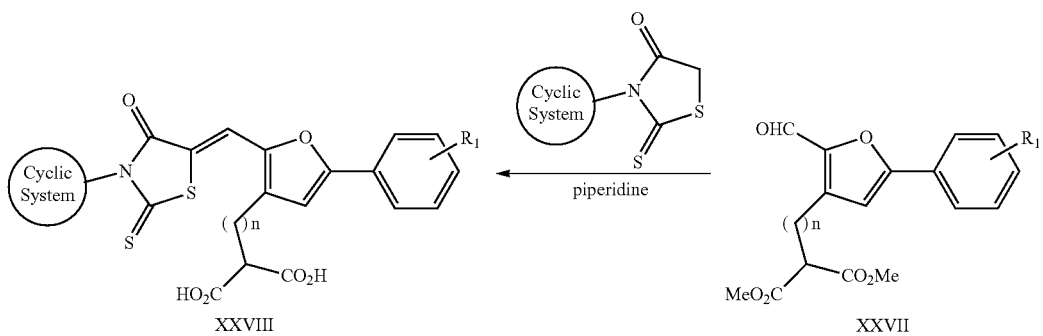

General Procedure of Mesylation Reaction

To a solution of the alcohol XVIII (10.0 mmol) made above in dry $CH_2Cl_2$ (50 mL) was added $Et_3N$ (5.05 g, 50.0 mmol) and methanesulfonyl chloride (1.37 g, 12.0 mmol) at 0° C., and the mixture was then stirred until the starting material disappeared. The reaction was quenched by addition of water, and then washed with saturated $NaHCO_3$, dried with $MgSO_4$. The solvent was removed under vacuum, and the residue was purified by a flash chromatography (PE/EA) on silica gel to give the corresponding mesylate products XXIV.

General Procedure of Malonation Reaction

To a solution of sodium dimethyl malonate in THF, prepared from 1.45 g of dimethyl malonate and 0.44 g of sodium hydride (60% in mineral oil) in 250 mL of anhydrous THF, were added mesylate compound XVIV (10.0 mmol) and NaI (15.0 mmol). The mixture was heated to reflux for 4 h and 60 mL of $H_2O$. The mixture was extracted with ethyl acetate (2×100 mL). The combined organic phase was first washed with brine, and then dried over anhydrous $Na_2SO_4$. After removing the solvent, the residue was purified by a flash chromatography (PE/EA) on silica gel to give the corresponding products XXV.

General Procedure of Formylation Reaction

To a solution of diester compound XXV (10.0 mmol) in N,N-dimethyl formamide (50 mL) was added a solution made by mixing of N,N-dimethylformamide (20 mL) and phosphorus oxychloride (1.53 g, 10.0 mmol) at 0° C. under nitrogen, and the formed reaction mixture was allowed to warm to room temperature, and then stirred for 30 min before the mixture was heated at 80° C. for 2 h. After the reaction mixture was cooled to 0° C., saturated $Na_2CO_3$ solution was added slowly and pH 6 was set. The mixture was extracted with diethyl ether twice, the organic layer was washed with saturated $NaHCO_3$, dried with $MgSO_4$, the solvent was removed under vacuum, and the residue was purified by a flash chromatography (PE/EA) on silica gel to give the corresponding aldehyde products XXVI.

General Procedure of Hydrolysis of Diester

A solution of diester aldehyde compound XXVI (10.0 mmol) in ethanol (50 mL) was added 100 mL of 1 N NaOH solution, and the mixture was stirred at room temperature until the starting material was fully consumed. Removing the ethanol and the residue was diluted by addition of water. The aqueous phased was extracted with EA twice, dried with $MgSO_4$. After removal of the solvent, the residue was purified by recrystallion from diethyl ether/PE to afford the corresponding products XXVII.

General Procedure of Condensation Reaction

To a solution of 3-N-cycloalkyl-2-thioxothiazolidin-4-one I (0.5 mmol) and aldehyde compound XXVII (0.5 mmol) in ethanol (20 mL) was added anhydrous piperidine (0.05 mmol) at room temperature, and the mixture was stirred for 16 h. Removing ethanol, and the residue was recrystallization from ethyl acetate-hexane or a flash chromatography ($CH_2Cl_2$) on silica gel to give the corresponding product XXVIII as illustrated below.

2,2'-((3-(2-((Z)-(3-(bicyclo[2.2.1]heptan-2-yl)-4-oxo-2-thioxothiazolidin-5-ylidene)methyl)-5-(3',5'-dimeth-oxyphenyl)furan-3-yl)propyl)azanediyl)diacetic acid

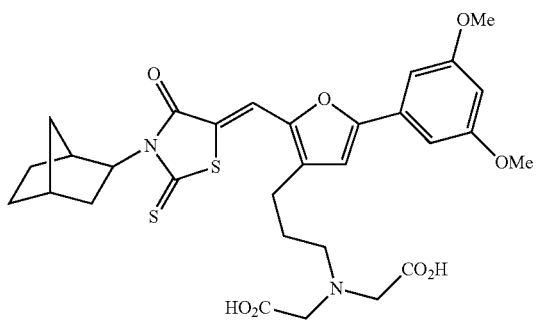 [SMILES: COc1cc(OC)cc(-c2cc(CCCN(CC(=O)O)CC(=O)O)c(/C=C3\SC(=S)N(C4CC5CCC4C5)C3=O)o2)c1]

$^1$H-NMR (300 MHz, $CDCl_3$): 7.51 (s, 1H), 7.37 (s, 1H), 6.98 (d, J=2.1, 2H), 6.59 (d, J=2.1, 1H), 4.86 (t, J=6.3, 1H), 3.83 (s, 6H), 2.7~2.72 (m, 5H), 2.6~2.35 (m, 2H), 1.73-1.70 (m, 2H), 1.5~1.53 (m, 2H). HRMS (ESI): 615.1808 (M+H).

2-(3-(2-((Z)-(3-(bicyclo[2.2.1]heptan-2-yl)-4-oxo-2-thioxothiazolidin-5-ylidene)methyl)-5-(3',5'-dimethoxy-phenyl)furan-3-yl)propyl)malonic acid

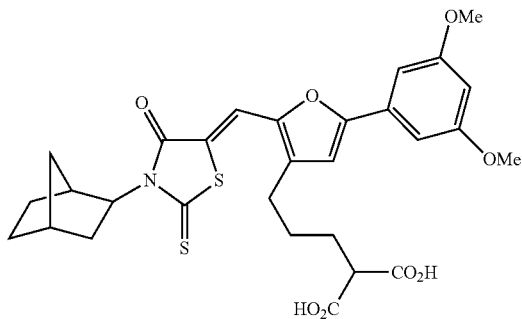 [SMILES: COc1cc(OC)cc(-c2cc(CCCC(C(=O)O)C(=O)O)c(/C=C3\SC(=S)N(C4CC5CCC4C5)C3=O)o2)c1]

¹H-NMR (300 MHz, DMSO-d6): 12.72 (s, 2H), 7.50 (s, 1H), 7.34 (s, 1H), 6.96 (s, 2H), 6.56 (s, 1H), 4.87 (t, J=2.1, 1H), 3.78 (s, 6H), 2.66 (d, J=2.1, 2H), 2.36 (m, 2H), 1.71 (m, 3H), 1.69 (m, 4H), 1.23 (m, 3H). HRMS (ESI): 585.1491 (M+H).

2-(3-(2-((Z)-(3-(adamantan-2-yl)-4-oxo-2-thioxothiazolidin-5-ylidene)methyl)-5-(3',5'-dimethoxy-phenyl)-furan-3-yl)propyl)malonic acid

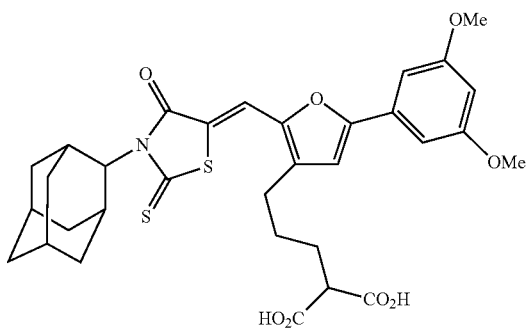 [SMILES: COc1cc(OC)cc(-c2cc(CCCC(C(=O)O)C(=O)O)c(/C=C3\SC(=S)N(C4C5CC6CC(C5)CC4C6)C3=O)o2)c1]

¹H-NMR (300 MHz, DMSO-d6): 7.51 (s, 1H), 7.32 (s, 1H), 6.96 (d, J=2.1, 2H), 6.55 (s, 1H), 5.03 (s, 1H), 3.78 (s, 6H), 3.76 (s, 2H), 2.65 (t, J=2.1, 3H), 2.47 (s, 5H), 1.86 (m, 6H), 1.74 (m, 7H), 1.53 (m, 3H).

2-(3-(2-((Z)-(3-(adamantan-2-yl)-4-oxo-2-thioxothiazolidin-5-ylidene)methyl)-5-(3'-hydroxy-5'-methoxy-phenyl)furan-3-yl)propyl)malonic acid

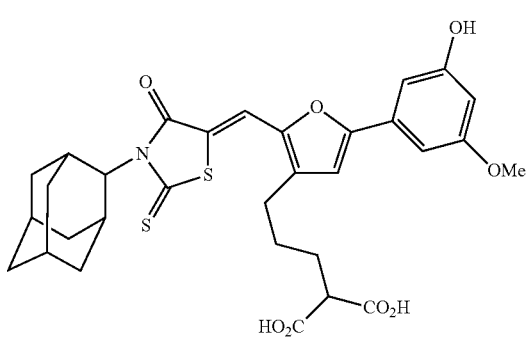 [SMILES: COc1cc(O)cc(-c2cc(CCCC(C(=O)O)C(=O)O)c(/C=C3\SC(=S)N(C4C5CC6CC(C5)CC4C6)C3=O)o2)c1]

¹H-NMR (300 MHz, DMSO-d6): 9.9 (s, 1H), 7.48 (s, 1H), 7.23 (s, 1H), 6.85 (m, 3H), 6.39 (m, 1H), 5.05 (s 1H), 3.77 (s, 3H), 3.20 (m, 1H), 2.42 (m, 4H), 1.97 (s, 7H), 1.74 (m, 8H). HRMS (ESI): 611.8031 (M).

2-(3-(2-((Z)-(3-(bicyclo[2.2.1]heptan-2-yl)-4-oxo-2-thioxothiazolidin-5-ylidene)methyl)-5-(3'-hydroxy-5'-methoxyphenyl)furan-3-yl)propyl)malonic acid

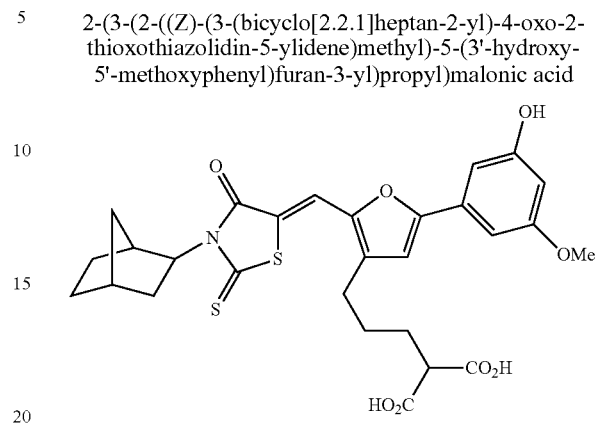

¹H-NMR (300 MHz, DMSO-d6): 9.9 (s, 1H), 7.48 (s, 1H), 7.23 (s, 1H), 6.85 (m, 3H), 6.39 (m, 1H), 4.89 (t, J=14.7, 1H), 3.77 (s, 3H), 3.23 (m, 1H), 2.69 (m, 2H), 2.37 (m, 4H), 1.76 (m, 3H).

2-(5-(2-((Z)-(3-(bicyclo[2.2.1]heptan-2-yl)-4-oxo-2-thioxothiazolidin-5-ylidene)methyl)-5-(3',5'-dimethoxy-phenyl)furan-3-yl)pentyl)malonic acid

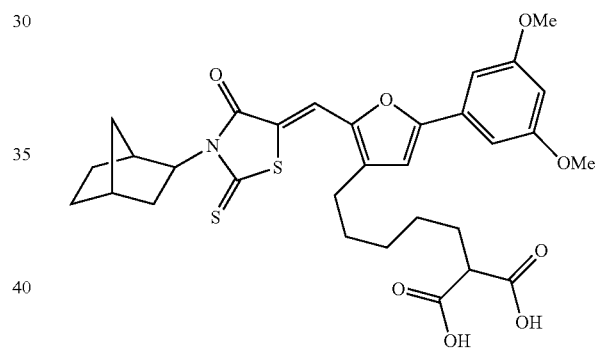

¹H-NMR (300 MHz, DMSO-d6): 12.64 (m, 2H), 7.46 (s, 1H), 7.35 (s, 1H), 6.96 (d, J=1.2, 2H), 6.56 (s, 1H), 4.84 (m, 1H), 3.80 (s, 6H), 3.16 (s, 1H), 2.61 (m, 2H), 2.34 (m, 3H), 1.66 (m, 3H), 1.54 (m, 4H), 1.25 (m, 8H). HRMS (ESI): 613.1804 (M).

2-(5-(2-((Z)-(3-(adamantan-2-yl)-4-oxo-2-thioxothiazolidin-5-ylidene)methyl)-5-(3',5'-dimethoxy-phenyl)-furan-3-yl)pentyl)malonic acid

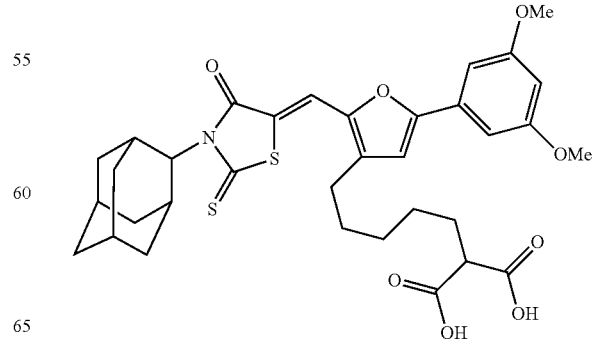

1H-NMR (300 MHz, DMSO-d6): 12.72 (m, 2H), 7.49 (s, 1H), 7.35 (s, 1H), 6.96 (d, J=2.4, 2H), 6.56 (d, J=2.1, 1H), 5.03 (s, 1H), 3.80 (s, 6H), 3.14 (d, J=7.2, 1H), 2.62 (m, 2H), 2.41 (m, 3H), 1.86 (m, 6H), 1.66 (m, 8H), 1.28 (m, 5H).

Synthesis of Type-8: Modification of Side Chain in C-Ring (Furan) with Amino Acid Moiety

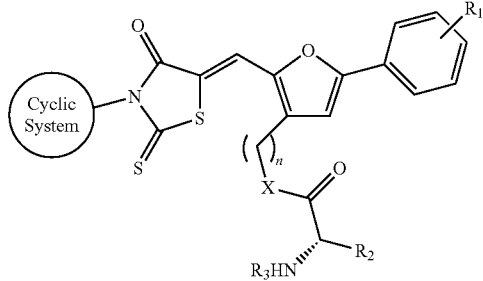

This type of compound was prepared according to the synthetic route below.

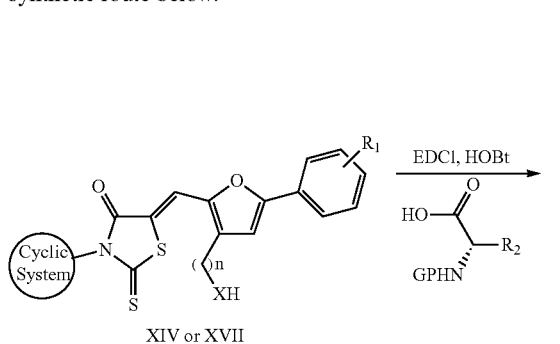

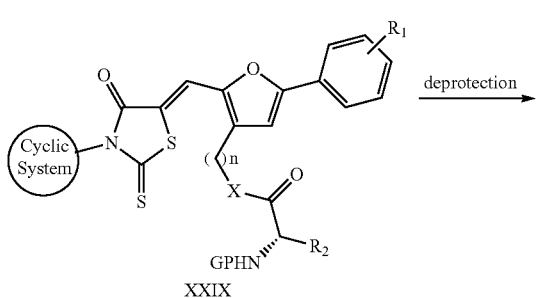

General Procedure for the Synthesis of XXIX

To a solution of (Z)-3-cycloalkyl-5-((5-aryl-3-(n-hydroxy (n-alkyl))-(furan-2-yl)methylene)-2-thioxo-thiazolidin-4-one XIV (10.0 mmol) or (Z)-3-cycloalkyl-5-((5-aryl-3-(n-amino(n-alkyl))-(furan-2-yl)methylene)-2-thioxothiazolidin-4-one XVII (10.0 mmol) in dry CH$_2$Cl$_2$ (80 mL) was added HOBt (1.62 g, 12.0 mmol), Boc- or Fmoc-amino acid (12.0 mmol) and EDCI (2.87 g, 15.0 mmol) at 0° C., and the formed mixture was stirred at room temperature for 24 h. The reaction was worked up addition of water, and the formed organic phase was washed sequentially with 5% diluted HCl, brine, saturated NaHCO$_3$ and brine, and then dried over anhydrous Na$_2$SO$_4$. After removal of the solvent, the residue was purified by a flash chromatography (PE/EA) to give the corresponding products XXIX.

(2S)-3-(2-((Z)-(3-(bicyclo[2.2.1]heptan-2-yl)-4-oxo-2-thioxothiazolidin-5-ylidene)methyl)-5-(3',5'-dimethoxy-phenyl)furan-3-yl)propyl 4-amino-2-((tert-butoxycarbonyl)amino)-4-oxobutanoate

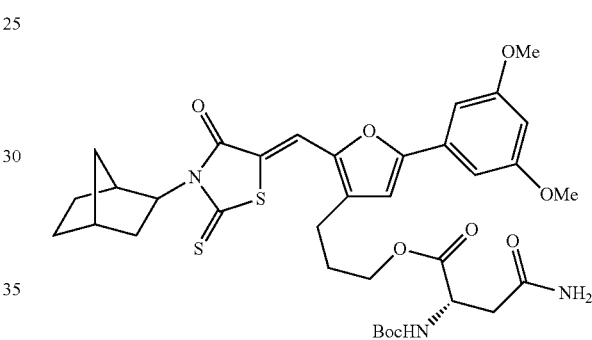

1H-NMR (300 MHz, CDCl$_3$): 7.61 (d, J=5.1, 1H), 6.92 (d, J=2.1, 2H), 6.74 (s, 1H), 6.49 (t, J=2.1, 1H), 6.25 (t, J=14.1, 1H), 5.93 (s, 1H), 5.81 (d, J=8.1, 1H), 4.97 (t, J=6.0, 1H), 4.60-4.54 (m, 1H), 4.40-4.28 (m, 1H), 4.23-4.16 (m, 1H), 3.89 (s, 6H), 3.19-3.10 (m, 1H), 2.85-2.78 (m, 3H), 2.54 (s, 1H), 2.44 (s, 1H), 2.39-2.30 (m, 2H), 1.20-1.96 (m, 2H), 1.79 (t, J=9.3, 1H), 1.68-1.60 (m, 5H), 1.40-1.36 (m, 3H).

(2S)-3-(2-((Z)-(3-(bicyclo[2.2.1]heptan-2-yl)-4-oxo-2-thioxothiazolidin-5-ylidene)methyl)-5-(3',5'-dimethoxy-phenyl)furan-3-yl)propyl 2,5-bis((tert-butoxycarbonyl)amino)pentanoate

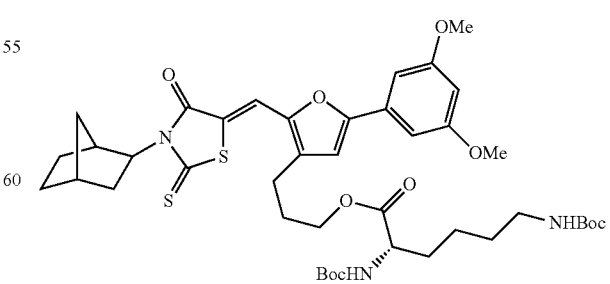

1H-NMR (300 MHz, CDCl$_3$): 7.36 (s, 1H), 6.89 (d, J=2.4, 2H), 6.72 (s, 1H), 6.46 (d, J=2.1, 1H), 5.30 (t, J=6.0, 1H), 4.94

(t, J=6.6, 1H), 4.60 (s, 1H), 4.24 (t, J=9.0, 1H), 4.15-4.12 (m, 2H), 3.86 (s, 6H), 3.09 (t, J=6.0, 2H), 2.68 (t, J=7.2, 2H), 2.52 (s, 1H), 2.43 (s, 1H), 2.28 (d, J=9.6, 2H), 1.96 (t, J=6.9, 2H), 1.74-1.71 (m, 4H), 1.41 (s, 18H), 1.28-1.24 (m, 4H), 1.05 (m, 2H). HRMS (ESI): 828.3640 (M+H).

(2R)-1-benzyl 4-(3-(2-((Z)-(3-(bicyclo[2.2.1]heptan-2-yl)-4-oxo-2-thioxothiazolidin-5-ylidene)methyl)-5-(3',5'-dimethoxyphenyl)furan-3-yl)propyl) 2-((tert-butoxycarbonyl)amino)succinate

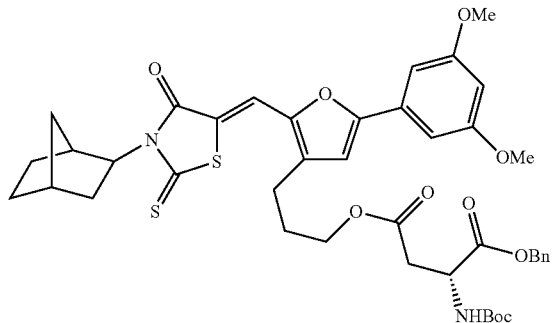 [SMILES: COc1cc(OC)cc(-c2cc(CCCOC(=O)C[C@@H](NC(=O)OC(C)(C)C)C(=O)OCc3ccccc3)c(/C=C3\SC(=S)N(C4CC5CCC4C5)C3=O)o2)c1]

$^1$H-NMR (300 MHz, CDCl$_3$): 7.37 (s, 1H), 7.32 (s, 5H), 6.92 (d, J=2.1, 2H), 6.72 (s, 1H), 6.50 (t, J=2.1, 1H), 5.57 (d, J=8.7, 1H), 5.25-5.13 (m, 2H), 4.99-4.94 (m, 1H), 4.67 (t, J=4.0, 1H), 4.07 (t, J=6.3, 2H), 3.09 (s, 1H), 3.04 (d, J=2.1, 1H), 2.93-2.85 (m, 1H), 2.65 (t, J=7.5, 2H), 2.54 (s, 1H), 2.45 (s, 1H), 2.33-2.23 (m, 3H), 1.91 (t, J=7.2, 2H), 1.78 (d, J=1.8, 1H), 1.60 (d, J=6.0, 2H), 1.43 (s, 9H), 1.31-0.83 (m, 2H).

(2S)-3-(2-((Z)-(3-(bicyclo[2.2.1]heptan-2-yl)-4-oxo-2-thioxothiazolidin-5-ylidene)methyl)-5-(3',5'-dimethoxy-phenyl)furan-3-yl)propyl 2-(((((9H-fluoren-9-yl)methoxy)carbonyl)amino)-4-methylpentanoate

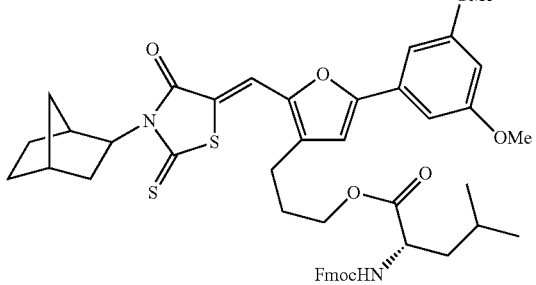

$^1$H-NMR (300 MHz, CDCl$_3$): 7.68 (t, J=7.2, 2H), 7.55 (t, J=6.3, 2H), 7.36-7.17 (m, 5H), 6.92 (d, J=1.8, 2H), 6.70 (s, 1H), 6.50 (s, 1H), 6.03 (d, J=0.6, 1H), 5.30 (s, 6H), 4.98-4.92 (m, 1H), 4.11-4.51 (m, 7H), 3.88 (s, 6H), 3.49 (s, 1H), 2.60 (t, J=6.3, 2H), 2.51 (d, J=1.8, 1H), 2.49 (s, 1H), 2.24 (d, J=3.9, 2H), 1.82-1.61 (m, 4H), 1.29-1.25 (m, 5H).

(2S)-3-(2-((Z)-(3-(bicyclo[2.2.1]heptan-2-yl)-4-oxo-2-thioxothiazolidin-5-ylidene)methyl)-5-(3',5'-dimethoxy-phenyl)furan-3-yl)propyl 2-((tert-butoxycarbonyl)amino)-3

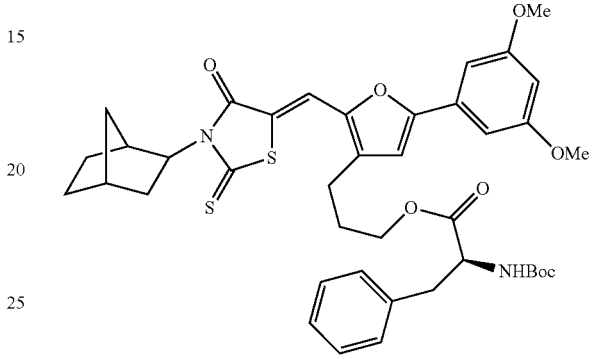

$^1$H-NMR (300 MHz, CDCl$_3$): 7.37 (s, 1H), 7.30-7.17 (m, 5H), 6.91 (d, J=2.1, 2H), 6.70 (s, 1H), 6.49 (t, J=2.1, 1H), 5.20-5.17 (m, 1H), 4.98-4.95 (m, 1H), 4.59-4.56 (m, 1H), 4.15-4.12 (m, 1H), 3.88 (s, 6H), 3.84-3.81 (m, 1H), 3.08 (t, J=5.1, 1H), 2.36 (s, 1H), 2.61-2.54 (3H), 2.32 (s, 1H), 2.19-2.16 (m, 2H), 1.93-1.89 (m, 2H), 1.80-1.78 (m, 2H), 2.34-2.31 (m, 2H), 1.40 (s, 9H), 1.28-1.25 (m, 3H). HRMS (ESI): 747.2603 (M+H).

(2S)-3-(2-((Z)-(3-(bicyclo[2.2.1]heptan-2-yl)-4-oxo-2-thioxothiazolidin-5-ylidene)methyl)-5-(3',5'-dimethoxyphenyl)furan-3-yl)propyl 3-(4-(tert-butoxy)phenyl)-2-((tert-butoxycarbonyl)amino) propanoate

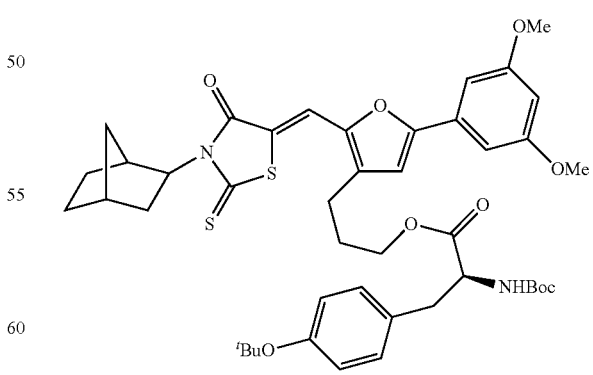

$^1$H-NMR (300 MHz, CDCl$_3$): 7.38 (s, 1H), 7.07 (d, J=8.4, 3H), 6.94-6.92 (m, 4H), 6.72 (s, 1H), 6.49 (m, 1H), 5.18 (d, J=8.1, 1H), 4.98-4.96 (m, 1H), 4.56-4.53 (m, 1H), 4.15-4.12 (m, 2H), 4.11 (s, 6H), 3.08-3.04 (m, 2H), 2.63 (t, J=7.5, 2H), 2.54 (s, 1H), 2.33 (s, 1H), 2.06-2.06 (m, 2H), 1.95-1.52 (m, 2H), 1.83-1.80 (m, 3H), 1.45 (s, 9H), 1.26-1.21 (m, 11H).

(2S)-3-(2-((Z)-(3-(bicyclo[2.2.1]heptan-2-yl)-4-oxo-2-thioxothiazolidin-5-ylidene)methyl)-5-(3',5'-dimethoxy-phenyl)furan-3-yl)propyl 2-((((9H-fluoren-9-yl)methoxy)carbonyl)amino)-3-(1-trityl-1H-imidazol-4-yl)-propanoate

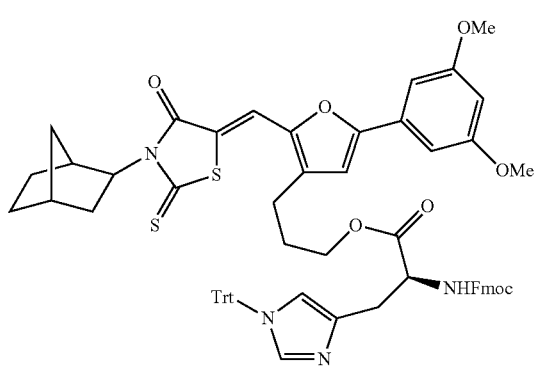

¹H-NMR (300 MHz, CDCl₃): 7.73 (d, J=7.5, 2H), 7.59 (t, J=6.6, 2H), 7.41-7.24 (m, 16H), 7.11-7.08 (m, 7H), 6.89 (d, J=2.1, 2H), 6.68-6.47 (4H), 4.94-4.92 (m, 1H), 4.66-4.30 (m, 5H), 3.87 (s, 6H), 3.10 (d, J=2.1, 2H), 2.62-2.59 (m, 2H), 2.59 (s, 1H), 2.57 (s, 1H), 2.37-2.21 (m, 2H), 1.96-1.70 (m, 3H), 1.57-1.50 (m, 4H).

(2S)-1-((9H-fluoren-9-yl)methyl) 2-(3-(2-((Z)-(3-(bicyclo[2.2.1]heptan-2-yl)-4-oxo-2-thioxothiazolidin-5-ylidene)methyl)-5-(3,5-dimethoxyphenyl)furan-3-yl)propyl)pyrrolidine-1,2-dicarboxylate

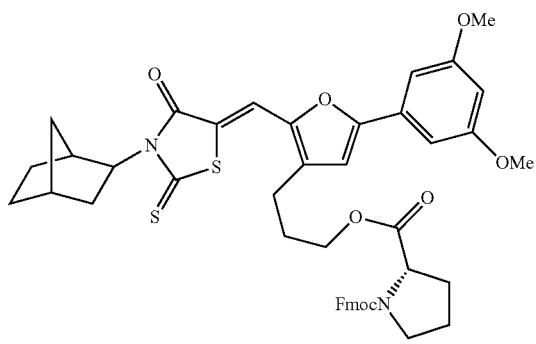

¹H-NMR (300 MHz, CDCl₃): 7.73 (d, J=7.5, 2H), 7.59 (t, J=6.6, 2H), 7.41-7.24 (m, 16H), 7.11-7.08 (m, 7H), 6.89 (d, J=2.1, 2H), 6.68-6.47 (4H), 4.94-4.92 (m, 1H), 4.66-4.30 (m, 5H), 3.87 (s, 6H), 3.10 (d, J=2.1, 2H), 2.62-2.59 (m, 2H), 2.59 (s, 1H), 2.57 (s, 1H), 2.37-2.21 (m, 2H), 1.96-1.70 (m, 3H), 1.57-1.50 (m, 4H).

(2S)-3-(2-((Z)-(3-(bicyclo[2.2.1]heptan-2-yl)-4-oxo-2-thioxothiazolidin-5-ylidene)methyl)-5-(3',5'-dimethoxy-phenyl)furan-3-yl)propyl 2-((tert-butoxycarbonyl)amino)-2-phenylacetate

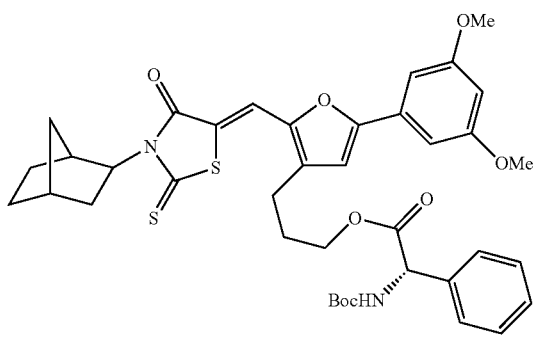 [SMILES: COc1cc(OC)cc(-c2cc(CCCOC(=O)[C@@H](NC(=O)OC(C)(C)C)c3ccccc3)c(/C=C3\SC(=S)N(C4CC5CCC4C5)C3=O)o2)c1]

¹H-NMR (300 MHz, CDCl₃): 7.31-7.43 (m, 6H), 6.88 (d, J=2.1, 2H), 6.56 (s, 1H), 6.49 (t, 1H), 5.69 (s, 1H), 5.35 (d, J=7.5, 1H), 4.97 (dd, J=6.0, 2.1, 1H), 4.11-4.23 (m, 3H), 3.88 (s, 6H), 3.84 (s, 1H), 2.47-2.55 (m, 4H), 2.40 (d, J=8.4, 2H), 1.89 (t, J=6.6, 2H), 1.79 (t, J=7.8, 2H), 1.65-1.58 (m, 6H), 1.23-1.32 (m, 5H).

(2S)-3-(2-((Z)-(3-(bicyclo[2.2.1]heptan-2-yl)-4-oxo-2-thioxothiazolidin-5-ylidene)methyl)-5-(4'-fluorophenyl)furan-3-yl)propyl 4-amino-2-((tert-butoxycarbonyl)amino)-4-oxobutanoate

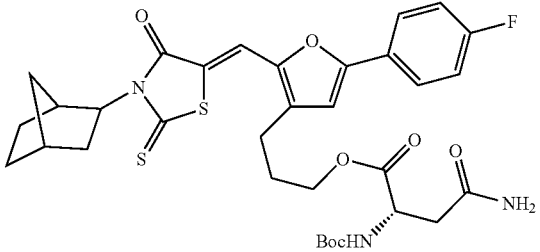 [SMILES: CC(C)(C)OC(=O)N[C@@H](CC(N)=O)C(=O)OCCCc1cc(-c2ccc(F)cc2)oc1/C=C1\SC(=S)N(C2CC3CCC2C3)C1=O]

¹H-NMR (300 MHz, DMSO-d6): 7.84 (dd, J=8.1, 5.4, 1H), 7.50 (s, 1H), 7.44-7.35 (m, 3H), 7.26 (s, 1H), 7.04 (d, J=8.1, 1H), 6.94 (m, 1H), 4.85 (t, J=6.6, 1H), 4.36-4.29 (m, 2H), 4.07-3.97 (m, 2H), 2.72 (t, J=7.5, 2H), 2.38 (m, 1H), 2.32-2.09 (m, 4H), 1.92-1.79 (m, 3H), 1.73-1.62 (m, 2H), 1.56-1.49 (m, 4H), 1.30 (s, 9H).

(2S)-3-(2-((Z)-(3-(bicyclo[2.2.1]heptan-2-yl)-4-oxo-2-thioxothiazolidin-5-ylidene)methyl)-5-(4'-chlorophenyl)furan-3-yl)propyl 4-amino-2-((tert-butoxycarbonyl)amino)-4-oxobutanoate

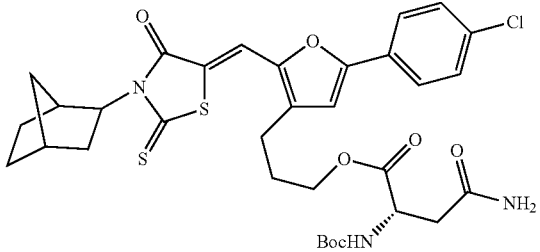

$^1$H-NMR (300 MHz, DMSO-d6): 7.79 (d, J=9.0, 2H), 7.62 (d, J=9.0, 1H), 7.51 (s, 1H), 7.34 (d, J=9.0, 1H), 7.03 (d, J=9.0, 1H), 6.94 (S, 1H), 4.85 (d, J=6.6, 1H), 4.38-4.22 (m, 1H), 4.12-3.94 (m, 2H), 2.74-2.60 (m, 2H), 2.56 (t, J=6.6, 2H), 2.38-2.15 (m, 3H), 1.87 (t, J=6.3, 2H), 1.73-1.62 (m, 1H), 1.56-1.50 (m, 2H), 1.30 (s, 9H), 1.30-1.23 (m, 3H).

(2S)-1-(3-(2-((Z)-(3-(bicyclo[2.2.1]heptan-2-yl)-4-oxo-2-thioxothiazolidin-5-ylidene)methyl)-5-(3'-hydroxy-5'-methoxyphenyl)furan-3-yl)propyl) 4-tert-butyl 2-((tert-butoxycarbonyl)amino)-succinate

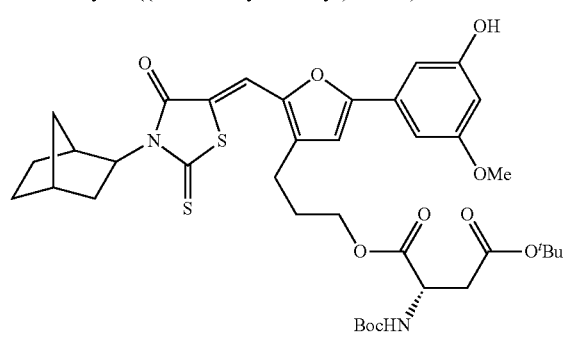

Red solid 50 mg (38%). $^1$H NMR (300 MHz, CDCl$_3$): 7.42 (s, 1H), 7.22 (s, 1H), 7.02 (s, 1H), 6.72 (s, 1H), 6.66 (t, J=1.8, 1H), 5.60 (d, J=8.7, 1H), 4.98-4.96 (m, 1H), 4.82-3.79 (m, 1H), 3.89 (s, 3H), 3.69 (t, J=6 Hz, 1H), 3.11-3.08 (m, 1H), 2.92-2.90 (m, 1H), 2.86-2.84 (m, 2H), 2.55 (s, 1H), 2.46 (s, 1H), 2.31-2.29 (m, 2H), 1.91-1.89 (m, 3H), 1.48 (s, 18H), 1.29-1.26 (m, 4H).

(2S)-5-(2-((Z)-(3-(bicyclo[2.2.1]heptan-2-yl)-4-oxo-2-thioxothiazolidin-5-ylidene)methyl)-5-(3',5'-dimethoxy-phenyl)furan-3-yl)pentyl 4-amino-2-((tert-butoxycarbonyl)amino)-4-oxobutanoate

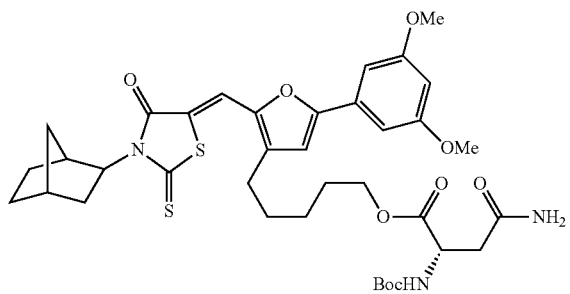 [SMILES: COc1cc(OC)cc(-c2cc(CCCCCOC(=O)[C@H](CC(N)=O)NC(=O)OC(C)(C)C)c(/C=C3\SC(=S)N(C4CC5CCC4C5)C3=O)o2)c1]

$^1$H-NMR (300 MHz, CDCl$_3$): 7.41 (s, 1H), 6.93 (d, J=2.1, 2H), 6.75 (s, 1H), 6.50 (t, J=2.1, 1H), 5.71 (s, 2H), 5.53 (s, 1H), 5.01-4.99 (m, 1H), 4.53-4.52 (m, 1H), 4.20-4.18 (m, 1H), 3.90 (s, 6H), 3.83 (d, J=3.9, 1H), 2.36 (s, 1H), 2.30-2.28 (m, 2H), 1.83-1.57 (m, 8H), 1.49-1.40 (m, 10H), 1.26-1.21 (m, 3H).

tert-butyl((2S)-4-amino-1-((3-(2-((Z)-(3-(bicyclo[2.2.1]heptan-2-yl)-4-oxo-2-thioxothiazolidin-5-ylidene)-methyl)-5-(3,5-dimethoxyphenyl)furan-3-yl)propyl)amino)-1,4-dioxobutan-2-yl)-carbamate

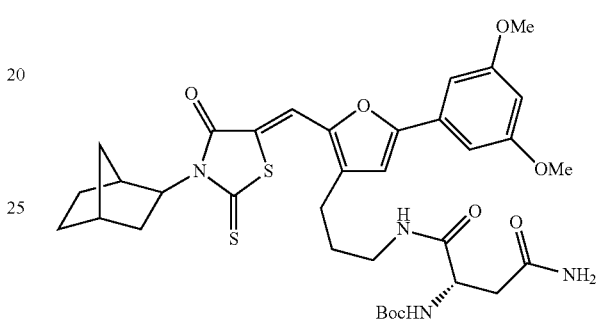

Red-brown solid in 46% yield. $^1$H-NMR (300 MHz, CDCl$_3$): 7.58 (d, J=2.7, 1H), 6.94 (m, 3H), 6.72 (s, 1H), 6.46 (m, 2H), 6.11 (m, 1H), 5.89 (d, J=1.5, 1H), 4.95 (m, 1H), 4.48 (m, 1H), 3.86 (s, 6H), 3.50 (m, 1H), 3.24 (m, 1H), 3.13 (m, 1H), 2.63 (m, 4H), 2.57 (s, 1H), 2.41 (s, 1H), 2.25 (m, 3H), 1.76 (m, 2H), 1.43 (s, 9H), 1.25 (m, 5H).

tert-butyl ((2S)-1-((3-(2-((Z)-(3-(bicyclo[2.2.1]heptan-2-yl)-4-oxo-2-thioxothiazolidin-5-ylidene)methyl)-5-(3',5'-dimethoxyphenyl)furan-3-yl)propyl)amino)-1-oxo-3-phenylpropan-2-yl)-carbamate

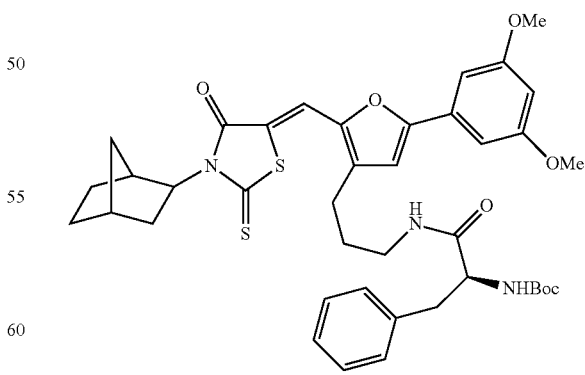

$^1$H-NMR (300 MHz, CDCl$_3$): 7.33-7.23 (m, 6H), 6.92 (d, J=2.1, 2H), 6.71 (s, 2H), 6.50 (t, J=2.4, 1H), 5.95 (s, 1H), 5.25 (s, 1H), 4.96 (dd, J=6.0, 2.3, 1H), 4.38-4.28 (m, 1H), 3.90 (s, 6H), 3.79 (t, J=6.3, 2H), 3.28-3.19 (m, 2H), 3.08 (d, J=6.9,

2H), 2.58-2.48 (m, 4H), 2.36-2.30 (m, 2H), 1.81-1.72 (m, 7H), 1.68-1.59 (d, J=5.1, 4H), 1.40 (s, 9H).

(3S)-tert-butyl 4-((3-(2-((Z)-(3-(bicyclo[2.2.1]heptan-2-yl)-4-oxo-2-thioxothiazolidin-5-ylidene)methyl)-5-(3',5'-dimethoxyphenyl)furan-3-yl)propyl)amino)-3-((tert-butoxycarbonyl)-amino)-4-oxobutanoate

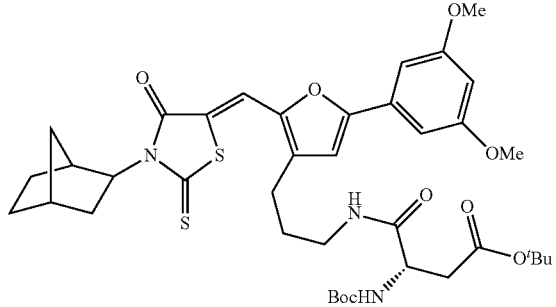 [SMILES: COc1cc(OC)cc(-c2cc(CCCNC(=O)[C@H](CC(=O)OC(C)(C)C)NC(=O)OC(C)(C)C)c(/C=C3\SC(=S)N(C4CC5CCC4C5)C3=O)o2)c1]

¹H-NMR (300 MHz, CDCl₃): 7.38 (s, 1H), 6.92 (d, J=3.9, 2H), 6.76 (s, 2H), 6.71-6.69 (m, 1H), 6.70 (s, 1H), 6.49 (t, J=2.4, 1H), 5.79 (d, J=3.6, 1H), 4.97-4.95 (m, 1H), 4.45 (d, J=3.3, 1H), 3.89 (s, 6H), 3.80 (d, J=3.9, 3H), 3.24-3.42 (m, 3H), 2.62-2.67 (m, 3H), 2.60 (s, 1H), 2.46 (s, 1H), 2.35-2.33 (m, 5H), 1.85-1.75 (m, 4H), 1.45-1.43 (m, 7H), 1.40-1.38 (m, 18H), 1.26-1.28 (m, 7H).

(9H-fluoren-9-yl)methyl 425)-1-((3-(2-((Z)-(3-(bicyclo[2.2.1]heptan-2-yl)-4-oxo-2-thioxo-thiazolidin-5-ylidene)methyl)-5-(3',5'-dimethoxyphenyl)furan-3-yl)propyl)amino)-4-methyl-1-oxopentan-2-yl)carbamate ¹H-NMR (300 MHz, CDCl₃): 7.71 (d, J=4.5, 2H), 7.54 (d, J=4.5, 2H), 7.34 (t, J=1.8, 2H), 7.25 (s, 2H), 6.92 (d, J=1.5, 1H), 6.71 (s, 1H), 6.50 (t, J=1.2, 1H), 6.21 (s, 1H), 5.60 (s, 1H), 4.93 (s, 1H), 4.46 (d, J=3.3, 2H), 4.20-4.12 (m, 2H), 3.89 (s, 6H), 3.80 (d, J=6.9, 2H), 3.40 (s, 1H), 3.18 (s, 1H), 2.56 (t, J=1.5, 2H), 2.51 (s, 1H), 2.43 (s, 2H), 2.26-2.32 (m, 3H), 1.65-1.90 (m, 7H), 1.29-1.27 (m, 5H).

tert-butyl ((2S)-1-((3-(2-((Z)-(3-(bicyclo[2.2.1]heptan-2-yl)-4-oxo-2-thioxothiazolidin-5-ylidene)methyl)-5-(3',5'-dimethoxyphenyl)furan-3-yl)propyl)amino)-3-(4-(tert-butoxy)phenyl)-1-oxopropan-2-yl)carbamate

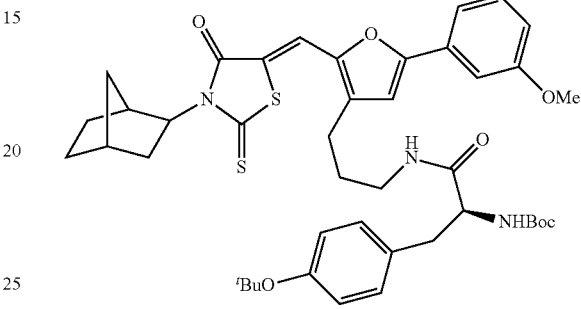

Red-brown solid in 51% yield. ¹H-NMR (300 MHz, CDCl₃): 7.50 (s, 1H), 7.10 (d, J=8.4, 2H), 6.91-6.88 (m, 4H), 6.70 (s, 1H), 6.47 (t, J=2.1, 1H), 5.91 (s, 1H), 5.20-5.18 (m, 1H), 4.96-4.94 (m, 1H), 4.23 (d, J=7.8, 1H), 3.85 (s, 6H), 3.80-3.78 (m, 2H), 3.24-3.22 (m, 2H), 3.00 (d, J=7.2, 2H), 2.52-2.50 (m, 3H), 2.44-2.42 (m, 4H), 1.73-1.70 (m, 2H), 1.38 (s, 9H), 1.28 (s, 9H), 0.85-0.81 (m, 5H).

(9H-fluoren-9-yl)methyl ((2S)-1-((3-(2-((Z)-(3-(bicyclo[2.2.1]heptan-2-yl)-4-oxo-2-thioxothiazolidin-5-ylidene)methyl)-5-(3',5'-dimethoxyphenyl)furan-3-yl)propyl)amino)-1-oxo-3-(1-trityl-1H-imidazol-4-yl)propan-2-yl)carbamate

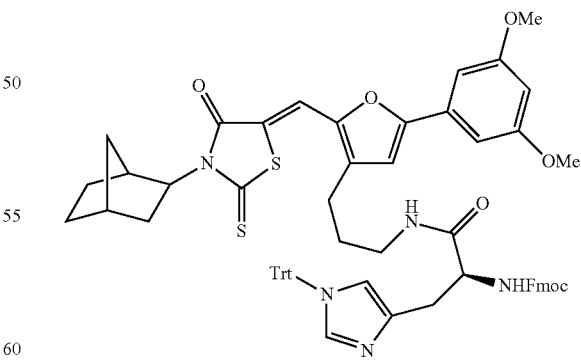

Red-brown solid in 46% yield. ¹H-NMR (300 MHz, CDCl₃): 7.71 (d, J=7.2, 2H), 7.56 (d, J=6.6, 2H), 7.29-7.28 (m, 11H), 7.06 (m, 6H), 6.87 (d, J=2.1, 2H), 6.67 (s, 3H), 6.46 (t, J=2.1, 1H), 4.91 (t, J=1.8, 1H), 4.47-4.45 (m, 1H), 4.34 (t, J=2.1, 2H), 4.19-4.18 (m, 1H), 3.85 (t, J=4.5, 6H), 3.46 (t, J=6.9, 3H), 3.26 (t, J=3.3, 2H), 3.06 (s, 2H), 2.54-2.52 (m, 3H), 2.38 (s, 1H), 2.25 (s, 2H), 1.77-1.75 (m, 9H), 1.24-1.21 (m, 8H).

tert-butyl ((1S)-2-((3-(2-((Z)-(3-(bicyclo[2.2.1]heptan-2-yl)-4-oxo-2-thioxothiazolidin-5-ylidene)methyl)-5-(3',5'-dimethoxyphenyl)furan-3-yl)propyl)amino)-2-oxo-1-phenylethyl)-carbamate

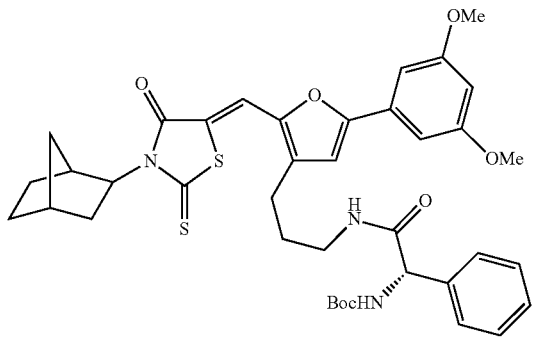 [SMILES: COc1cc(OC)cc(-c2cc(CCCNC(=O)[C@@H](NC(=O)OC(C)(C)C)c3ccccc3)c(/C=C3\SC(=S)N(C4CC5CCC4C5)C3=O)o2)c1]

Red-brown solid in 68% yield. ¹H-NMR (300 MHz, CDCl₃): 7.34 (dd, J=7.5, 2.1, 6H), 6.88 (d, J=2.1, 2H), 6.65 (s, 1H), 6.47 (s, 1H), 5.83-5.81 (m, 2H), 5.10-5.08 (m, 1H), 4.95 (t, J=7.2, 1H), 3.86 (s, 6H), 3.28 (d, J=6.3, 2H), 2.48-2.46 (m, 4H), 2.31 (d, J=1.8, 2H), 1.76 (t, J=6.6, 4H), 1.38-1.36 (m, 10H), 1.25-1.23 (m, 5H).

tert-butyl ((2S)-4-amino-1-((3-(2-((Z)-(3-(bicyclo[2.2.1]heptan-2-yl)-4-oxo-2-thioxothiazolidin-5-ylidene)-methyl)-5-(3'-hydroxy-5'-methoxyphenyl)furan-3-yl)propyl)amino)-1,4-dioxobutan-2-yl)carbamate

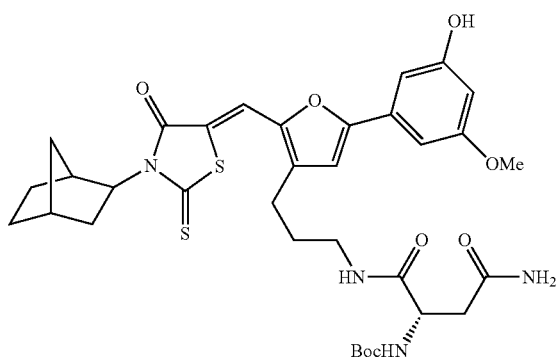 [SMILES: COc1cc(O)cc(-c2cc(CCCNC(=O)[C@H](CC(N)=O)NC(=O)OC(C)(C)C)c(/C=C3\SC(=S)N(C4CC5CCC4C5)C3=O)o2)c1]

¹H NMR (300 MHz, DMSO-d6): 9.93 (s, 1H), 7.86 (s, 1H), 7.50 (s, 1H), 7.26-7.24 (m, 2H), 6.86-6.84 (m, 3H), 6.40 (s, 1H), 4.88-4.86 (m, 1H), 4.17 (d, J=6.3, 1H), 3.77 (s, 3H), 3.82 (s, 6H), 3.10 (d, J=5.7, 2H), 2.65-2.64 (m, 2H), 2.23-2.37 (m, 5H), 1.69-1.67 (m, 3H), 1.54-1.52 (m, 2H), 1.35 (s, 9H), 1.22-1.20 (m, 4H). HRMS (ESI): 699.2493 (M+H).

tert-butyl ((2S)-1-((3-(2-((Z)-3-(bicyclo[2.2.1]heptan-2-yl)-4-oxo-2-thioxothiazolidin-5-ylidene)methyl)-5-(3'-hydroxy-5'-methoxyphenyl)furan-3-yl)propyl)amino)-3-(4-(tert-butoxy)phenyl)-1-oxopropan-2-yl)carbamate

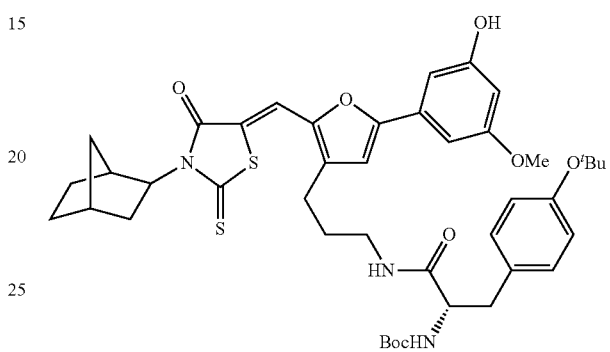

Red solid, 53%. ¹H NMR (300 MHz, CDCl₃): 7.22 (s, 1H), 7.12 (d, J=8.7, 2H), 7.03 (s, 1H), 6.92 (d, J=8.4, 2H), 6.76 (d, J=2.1, 2H), 6.59 (s, 1H), 6.44 (t, J=2.1, 1H), 6.17 (s, 1H), 5.36 (s, 1H), 4.94-4.93 (m, 1H), 4.36-4.35 (m, 1H), 3.84 (s, 3H), 3.27-3.26 (m, 2H), 3.03 (d, J=7.2, 2H), 2.64 (s, 1H), 2.57-2.56 (m, 3H), 2.33-2.31 (m, 3H), 1.76-1.74 (m, 4H), 1.61-1.60 (m, 4H), 1.38 (s, 9H), 1.35 (s, 9H).

(3S)-tert-butyl 4-((3-(2-((Z)-(3-(bicyclo[2.2.1]heptan-2-yl)-4-oxo-2-thioxothiazolidin-5-ylidene)methyl)-5-(3'-hydroxy-5'-methoxyphenyl)furan-3-yl)propyl)amino)-3-((tert-butoxycarbonyl)amino)-4-oxobutanoate

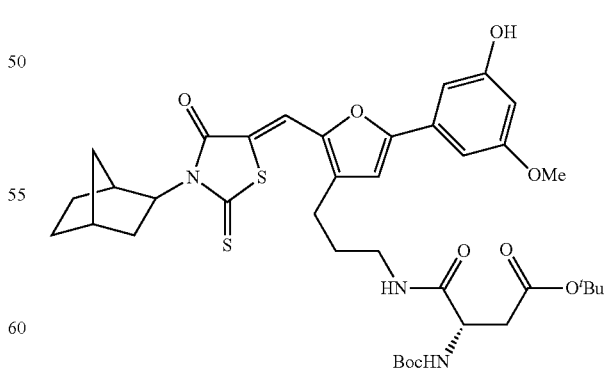

Red solid, 63%. ¹H NMR (300 MHz, DMSO-d6): 9.94 (s, 1H), 7.89 (t, J=5.1, 1H), 7.48 (s, 1H), 7.24 (s, 1H), 7.21 (d, J=3.6, 1H), 6.84 (d, J=1.2, 2H). 6.40 (d, J=2.1, 1H), 4.88-4.86 (m, 1H), 4.25-4.23 (m, 1H), 3.77 (s, 3H), 3.55 (s, 1H), 3.09 (t, J=6.0, 2H), 2.72-2.70 (m, 3H), 2.38-2.36 (m, 3H), 2.26-2.24 (m, 2H), 1.73-1.71 (m, 4H), 1.41-1.39 (m, 3H), 1.36 (s, 18H).

(3S)-tert-butyl 4-((3-(2-((Z)-(3-(bicyclo[2.2.1]heptan-2-yl)-4-oxo-2-thioxothiazolidin-5-ylidene)methyl)-5-(3'-hydroxy-5'-methoxyphenyl)furan-3-yl)propyl)amino)-3-((tert-butoxycarbonyl)amino)-4-oxobutanoate

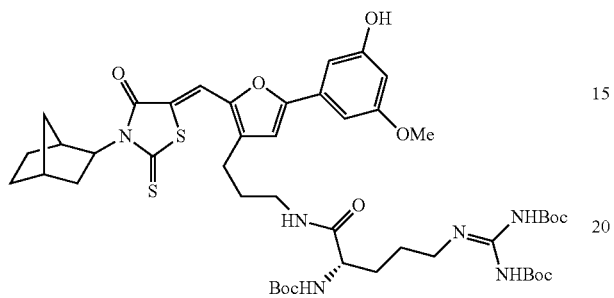

Red solid, 64%. ¹H NMR (300 MHz, DMSO-d6): 9.95 (s, 1H), 9.06 (s, 2H), 7.91 (s, 1H), 7.47 (s, 1H), 7.23 (s, 1H), 6.84-6.82 (m, 2H), 6.40 (s, 1H), 4.86-4.84 (m, 1H), 3.79-3.76 (m, 1H), 3.77 (s, 3H), 3.09 (s, J=6.6, 2H), 2.65-2.63 (m, 2H), 2.26-2.36 (m, 3H), 1.73-1.71 (m, 3H), 1.53-1.52 (m, 5H), 1.35-1.33 (m, 27H), 1.19-1.17 (m, 7H). HRMS (ESI): 941.4074 (M+H).

General procedure for the synthesis of the above compound XXX

The above compound XXIX (5.0 mmol) was resolved in CH₂Cl₂ (60 mL), and was added TFA (10.0 equiv) or Et₂NH (10.0 equiv) at 0° C. The resulting mixture was stirred at room temperature until the starting material was fully consumed. The reaction mixture was concentrated to dryness, and the residue was purified by recrystallization from diethyl ether to give the corresponding product as illustrated above.

(2S)-3-(2-((Z)-(3-(bicyclo[2.2.1]heptan-2-yl)-4-oxo-2-thioxothiazolidin-5-ylidene)methyl)-5-(3',5'-dimethoxyphenyl)furan-3-yl)propyl 2-amino-3-(4-hydroxyphenyl)propanoate

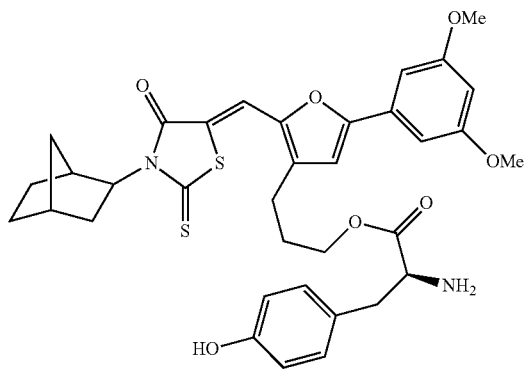 [SMILES: COc1cc(OC)cc(-c2cc(CCCOC(=O)[C@@H](N)Cc3ccc(O)cc3)c(/C=C3\SC(=S)N(C4CC5CCC4C5)C3=O)o2)c1]

¹H-NMR (300 MHz, DMSO-d6): 9.89 (w, 1H), 7.46 (s, 1H), 7.22 (s, 1H), 6.83 (t, J=2.4, 2H), 6.38 (t, J=2.1, 1H), 5.04 (s, 1H), 4.54-5.53 (m, 1H), 3.76 (s, 3H), 3.42-3.41 (m, 2H), 2.66 (t, J=7.5, 2H), 2.41 (m, 3H), 1.87 (w, 6H), 1.76 (m, 3H), 1.62 (t, J=12.3, 2H).

(2S)-3-(2-((Z)-(3-(bicyclo[2.2.1]heptan-2-yl)-4-oxo-2-thioxothiazolidin-5-ylidene)methyl)-5-(3,5-dimethoxy-phenyl)furan-3-yl)propyl 2-amino-4-methylpentanoate

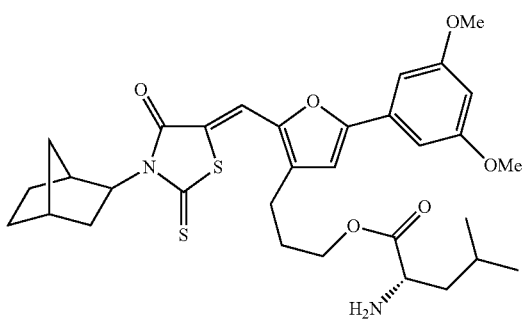 [SMILES: COc1cc(OC)cc(-c2cc(CCCOC(=O)[C@@H](N)CC(C)C)c(/C=C3\SC(=S)N(C4CC5CCC4C5)C3=O)o2)c1]

¹H-NMR (300 MHz, CDCl₃): 7.23 (s, 1H), 6.84 (s, 2H), 6.72 (s, 1H), 6.42 (s, 1H), 4.92 (t, J=5.4, 2H), 4.18-4.10 (m, 3H), 3.90 (s, 6H), 2.63-2.24 (m, 7H), 1.95 (s, 2H), 1.82-1.75 (m, 4H), 1.60-1.53 (m, 3H), 0.95-0.87 (m, 7H). HRMS (ESI): 6.13.2391 (M+H).

(2S)-3-(2-((Z)-(3-(bicyclo[2.2.1]heptan-2-yl)-4-oxo-2-thioxothiazolidin-5-ylidene)methyl)-5-(3',5'-dimethoxy-phenyl)furan-3-yl)propyl 2-amino-3-phenylpropanoate

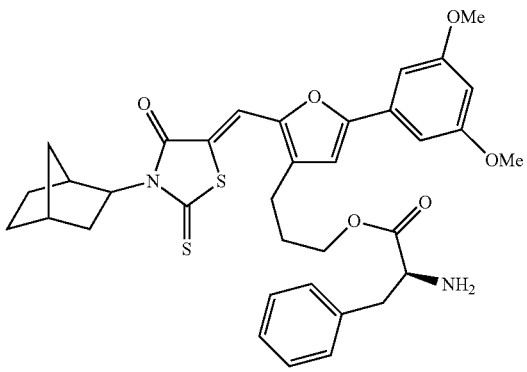 [SMILES: COc1cc(OC)cc(-c2cc(CCCOC(=O)[C@@H](N)Cc3ccccc3)c(/C=C3\SC(=S)N(C4CC5CCC4C5)C3=O)o2)c1]

¹H-NMR (300 MHz, CDCl₃): 7.35-7.21 (m, 6H), 6.91 (d, J=2.1, 2H), 6.70 (s, 1H), 6.50 (t, J=2.1, 1H), 4.98-4.96 (m, 1H), 4.12 (t, J=6.0, 2H), 3.87-3.80 (m, 8H), 3.14-3.12 (m, 1H), 2.95-2.93 (m, 1H), 2.61-2.59 (m, 2H), 2.58 (s, 1H), 2.54

(s, 1H), 2.36-2.28 (m, 3H), 1.95-1.75 (m, 2H), 1.61-1.55 (m, 4H), 1.41-1.91 (m, 3H). HRMS (ESI): 647.2244 (M+H).

(2S)-3-(2-((Z)-(3-(bicyclo[2.2.1]heptan-2-yl)-4-oxo-2-thioxothiazolidin-5-ylidene)methyl)-5-(3',5'-dimethoxy-phenyl)furan-3-yl)propyl 2-amino-2-phenylacetate

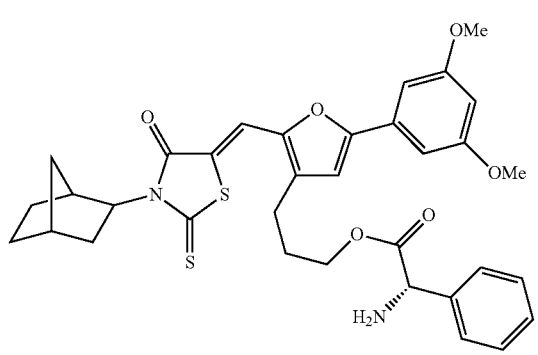 [SMILES: COc1cc(OC)cc(-c2cc(CCCOC(=O)[C@@H](N)c3ccccc3)c(/C=C3\SC(=S)N(C4CC5CCC4C5)C3=O)o2)c1]

¹H-NMR (300 MHz, CDCl₃): 7.47-7.37 (m, 5H), 7.30 (s, 1H), 6.89 (d, J=2.1, 2H), 6.57 (s, 1H), 6.49 (t, J=2.1, 1H), 4.98 (dd, J=6.0, 2.1, 1H), 4.71 (s, 1H), 4.20-4.12 (m, 2H), 3.89 (s, 6H), 2.58-2.48 (m, 4H), 2.40-2.31 (m, 2H), 1.89-1.80 (m, 4H), 1.67-1.62 (m, 2H), 1.51-1.44 (m, 2H). HRMS (ESI): 633.2083 (M+H).

(2S)-3-(2-((Z)-(3-(bicyclo[2.2.1]heptan-2-yl)-4-oxo-2-thioxothiazolidin-5-ylidene)methyl)-5-(3',5'-dimeth-oxyphenyl)furan-3-yl)propyl 2,4-diamino-4-oxobutanoate

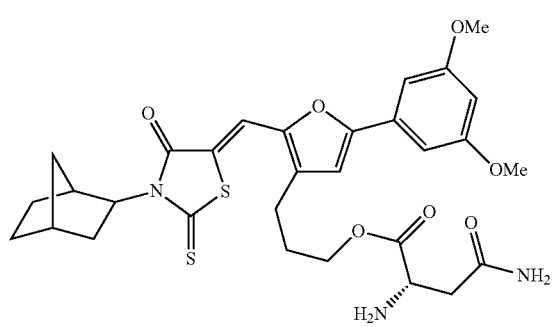 [SMILES: COc1cc(OC)cc(-c2cc(CCCOC(=O)[C@@H](N)CC(N)=O)c(/C=C3\SC(=S)N(C4CC5CCC4C5)C3=O)o2)c1]

¹H-NMR (300 MHz, DMSO-d6): 8.37 (t, J=3.6, 1H), 8.04 (m, 2H), 7.58 (s, 1H), 7.44 (s, 1H), 7.28 (d, J=6.0, 1H), 7.17 (s, 1H), 6.94 (d, J=2.1, 2H), 6.50-6.47 (m, 1H), 4.85-4.83 (m, 1H), 3.99-3.97 (m, 1H), 3.85 (s, 6H), 3.07-3.01 (m, 6H), 2.69-2.61 (m, 4H), 2.28-2.20 (m, 3H), 1.78-1.72 (m, 3H), 1.54-1.51 (m, 2H), 1.26-1.25 (m, 4H).

(2S)-2-amino-N¹-(3-(2-((Z)-(3-(bicyclo[2.2.1]heptan-2-yl)-4-oxo-2-thioxothiazolidin-5-ylidene)methyl)-5-(3',5'-dimethoxyphenyl)furan-3-yl)propyl)-3-(4-hydroxyphenyl)propanamide

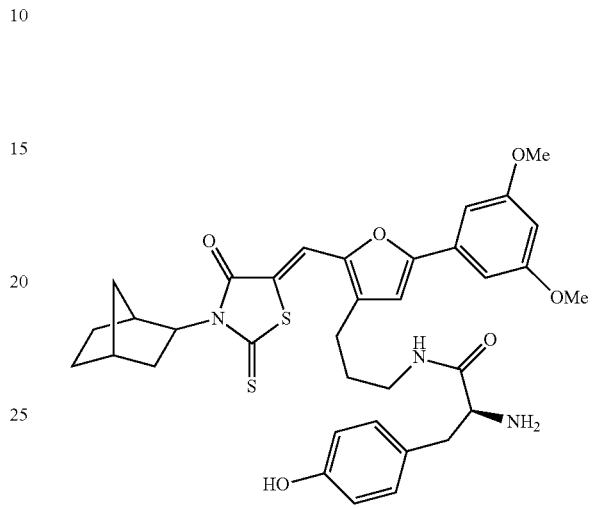

Yellow brown solid in 78% yield. ¹H-NMR (300 MHz, DMSO-d6): 9.12 (s, 1H), 7.86-7.84 (m, 1H), 7.43 (s, 1H), 7.31 (s, 1H), 6.94-6.92 (m, 5H), 6.57-6.55 (m, 4H), 4.84-4.82 (m, 1H), 3.80 (s, 6H), 3.62 (s, 1H), 3.09-3.07 (m, 2H), 2.79-2.78 (m, 1H), 2.58-2.56 (m, 2H), 2.24-2.22 (m, 4H), 1.65-1.63 (m, 4H).

(2S)-2-amino-N¹-(3-(2-((Z)-(3-(bicyclo[2.2.1]heptan-2-yl)-4-oxo-2-thioxothiazolidin-5-ylidene)methyl)-5-(3',5'-dimethoxyphenyl)furan-3-yl)propyl)succinamide

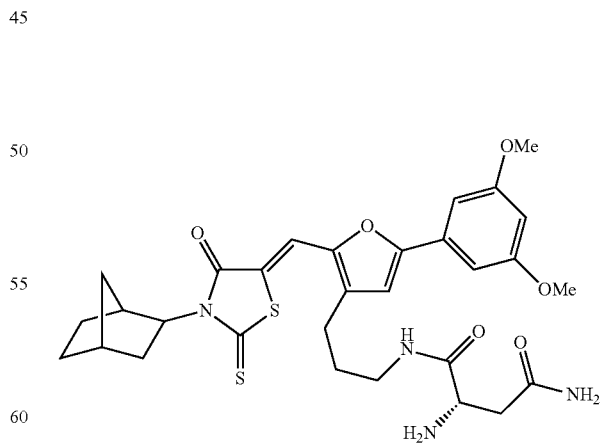

Yellow brown solid in 72% yield. ¹H-NMR (300 MHz, DMSO-d₆): 8.40 (t, J=3.6, 1H), 8.08-8.06 (m, 2H), 7.61 (s, 1H), 7.51 (s, 1H), 7.34 (d, J=5.4, 1H), 7.23 (s, 1H), 6.95 (d, J=2.1, 2H), 6.59-6.56 (m, 1H), 4.85-4.83 (m, 1H), 3.99-3.87

(m, 1H), 3.85 (s, 6H), 3.07-3.04 (m, 6H), 2.67-2.63 (m, 4H), 2.34-2.33 (m, 3H), 1.76-1.73 (m, 3H), 1.56-1.51 (m, 2H), 1.21-1.17 (m, 4H).

(3S)-3-amino-4-((3-(2-((Z)-(3-(bicyclo[2.2.1]heptan-2-yl)-4-oxo-2-thioxothiazolidin-5-ylidene)methyl)-5-(3',5'-dimethoxyphenyl)furan-3-yl)propyl)amino)-4-oxobutanoic acid

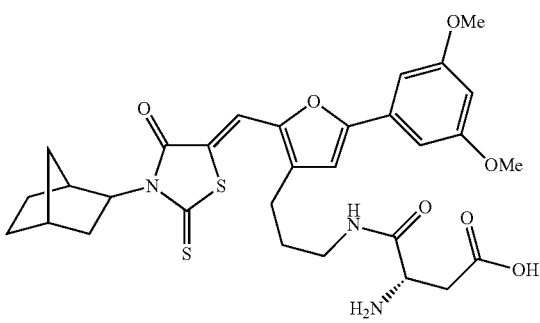 [SMILES: COc1cc(OC)cc(-c2cc(CCCNC(=O)[C@@H](N)CC(=O)O)c(/C=C3\SC(=S)N(C4CC5CCC4C5)C3=O)o2)c1]

Yellow brown solid in 42% yield. $^1$H-NMR (300 MHz, DMSO-d6): 8.36 (t, J=4.0, 1H), 8.04-8.02 (m, 2H), 7.54 (s, 1H), 7.46 (s, 1H), 7.34 (d, J=5.8, 1H), 7.19 (s, 1H), 6.90 (d, J=2.7, 2H), 6.59-6.56 (m, 1H), 4.87-4.85 (m, 1H), 3.99-3.87 (m, 1H), 3.84 (s, 6H), 3.09-3.03 (m, 6H), 2.67-2.61 (m, 4H), 2.36-2.33 (m, 3H), 1.74-1.71 (m, 3H), 1.56-1.53 (m, 3H), 1.21-1.13 (m, 4H).

(2S)-2-amino-N$^1$-(3-(2-((Z)-(3-(bicyclo[2.2.1]heptan-2-yl)-4-oxo-2-thioxothiazolidin-5-ylidene)methyl)-5-(3',5'-dimethoxyphenyl)furan-3-yl)propyl)-2-phenylacetamide

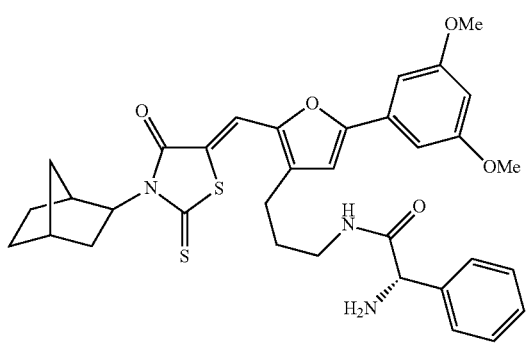 [SMILES: COc1cc(OC)cc(-c2cc(CCCNC(=O)[C@@H](N)c3ccccc3)c(/C=C3\SC(=S)N(C4CC5CCC4C5)C3=O)o2)c1]

Red-brown solid in 58% yield. $^1$H-NMR (300 MHz, DMSO-d6): 8.45 (t, J=4.8, 1H), 7.39-7.37 (m, 9H), 6.93 (d, J=2.1, 2H), 6.56 (s, 1H), 4.85-4.83 (m, 1H), 3.80 (s, 6H), 3.04 (d, J=7.5, 5H), 2.39-2.37 (m, 4H), 1.69-1.67 (m, 3H), 1.52-1.50 (m, 3H), 1.14-1.12 (m, 4H).

(2S)-2-amino-N$^1$-(3-(2-((Z)-(3-(bicyclo[2.2.1]heptan-2-yl)-4-oxo-2-thioxothiazolidin-5-ylidene)methyl)-5-(3',5'-dimethoxyphenyl)furan-3-yl)propyl)-3-phenylpropanamide

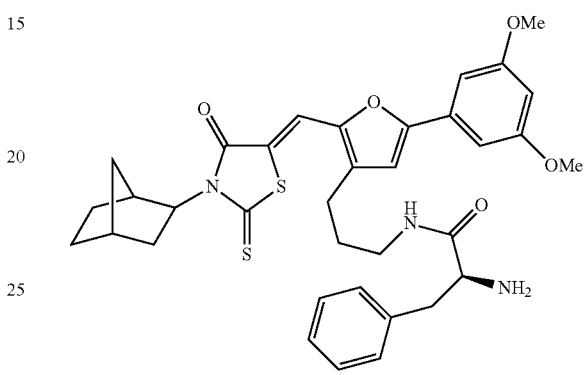

$^1$H-NMR (300 MHz, DMSO-d6): 7.38-7.26 (m, 6H), 6.94 (d, J=2.4, 2H), 6.73 (s, 1H), 6.54 (t, J=2.7, 1H), 5.02-4.99 (m, 1H), 4.15 (t, J=6.0, 2H), 3.89-3.83 (m, 8H), 3.16-3.14 (m, 1H), 2.98-2.92 (m, 1H), 2.61-2.59 (m, 2H), 2.58 (s, 1H), 2.54 (s, 1H), 2.36-2.28 (m, 3H), 1.95-1.75 (m, 2H), 1.61-1.55 (m, 4H), 1.41-1.91 (m, 3H).

(2S)—N$^1$-(3-(2-((Z)-(3-(bicyclo[2.2.1]heptan-2-yl)-4-oxo-2-thioxothiazolidin-5-ylidene)methyl)-5-(3',5'-dimethoxyphenyl)furan-3-yl)propyl)pyrrolidine-2-carboxamide

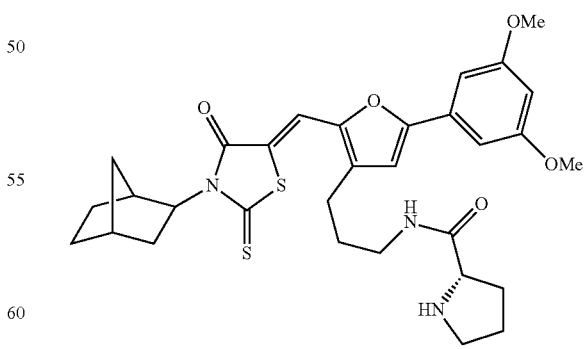

$^1$H-NMR (300 MHz, DMSO-d6): 7.38-7.26 (m, 6H), 6.94 (d, J=2.4, 2H), 6.73 (s, 1H), 6.54 (t, J=2.7, 1H), 5.02-4.99 (m, 1H), 4.15 (t, J=6.0, 2H), 3.89-3.83 (m, 8H), 3.16-3.14 (m, 1H), 2.98-2.92 (m, 1H), 2.61-2.59 (m, 2H), 2.58 (s, 1H), 2.54

(s, 1H), 2.36-2.28 (m, 3H), 1.95-1.75 (m, 2H), 1.61-1.55 (m, 4H), 1.41-1.91 (m, 3H). HRMS (ESI): 596.2240 (M+H).

(2S)-2-amino-N[1]-(3-(2-((Z)-(3-(bicyclo[2.2.1]heptan-2-yl)-4-oxo-2-thioxothiazolidin-5-ylidene)methyl)-5-(3'-hydroxy-5'-methoxyphenyl)furan-3-yl)propyl)-3-(4-hydroxyphenyl)propanamide

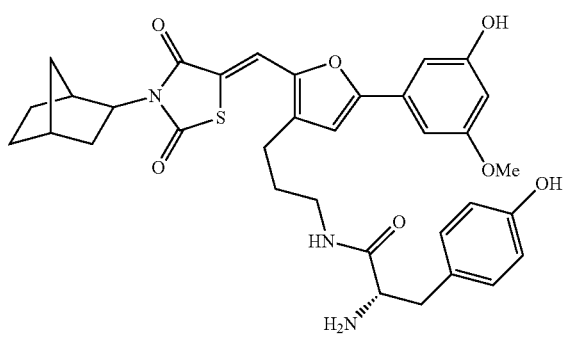 [SMILES: COc1cc(O)cc(-c2cc(CCCNC(=O)[C@@H](N)Cc3ccc(O)cc3)c(/C=C3\SC(=O)N(C4CC5CCC4C5)C3=O)o2)c1]

$^1$H-NMR (300 MHz, DMSO-d6): 9.93 (s, 1H), 9.16 (s, 1H), 9.96 (s, 1H), 7.44 (s, 1H), 7.21 (s, 1H), 6.97 (t, J=8.1, 2H), 6.85 (s, 1H), 6.63 (s, J=8.4, 2H), 6.40 (t, J=2.1, 1H), 4.88-4.86 (m, 1H), 3.76 (s, 3H), 3.10-3.08 (m, 2H), 2.79-2.77 (m, 1H), 2.58-2.56 (m, 4H), 2.37 (s, 1H), 2.27-2.26 (m, 2H), 1.69-1.67 (m, 3H), 1.54-1.52 (m, 2H), 1.22-1.20 (m, 4H).

(2S)-2-amino-N[1]-(3-(2-((Z)-(3-(bicyclo[2.2.1]heptan-2-yl)-4-oxo-2-thioxothiazolidin-5-ylidene)methyl)-5-(3'-hydroxy-5'-methoxyphenyl)furan-3-yl)propyl)succinamide

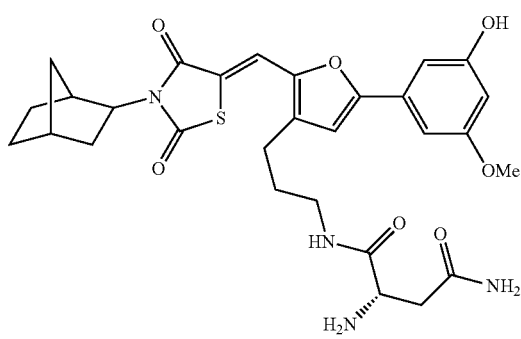 [SMILES: COc1cc(O)cc(-c2cc(CCCNC(=O)[C@@H](N)CC(N)=O)c(/C=C3\SC(=O)N(C4CC5CCC4C5)C3=O)o2)c1]

$^1$H NMR (300 MHz, DMSO-d6): 9.93-9.91 (m, 1H), 8.03-8.01 (m, 1H), 7.48 (s, 1H), 7.41 (s, 1H), 7.22 (s, 1H), 6.87-6.85 (m, 2H), 6.38 (d, J=1.8, 1H), 4.87-4.85 (m, 1H), 3.75 (s, 3H), 3.51-3.49 (m, 1H), 3.10-3.08 (m, 2H), 2.64-2.62 (m, 2H), 2.24-2.36 (m, 4H), 1.73-1.71 (m, 2H), 1.52-1.50 (m, 2H), 1.35 (s, 9H), 1.22-1.20 (m, 5H).

(2S)-2-amino-N[1]-(3-(2-((Z)-(3-(bicyclo[2.2.1]heptan-2-yl)-4-oxo-2-thioxothiazolidin-5-ylidene)methyl)-5-(3'-hydroxy-5'-methoxyphenyl)furan-3-yl)propyl)-5-((diaminomethylene)amino)pentanamide dihydrochloride

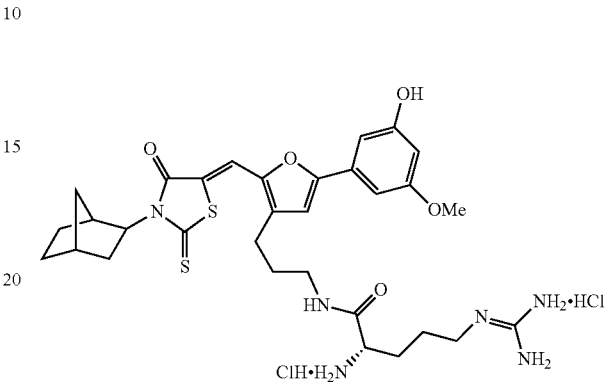

HRMS (ESI): 641.2578 (M+H).

Synthesis of Type-9: Modification of Side Chain in C-Ring (Furan) with Tartrate Moiety

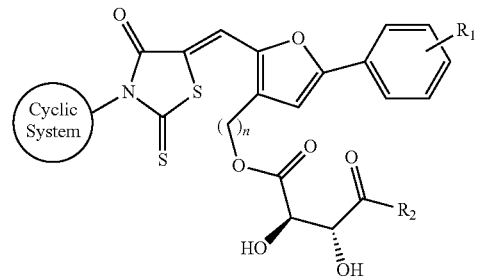

This type of compound was prepared according to the synthetic route below.

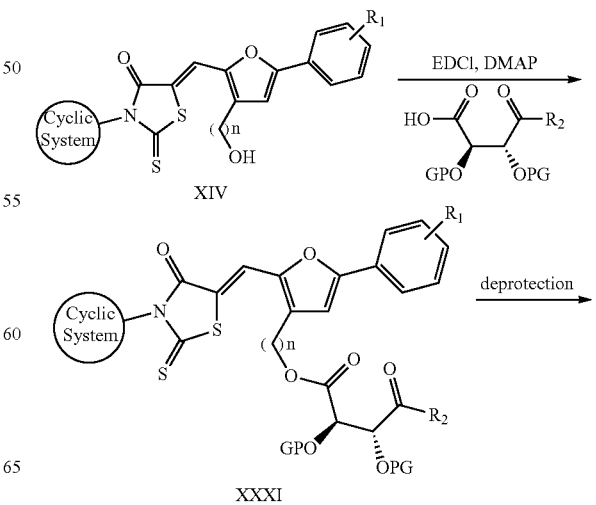

-continued

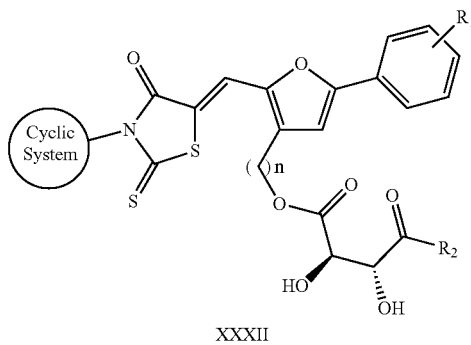

XXXII

General Procedure of Coupling Reaction

To a solution of XIV (10.0 mmol) in dry $CH_2Cl_2$ (80 mL) was added HOBt (1.62 g, 12.0 mmol), protecting α-hydroxy acid (12.0 mmol) and EDCI (2.87 g, 15.0 mmol) at 0° C., and the formed mixture was stirred at room temperature for 24 h. The reaction was worked up addition of water, and the formed organic phase was washed sequentially with 5% diluted HCl, brine, saturated $NaHCO_3$ and brine, and then dried over anhydrous $Na_2SO_4$. After removal of the solvent, the residue was purified by a flash chromatography (PE/EA) to give the corresponding products XXXI.

General Procedure of Deprotection Reaction

The above compound XXXI (5.0 mmol) was resolved in $CH_2Cl_2$ (60 mL), and was added TFA (10.0 equiv) at 0° C. The resulting mixture was stirred at room temperature until the starting material was fully consumed. The reaction mixture was concentrated to dryness, and the residue was purified by recrystallization from diethyl ether to give the corresponding product XXXII as illustrated below.

(2S,3S)-1-(3-(2-((Z)-(3-(bicyclo[2.2.1]heptan-2-yl)-4-oxo-2-thioxothiazolidin-5-ylidene)methyl)-5-(4'-chlorophenyl)furan-3-yl)propyl)4-methyl 2,3-dihydroxysuccinate

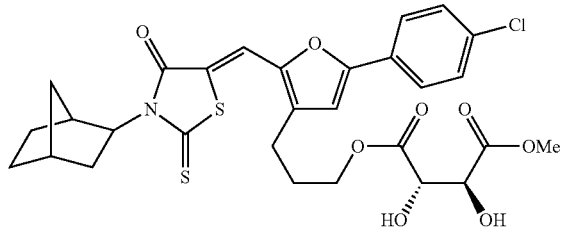

$^1$H-NMR (300 MHz, $CDCl_3$): 7.67 (d, J=8.7, 2H), 7.43 (t, J=8.7, 2H), 7.36 (s, 1H), 6.73 (s, 1H), 4.95 (t, J=1.5, 1H), 4.81 (t, J=2.4, 2H), 4.24 (m, 2H), 3.83 (s, 3H), 2.72 (t, J=7.2, 2H), 2.53 (s, 1H), 2.43 (s, 1H), 2.32 (m, 3H), 2.01 (m, 2H), 1.78 (m, 2H), 1.59 (s, 3H), 1.52 (s, 3H), 1.24 (m, 5H). HRMS (ESI): 620.1168 (M+H).

(2S,3S)-1-(3-(2-((Z)-(3-(bicyclo[2.2.1]heptan-2-yl)-4-oxo-2-thioxothiazolidin-5-ylidene)methyl)-5-(4'-fluorophenyl)furan-3-yl)propyl)4-methyl 2,3-dihydroxysuccinate

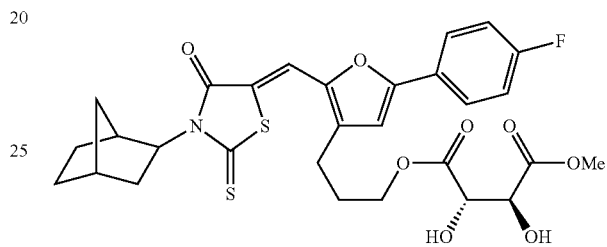

$^1$H-NMR (300 MHz, DMSO-d6): 7.84 (m, 2H), 7.49 (s, 1H), 7.41 (m, 2H), 7.29 (s, 1H), 5.53 (m, 2H), 4.84 (m, 1H), 4.42 (m, 2H), 4.10 (m, 2H), 3.62 (s, 3H), 2.72 (m, 2H), 2.35 (m, 1H), 2.24 (d, J=1.2, 2H), 1.91 (m, 3H), 1.71 (d, J=1.5, 1H), 1.68 (t, J=1.5, 2H), 1.21 (m, 3H). HRMS (ESI): 604.1496 (M+H).

(2R,3R)-1-(3-(2-((Z)-(3-(adamantan-2-yl)-4-oxo-2-thioxothiazolidin-5-ylidene)methyl)-5-(3',5'-dimethoxy-phenyl)furan-3-yl)propoxy)-4-amino-1,4-dioxobutane-2,3-diyldiacetate

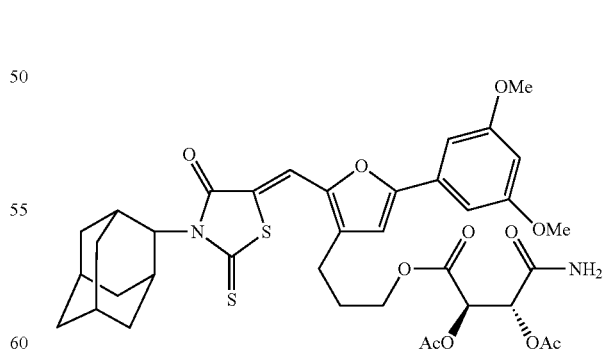

$^1$H-NMR (300 MHz, $CDCl_3$): 7.43 (s, 1H), 6.92 (d, J=2.1, 2H), 6.76 (s, 1H), 6.47 (s, 1H), 6.39 (s, 1H), 5.91 (s, 1H), 5.81 (d, J=2.4, 1H), 5.61 (d, J=2.4, 1H), 5.14 (s, 1H), 4.18 (d, J=2.4, 1H), 3.87 (s, 6H), 2.72 (d, J=2.4, 2H), 2.48 (m, 4H), 2.17 (d, J=6.0, 6H), 1.92 (m, 6H), 1.72 (m, 2H), 1.68 (m, 2H).

Synthesis of Type-10: Modification of Side Chain in C-Ring (Furan) with Morphiline Moiety

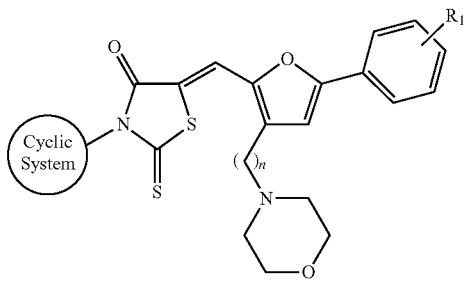

This type of compound was prepared according to the synthetic route below.

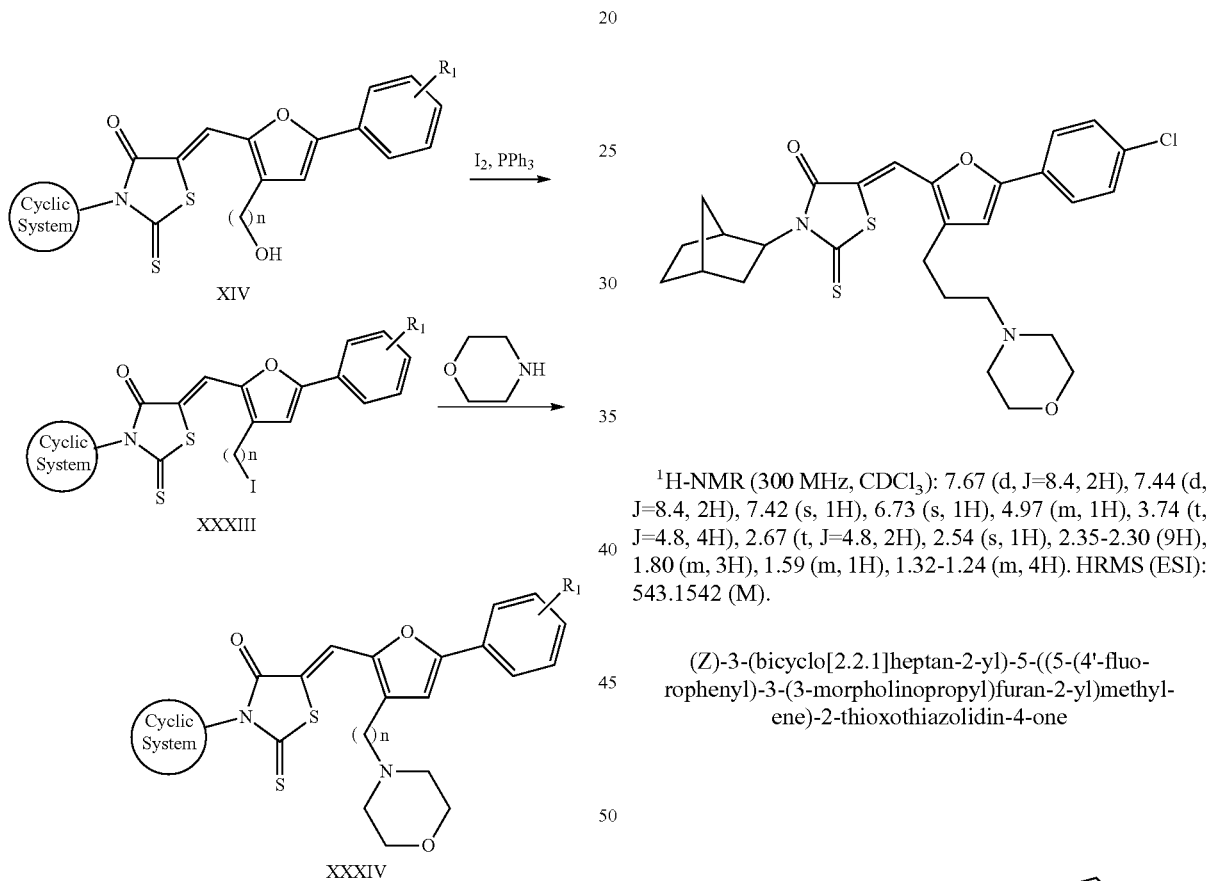

General Procedure of Iodonation Reaction

The solution of alcohol compound XIV (10 mmol) and PPh$_3$ (2.62 g, 10 mmol) in THF (60 mL) was added I$_2$ (2.79 g, 11 mmol), the resulting brown mixture was stirred for 2 h at room temperature. The solvent were removed, and the residue was extracted with EA, washed with saturated Na$_2$S$_2$O$_3$. The combined organic phases were dried MgSO$_4$. The solvent was removed under vacuum, and the residue was purified by a flash chromatography (PE/EA) on silica gel to give the corresponding iodo compound XXXIII as yellow solid.

General Procedure of Morpholine Substituted Reaction

To a solution of iodo compound XXXIII (10.0 mmol) made above in dry CH$_2$Cl$_2$ (50 mL) was added morpholine (4.35 g, 50.0 mmol), and the mixture was then refluxed until the starting material disappeared. The reaction was quenched by addition of water, and then washed with saturated NaHCO$_3$, dried with MgSO$_4$. The solvent was removed under vacuum, and the residue was purified by a flash chromatography (PE/EA/TEA) on silica gel to give the corresponding products XXXIV.

(Z)-3-(bicyclo[2.2.1]heptan-2-yl)-5-((5-(4'-chlorophenyl)-3-(3-morpholinopropyl)furan-2-yl)methylene)-2-thioxothiazolidin-4-one

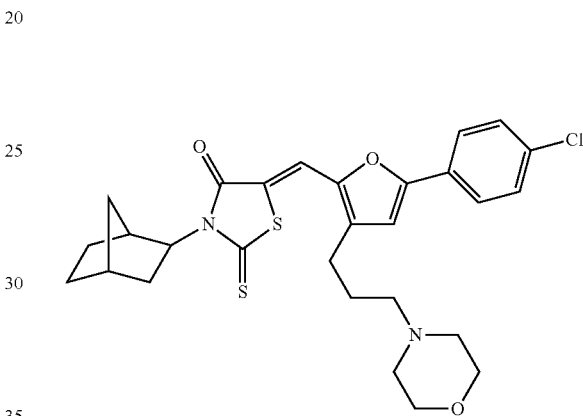

$^1$H-NMR (300 MHz, CDCl$_3$): 7.67 (d, J=8.4, 2H), 7.44 (d, J=8.4, 2H), 7.42 (s, 1H), 6.73 (s, 1H), 4.97 (m, 1H), 3.74 (t, J=4.8, 4H), 2.67 (t, J=4.8, 2H), 2.54 (s, 1H), 2.35-2.30 (9H), 1.80 (m, 3H), 1.59 (m, 1H), 1.32-1.24 (m, 4H). HRMS (ESI): 543.1542 (M).

(Z)-3-(bicyclo[2.2.1]heptan-2-yl)-5-((5-(4'-fluorophenyl)-3-(3-morpholinopropyl)furan-2-yl)methylene)-2-thioxothiazolidin-4-one

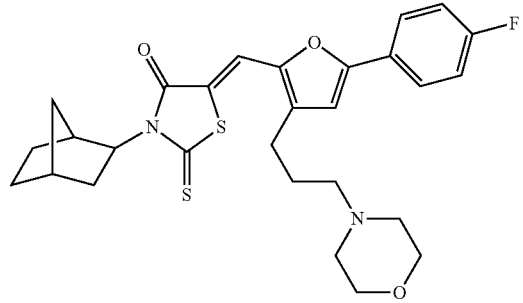 [SMILES: O=C1/C(=C/c2oc(-c3ccc(F)cc3)cc2CCCN2CCOCC2)SC(=S)N1C1CC2CCC1C2]

$^1$H-NMR (300 MHz, CDCl$_3$): 7.77-7.72 (m, 2H), 7.46 (s, 1H), 7.22-7.15 (m, 2H), 6.70 (s, 1H), 4.98 (d, J=2.7, 1H), 3.76

(t, J=4.5, 4H), 2.68 (t, J=7.2, 2H), 2.55 (s, 1H), 2.46-2.22 (m, 9H), 1.87-1.69 (m, 4H), 1.38-1.15 (m, 4H).

(Z)-3-(bicyclo[2.2.1]heptan-2-yl)-5-((5-(3',5'-dimethoxyphenyl)-3-(3-morpholinopropyl)furan-2-yl)methyl-ene)-2-thioxothiazolidin-4-one

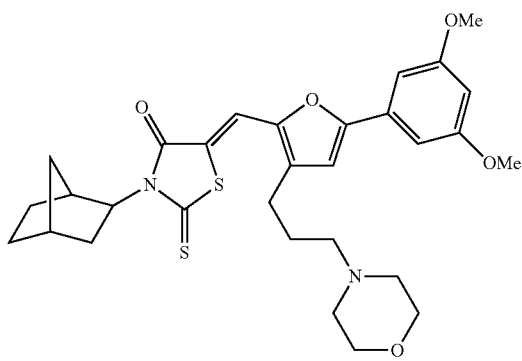 [SMILES: COc1cc(OC)cc(-c2cc(CCCN3CCOCC3)c(/C=C3\SC(=S)N(C4CC5CCC4C5)C3=O)o2)c1]

$^{1}$H-NMR (300 MHz, CDCl$_{3}$): 7.44 (s, 1H), 9.62 (d, J=2.1, 2H), 6.74 (s, 1H), 6.49 (t, J=2.1, 1H), 4.97 (m, 1H), 3.96 (s, 2H), 3.89 (s, 6H), 3.77 (t, J=4.8, 2H), 3.20 (s, 2H), 2.68 (s, 2H), 2.68 (t, J=4.8, 2H), 2.55 (s, 1H), 2.47 (s, 4H), 2.38 (m, 4H), 1.65 (m, 3H), 1.60 (m, 2H), 1.38 (m, 2H). HRMS (ESI): 569.2145 (M+H).

(Z)-3-(adamantan-2-yl)-5-((5-(3',5'-dimethoxyphenyl)-3-(3-morpholinopropyl)furan-2-yl)methylene)-2-thioxothiazolidin-4-one

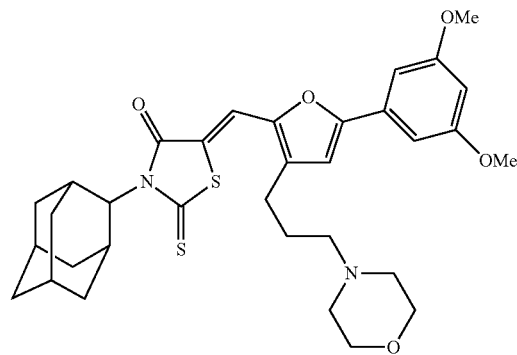 [SMILES: COc1cc(OC)cc(-c2cc(CCCN3CCOCC3)c(/C=C3\SC(=S)N(C4C5CC6CC(C5)CC4C6)C3=O)o2)c1]

$^{1}$H-NMR (300 MHz, CDCl$_{3}$): 7.45 (s, 1H), 6.89 (d, J=2.4, 2H), 6.47 (t, J=2.1, 1H), 5.15 (s, 1H), 3.87 (s, 6H), 3.80 (d, J=5.4, 1H), 3.75 (t, J=4.5, 4H), 3.15 (m, 1H), 2.65 (t, J=4.2, 2H), 2.48-2.35 (m, 10H), 2.00-1.79 (m, 10H), 1.66-1.58 (m, 1H). HRMS (ESI): 609.2449 (M+H).

(Z)-3-(adamantan-2-yl)-5-((5-(4'-fluorophenyl)-3-(3-morpholinopropyl)furan-2-yl)methylene)-2-thioxothi-azolidin-4-one

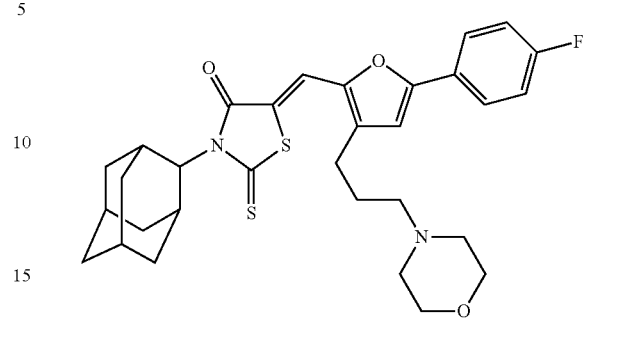

$^{1}$H-NMR (300 MHz, CDCl$_{3}$): 7.76 (m, 2H), 7.46 (s, 1H), 7.18 (t, J=8.4, 2H), 6.73 (s, 1H), 5.16 (s, 1H), 3.75 (t, J=4.8, 4H), 2.69 (t, J=8.1, 2H), 2.50-2.42 (m, 8H), 2.00-1.71 (m, 14H). HRMS (ESI): 567.2144 (M+H).

(Z)-3-(adamantan-2-yl)-5-((5-(4'-chlorophenyl)-3-(3-morpholinopropyl)furan-2-yl)methylene)-2-thioxothi-azolidin-4-one

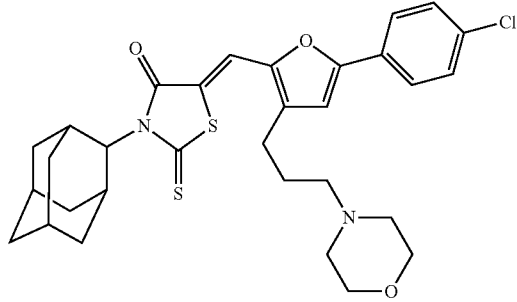 [SMILES: O=C1/C(=C/c2oc(-c3ccc(Cl)cc3)cc2CCCN2CCOCC2)SC(=S)N1C1C2CC3CC(C2)CC1C3]

$^{1}$H-NMR (300 MHz, CDCl$_{3}$): 7.68 (d, J=2.4, 2H), 7.45 (d, J=4.2, 2H), 7.40 (s, 1H), 6.71 (s, 1H), 5.15 (s, 1H), 3.73 (t, J=4.8, 4H), 2.67 (t, J=3.0, 2H), 2.52-2.33 (m, 8H), 2.32 (t, J=7.2, 2H), 2.06-1.86 (m, 6H), 1.85-1.64 (m, 6H). HRMS (ESI): 583.1857 (M).

(Z)-3-(bicyclo[2.2.1]heptan-2-yl)-5-((5-(4'-chlorophenyl)-3-(3-morpholinopentyl)furan-2-yl)methyl-ene)-2-thioxothiazolidin-4-one

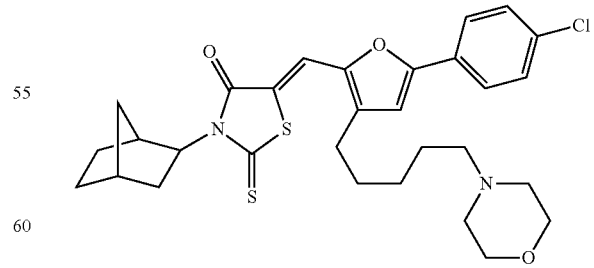

$^{1}$H-NMR (300 MHz, CDCl$_{3}$): 7.66 (d, J=8.7, 2H), 7.41 (d, J=8.7, 2H), 7.36 (s, 1H), 6.71 (s, 1H), 4.96 (dd, J=6.0, 4.5, 1H), 3.71 (t, J=4.8, 4H), 2.59 (t, J=4.5, 2H), 2.54 (s, 1H), 2.45-2.40 (m, 5H), 2.35-2.27 (m, 4H), 1.80-1.13 (m, 12H).

Synthesis of Type-11: Modification of Side Chain in C-Ring with Piperazine Moiety

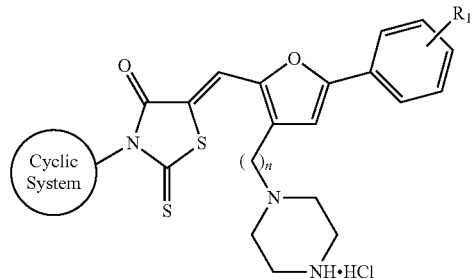

This type of compound was prepared according to the synthetic route below.

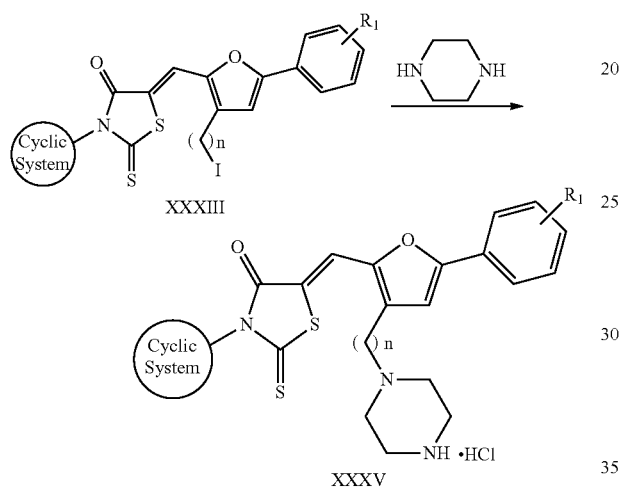

General Procedure of Piperazine Substituted Reaction

To a solution of iodo compound XXXIII (10.0 mmol) made above in dry $CH_2Cl_2$ (50 mL) was added piperazine (4.35 g, 50.0 mmol), and the mixture was then refluxed until the starting material disappeared. The reaction was quenched by addition of water, and then washed with saturated $NaHCO_3$, dried with $MgSO_4$. The solvent and excessive piperazine were removed under vacuum, and the residue was added dil. HCl, and collected the solid. The crude product was purified by recrystallization from ether/MeOH to give the corresponding products XXXV.

(Z)-3-(bicyclo[2.2.1]heptan-2-yl)-5-((5-(4'-chlorophenyl)-3-(3-(piperazin-1-yl)propyl)furan-2-yl)-methylene)-2-thioxothiazolidin-4-one hydrochloride

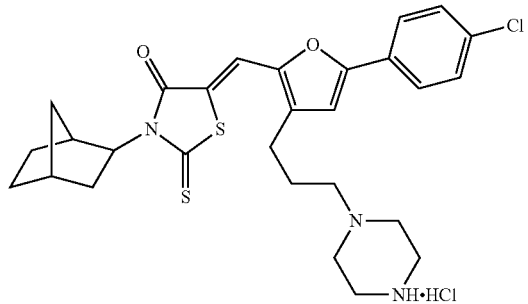

$^1$H-NMR (300 MHz, DMSO-d6): 9.63 (s, 2H), 7.80 (d, J=8.7, 2H), 7.64 (d, J=8.7, 2H), 7.53 (s, 1H), 7.39 (s, 1H), 4.88-4.84 (m, 1H), 3.71-3.59 (m, 2H), 3.15 (s, 6H), 2.37 (s, 1H), 2.36-2.25 (m, 2H), 2.11-1.84 (m, 3H), 2.00 (t, J=1.8, 1H), 1.58-1.40 (m, 2H), 1.31-1.12 (m, 5H).

(Z)-3-(bicyclo[2.2.1]heptan-2-yl)-5-((5-(4'-fluorophenyl)-3-(3-(piperazin-1-yl)propyl)furan-2-yl)-methylene)-2-thioxothiazolidin-4-one hydrochloride $^1$H-NMR (300 MHz, DMSO-d6)): 9.41-9.30 (broad, 2H), 7.85 (d, J=5.4, 2H), 7.52 (s, 1H), 7.49-7.30 (m, 2H), 7.30 (s, 1H), 4.88-4.79 (m, 1H), 3.70-3.48 (m, 4H), 3.38-3.05 (m, 4H), 2.78-2.64 (m, 2H), 1.74-1.67 (m, 1H), 1.61-1.50 (m, 2H), 1.22-1.13 (m, 4H). HRMS (ESI): 526.1989 (M−HCl+H).

(Z)-3-(bicyclo[2.2.1]heptan-2-yl)-5-((5-(3',5'-dimethoxyphenyl)-3-(3-(piperazin-1-yl)propyl)furan-2-yl)-methylene)-2-thioxothiazolidin-4-one hydrochloride

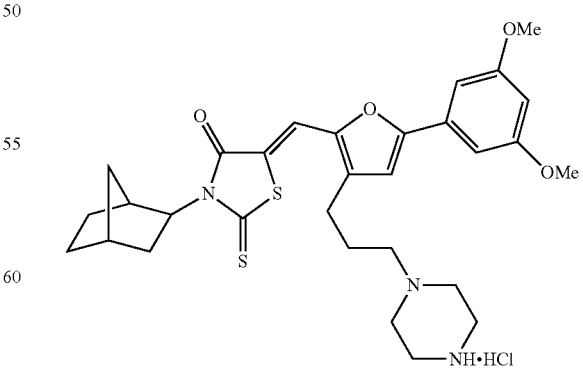

$^1$H-NMR (300 MHz, DMSO-d6): 9.36 (broad, 2H), 7.53 (s, 1H), 7.39 (s, 1H), 7.95 (d, J=2.1, 2H), 4.85 (m, 1H), 3.82

(s, 6H), 3.78-3.21 (m, 8H), 2.72 (m, 1H), 2.49-2.15 (m, 7H), 2.10-1.82 (m, 6H), 1.32-1.15 (m, 3H). HRMS (ESI): 568.2276 (M−HCl+H).

(Z)-3-(adamantan-2-yl)-5-((5-(4'-fluoroyphenyl)-3-(3-(piperazin-1-yl)propyl)furan-2-yl)methylene)-2-thio-xothiazolidin-4-one hydrochloride

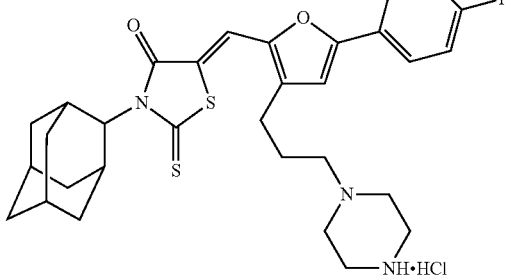

¹H-NMR (300 MHz, CDCl₃): 9.41-9.30 (broad, 1H), 7.85 (dd, J=5.4, 2H), 7.52 (s, 1H), 7.49-7.30 (m, 2H), 7.30 (s, 1H), 4.88-4.79 (m, 1H), 3.28-3.00 (m, 4H), 2.76 (t, J=6.9, 2H), 2.60-2.47 (m, 9H), 2.11-1.97 (m, 2H), 1.90 (s, 5H), 1.75-1.63 (m, 4H), 1.22-1.13 (m, 2H). HRMS (ESI): 566.2293 (M−HCl+H).

(Z)-3-(adamantan-2-yl)-5-((5-(3',5'-dimethoxyphenyl)-3-(3-(piperazin-1-yl)propyl)furan-2-yl)methylene)-2-thioxothiazolidin-4-one hydrochloride

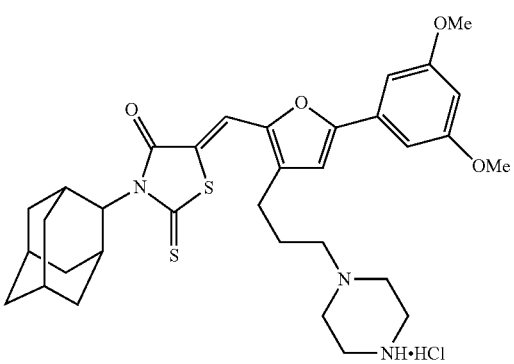

¹H-NMR (300 MHz, DMSO-d6): 9.42 (broad, 2H), 7.60 (m, 1H), 7.39 (s, 1H), 6.95 (d, J=2.1, 2H), 6.57 (s, 1H), 5.09 (s, 1H), 3.82 (s, 6H), 3.74-3.30 (5H), 3.28-3.00 (m, 2H), 2.73 (m, 2H), 2.48-2.37 (m, 3H), 2.11-1.97 (m, 7H), 190 (s, 5H), 1.75-1.52 (m, 4H). HRMS (ESI): 608.2627 (M−HCl+H).

(Z)-3-(adamantan-2-yl)-5-((5-(4'-chlorophenyl)-3-(3-(piperazin-1-yl)propyl)furan-2-yl)methylene)-2-thioxothiazolidin-4-one hydrochloride

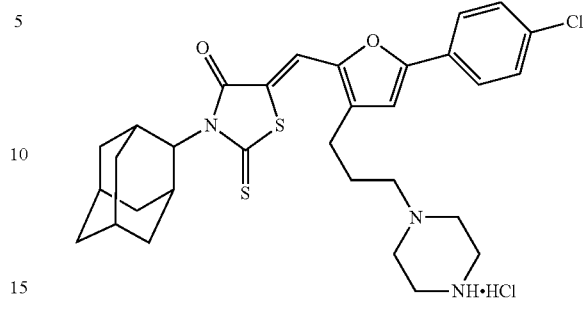

¹H-NMR (300 MHz, DMSO-d6): 7.82 (d, J=8.4, 2H), 7.67-7.58 (m, 2H), 7.56 (d, J=3.0, 1H), 7.38 (d, J=3.3, 1H), 4.84 (d, J=7.2, 1H), 3.28-3.00 (m, 4H), 2.76 (t, J=6.9, 2H), 2.60-2.47 (m, 9H), 2.11-1.97 (m, 2H), 1.90 (s, 5H), 1.75-1.63 (m, 4H), 1.22-1.13 (m, 2H).

(Z)-3-(bicyclo[2.2.1]heptan-2-yl)-5-((5-(4'-chlorophenyl)-3-(3-(piperazin-1-yl)pentyl)furan-2-yl)-methylene)-2-thioxothiazolidin-4-one hydrochloride

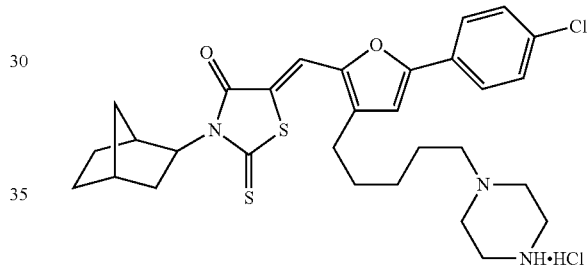

¹H NMR (300 MHz, DMSO-d6)): 9.72-9.51 (broad, 2H), 7.80 (d, J=2.4, 2H), 7.61 (d, J=2.4, 2H), 7.45 (s, 1H), 7.35 (s, 1H), 4.84 (d, J=7.2, 1H), 3.75-2.98 (m, 10H), 2.66 (d, J=6.9, 2H), 2.37 (s, 1H), 2.31-2.18 (m, 2H), 1.80-1.39 (m, 7H), 1.38-1.15 (m, 6H).

(Z)-3-(bicyclo[2.2.1]heptan-2-yl)-5-((5-(3-methoxyphenyl)-3-(5-(piperazin-1-yl)pentyl)furan-2-yl)methylene)-2-thioxothiazolidin-4-one dihydrochloride

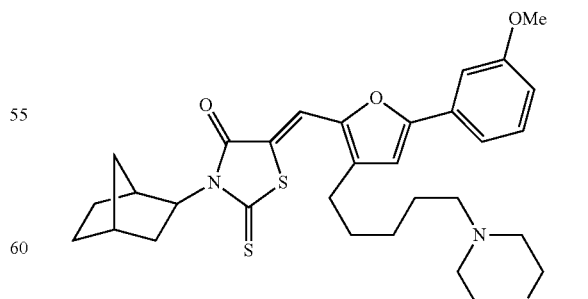

¹H-NMR (300 MHz, DMSO-d₆): 11.6 (board, 1H), 9.57 (board, 2H), 7.50 (s, 1H), 7.36 (m=7.47-7.36, 3H), 7.32 (s, 1H), 7.01 (dd, J=1.5 Hz, 1H), 4.85 (t, J=6.6 Hz, 1H), 3.86 (s, 3H), 3.46 (board, 2H), 3.46 (m=3.49-3.46, 4H), 3.09 (m=3.12-3.09, 2H), 2.67 (t, J=7.2 Hz, 2H), 2.30 (s, 1H), 2.21 (m=2.29-2.21, 2H), 1.70 (m=1.73-1.70, 2H), 1.63 (m=1.68-1.63, 2H), 1.54 (m=1.59-1.54, 2H), 1.34 (m=1.40-1.34, 2H), 1.34 (m=1.40-1.34, 2H), 1.20 (m=1.29-1.20, 2H). HRMS (ESI): 565.2438 (M+H).

The sides chain of C-ring containing N or S are also modified using methods known to those skilled in the art in view of the present disclosure.

(Z)-3-(bicyclo[2.2.1]heptan-2-yl)-5-((5-(4-chlorophenyl)-3-(5-(piperazin-1-yl)pentyl)-1H-pyrrol-2-yl)methylene)-2-thioxothiazolidin-4-one dihydrochloride

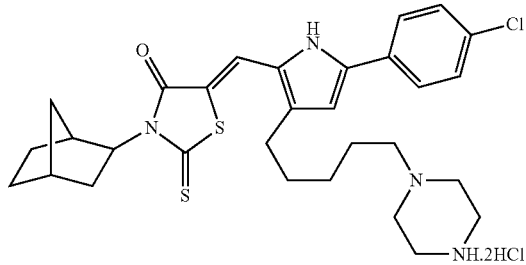

$^1$H-NMR (300 MHz, DMSO-$d_6$): 13.02 (s, 1H), 11.6 (board, 1H), 7.70 (dd, J=6.0 Hz, 2H), 7.62 (s, 1H), 7.60 (dd, J=6.0 Hz, 2H), 6.92 (d, J=2.4 Hz, 1H), 4.98 (t, J=7.5 Hz, 1H), 3.64 (t, J=6.6 Hz, 1H), 3.13 (board, 1H), 2.63 (m=2.72-2.63, 2H), 2.28 (m=2.33-2.28, 4H), 1.68 (m=1.75-1.68, 2H), 3.12 (t, J=5.4 Hz, 2H), 2.82 (t, J=7.2 Hz, 2H), 2.37 (s, 1H), 2.19 (m=2.28-2.19, 2H), 1.56 (m=1.63-1.56, 4H), 1.43 (m=1.47-1.43, 1H), 1.22 (m=1.30-1.22, 5H). HRMS (ESI): 567.2019 (M−H-2HCl).

(Z)-3-(bicyclo[2.2.1]heptan-2-yl)-5-((5-(3-methoxyphenyl)-3-(5-(piperazin-1-yl)pentyl)-1H-pyrrol-2-yl)methylene)-2-thioxothiazolidin-4-one dihydrochloride

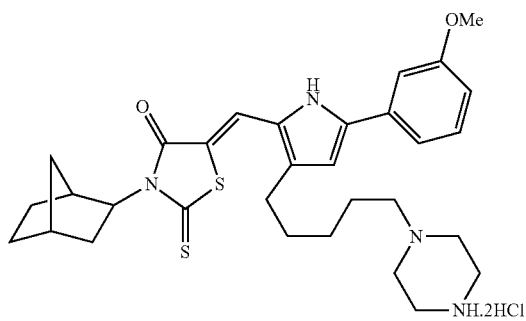

$^1$H-NMR (300 MHz, DMSO-$d_6$): 13.25 (s, 1H), 11.8 (board, 1H), 9.78 (board, 2H), 7.62 (s, 1H), 7.39 (m=7.43-7.39, 1H), 7.23 (m=7.32-7.23, 2H), 6.98 (m=7.23-6.98, 2H), 4.98 (t, J=7.5 Hz, 1H), 3.82 (s, 3H), 3.42 (m=3.51-3.42, 4H), 3.13 (m=3.28-3.13, 2H), 2.68 (m=2.71-2.68, 2H), 2.43 (s, 1H), 2.26 (m=2.35-2.26, 1H), 1.62 (m=1.73-1.62, 2H), 1.52 (m=1.61-1.53, 4H), 1.26 (m=1.35-1.26, 5H). HRMS (ESI): 565.2671 (M+H−2HCl).

(Z)-3-(bicyclo[2.2.1]heptan-2-yl)-5-((5-(4-chlorophenyl)-1-methyl-3-(5-(piperazin-1-yl)pentyl)-1H-pyrrol-2-yl)methylene)-2-thioxothiazolidin-4-one dihydrochloride

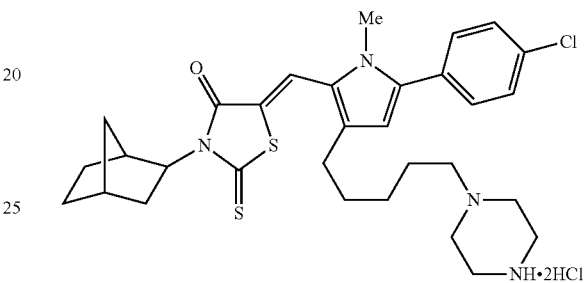

$^1$H-NMR (300 MHz, DMSO-$d_6$): 11.80 (board, 1H), 9.85 (board, 2H), 7.63 (s, 1H), 7.46 (m=7.50-7.43, 4H), 6.39 (s, 1H), 5.04 (s, 1H), 3.56 (s, 3H), 3.09 (s, 2H), 2.48 (m=2.51-2.48, 4H), 2.35 (m=2.42-2.35, 2H), 1.85 (m=1.93-2.85, 6H), 1.71 (m=1.78-1.71, 4H), 1.60 (m=1.68-1.60, 2H), 1.35 (m=1.42-1.35, 2H), 1.22 (m=1.30-1.22, 2H). HRMS (ESI): 583.2340 (M−2HCl).

(Z)-3-(bicyclo[2.2.1]heptan-2-yl)-5-((5-(4-chlorophenyl)-3-(5-(piperazin-1-yl)pentyl)thiophen-2-yl)methylene)-2-thioxothiazolidin-4-one dihydrochloride

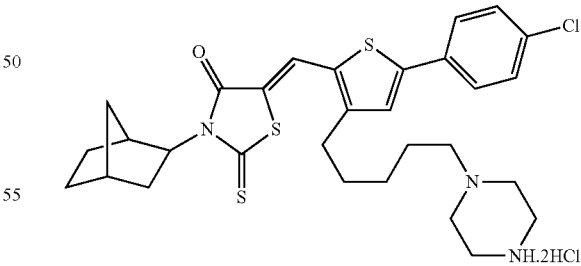

$^1$H-NMR (300 MHz, DMSO-$d_6$): 11.6 (board, 1H), 9.56 (s, 1H), 7.83 (s, 1H), 7.80 (d, J=5.4 Hz, 2H), 7.74 (s, 1H), 7.51 (d, J=5.7 Hz, 2H), 4.83 (s, 1H), 3.53 (m=3.56-3.53, 2H), 3.39 (m=3.48-3.39, 4H), 3.19 (m=3.26-3.19, 2H), 3.12 (t, J=5.4 Hz, 2H), 2.82 (t, J=7.2 Hz, 2H), 2.37 (s, 1H), 2.19 (m=2.28-2.19, 2H), 1.63 (m=1.74-1.63, 6H), 1.53 (m=1.54-1.53, 2H), 1.36 (m=1.40-1.36, 2H), 1.22 (m=1.25-1.22, 5H). HRMS (ESI): 586.1799 (M+H-2HCl).

123

(Z)-3-(bicyclo[2.2.1]heptan-2-yl)-5-((5-(3-methoxyphenyl)-3-(5-(piperazin-1-yl)pentyl)thiophen-2-yl)methylene)-2-thioxothiazolidin-4-one dihydrochloride

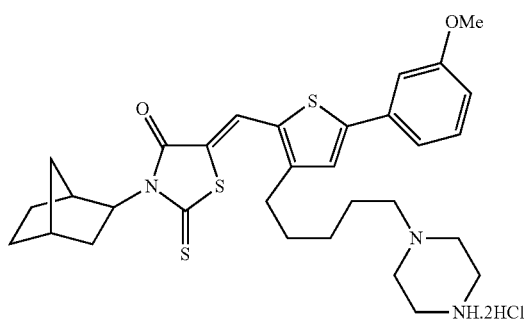

$^1$H-NMR (300 MHz, DMSO-$d_6$): 11.7 (board, 1H), 9.64 (board, 2H), 7.78 (s, 1H), 7.74 (s, 1H), 7.30 (m=7.39-7.30, 3H), 6.96 (m=6.98-6.96, 1H), 4.82 (dd, J=6.0 Hz, 1H), 3.83 (s, 3H), 3.60 (m=3.65-3.60, 2H), 3.19 (m=3.28-3.19, 4H), 2.81 (t, J=7.5 Hz, 2H), 2.43 (s, 1H), 2.30 (m=2.32-2.30, 2H), 1.75 (m=1.79-1.75, 4H), 1.69 (m=1.73-1.69, 3H), 1.60 (m=1.65-1.60, 5H), 1.46 (m=1.49-1.45, 2H), 1.26 (m=1.38-1.26, 4H). HRMS (ESI): 582.2240 (M+H-2HCl).

Synthesis of Type-12: Modification of Side Chain in C-Ring (Furan) with Guanidine Moiety

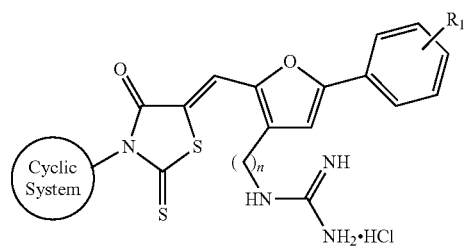

This type of compound was prepared according to the synthetic route below.

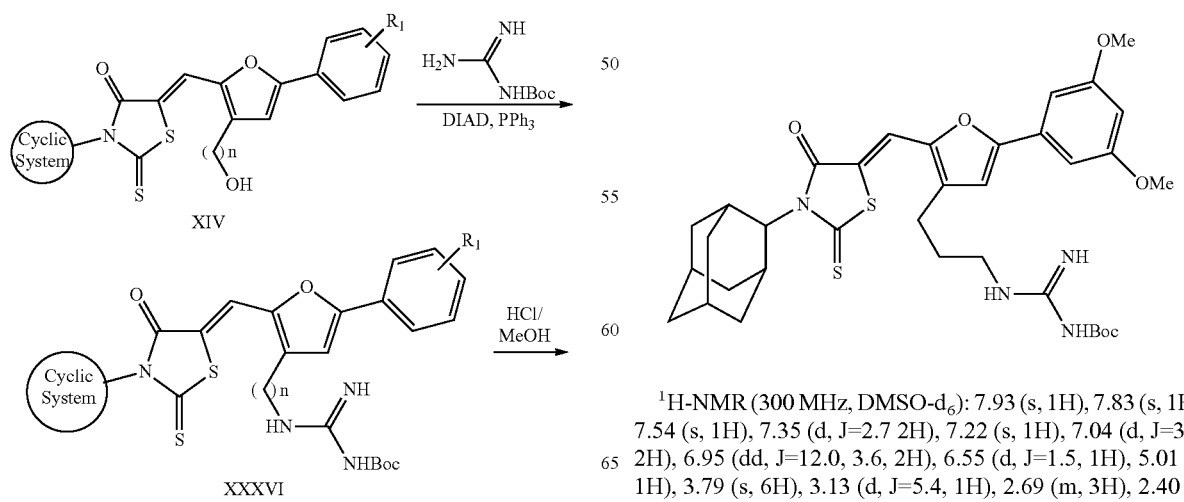

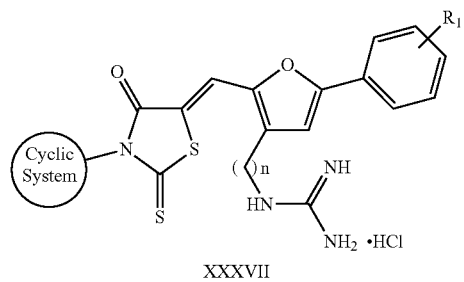

XXXVII

General Procedure of Mitsunobu Reaction

Diisopropylazodicarboxylate (DIAD) (0.80 mmol) was added dropwise to a solution of alcohol compound XIV (0.40 mmol), N,N-bis-(tert-butyloxycarbonyl)guanidine (0.19 g, 1.20 mmol) and PPh$_3$ (0.23 g, 0.88 mmol) in dried THF (15 mL), and the mixture was stirred overnight at room temperature. The THF was evaporated, and the residual oil was purified by a flash chromatography (PE/EA) on silica gel to give the corresponding Boc-gunadine products XXXVI.

General Procedure of Deprotection Reaction

To solution of Boc-gunadine product XXXVI (0.16 mmol) in 20 ml of methanol solution was stirred overnight at room temperature. After the solvent was evaporated, and the residue was purified by a recrystallization from diethyl ether to give the corresponding product XXXVII as illustrated below.

N-1-(3-(2-((Z)-(3-(bicyclo[2.2.1]heptan-2-yl)-4-oxo-2-thioxothiazolidin-5-ylidene)methyl)-5-(3',5'-dimeth-oxyphenyl)furan-3-yl)propyl)-N-Boc guanidine $^1$H-NMR (300 MHz, DMSO-$d_6$): 7.93 (s, 1H), 7.83 (s, 1H), 7.54 (s, 1H), 7.35 (d, J=2.7 2H), 7.22 (s, 1H), 7.04 (d, J=3.0, 2H), 6.95 (dd, J=12.0, 3.6, 2H), 6.55 (d, J=1.5, 1H), 5.01 (s, 1H), 3.79 (s, 6H), 3.13 (d, J=5.4, 1H), 2.69 (m, 3H), 2.40 (s, 3H), 1.86 (m, 6H), 1.71 (s, 2H), 1.60 (m, 2H), 1.15 (m, 1H).

N-1-(3-(2-((Z)-(3-(bicyclo[2.2.1]heptan-2-yl)-4-oxo-2-thioxothiazolidin-5-ylidene)methyl)-5-(3'-hydroxy-5'-methoxyphenyl)furan-3-yl)propyl)guanidine hydrochloride

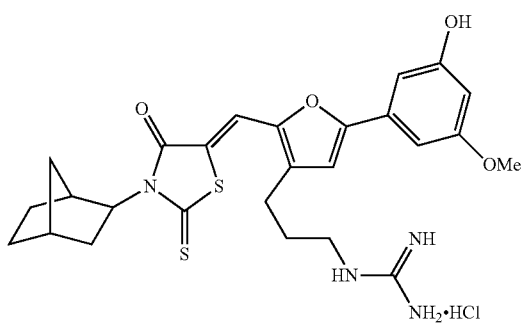

Red-brown solid in 80% yield, $^1$H NMR (DMSO-d6, 300 MHz): 10.01 (s, 1H), 7.51 (s, 1H), 7.26 (s, 1H), 7.13-7.11 (m, 2H), 6.83 (d, J=1.8, 1H), 6.42 (s, 1H), 4.82-4.80 (m, 1H), 3.75 (s, 3H), 2.82-2.80 (m, 4H), 2.30 (s, 1H), 2.24-2.22 (m, 2H), 1.97-1.95 (m, 2H), 1.73-1.71 (m, 1H), 1.57-1.55 (m, 2H), 1.13-1.11 (m, 3H).

N-1-(3-(2-((Z)-(3-(bicyclo[2.2.1]heptan-2-yl)-4-oxo-2-thioxothiazolidin-5-ylidene)methyl)-5-(3',5'-dimeth-oxyphenyl)furan-3-yl)propyl)guanidine hydrochloride

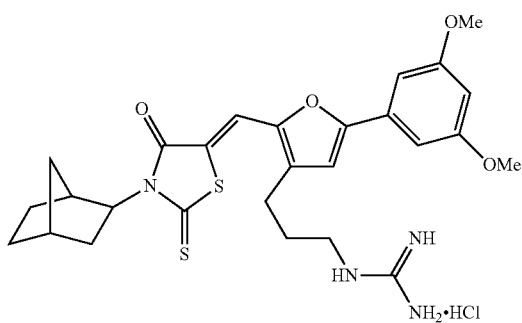

$^1$H-NMR (300 MHz, DMSO-d6): 8.10 (s, 2H), 7.48 (m, 3H), 7.28 (s, 1H), 7.11 (s, 1H), 6.95 (d, J=2.1, 2H), 6.56 (s, 1H), 4.82 (m, 1H), 3.80 (s, 6H), 3.19 (m, 2H), 2.70 (m, 2H), 2.34 (m, 4H), 1.72 (m, 3H), 1.50 (m, 4H), 1.22 (m, 6H).

N-1-(3-(2-((Z)-(3-(adamantan-2-yl)-4-oxo-2-thioxothiazolidin-5-ylidene)methyl)-5-(3',5'-dimethoxy-phenyl)furan-3-yl)propyl)guanidine hydrochloride

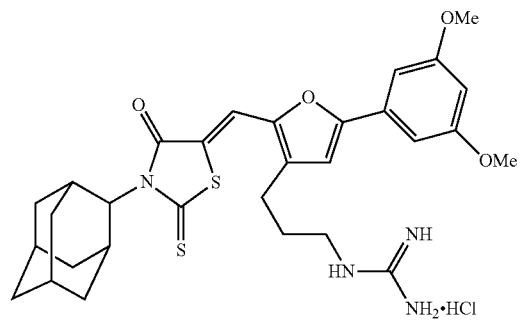

$^1$H-NMR (300 MHz, DMSO-d6): 7.93 (s, 1H), 7.83 (s, 1H), 7.54 (s, 1H), 7.35 (d, J=2.7 2H), 7.22 (s, 1H), 7.04 (d, J=3.0, 2H), 6.95 (d, J=12.0, 2H), 6.55 (d, J=1.5, 1H), 5.01 (s, 1H), 3.79 (s, 6H), 3.13 (d, J=5.4, 1H), 2.69 (m, 3H), 2.40 (s, 3H), 1.86 (m, 6H), 1.71 (s, 2H), 1.60 (m, 2H), 1.15 (m, 1H). HRMS (ESI):

N-1-(3-(2-((Z)-(3-(bicyclo[2.2.1]heptan-2-yl)-4-oxo-2-thioxothiazolidin-5-ylidene)methyl)-5-(4'-chlorophenyl)furan-3-yl)propyl)guanidine hydrochloride

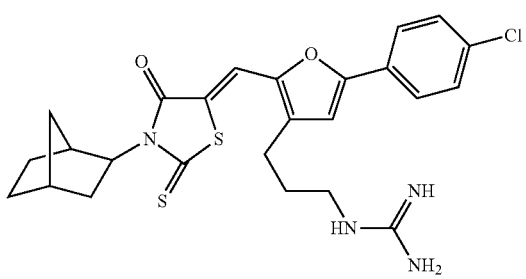 [SMILES: N=C(N)NCCCc1cc(-c2ccc(Cl)cc2)oc1/C=C1\SC(=S)N(C2CC3CCC2C3)C1=O]

$^1$H-NMR (300 MHz, DMSO-d6): 8.02 (s, 2H), 7.80 (d, J=8.4, 2H), 7.67-7.63 (m, 2H), 7.61 (s, 2H), 7.54-7.52 (s, 1H), 7.42 (s, 1H), 7.35-7.24 (s, 2H), 7.08 (s, 2H), 4.86 (dd, J=5.7, 2.6, 1H), 2.88-2.81 (m, 2H), 2.76 (t, J=15.3, 2H), 2.64 (s, 1H), 2.38 (s, 2H), 1.07-1.02 (m, 5H). HRMS (ESI): 515.1332 (M).

Synthesis of Type-13: Modification of Side Chain in C-Ring (Furan) with Heterocyclic

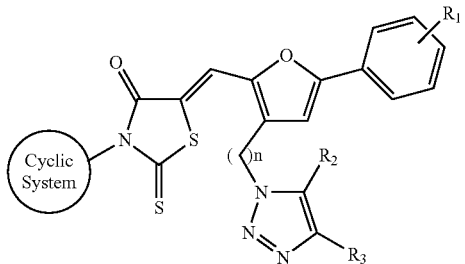

This type of compound was prepared according to the synthetic route below.

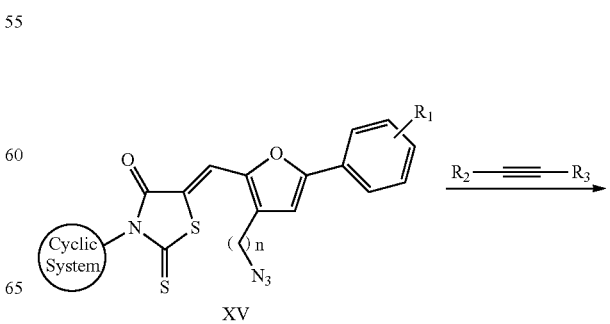

-continued

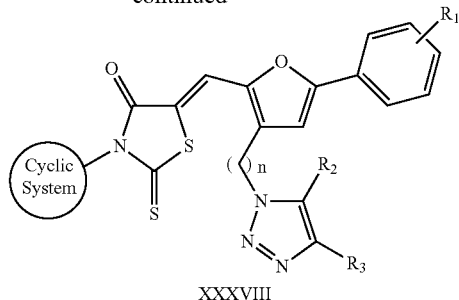

XXXVIII

General Procedure of Click Reaction

A solution of azide compound XV (10.0 mmol), propargyl alcohol (0.67 g, 12.0 mmol) in 50 ml of THF/H$_2$O (v/v=4/1) was added CuSO$_4$ (0.16 g, 1.0 mmol), and sodium ascorbate (1.0 mmol). The resulting mixture was stirred vigorously at room temperature for 2-4 h (as monitored by TLC analysis). Some precipitate was formed and collected by a simple filtration. After the precipitate was washed with water (3×25 mL), it was dried in air or further purified by flash chromatography to afford the pure product.

(Z)-3-(bicyclo[2.2.1]heptan-2-yl)-5-((5-(3',5'-dimethoxyphenyl)-3-(3-(4'-(hydroxymethyl)-1H-1',2',3'-triazol-1-yl)propyl)furan-2-yl)methylene)-2-thioxothiazolidin-4-one

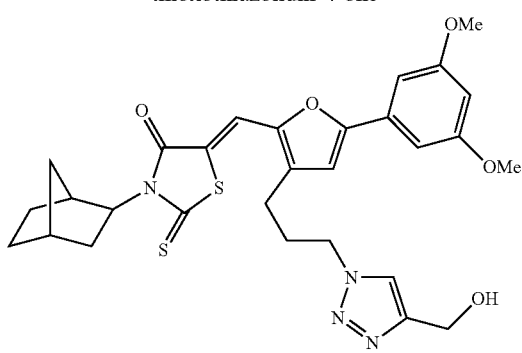

$^1$H-NMR (300 MHz, DMSO-d6): 8.00 (s, 1H), 7.41 (s, 1H), 7.34 (s, 1H), 6.93 (s, 2H), 6.5 (d, J=1.8, 1H), 5.19 (s, 1H), 4.84 (t, J=6.3, 1H), 4.50 (s, 2H), 4.00 (t, J=1.8, 1H), 3.85 (s, 6H), 2.71 (t, 2H), 2.37 (s, 1H), 2.12-2.24 (m, 4H), 1.70 (t, J=9.9, 1H), 1.53 (m, 2H), 1.20 (m, 2H). HRMS (ESI): 581.1901 (M+H).

(Z)-3-(adamantan-2-yl)-5-((5-(3',5'-dimethoxyphenyl)-3-(3-(4'-(hydroxymethyl)-1H-1',2',3'-triazol-1-yl)-propyl)furan-2-yl)methylene)-2-thioxothiazolidin-4-one

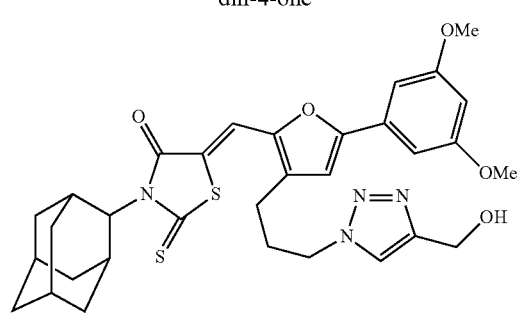

Red solid, 80%. $^1$H-NMR (300 MHz, DMSO-d6): 8.02 (s, 1H), 7.43 (s, 1H), 7.36 (s, 1H), 6.95 (s, 2H), 6.7 (d, J=1.8, 1H), 5.21 (s, 1H), 4.85 (t, J=6.3, 1H), 4.55 (s, 2H), 4.00 (t, J=1.8, 1H), 3.85 (s, 6H), 2.72 (t, 2H), 2.45-2.43 (m, 3H), 2.18-2.16 (m, 2H), 1.90-1.87 (m, 6H), 1.74-1.63 (m, 4H).

General Procedure of Hügens Reaction

A solution of azide compound (10.0 mmol), but-2-yne-1,4-diol (1.03 g, 12.0 mmol) in 50 ml of DMF was heated to 120° C. for 12 h (as monitored by TLC analysis). Removing the DMF, and the residue was purified by a recrystallization from diethyl ether or a flash chromatography (CH$_2$Cl$_2$/HOAc) on silica gel to give the corresponding product as illustrated above.

(Z)-3-(bicyclo[2.2.1]heptan-2-yl)-5-((3-(3-(4',5'-bis(hydroxymethyl)-1H-1',2',3'-triazol-1-yl)propyl)-5-(3',5'-dimethoxyphenyl)furan-2-yl)methylene)-2-thioxothiazolidin-4-one

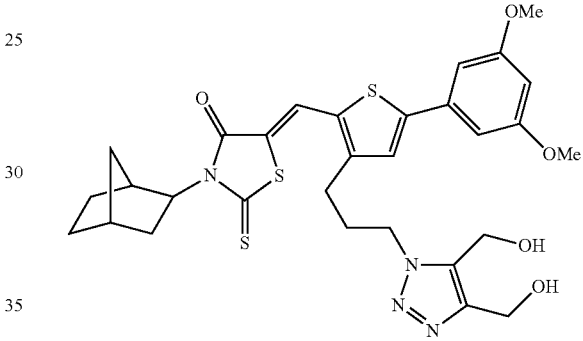

$^1$H-NMR (300 MHz, DMSO-d6): 7.46 (s, 1H), 7.36 (s, 1H), 6.93 (s, 1H), 6.94 (s, 1H), 6.55 (t, J=2.1, 1H), 5.36 (t, J=5.4, 1H), 5.00 (t, J=5.7, 1H), 4.85 (m, 1H), 4.58 (d, J=5.7, 2H), 4.46 (d, J=5.7, 2H), 4.50 (s, 2H), 4.40 (t, J=7.2, 2H), 4.35 (t, J=6.9, 2H), 3.80 (s, 6H), 2.70 (t, 2H), 2.30 (s, 1H), 2.12-2.24 (m, 4H), 1.52 (m, 1H), 1.50 (m, 2H), 1.20 (m, 4H). HRMS (ESI): 611.2006 (M+H).

(Z)-3-(adamantan-2-yl)-5-((3-(3-(4',5'-bis(hydroxymethyl)-1H-1',2',3'-triazol-1-yl)propyl)-5-(3',5'-dimetho-xyphenyl)furan-2-yl)methylene)-2-thioxothiazolidin-4-one

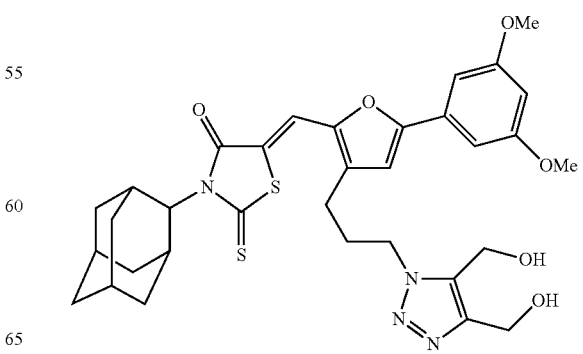

¹H-NMR (300 MHz, DMSO-d6): 7.51 (s, 1H), 7.38 (s, 1H), 6.96 (s, 2H), 6.57 (s, 1H), 5.36 (s, 1H), 5.04 (s, 2H), 4.60 (d, J=4.5, 1H), 4.49 (d, J=5.1, 2H), 4.40 (d, J=4.5, 2H), 3.82 (s, 6H), 2.72 (m, 2H), 2.44 (m, 3H), 2.17 (m, 2H), 1.89 (m, 6H), 1.73-1.64 (m, 4H).

Synthesis of Type-14: Modification of Side Chain in C-Ring (Furan) with Ether Moiety

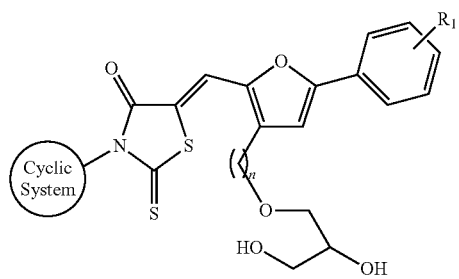

This type of compound was prepared according to the synthetic route below.

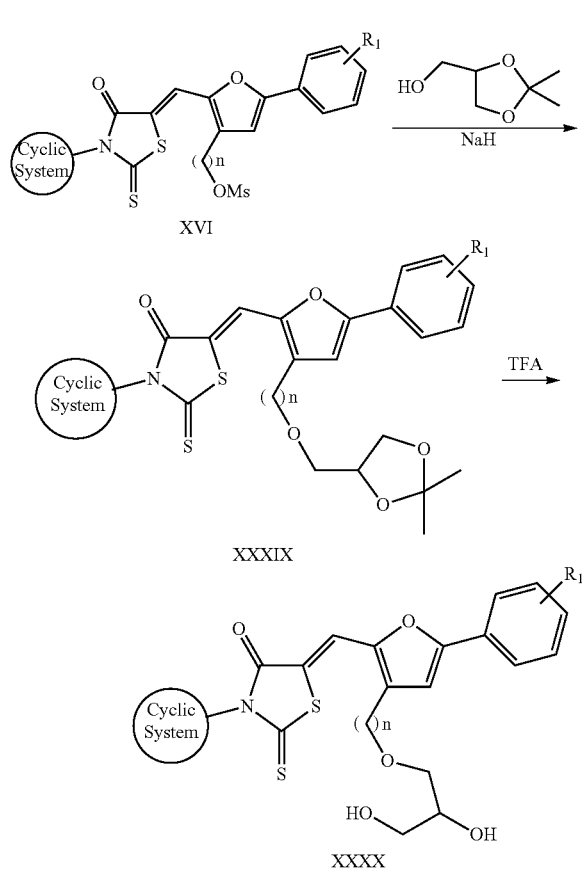

General Procedure of the Synthesis of Ether Compound XXXIX

To a solution of alcohol compound (0.13 g, 1.0 mmol) in DMF (10 mL) was added NaH (40 mg, 60% in mineral oil, 1.0 mmol), and the mixture was stirred at 0° C. for 30 min. Then mesylate compound XVI (1.1 mmol) was added and stirred until the starting material disappeared. The reaction was quenched by addition of water, and then extracted with saturated diethyl ether, dried with $MgSO_4$. The solvent was removed under vacuum, and the residue was purified by a flash chromatography (PE/EA) on silica gel to afford the corresponding ether products XXXIX.

General Procedure of Deprotection Reaction

To a solution of the compound made above in saturated HCl in methanol (20 mL) at 0° C., and then formed mixture was stirred at room temperature until the starting material was fully consumed. The reaction mixture was concentrated, and the residue was purified by a recrystallization from diethyl ether to give the corresponding product XXXX as illustrated below.

(Z)-3-(bicyclo[2.2.1]heptan-2-yl)-5-((3-(3-((S)-2,3-dihydroxypropoxy)propyl)-5-(3',5'-dimethoxy-phenyl)-furan-2-yl)methylene)-2-thioxothiazolidin-4-one

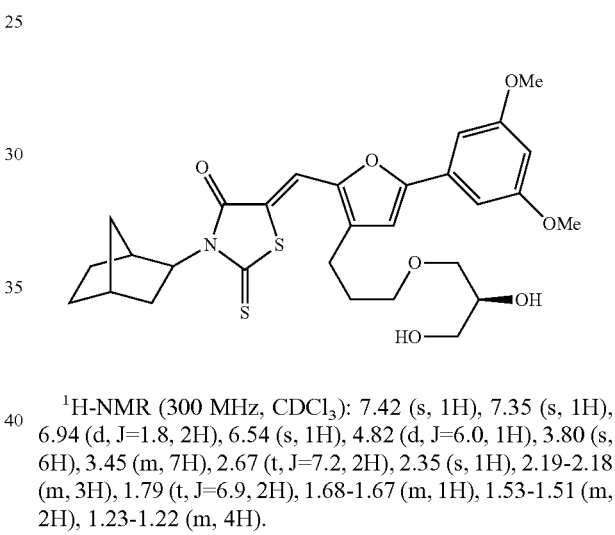

¹H-NMR (300 MHz, CDCl₃): 7.42 (s, 1H), 7.35 (s, 1H), 6.94 (d, J=1.8, 2H), 6.54 (s, 1H), 4.82 (d, J=6.0, 1H), 3.80 (s, 6H), 3.45 (m, 7H), 2.67 (t, J=7.2, 2H), 2.35 (s, 1H), 2.19-2.18 (m, 3H), 1.79 (t, J=6.9, 2H), 1.68-1.67 (m, 1H), 1.53-1.51 (m, 2H), 1.23-1.22 (m, 4H).

(Z)-3-(bicyclo[2.2.1]heptan-2-yl)-5-((3-(3-((S)-2,3-dihydroxypropoxy)propyl)-5-(4'-chlorophenyl)-furan-2-yl)methylene)-2-thioxothiazolidin-4-one

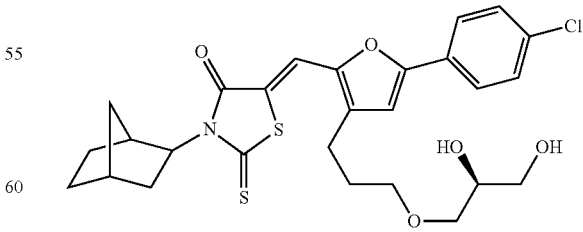

¹H-NMR (300 MHz, CDCl₃): 7.69-7.68 (m, 2H), 7.43-7.42 (m, 3H), 6.74 (s, 1H), 4.97 (d, J=6.3, 1H), 3.96 (t, J=4.5, 1H), 3.78-3.77 (m, 2H), 3.50 (d, J=4.2, 2H), 3.46 (t, J=5.7, 2H), 2.95 (d, J=3.6, 1H), 2.74 (t, J=7.2, 2H), 2.56 (s, 1H), 2.47

(s, 1H), 2.34-2.32 (m, 3H), 1.92 (t, J=6.0, 2H), 1.87-1.85 (m, 1H), 1.35-1.34 (m, 4H), 1.23-1.22 (m, 2H).

(Z)-3-(bicyclo[2.2.1]heptan-2-yl)-5-((3-(3-((S)-2,3-dihydroxypropoxy)propyl)-5-(4'-fluorophenyl)-furan-2-yl)methylene)-2-thioxothiazolidin-4-one

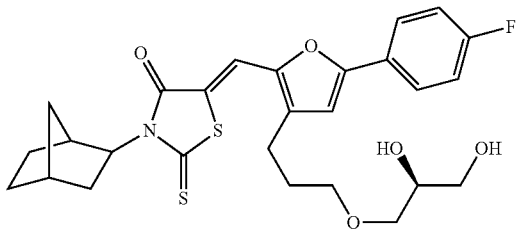 [SMILES: O=C1/C(=C/c2oc(-c3ccc(F)cc3)cc2CCCOC[C@@H](O)CO)SC(=S)N1C1CC2CCC1C2]

$^1$H-NMR (300 MHz, CDCl$_3$): 7.75 (dd, J=8.7, 5.1, 2H), 7.47 (s, 1H), 7.18 (t, J=8.7, 2H), 6.70 (s, 1H), 4.97 (t, J=7.8, 1H), 3.96 (t, J=4.5, 1H), 3.75 (m, 2H), 3.52 (d, J=4.8, 2H), 3.96 (t, J=4.8, 2H), 2.74 (t, J=6.9, 2H), 2.56 (s, 1H), 2.46 (s, 1H), 2.34 (m, 2H), 1.90 (t, J=6.6, 2H), 1.84 (m, 2H), 1.36 (m, 1H), 1.29 (m, 3H).

Synthesis of Type-15: Missing C-Ring

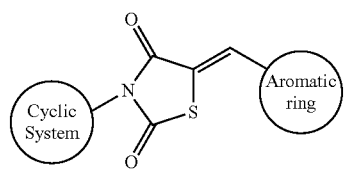

This type of compound was prepared according to the synthetic route below.

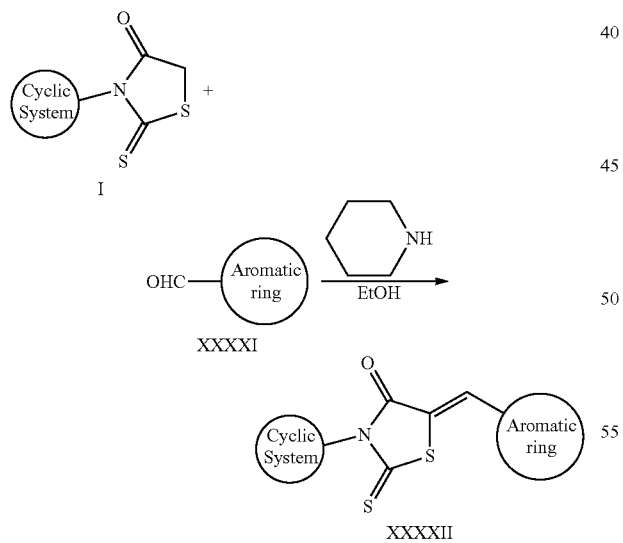

General procedure for the Synthesis of (Z)-3-cycloalkyl-5-((5-arylfuran-2-yl)methylene)-2-thioxothiazolidin-4-one III To a solution of 3-N-cycloalkyl-2-thioxothiazolidin-4-one I (0.5 mmol) and 5-substituted arylfuran-2-yl carboxaldehyde XXXXI (0.5 mmol) in EtOH (5 mL) was added anhydrous piperidine (43 mg, 0.5 mmol) at room temperature, and the mixture was refluxed for 16 h. After cooling to room temperature, the mixture was diluted with ethyl acetate (50 mL), and the organic phase was washed with water (3×10 mL), and then dried over anhydrous Na$_2$SO$_4$. The solvent was removed under vacuum, and the residue was recrystallized from ethyl acetate-hexane or a flash chromatography (CH$_2$Cl$_2$) on silica gel to afford the desired products XXXXII as illustrated below.

(Z)-5-(benzofuran-2-ylmethylene)-3-(decahydronaphthalen-2-yl)-2-thioxothiazolidin-4-one

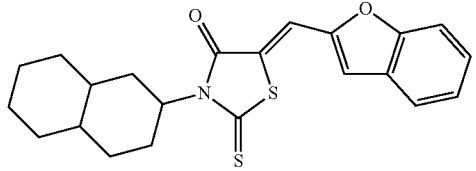 [SMILES: O=C1/C(=C/c2cc3ccccc3o2)SC(=S)N1C1CCC2CCCCC2C1]

$^1$H-NMR (300 MHz, CDCl$_3$): 7.63 (d, J=7.5, 1H), 7.54 (d, J=7.5, 1H), 7.46 (s, 1H), 7.43-7.42 (m, 1H), 7.30-7.29 (m, 1H), 7.12 (s, 1H), 5.28-5.07 (m, 1H), 2.83-2.61 (m, 2H), 1.90-1.85 (m, 2H), 1.81-1.75 (m, 4H), 1.70-1.61 (m, 3H), 1.48-1.43 (m, 3H), 1.38-1.21 (m, 8H).

(Z)-5-((6-bromo-4-oxo-4H-chromen-3-yl)methylene)-3-(decahydronaphthalen-2-yl)-2

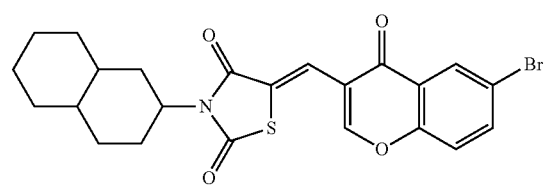 [SMILES: O=C1S/C(=C\c2coc3ccc(Br)cc3c2=O)C(=O)N1C1CCC2CCCCC2C1]

$^1$H-NMR (300 MHz, CDCl$_3$): 8.41 (t, J=2.3, 1H), 8.14 (s, 1H), 7.82 (q, J=3.8, 1H), 7.45 (d, J=13.1, 1H), 7.41 (d, J=8.9, 1H), 5.05 (s, 1H), 3.52 (s, 1H), 2.60 (d, J=12.3, 2H), 1.70 (m, 6H), 1.38 (m, 8H).

(Z)-3-(bicyclo[2.2.1]heptan-2-yl)-5-(furan-2-ylmethylene)-2-thioxothiazolidin-4-one

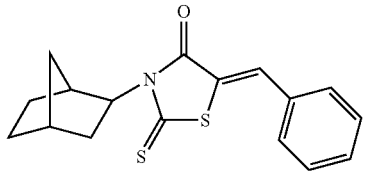 [SMILES: O=C1/C(=C/c2ccccc2)SC(=S)N1C1CC2CCC1C2]

¹H-NMR (300 MHz, CDCl₃): 7.61 (s, 1H), 7.45 (m, 5H), 4.95 (m, 1H), 2.56 (s, 1H), 2.47 (s, 1H), 2.36-2.28 (m, 2H), 1.79 (t, J=10.8, 1H), 1.70-1.50 (m, 2H), 1.48-1.20 (m, 3H).

(Z)-5-((6-bromo-4-oxo-4H-chromen-3-yl)methylene)-2-thioxo-3-(1,7,7-trimethylbicyclo[2.2.1]heptan-2-yl)-thiazolidin-4-one

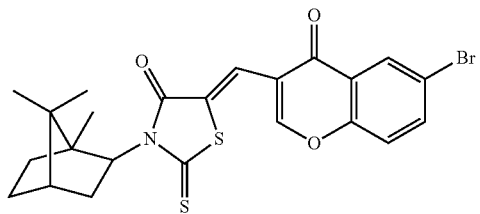 [SMILES: CC1(C)C2CCC1(C)C(N1C(=O)/C(=C/c3coc4ccc(Br)cc4c3=O)SC1=S)C2]

¹H-NMR (300 MHz, CDCl₃): 8.40 (d, J=1.9, 1H), 8.14 (s, 1H), 7.81 (q, J=3.5, 1H), 7.41 (t, J=6.4, 2H), 5.27 (t, J=9.0, 1H), 3.65 (q, J=6.81, 1H), 2.17 (s, 1H), 1.87 (s, 2H), 1.67 (t, J=10.1, 2H), 1.56 (s, 2H), 1.31 (t, J=4.2, 1H), 1.15 (s, 2H), 0.86 (d, J=25.3, 6H).

(Z)-3-(adamantan-2-yl)-5-(furan-2-ylmethylene)-2-thioxothiazolidin-4-one

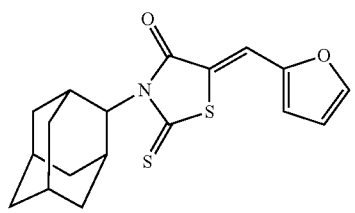 [SMILES: O=C1/C(=C/c2ccco2)SC(=S)N1C1C2CC3CC(C2)CC1C3]

¹H-NMR (300 MHz, CDCl₃): 7.69 (s, 1H), 7.38 (d, J=3.0, 1H), 6.79 (s, 1H), 6.58 (s, 1H), 5.14 (s, 1H), 2.58-2.32 (m, 5H), 2.09-1.88 (m, 8H), 1.83-1.65 (m, 6H).

3-adamantan-2-yl-5-(6-bromo-4-oxo-4H-chromen-3-ylmethylene)-2-thioxo-thiazolidin-4-one

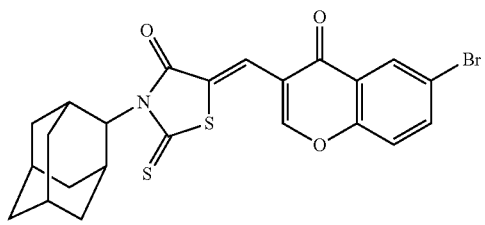 [SMILES: O=C1/C(=C/c2coc3ccc(Br)cc3c2=O)SC(=S)N1C1C2CC3CC(C2)CC1C3]

¹H-NMR (300 MHz, CDCl₃): 8.41 (d, J=2.4, 1H), 8.14 (s, 1H), 7.83 (q, J=3.80, 1H), 7.46 (d, J=0.6, 1H), 7.41 (d, J=9.0, 1H), 5.13 (s, 1H), 2.45 (t, J=13.2, 4H), 1.96 (d, J=8.1, 6H), 1.75 (t, J=14.4, 4H).

3-adamantan-2-yl-5-benzo[b]thiophen-3-ylmethylene-2-thioxo-thiazolidin-4-one

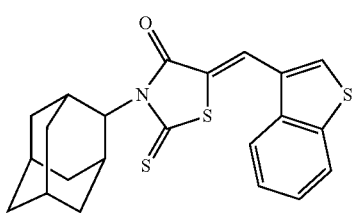

¹H-NMR (300 MHz, CDCl₃): 7.83 (m, 2H), 7.66 (s, 1H), 7.51-7.28 (m, 3H), 5.16 (s, 1H), 2.53 (m, 6H), 1.99-1.35 (m, 8H).

3-adamantan-2-yl-5-(5-bromo-1H-indol-2-ylmethylene)-2-thioxo-thiazolidin-4-one

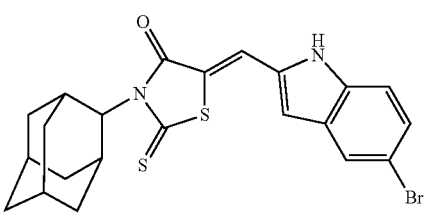 [SMILES: O=C1/C(=C/c2cc3cc(Br)ccc3[nH]2)SC(=S)N1C1C2CC3CC(C2)CC1C3]

¹H-NMR (300 MHz, CDCl₃): 8.82 (s, 1H), 8.03 (m, 2H), 7.85 (d, J=7.2, 1H), 7.47 (m, 1H), 7.38 (m, 1H), 5.18 (s, 1H), 2.53 (m, 6H), 1.99-1.35 (m, 8H).

(Z)-5-(benzo[b]thiophen-2-ylmethylene)-3-(bicyclo[2.2.1]heptan-2-yl)-2-thioxothiazolidin-4-one

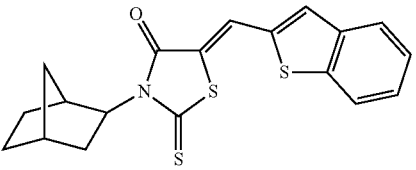

¹H-NMR (300 MHz, CDCl₃): 7.87 (d, J=6.0, 2H), 7.80 (s, 1H), 7.60 (s, 1H), 7.43 (t, J=4.5, 2H), 4.97-4.92 (t, J=6.6, 1H), 2.57 (s, 1H), 2.47 (s, 1H), 2.38-2.22 (m, 3H), 1.79 (t, J=11.1, 1H), 1.39-1.26 (m, 4H).

3-adamantan-2-yl-5-(1H-indol-3-ylmethylene)-2-thioxo-thiazolidin-4-one

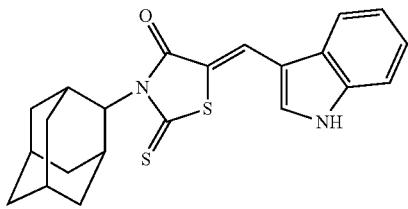 [SMILES: O=C1/C(=C/c2c[nH]c3ccccc23)SC(=S)N1C1C2CC3CC(C2)CC1C3]

¹H-NMR (300 MHz, CDCl₃): 8.82 (s, 1H), 8.03 (s, 1H), 7.85 (d, J=7.2, 1H), 7.47 (m, 2H), 7.38 (m, 2H), 5.18 (s, 1H), 2.53 (m, 4H), 2.06-1.92 (m, 6H), 1.82-1.73 (m, 4H).

(Z)-5-((1H-indol-3-yl)methylene)-3-(bicyclo[2.2.1]heptan-2-yl)-2-thioxothiazolidin-4-one

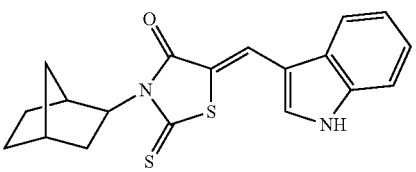 [SMILES: O=C1/C(=C/c2c[nH]c3ccccc23)SC(=S)N1C1CC2CCC1C2]

¹H-NMR (300 MHz, CDCl₃): 8.83-8.78 (m, 1H), 8.01 (s, 1H), 7.86 (d, J=9.0, 1H), 7.50-7.39 (m, 2H), 7.34-7.24 (m, 1H), 5.05-4.96 (m, 1H), 2.57 (s, 1H), 2.45 (s, 1H), 2.39-2.21 (m, 3H), 1.82-1.68 (m, 1H), 1.60-1.42 (m, 2H), 1.38-1.20 (m, 2H).

(Z)-5-(benzofuran-2-ylmethylene)-3-(bicyclo[2.2.1]heptan-2-yl)-2-thioxothiazolidin-4

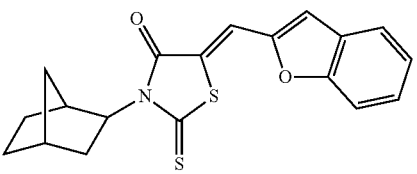 [SMILES: O=C1/C(=C/c2cc3ccccc3o2)SC(=S)N1C1CC2CCC1C2]

¹H-NMR (300 MHz, CDCl₃): 7.64 (d, J=6.0, 1H), 7.55 (d, J=9.0, 1H), 7.46 (d, J=3.0, 1H), 7.42 (d, J=1.2, 1H), 7.31 (d, J=3.0, 1H), 7.12 (m, 1H), 4.98-4.85 (m, 1H), 2.57 (s, 1H), 2.47 (s, 1H), 2.38-2.22 (m, 3H), 1.79 (t, J=12.0, 1H), 1.65-1.46 (m, 2H), 1.41-1.24 (m, 2H).

3-adamantan-2-yl-5-benzofuran-2-ylmethylene-2-thioxo-thiazolidin-4-one

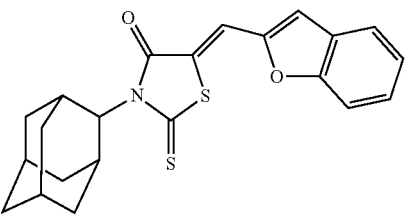 [SMILES: O=C1/C(=C/c2cc3ccccc3o2)SC(=S)N1C1C2CC3CC(C2)CC1C3]

¹H-NMR (300 MHz, CDCl₃): 7.63 (d, J=6.0, 1H), 7.55 (d, J=6.0, 1H), 7.47 (d, J=1.8, 1H), 7.44-7.36 (m, 1H), 7.30-7.26 (m, 1H), 7.10 (s, 1H), 5.16 (s, 1H), 2.51 (s, 2H), 2.45 (d, J=9.0, 2H), 2.02-1.86 (m, 6H), 1.80 (s, 2H), 1.73 (d, J=9.0, 2H).

(Z)-3-cycloheptyl-5-(furan-2-ylmethylene)-2-thioxothiazolidin-4-one

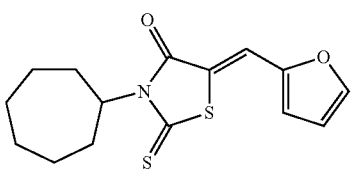 [SMILES: O=C1/C(=C/c2ccco2)SC(=S)N1C1CCCCCC1]

¹H-NMR (300 MHz, CDCl₃): 7.66 (d, J=1.8, 1H), 7.35 (s, 1H), 6.78 (d, J=3.0, 1H), 6.55 (q, J=1.8, 1H), 5.21-5.05 (m, 1H), 2.48-2.21 (m, 2H), 1.89-1.71 (m, 4H), 1.70-1.37 (m, 6H).

(Z)-3-cycloheptyl-5-(furan-2-ylmethylene)-2-thioxothiazolidin-4-one

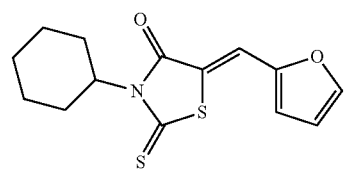 [SMILES: O=C1/C(=C/c2ccco2)SC(=S)N1C1CCCCC1]

¹H-NMR (500 MHz, CDCl₃): 7.68 (d, J=0.9, 1H), 7.36 (s, 1H), 6.79 (d, J=2.1, 1H), 6.57 (q, J=1.1, 1H), 5.08-4.95 (m, 1H), 2.41 (d, J=6.0, 2H), 1.88 (d, J=6.0, 2H), 1.70-1.68 (m, 3H), 1.45-1.21 (m, 3H).

Synthesis of Type-16: Modification of Aliphatic Chain as D-Ring

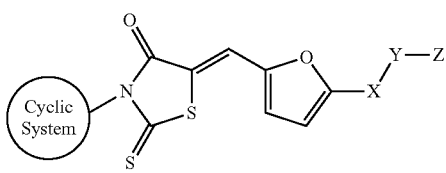

This type of compound was prepared according to the synthetic route below.

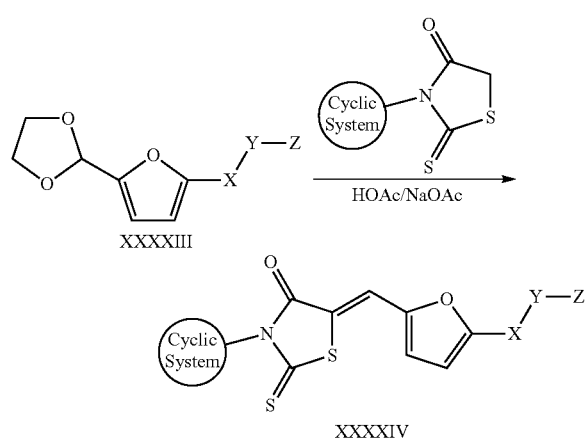

X = H, CH, CH₂; Y = CH, CH₂
Z = CO₂H, CO₂R, CONH—AA—OR, CH₂OH, CONH₂

General Procedure of Condensation Reaction

To a solution of 3-N-cycloalkyl-2-thioxothiazolidin-4-one I (0.5 mmol) and acetal XXXXIII (0.5 mmol) in AcOH (5 mL) was added anhydrous AcONa (123 mg, 1.5 mmol) at room temperature, and the mixture was refluxed for 16 h. After cooling to room temperature, the mixture was diluted with ethyl acetate (50 mL), and the organic phase was washed with water (3×10 mL), and then dried over anhydrous Na₂SO₄. The solvent was removed under vacuum, and the residue was recrystallized from ethyl acetate-hexane to give the corresponding products XXXXIV.

(E)-Methyl 3-(5-((Z)-(3-(bicyclo[2.2.1]heptan-2-yl)-4-oxo-2-thioxothiazolidin-5-ylidene)methyl)-furan-2-yl)acrylate

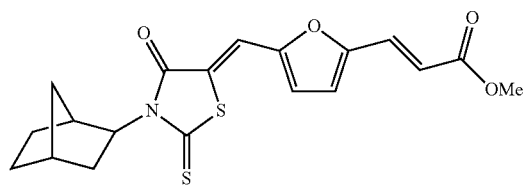 [SMILES: COC(=O)/C=C/c1ccc(/C=C2\SC(=S)N(C3CC4CCC3C4)C2=O)o1]

$^1$H-NMR (300 MHz, CDCl₃): 7.45 (d, J=15, 2H), 7.32 (s, 1H), 6.85 (d, J=3.0, 1H), 6.74 (d, J=3.0, 1H), 6.49 (d, J=15, 1H), 4.97-4.92 (m, 1H), 3.55 (s, 1H), 2.55 (s, 1H), 2.46 (s, 1H), 2.39-2.21 (m, 3H), 1.79-1.52 (m, 5H).

(E)-ethyl 3-(5-((Z)-(3-(decahydronaphthalen-2-yl)-4-oxo-2-thioxothiazolidin-5-ylidene)methyl)-furan-2-yl)acrylate

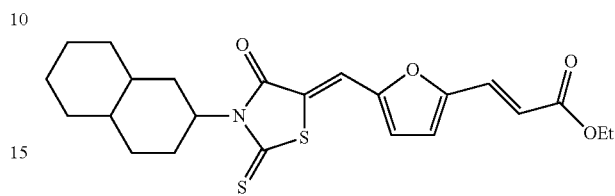

$^1$H-NMR (300 MHz, CDCl₃): 7.45 (d, J=15.9, 1H), 7.32 (d, J=4.2, 1H), 6.85 (d, J=3.6, 1H), 6.73 (d, J=3.9, 1H), 6.48 (d, J=9.5, 1H), 5.27 and 5.05 (m, total 1H,), 4.30 (q, J=4.3, 2H), 2.82 and 2.58 (m, total 2H), 1.89-1.25 (m, 17H).

(E)-Ethyl 3-(5-((Z)-(3-(adamantan-2-yl)-4-oxo-2-thioxothiazolidin-5-ylidene)methyl)furan-2-yl)acrylate

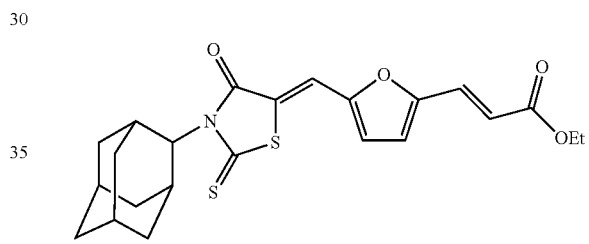

$^1$H-NMR (300 MHz, CDCl₃): 7.45 (d, J=15.9, 1H), 7.34 (d, J=4.2, 1H), 6.84 (d, J=3.6, 1H), 6.74 (d, J=3.9, 1H), 6.51 (d, J=3.9, 1H), 5.14 (s, 1H,), 4.31 (q, J=4.3, 2H), 2.45 (d, J=7.7, 4H), 1.98 (d, J=0.9, 6H), 1.75 (q, J=9.4, 4H), 1.39 (q, J=3.7, 3H).

(E)-Ethyl 3-(5-((Z)-(3-(adamantan-2-yl)-4-oxo-2-thioxothiazolidin-5-ylidene)methyl)furan-2-yl)acrylate

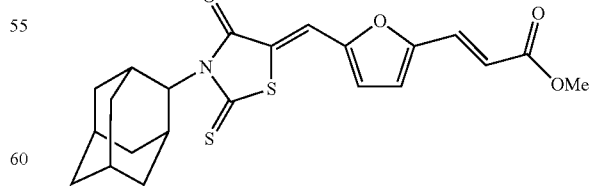

$^1$H-NMR (300 MHz, CDCl₃): 7.45 (d, J=15, 1H), 7.33 (s, 1H), 6.83 (d, J=3.0, 1H), 6.74 (d, J=3.0, 1H), 6.48 (d, J=18, 1H), 5.14 (s, 1H), 3.86 (s, 3H), 2.54-2.38 (m, 4H), 2.08-1.84 (m, 7H), 1.80-1.65 (m, 3H).

(E)-Ethyl 3-(5-((Z)-(3-(adamantan-2-yl)-4-oxo-2-thioxothiazolidin-5-ylidene)methyl)furan-2-yl)acrylate

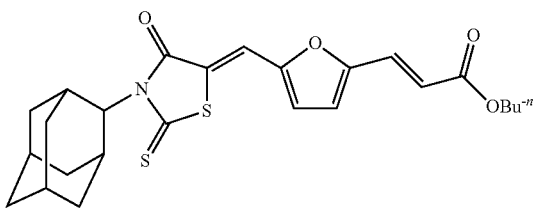

$^1$H-NMR (300 MHz, CDCl$_3$): 7.49 (d, J=15.6, 1H), 7.34 (s, 1H), 6.84 (d, J=3.6, 1H), 6.74 (d, J=3.3, 1H), 6.48 (d, J=15.9, 1H), 5.14 (s, 1H), 4.24 (d, J=6.6, 2H), 2.45 (d, J=7.0, 4H), 1.98 (d, J=4.2, 6H), 1.81 (m, 2H), 1.73 (m, 4H), 1.45 (m, 2H), 0.98 (t, J=7.5, 3H).

Table 1 lists compounds according to embodiments of the present invention. The EC$_{50}$ and virus yield classifications are based on assays for inhibiting influenza virus infection.

TABLE 1

| Compound No | Structure | MW | EC$_{50}$ | Virus Yield |
|---|---|---|---|---|
| | Type-1 Basic Skeleton | | | |
| 1 | 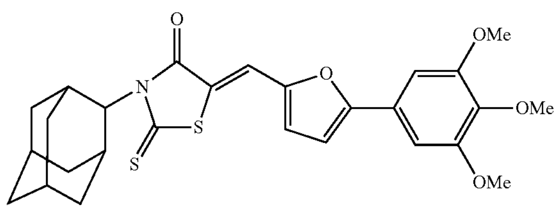 [SMILES: COc1cc(-c2ccc(/C=C3\SC(=S)N(C4C5CC6CC(C5)CC4C6)C3=O)o2)cc(OC)c1OC] | C27H29NO5S2 Exact Mass: 511.1487 Molecular Weight: 511.6529 | A | A |
| 2 | 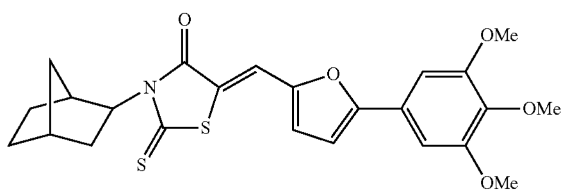 [SMILES: COc1cc(-c2ccc(/C=C3\SC(=S)N(C4CC5CCC4C5)C3=O)o2)cc(OC)c1OC] | C24H25NO5S2 Exact Mass: 471.1174 Molecular Weight: 471.5890 | A | B |
| 3 | 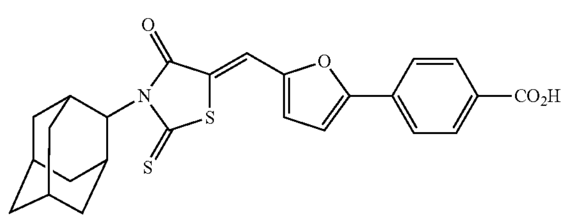 [SMILES: O=C(O)c1ccc(-c2ccc(/C=C3\SC(=S)N(C4C5CC6CC(C5)CC4C6)C3=O)o2)cc1] | C25H23NO4S2 Exact Mass: 465.1068 Molecular Weight: 465.5844 | A | B |
| 4 | 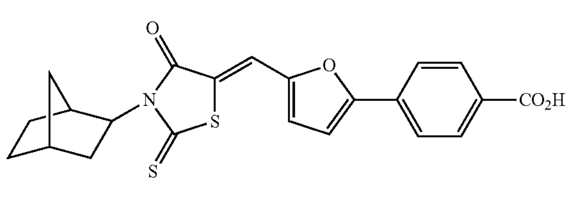 [SMILES: O=C(O)c1ccc(-c2ccc(/C=C3\SC(=S)N(C4CC5CCC4C5)C3=O)o2)cc1] | C22H19NO4S2 Exact Mass: 425.0755 Molecular Weight: 425.5206 | A | C |

TABLE 1-continued

| Compound No | Structure | MW | EC$_{50}$ | Virus Yield |
|---|---|---|---|---|
| 5 | 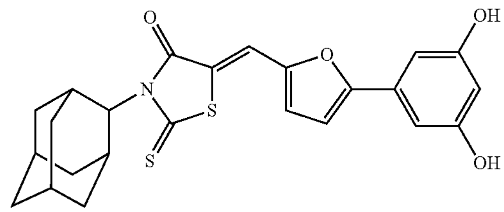 [SMILES: O=C1/C(=C/c2ccc(-c3cc(O)cc(O)c3)o2)SC(=S)N1C1C2CC3CC(C2)CC1C3] | C24H23NO4S2<br>Exact Mass: 453.1068<br>Molecular Weight: 453.5737 | A | A |
| 6 | 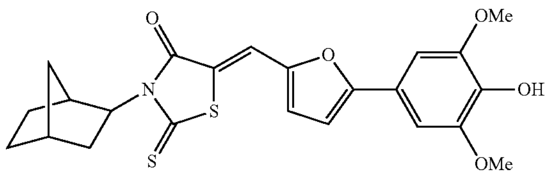 [SMILES: COc1cc(-c2ccc(/C=C3\SC(=S)N(C4CC5CCC4C5)C3=O)o2)cc(OC)c1O] | C23H23NO5S2<br>Exact Mass: 457.1018<br>Molecular Weight: 457.5624 | NA** | A |
| 7 | 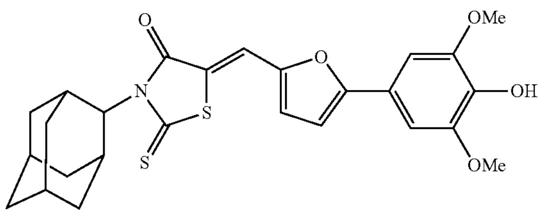 [SMILES: COc1cc(-c2ccc(/C=C3\SC(=S)N(C4C5CC6CC(C5)CC4C6)C3=O)o2)cc(OC)c1O] | C26H27NO5S2<br>Exact Mass: 497.1331<br>Molecular Weight: 497.6263 | A | C |
| 8 | 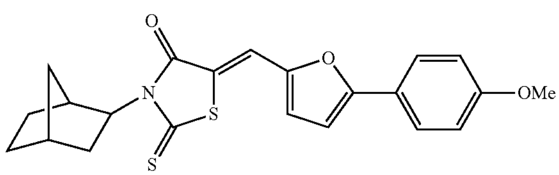 [SMILES: COc1ccc(-c2ccc(/C=C3\SC(=S)N(C4CC5CCC4C5)C3=O)o2)cc1] | C22H21NO3S2<br>Exact Mass: 411.0963<br>Molecular Weight: 411.5370 | A | A |
| 9 | 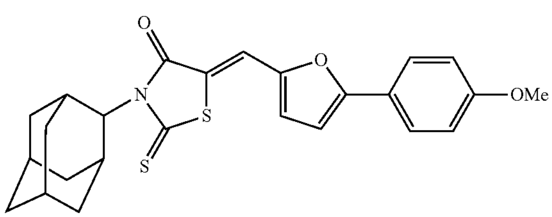 [SMILES: COc1ccc(-c2ccc(/C=C3\SC(=S)N(C4C5CC6CC(C5)CC4C6)C3=O)o2)cc1] | C25H25NO3S2<br>Exact Mass: 451.1276<br>Molecular Weight: 451.6009 | A | A |
| 10 | 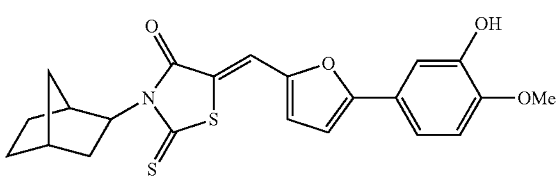 [SMILES: COc1ccc(-c2ccc(/C=C3\SC(=S)N(C4CC5CCC4C5)C3=O)o2)cc1O] | C22H21NO4S2<br>Exact Mass: 427.0912<br>Molecular Weight: 427.5364 | A | A |
| 11 | 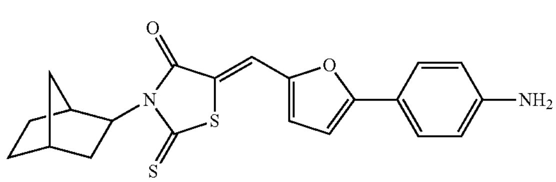 [SMILES: Nc1ccc(-c2ccc(/C=C3\SC(=S)N(C4CC5CCC4C5)C3=O)o2)cc1] | C21H20N2O2S2<br>Exact Mass: 396.0966<br>Molcular Weight: 396.5257 | A | C |
| 12 | 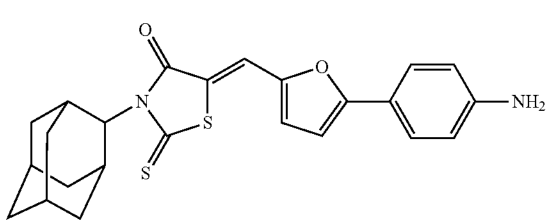 [SMILES: Nc1ccc(-c2ccc(/C=C3\SC(=S)N(C4C5CC6CC(C5)CC4C6)C3=O)o2)cc1] | C24H24N2O2S2<br>Exact Mass: 436.1279<br>Molecular Weight: 436.5896 | A | B |

TABLE 1-continued

| Compound No | Structure | MW | EC$_{50}$ | Virus Yield |
|---|---|---|---|---|
| 13 | 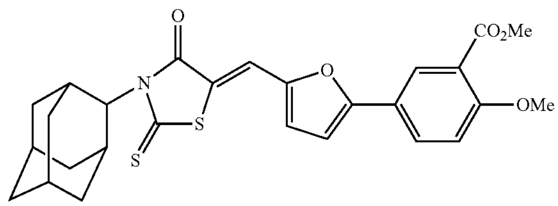 | C27H27NO5S2<br>Exact Mass: 509.1331<br>Molecular Weight: 509.6370 | A | A |
| 14 | 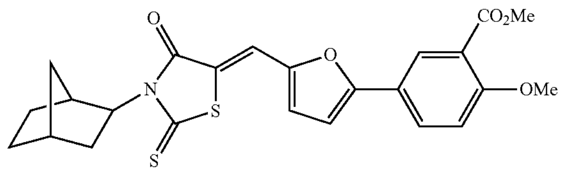 | C24H23NO5S2<br>Exact Mass: 469.1018<br>Molecular Weight: 469.5731 | A | A |
| 15 | 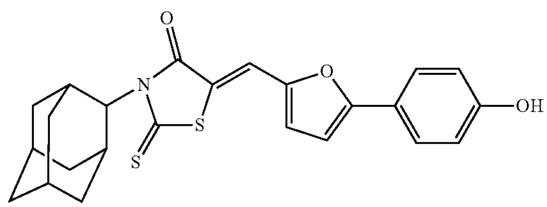 [SMILES: O=C1/C(=C/c2ccc(-c3ccc(O)cc3)o2)SC(=S)N1C1C2CC3CC(C2)CC1C3] | C24H23NO3S2<br>Exact Mass: 437.1119<br>Molecular Weight: 437.5743 | A | A |
| 16 | 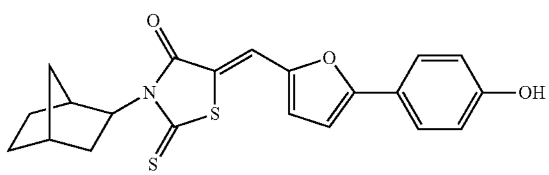 [SMILES: O=C1/C(=C/c2ccc(-c3ccc(O)cc3)o2)SC(=S)N1C1CC2CCC1C2] | C21H19NO3S2<br>Exact Mass: 397.0806<br>Molecular Weight: 397.5105 | NA | A |
| 17 | 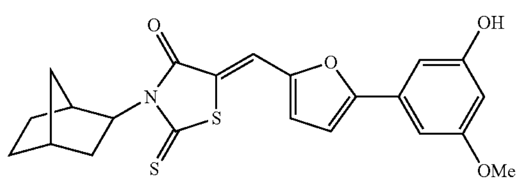 | C22H21NO4S2<br>Exact Mass: 427.0912<br>Molecular Weight: 427.5364 | A | A |
| 18 | 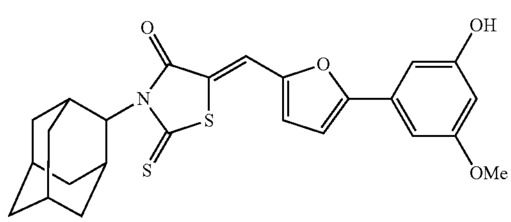 [SMILES: COc1cc(O)cc(-c2ccc(/C=C3\SC(=S)N(C4C5CC6CC(C5)CC4C6)C3=O)o2)c1] | C25H25NO4S2<br>Exact Mass: 467.1225<br>Molecular Weight: 467.6003 | A | A |
| 19 | 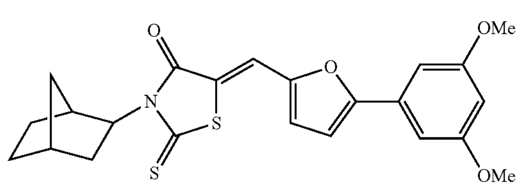 [SMILES: COc1cc(OC)cc(-c2ccc(/C=C3\SC(=S)N(C4CC5CCC4C5)C3=O)o2)c1] | C23H23NO4S2<br>Exact Mass: 441.1068<br>Molecular Weight: 441.5630 | A | A |

TABLE 1-continued

| Compound No | Structure | MW | EC$_{50}$ | Virus Yield |
|---|---|---|---|---|
| 20 | 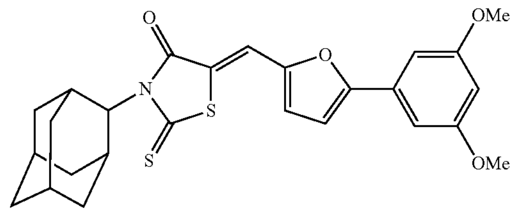 [SMILES: COc1cc(OC)cc(-c2ccc(/C=C3\SC(=S)N(C4C5CC6CC(C5)CC4C6)C3=O)o2)c1] | C26H27NO4S2<br>Exact Mass: 481.1381<br>Molecular Weight: 481.6269 | A | A |
| 21 | 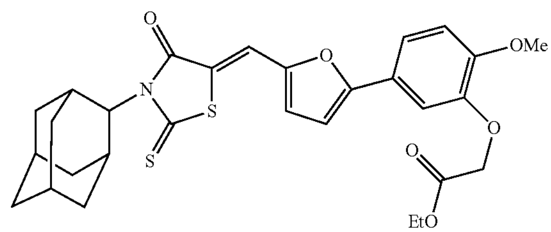 [SMILES: CCOC(=O)COc1cc(-c2ccc(/C=C3\SC(=S)N(C4C5CC6CC(C5)CC4C6)C3=O)o2)ccc1OC] | C29H31NO6S2<br>Exact Mass: 553.1593<br>Molecular Weight: 553.6895 | A | A |
| 22 | 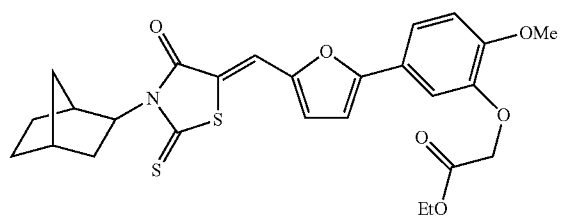 | C26H27NO6S2<br>Exact Mass: 513.1280<br>Molecular Weight: 513.6257 | A | A |
| 23 | 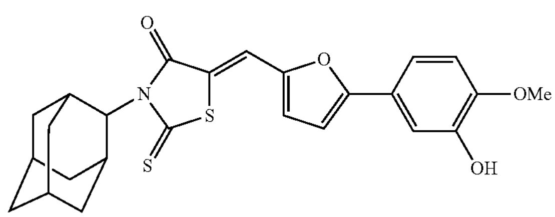 [SMILES: COc1ccc(-c2ccc(/C=C3\SC(=S)N(C4C5CC6CC(C5)CC4C6)C3=O)o2)cc1O] | C25H25NO4S2<br>Exact Mass: 467.1225<br>Molecular Weight: 467.6003 | A | A |
| 24 | 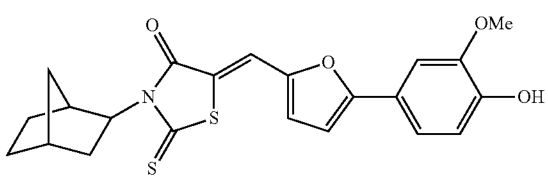 [SMILES: COc1cc(-c2ccc(/C=C3\SC(=S)N(C4CC5CCC4C5)C3=O)o2)ccc1O] | C22H21NO4S2<br>Exact Mass: 427.0912<br>Molecular Weight: 427.5364 | A | A |
| 25 | 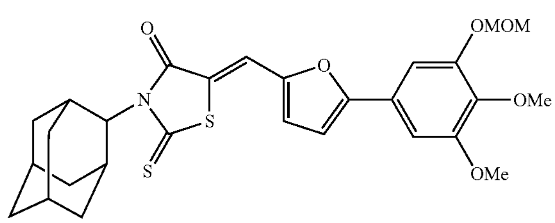 | C28H31NO6S2<br>Exact Mass: 541.1593<br>Molecular Weight: 541.6788 | A | A |
| 26 | 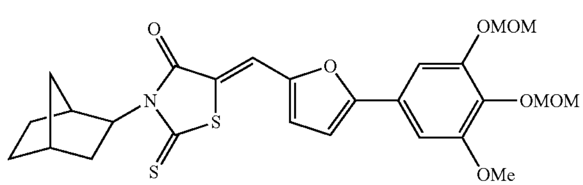 | C26H29NO7S2<br>Exact Mass: 531.1385<br>Molecular Weight: 531.6410 | A | A |

TABLE 1-continued

| Compound No | Structure | MW | EC$_{50}$ | Virus Yield |
|---|---|---|---|---|
| 27 | 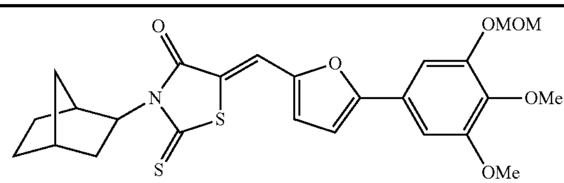 | C25H27NO6S2<br>Exact Mass: 501.1280<br>Molecular Weight: 501.6150 | A | A |
| 28 | 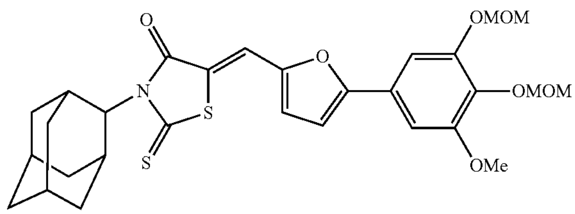 | C29H33NO7S2<br>Exact Mass: 571.1698<br>Molecular Weight: 571.7048 | NA | A |
| 29 | 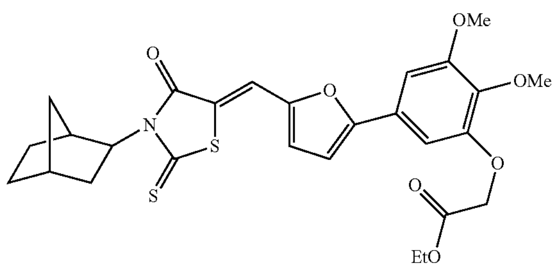 [SMILES: CCOC(=O)COc1cc(-c2ccc(/C=C3\SC(=S)N(C4CC5CCC4C5)C3=O)o2)cc(OC)c1OC] | C27H29NO7S2<br>Exact Mass: 543.1385<br>Molecular Weight: 543.6517 | A | A |
| 30 | 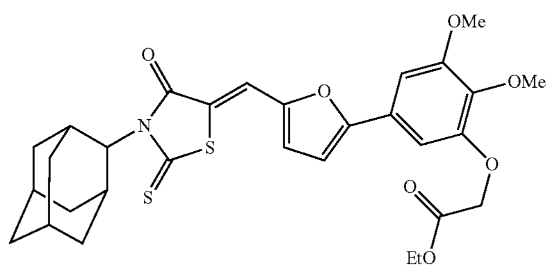 [SMILES: CCOC(=O)COc1cc(-c2ccc(/C=C3\SC(=S)N(C4C5CC6CC(C5)CC4C6)C3=O)o2)cc(OC)c1OC] | C30H33NO7S2<br>Exact Mass: 583.1698<br>Molecular Weight: 583.7155 | A | A |
| 31 | 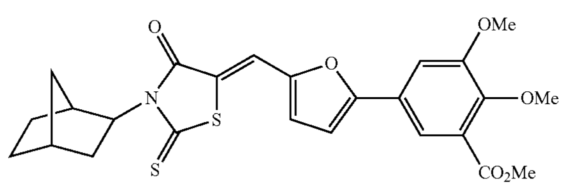 [SMILES: COC(=O)c1cc(-c2ccc(/C=C3\SC(=S)N(C4CC5CCC4C5)C3=O)o2)cc(OC)c1OC] | C25H25NO6S2<br>Exact Mass: 499.1123<br>Molecular Weight: 499.5991 | A | A |
| 32 | 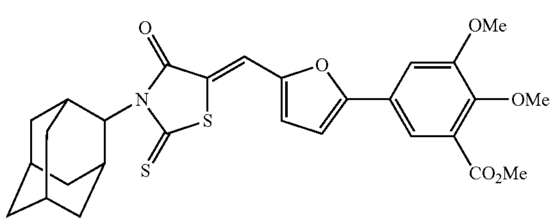 [SMILES: COC(=O)c1cc(-c2ccc(/C=C3\SC(=S)N(C4C5CC6CC(C5)CC4C6)C3=O)o2)cc(OC)c1OC] | C28H29NO6S2<br>Exact Mass: 539.1436<br>Molecular Weight: 539.6630 | A | A |
| 33 | 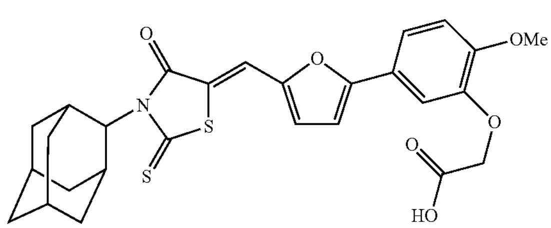 [SMILES: COc1ccc(-c2ccc(/C=C3\SC(=S)N(C4C5CC6CC(C5)CC4C6)C3=O)o2)cc1OCC(=O)O] | C27H27NO6S2<br>Exact Mass: 525.1280<br>Molecular Weight: 525.6364 | A | A |

TABLE 1-continued

| Compound No | Structure | MW | EC$_{50}$ | Virus Yield |
|---|---|---|---|---|
| 34 | 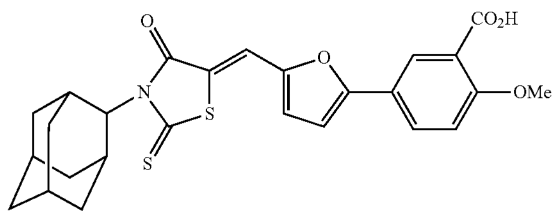 [SMILES: COc1ccc(-c2ccc(/C=C3\SC(=S)N(C4C5CC6CC(C5)CC4C6)C3=O)o2)cc1C(=O)O] | C26H25NO5S2<br>Exact Mass: 495.1174<br>Molecular Weight: 495.6104 | A | A |
| 35 | 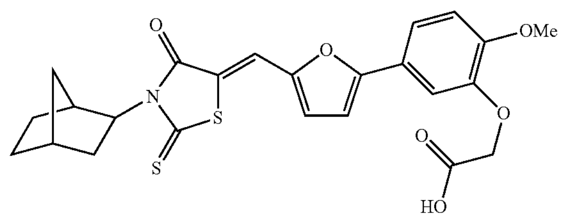 | C24H23NO6S2<br>Exact Mass: 485.0967<br>Molecular Weight: 485.5725 | A | B |
| 36 | 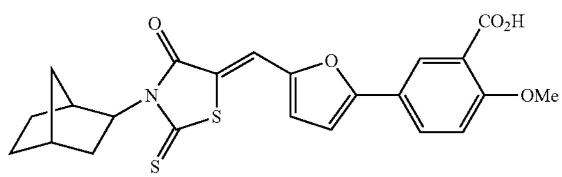 [SMILES: COc1ccc(-c2ccc(/C=C3\SC(=S)N(C4CC5CCC4C5)C3=O)o2)cc1C(=O)O] | C23H21NO5S2<br>Exact Mass: 455.0861<br>Molecular Weight: 455.5465 | A | B |
| 37 | 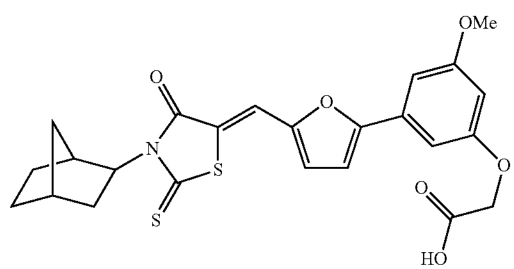 [SMILES: COc1cc(OCC(=O)O)cc(-c2ccc(/C=C3\SC(=S)N(C4CC5CCC4C5)C3=O)o2)c1] | C24H23NO6S2<br>Exact Mass: 485.0967<br>Molecular Weight: 485.5725 | A | B |
| 38 | 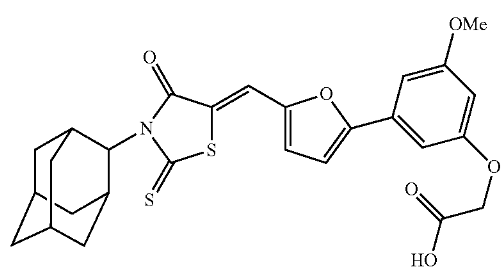 [SMILES: COc1cc(OCC(=O)O)cc(-c2ccc(/C=C3\SC(=S)N(C4C5CC6CC(C5)CC4C6)C3=O)o2)c1] | C27H27NO6S2<br>Exact Mass: 525.1280<br>Molecular Weight: 525.6364 | A | A |
| 39 | 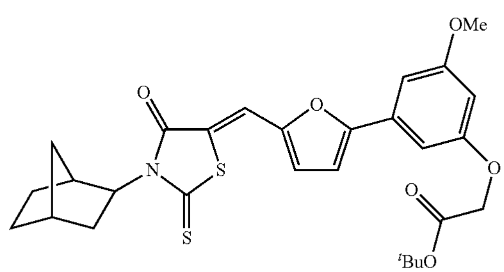 [SMILES: COc1cc(OCC(=O)OC(C)(C)C)cc(-c2ccc(/C=C3\SC(=S)N(C4CC5CCC4C5)C3=O)o2)c1] | C28H31NO6S2<br>Exact Mass: 541.1593<br>Molecular Weight: 541.6788 | A | A |

TABLE 1-continued

| Compound No | Structure | MW | EC$_{50}$ | Virus Yield |
|---|---|---|---|---|
| 40 | 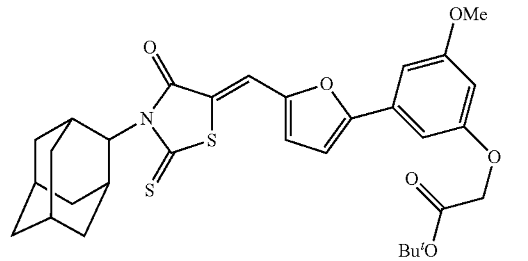 | C31H35NO6S2<br>Exact Mass: 581.1906<br>Molecular Weight: 581.7427 | A | B |
| 41 | 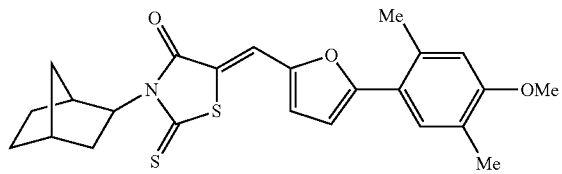 [SMILES: COc1cc(C)c(-c2ccc(/C=C3\SC(=S)N(C4CC5CCC4C5)C3=O)o2)cc1C] | C24H25NO3S2<br>Exact Mass: 439.1276<br>Molecular Weight: 439.5902 | NA | A |
| 42 | 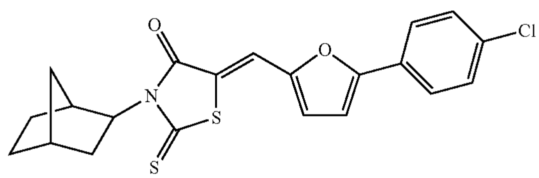 [SMILES: O=C1/C(=C/c2ccc(-c3ccc(Cl)cc3)o2)SC(=S)N1C1CC2CCC1C2] | C21H18ClNO2S2<br>Exact Mass: 415.0467<br>Molecular Weight: 415.9561 | NA | B |
| 43 | 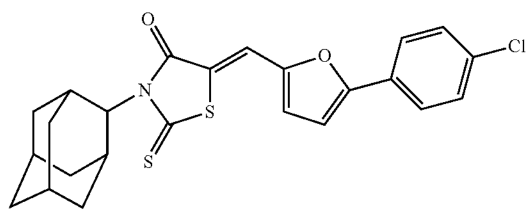 [SMILES: O=C1/C(=C/c2ccc(-c3ccc(Cl)cc3)o2)SC(=S)N1C1C2CC3CC(C2)CC1C3] | C24H22ClNO2S2<br>Exact Mass: 455.0780<br>Molecular Weight: 456.0200 | A | A |
| 44 | 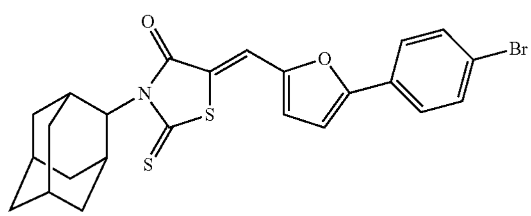 [SMILES: O=C1/C(=C/c2ccc(-c3ccc(Br)cc3)o2)SC(=S)N1C1C2CC3CC(C2)CC1C3] | C24H22BrNO2S2<br>Exact Mass: 499.0275<br>Molecular Weight: 500.4710 | NA | A |
| 45 | 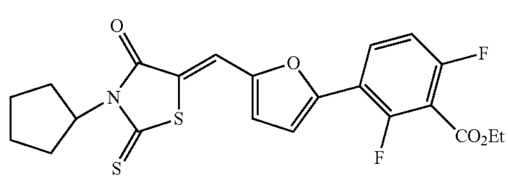 [SMILES: CCOC(=O)c1c(F)ccc(-c2ccc(/C=C3\SC(=S)N(C4CCCC4)C3=O)o2)c1F] | C22H19F2NO4S2<br>Exact Mass: 463.0724<br>Molecular Weight: 463.5174 | A | NA |
| 46 | 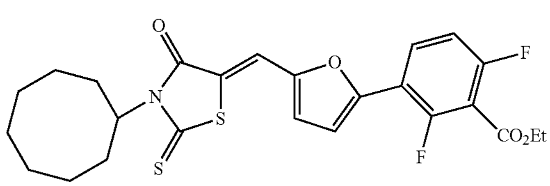 [SMILES: CCOC(=O)c1c(F)ccc(-c2ccc(/C=C3\SC(=S)N(C4CCCCCCC4)C3=O)o2)c1F] | C25H25F2NO4S2<br>Exact Mass: 505.1193<br>Molecular Weight: 505.5971 | A | NA |

TABLE 1-continued

| Compound No | Structure | MW | EC$_{50}$ | Virus Yield |
|---|---|---|---|---|
| 47 | 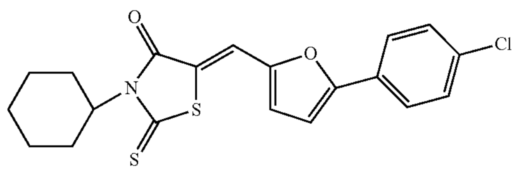 [SMILES: O=C1/C(=C/c2ccc(-c3ccc(Cl)cc3)o2)SC(=S)N1C1CCCCC1] | C20H18ClNO2S2<br>Exact Mass: 403.0467<br>Molecular Weight: 403.9454 | A | NA |
| 48 | 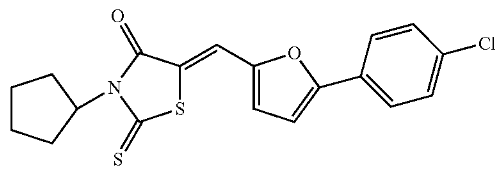 [SMILES: O=C1/C(=C/c2ccc(-c3ccc(Cl)cc3)o2)SC(=S)N1C1CCCC1] | C19H16ClNO2S2<br>Exact Mass: 389.0311<br>Moelcular Weight: 389.9188 | A | NA |
| 49 | 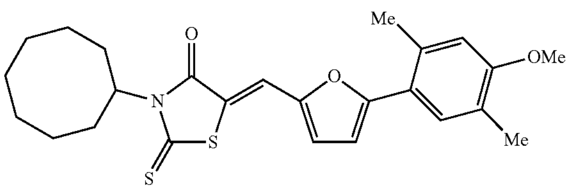 [SMILES: COc1cc(C)c(-c2ccc(/C=C3\SC(=S)N(C4CCCCCCC4)C3=O)o2)cc1C] | C25H29NO3S2<br>Exact Mass: 455.1589<br>Molecular Weight: 455.6327 | A | NA |
| 50 | 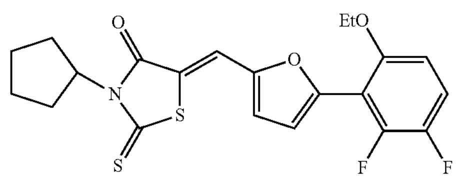 [SMILES: CCOc1ccc(F)c(F)c1-c1ccc(/C=C2\SC(=S)N(C3CCCC3)C2=O)o1] | C21H19F2NO3S2<br>Exact Mass: 435.0774<br>Molecular Weight: 435.5073 | A | NA |
| 51 | 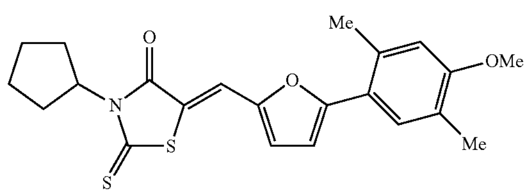 [SMILES: COc1cc(C)c(-c2ccc(/C=C3\SC(=S)N(C4CCCC4)C3=O)o2)cc1C] | C22H23NO3S2<br>Exact Mass: 413.1119<br>Molecular Weight: 413.5529 | A | NA |
| 52 | 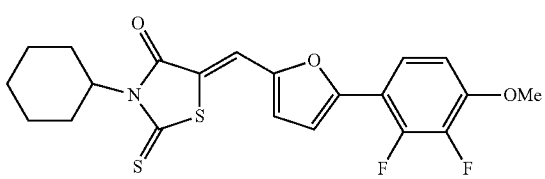 [SMILES: COc1ccc(-c2ccc(/C=C3\SC(=S)N(C4CCCCC4)C3=O)o2)c(F)c1F] | C21H19F2NO3S2<br>Exact Mass: 435.0774<br>Molecular Weight: 435.5073 | A | NA |
| 53 | 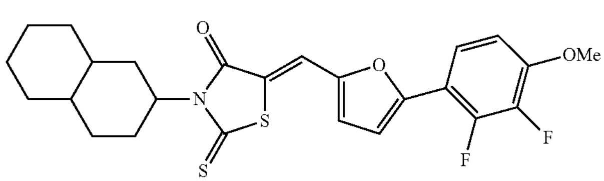 [SMILES: COc1ccc(-c2ccc(/C=C3\SC(=S)N(C4CCC5CCCCC5C4)C3=O)o2)c(F)c1F] | C25H25F2NO3S2<br>Exact Mass: 489.1244<br>Molecular Weight: 489.59777 | NA | A |
| 54 | 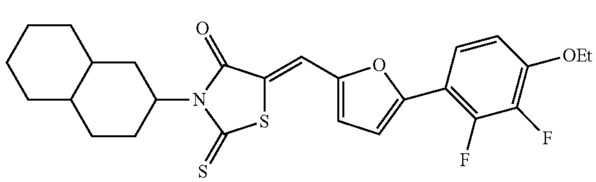 [SMILES: CCOc1ccc(-c2ccc(/C=C3\SC(=S)N(C4CCC5CCCCC5C4)C3=O)o2)c(F)c1F] | C26H27F2NO3S2<br>Exact Mass: 503.1400<br>Molecular Weight: 503.6243 | NA | A |

TABLE 1-continued

| Compound No | Structure | MW | EC$_{50}$ | Virus Yield |
|---|---|---|---|---|
| 55 | 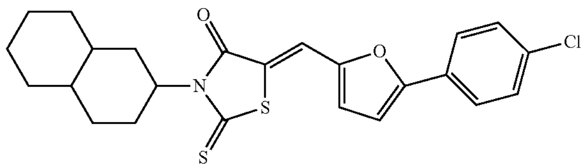 [SMILES: O=C1/C(=C/c2ccc(-c3ccc(Cl)cc3)o2)SC(=S)N1C1CCC2CCCCC2C1] | C24H24ClNO2S2<br>Exact Mass: 457.0937<br>Molecular Weight: 458.0359 | NA | A |
| 56 | (pure isomer) | C26H29NO4S2<br>Exact Mass: 483.1538<br>Molecular Weight: 483.6428 | NA | A |
| 57 | (two isomers) | C26H29NO4S2<br>Exact Mass: 483.1538<br>Molecular Weight: 483.6428 | NA | A |

Type-2
Modification of
C-ring

| Compound No | Structure | MW | EC$_{50}$ | Virus Yield |
|---|---|---|---|---|
| 58 | | C23H24N2O3S2<br>Exact Mass: 440.1228<br>Molecular Weight: 440.5783 | A | A |
| 59 | | C26H28N2O3S2<br>Exact Mass: 480.1541<br>Molecular Weight: 480.6421 | A | B |
| 60 | | C23H21F2NO2S3<br>Exact Mass: 477.0702<br>Molecular Weight: 477.6101 | NA | C |

TABLE 1-continued
| Compound No | Structure | MW | EC$_{50}$ | Virus Yield |
|---|---|---|---|---|
| 61 | 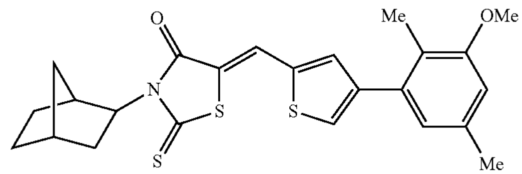 [SMILES: COc1cc(C)cc(-c2csc(/C=C3\SC(=S)N(C4CC5CCC4C5)C3=O)c2)c1C] | C24H25NO2S3 Exact Mass: 455.1047 Molecular Weight: 455.6558 | NA | C |
| 62 | 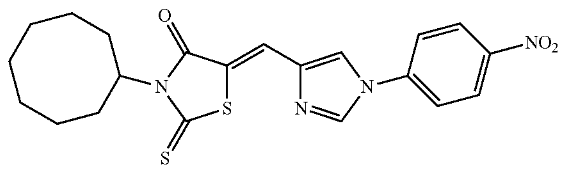 [SMILES: O=C1/C(=C/c2cn(-c3ccc([N+](=O)[O-])cc3)cn2)SC(=S)N1C1CCCCCCC1] | C21H22N4O3S2 Exact Mass: 442.1133 Molecular Weight: 442.5544 | C | NA |
| 63 | 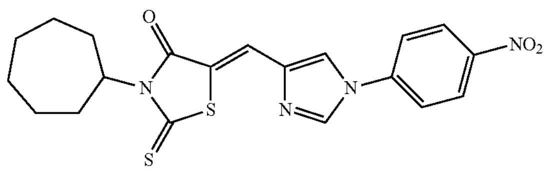 [SMILES: O=C1/C(=C/c2cn(-c3ccc([N+](=O)[O-])cc3)cn2)SC(=S)N1C1CCCCCC1] | C20H20N4O3S2 Exact Mass: 428.0977 Molecular Weight: 428.5278 | C | NA |
| 64 | 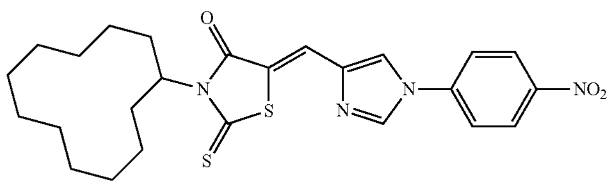 [SMILES: O=C1/C(=C/c2cn(-c3ccc([N+](=O)[O-])cc3)cn2)SC(=S)N1C1CCCCCCCCCCC1] | C25H30N4O3S2 Exact Mass: 498.1759 Molecular Weight: 498.6607 | A | NA |
| 65 | 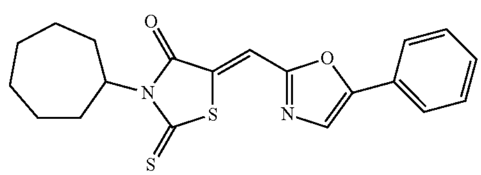 [SMILES: O=C1/C(=C/c2ncc(-c3ccccc3)o2)SC(=S)N1C1CCCCCC1] | C20H20N2O2S2 Exact Mass: 384.0966 Molecular Weight: 384.5150 | A | NA |
| 66 | 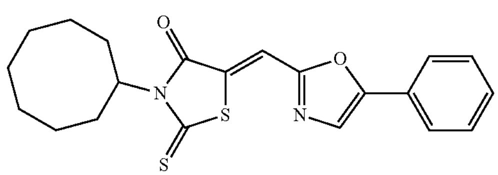 [SMILES: O=C1/C(=C/c2ncc(-c3ccccc3)o2)SC(=S)N1C1CCCCCCC1] | C21H22N2O2S2 Exact Mass: 398.1123 Molecular Weight: 398.5416 | A | NA |
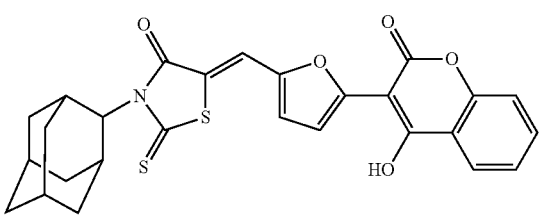 [SMILES: O=C1/C(=C/c2ccc(-c3c(O)c4ccccc4oc3=O)o2)SC(=S)N1C1C2CC3CC(C2)CC1C3]
Type-3a Coumarin
as D-ring
| 67 | | C27H23NO5S2 Exact Mass: 505.1018 Molecular Weight: 505.6052 | NA | A |

TABLE 1-continued

| Compound No | Structure | MW | EC$_{50}$ | Virus Yield |
|---|---|---|---|---|
| 68 | 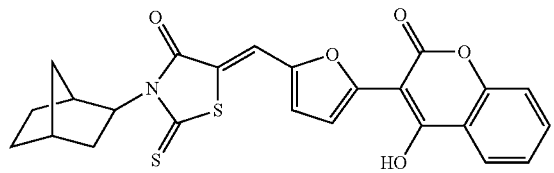 [SMILES: O=C1/C(=C/c2ccc(-c3c(O)c4ccccc4oc3=O)o2)SC(=S)N1C1CC2CCC1C2] | C24H19NO5S2<br>Exact Mass: 465.0705<br>Molecular Weight: 465.5414 | NA | A |
| 69 | 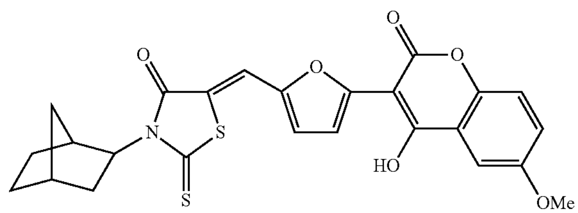 [SMILES: COc1ccc2oc(=O)c(-c3ccc(/C=C4\SC(=S)N(C5CC6CCC5C6)C4=O)o3)c(O)c2c1] | C25H21NO6S2<br>Exact Mass: 495.0810<br>Molecular Weight: 495.5673 | B | A |
| 70 | 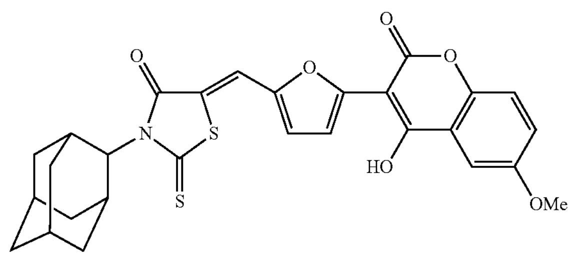 [SMILES: COc1ccc2oc(=O)c(-c3ccc(/C=C4\SC(=S)N(C5C6CC7CC(C6)CC5C7)C4=O)o3)c(O)c2c1] | C28H25NO6S2<br>Exact Mass: 535.1123<br>Molecular Weight: 535.6312 | B | A |
| 71 | 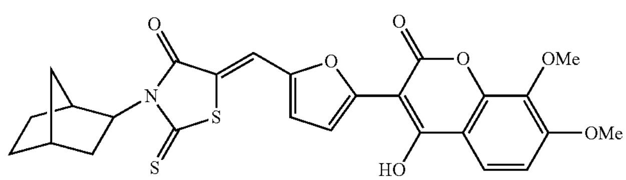 [SMILES: COc1ccc2c(O)c(-c3ccc(/C=C4\SC(=S)N(C5CC6CCC5C6)C4=O)o3)c(=O)oc2c1OC] | C26H23NO7S2<br>Exact Mass: 525.0916<br>Molecular Weight: 525.5933 | B | A |
| 72 | 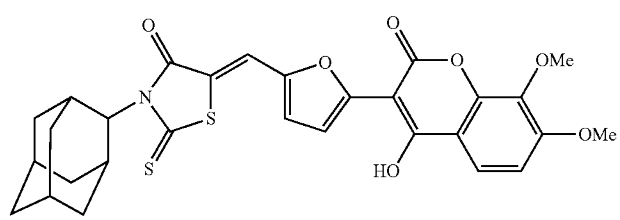 [SMILES: COc1ccc2c(O)c(-c3ccc(/C=C4\SC(=S)N(C5C6CC7CC(C6)CC5C7)C4=O)o3)c(=O)oc2c1OC] | C29H27NO7S2<br>Exact Mass: 565.1229<br>Molecular Weight: 565.6572 | B | A |
| 73 | 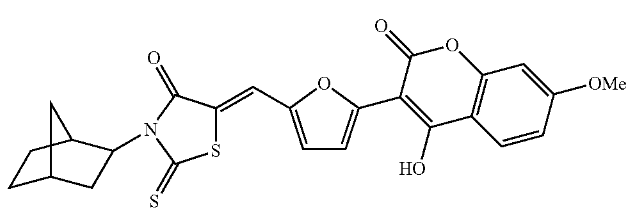 [SMILES: COc1ccc2c(O)c(-c3ccc(/C=C4\SC(=S)N(C5CC6CCC5C6)C4=O)o3)c(=O)oc2c1] | C25H21NO6S2<br>Exact Mass: 495.0810<br>Molecular Weight: 495.5673 | B | A |
| 74 | 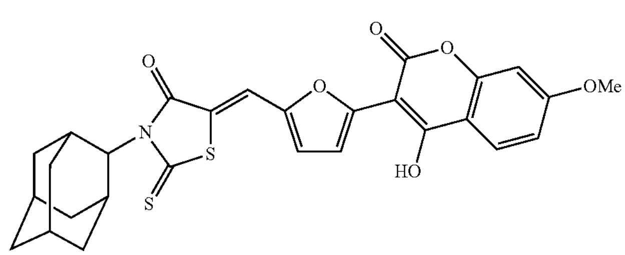 [SMILES: COc1ccc2c(O)c(-c3ccc(/C=C4\SC(=S)N(C5C6CC7CC(C6)CC5C7)C4=O)o3)c(=O)oc2c1] | C28H25NO6S2<br>Exact Mass: 535.1123<br>Molecular Weight: 535.6312 | B | A |

TABLE 1-continued

| Compound No | Structure | MW | EC$_{50}$ | Virus Yield |
|---|---|---|---|---|
| | Type-3b Coumarin as D-ring | | | |
| 75 | 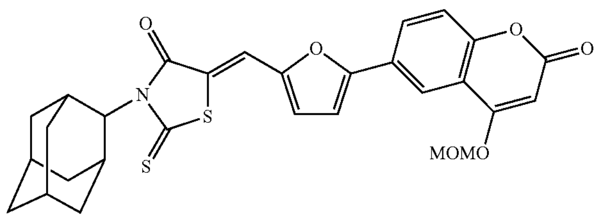 | C29H27NO6S2<br>Exact Mass: 549.1280<br>Molecular Weight: 549.6578 | C | C |
| 76 | 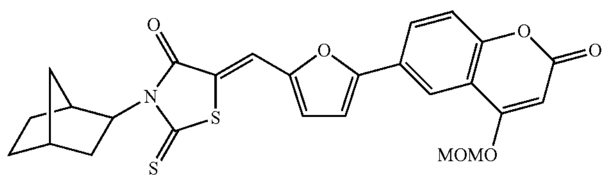 | C26H23NO6S2<br>Exact Mass: 509.0967<br>Molecular Weight: 509.5939 | C | C |
| | Type-4 Modification of D-ring with amino acid | | | |
| 77 | 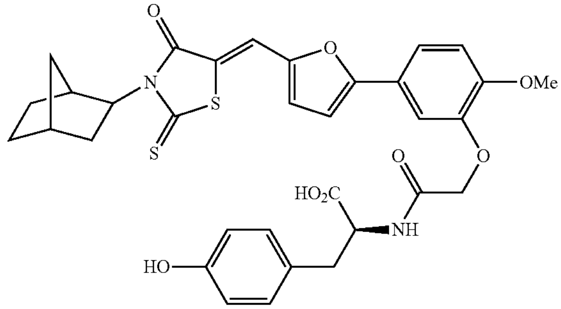 [SMILES: COc1ccc(-c2ccc(/C=C3\SC(=S)N(C4CC5CCC4C5)C3=O)o2)cc1OCC(=O)N[C@@H](Cc1ccc(O)cc1)C(=O)O] | C33H32N2O8S2<br>Exact Mass: 648.1600<br>Molecular Weight: 648.7458 | B | B |

TABLE 1-continued

| Compound No | Structure | MW | EC$_{50}$ | Virus Yield |
|---|---|---|---|---|
| 78 | 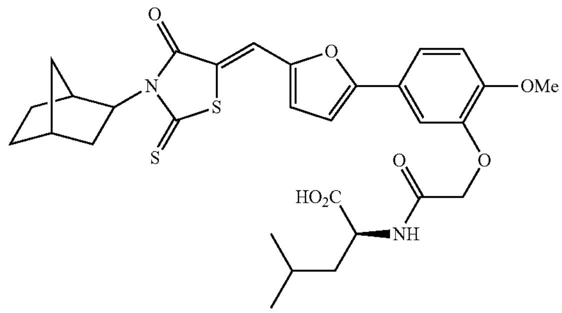 [SMILES: COc1ccc(-c2ccc(/C=C3\SC(=S)N(C4CC5CCC4C5)C3=O)o2)cc1OCC(=O)N[C@@H](CC(C)C)C(=O)O] | C30H34N2O7S2<br>Exact Mass: 598.1807<br>Molecular Weight: 598.7302 | A | A |
| 79 | 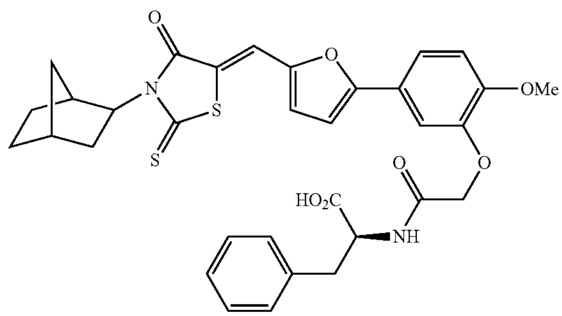 [SMILES: COc1ccc(-c2ccc(/C=C3\SC(=S)N(C4CC5CCC4C5)C3=O)o2)cc1OCC(=O)N[C@@H](Cc1ccccc1)C(=O)O] | C33H32N2O7S2<br>Exact Mass: 632.1651<br>Molecular Weight: 632.7464 | A | A |
| 80 | 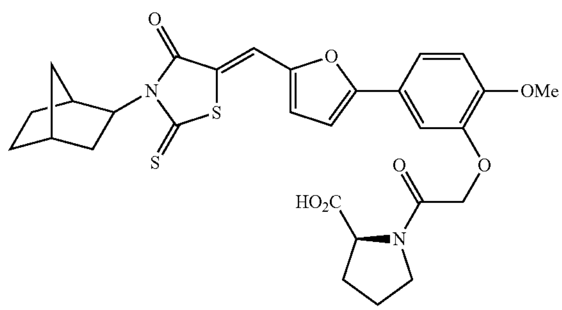 [SMILES: COc1ccc(-c2ccc(/C=C3\SC(=S)N(C4CC5CCC4C5)C3=O)o2)cc1OCC(=O)N1CCC[C@H]1C(=O)O] | C29H30N2O7S2<br>Exact Mass: 582.1494<br>Molecular Weight: 582.6877 | A | A |
| 81 | 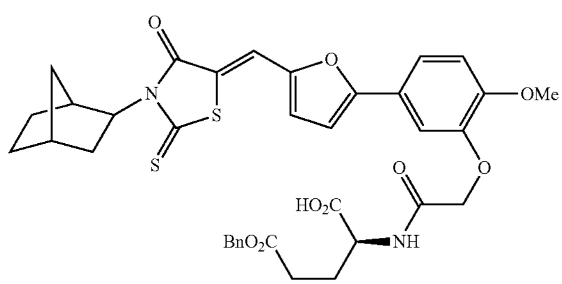 | C36H36N2O9S2<br>Exact Mass: 704.1862<br>Molecular Weight: 704.8090 | A | B |
| 82 | 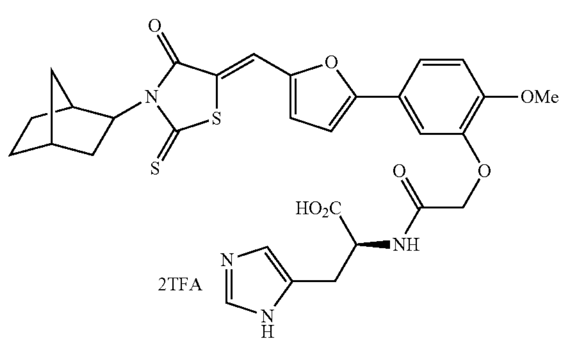 [SMILES: COc1ccc(-c2ccc(/C=C3\SC(=S)N(C4CC5CCC4C5)C3=O)o2)cc1OCC(=O)N[C@@H](Cc1cnc[nH]1)C(=O)O] | C34H30F6N4O9S2<br>Exact Mass: 816.1358<br>Molecular Weight: 816.7438 | A | B |

TABLE 1-continued

| Compound No | Structure | MW | EC$_{50}$ | Virus Yield |
|---|---|---|---|---|
| 83 | 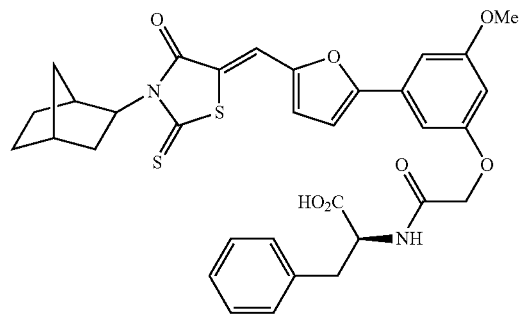 [SMILES: COc1cc(OCC(=O)N[C@@H](Cc2ccccc2)C(=O)O)cc(-c2ccc(/C=C3\SC(=S)N(C4CC5CCC4C5)C3=O)o2)c1] | C33H32N2O7S2<br>Exact Mass: 632.1651<br>Molecular Weight: 632.7464 | A | B |
| 84 | 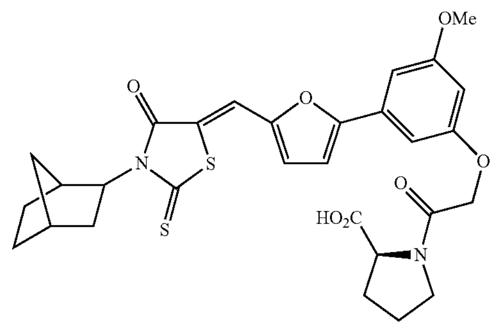 [SMILES: COc1cc(OCC(=O)N2CCC[C@H]2C(=O)O)cc(-c2ccc(/C=C3\SC(=S)N(C4CC5CCC4C5)C3=O)o2)c1] | C29H30N2O7S2<br>Exact Mass: 582.1494<br>Molecular Weight: 582.6877 | A | B |
| 85 | 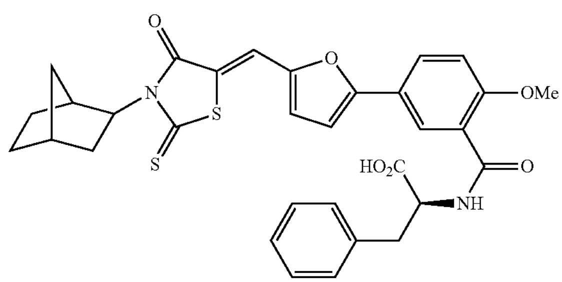 [SMILES: COc1ccc(-c2ccc(/C=C3\SC(=S)N(C4CC5CCC4C5)C3=O)o2)cc1C(=O)N[C@@H](Cc1ccccc1)C(=O)O] | C32H30N2O6S2<br>Exact Mass: 602.1545<br>Molecular Weight: 602.7204 | A | A |
| 86 | 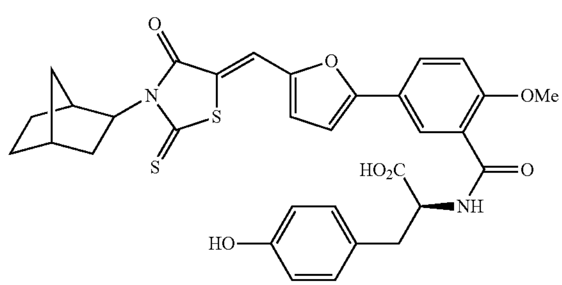 [SMILES: COc1ccc(-c2ccc(/C=C3\SC(=S)N(C4CC5CCC4C5)C3=O)o2)cc1C(=O)N[C@@H](Cc1ccc(O)cc1)C(=O)O] | C32H30N2O7S2<br>Exact Mass: 618.1494<br>Molecular Weight: 618.7198 | A | A |
| 87 | 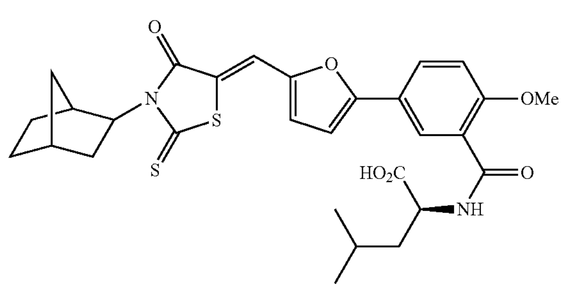 [SMILES: COc1ccc(-c2ccc(/C=C3\SC(=S)N(C4CC5CCC4C5)C3=O)o2)cc1C(=O)N[C@@H](CC(C)C)C(=O)O] | C29H32N2O6S2<br>Exact Mass: 568.2703<br>Molecular Weight: 568.7042 | A | A |

TABLE 1-continued

| Compound No | Structure | MW | EC$_{50}$ | Virus Yield |
|---|---|---|---|---|
| 88 | 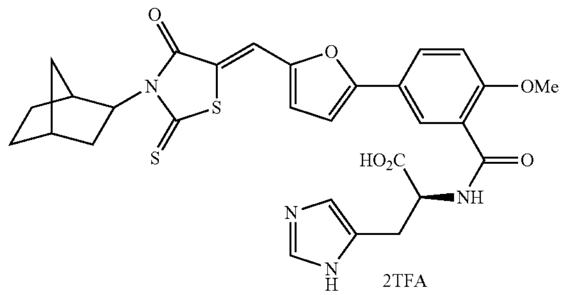 [SMILES: COc1ccc(-c2ccc(/C=C3\SC(=S)N(C4CC5CCC4C5)C3=O)o2)cc1C(=O)N[C@@H](Cc1cnc[nH]1)C(=O)O] | C33H28F6N4O8S2<br>Exact Mass: 786.1253<br>Molecular Weight: 786.7178 | A | A |
| 89 | 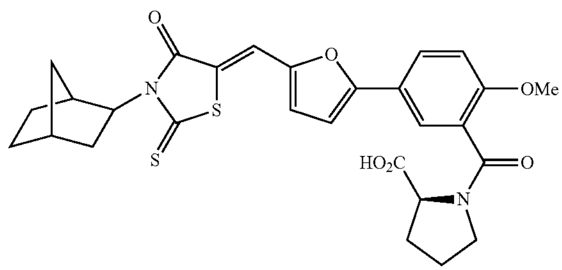 [SMILES: COc1ccc(-c2ccc(/C=C3\SC(=S)N(C4CC5CCC4C5)C3=O)o2)cc1C(=O)N1CCC[C@H]1C(=O)O] | C28H28N2O6S2<br>Exact Mass: 552.1389<br>Molecular Weight: 552.6617 | A | A |
| 90 | 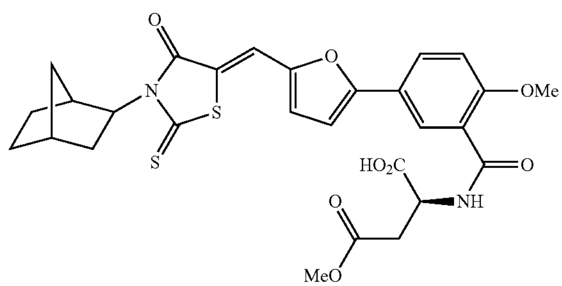 [SMILES: COC(=O)C[C@H](NC(=O)c1cc(-c2ccc(/C=C3\SC(=S)N(C4CC5CCC4C5)C3=O)o2)ccc1OC)C(=O)O] | C28H28N2O8S2<br>Exact Mass: 584.1287<br>Molecular Weight: 584.6605 | B | C |
| 91 | 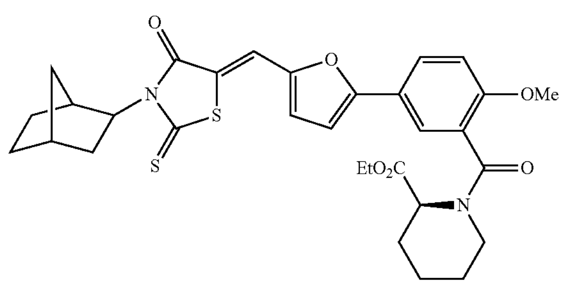 [SMILES: CCOC(=O)[C@@H]1CCCCN1C(=O)c1cc(-c2ccc(/C=C3\SC(=S)N(C4CC5CCC4C5)C3=O)o2)ccc1OC] | C31H34N2O6S2<br>Exact Mass: 594.1858<br>Molecular Weight: 594.7415 | A | A |

Type-5 Modification of side chain in C-ring (furan) with alcohol moiety

TABLE 1-continued

| Compound No | Structure | MW | EC$_{50}$ | Virus Yield |
|---|---|---|---|---|
| 92 | 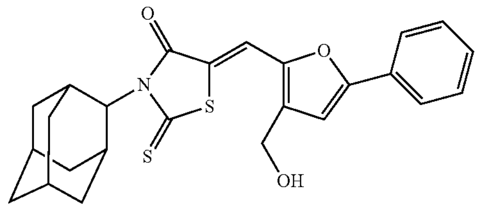 [SMILES: O=C1/C(=C/c2oc(-c3ccccc3)cc2CO)SC(=S)N1C1C2CC3CC(C2)CC1C3] | C25H25NO3S2<br>Exact Mass: 451.1276<br>Molecular Weight: 451.6009 | A | A |
| 93 | 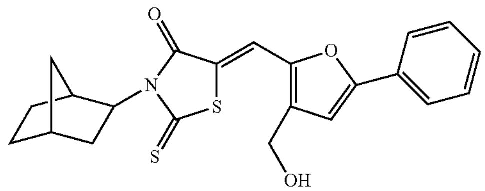 [SMILES: O=C1/C(=C/c2oc(-c3ccccc3)cc2CO)SC(=S)N1C1CC2CCC1C2] | C22H21NO3S2<br>Exact Mass: 411.0963<br>Molecular Weight: 411.5370 | A | A |
| 94 | 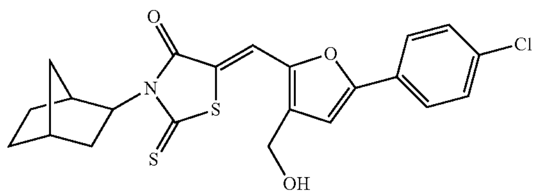 [SMILES: O=C1/C(=C/c2oc(-c3ccc(Cl)cc3)cc2CO)SC(=S)N1C1CC2CCC1C2] | C22H20ClNO3S2<br>Exact Mass: 445.0573<br>Molecular Weight: 445.9821 | NA | C |
| 95 | 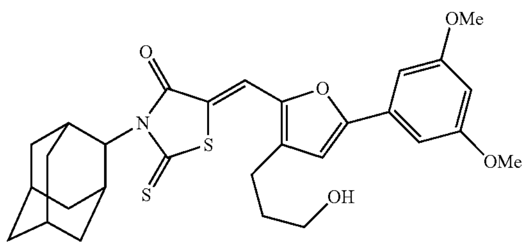 [SMILES: COc1cc(OC)cc(-c2cc(CCCO)c(/C=C3\SC(=S)N(C4C5CC6CC(C5)CC4C6)C3=O)o2)c1] | C29H33NO5S2<br>Exact Mass: 539.1800<br>Molecular Weight: 539.7060 | A | A |
| 96 | 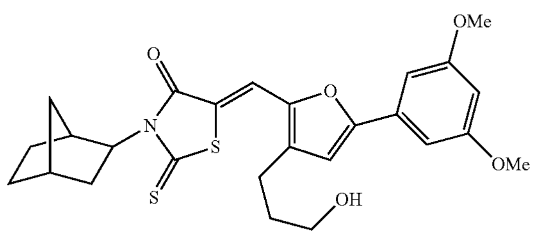 [SMILES: COc1cc(OC)cc(-c2cc(CCCO)c(/C=C3\SC(=S)N(C4CC5CCC4C5)C3=O)o2)c1] | C26H29NO5S2<br>Exact Mass: 499.1487<br>Molecular Weight: 499.6422 | A | A |
| 97 | 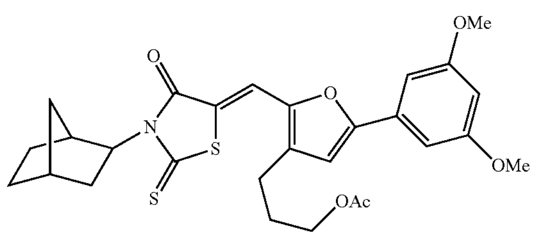 [SMILES: COc1cc(OC)cc(-c2cc(CCCOC(C)=O)c(/C=C3\SC(=S)N(C4CC5CCC4C5)C3=O)o2)c1] | C28H31NO6S2<br>Exact Mass: 541.1593<br>Molecular Weight: 541.6788 | A | A |
| 98 | 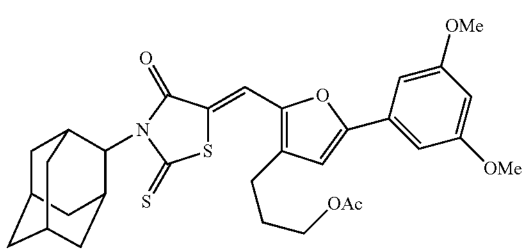 [SMILES: COc1cc(OC)cc(-c2cc(CCCOC(C)=O)c(/C=C3\SC(=S)N(C4C5CC6CC(C5)CC4C6)C3=O)o2)c1] | C31H35NO6S2<br>Exact Mass: 581.1906<br>Molecular Weight: 581.7427 | A | A |

TABLE 1-continued
| Compound No | Structure | MW | EC$_{50}$ | Virus Yield |
|---|---|---|---|---|
| 99 | 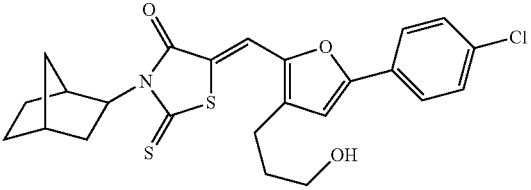 [SMILES: O=C1/C(=C/c2oc(-c3ccc(Cl)cc3)cc2CCCO)SC(=S)N1C1CC2CCC1C2] | C24H24ClNO3S2<br>Exact Mass: 473.0886<br>Mol. Wt.: 474.0353 | A | A |
| 100 | 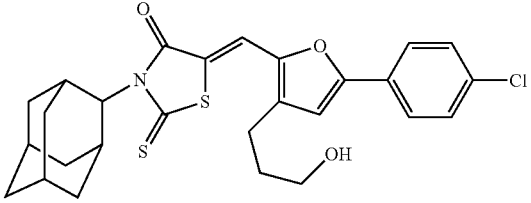 [SMILES: O=C1/C(=C/c2oc(-c3ccc(Cl)cc3)cc2CCCO)SC(=S)N1C1C2CC3CC(C2)CC1C3] | C27H28ClNO3S2<br>Exact Mass: 513.1199<br>Mol. Wt.: 514.0991 | A | A |
| 101 | 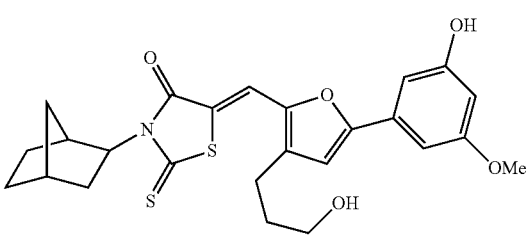 [SMILES: COc1cc(O)cc(-c2cc(CCCO)c(/C=C3\SC(=S)N(C4CC5CCC4C5)C3=O)o2)c1] | C25H27NO5S2<br>Exact Mass: 485.1331<br>Molecular Weight: 485.6156 | A | B |
| 102 | 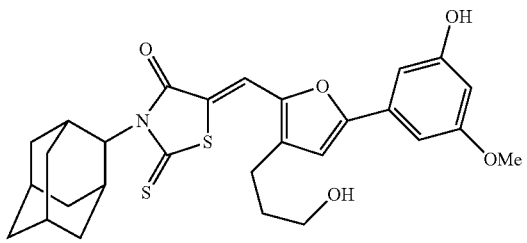 [SMILES: COc1cc(O)cc(-c2cc(CCCO)c(/C=C3\SC(=S)N(C4C5CC6CC(C5)CC4C6)C3=O)o2)c1] | C28H31NO5S2<br>Exact Mass: 525.1644<br>Molecular Weight: 525.6794 | A | C |
| 103 | 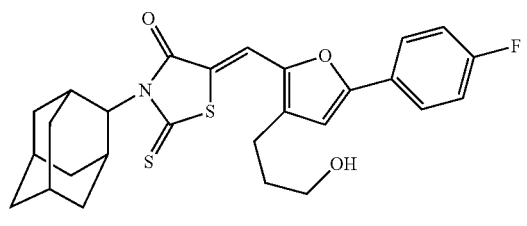 [SMILES: O=C1/C(=C/c2oc(-c3ccc(F)cc3)cc2CCCO)SC(=S)N1C1C2CC3CC(C2)CC1C3] | C27H28FNO3S2<br>Exact Mass: 497.1495<br>Molecular Weight: 497.6445 | A | A |
| 104 | 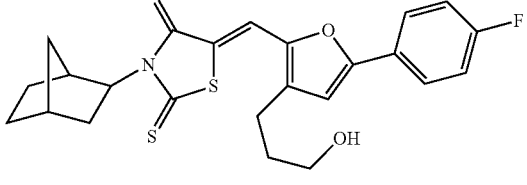 | C24H24FNO3S2<br>Exact Mass: 457.1182<br>Molecular Weight: 457.5807 | A | B |
| 105 | 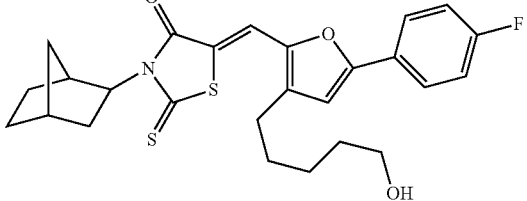 | C26H28FNO3S2<br>Exact Mass: 485.1495<br>Molecular Weight: 485.6338 | A | A |

TABLE 1-continued

| Compound No | Structure | MW | EC$_{50}$ | Virus Yield |
|---|---|---|---|---|
| 106 | 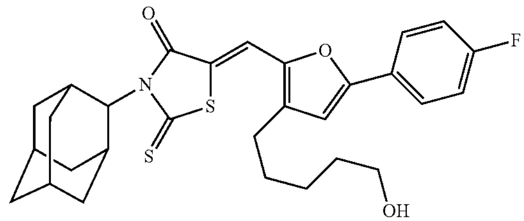 [SMILES: O=C1/C(=C/c2oc(-c3ccc(F)cc3)cc2CCCCCO)SC(=S)N1C1C2CC3CC(C2)CC1C3] | C29H32FNO3S2<br>Exact Mass: 525.1808<br>Molecular Weight: 525.6977 | A | A |
| 107 | 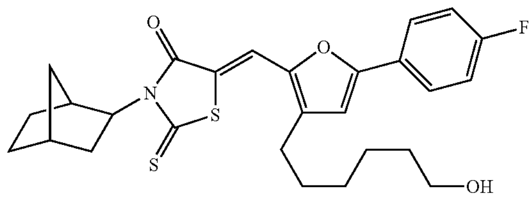 [SMILES: O=C1/C(=C/c2oc(-c3ccc(F)cc3)cc2CCCCCCO)SC(=S)N1C1CC2CCC1C2] | C27H30FNO3S2<br>Exact Mass: 499.1651<br>Molecular Weight: 499.6604 | A | A |
| 108 | 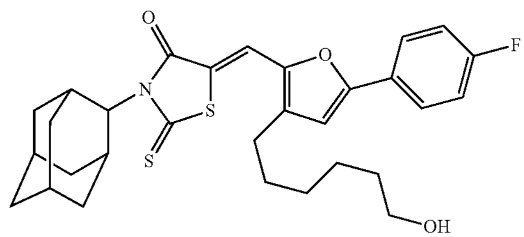 [SMILES: O=C1/C(=C/c2oc(-c3ccc(F)cc3)cc2CCCCCCO)SC(=S)N1C1C2CC3CC(C2)CC1C3] | C30H34FNO3S2<br>Exact Mass: 539.1964<br>Molecular Weight: 539.7243 | A | A |
| 109 | 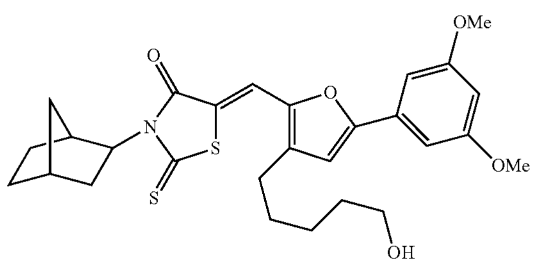 [SMILES: COc1cc(OC)cc(-c2cc(CCCCCO)c(/C=C3\SC(=S)N(C4CC5CCC4C5)C3=O)o2)c1] | C28H33NO5S2<br>Exact Mass: 527.1800<br>Molecular Weight: 527.6953 | A | A |
| 110 | 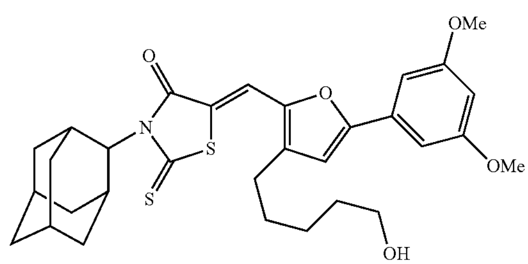 [SMILES: COc1cc(OC)cc(-c2cc(CCCCCO)c(/C=C3\SC(=S)N(C4C5CC6CC(C5)CC4C6)C3=O)o2)c1] | C31H37NO5S2<br>Exact Mass: 567.2113<br>Molecular Weight: 567.7592 | A | A |
| 111 | 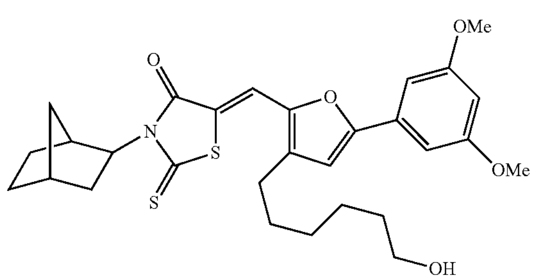 [SMILES: COc1cc(OC)cc(-c2cc(CCCCCCO)c(/C=C3\SC(=S)N(C4CC5CCC4C5)C3=O)o2)c1] | C29H35NO5S2<br>Exact Mass: 541.1957<br>Molecular Weight: 541.7219 | A | A |

TABLE 1-continued

| Compound No | Structure | MW | EC$_{50}$ | Virus Yield |
|---|---|---|---|---|
| 112 | 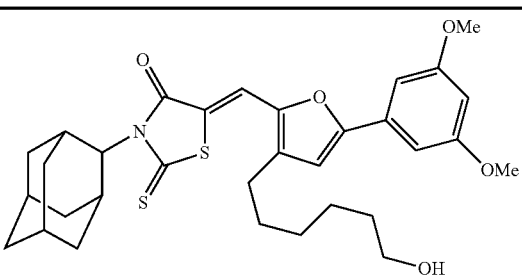 | C32H39NO5S2<br>Exact Mass: 581.2270<br>Molecular Weight: 581.7858 | A | A |
| 113 | 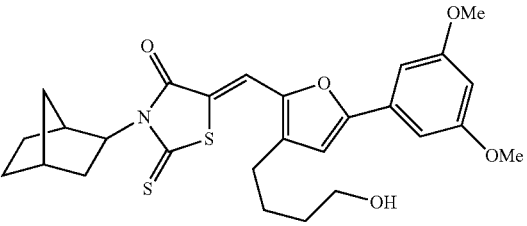 [SMILES: COc1cc(OC)cc(-c2cc(CCCCO)c(/C=C3\SC(=S)N(C4CC5CCC4C5)C3=O)o2)c1] | C27H31NO5S2<br>Exact Mass: 513.1644<br>Molecular Weight: 513.6687 | A | A |
| 114 | 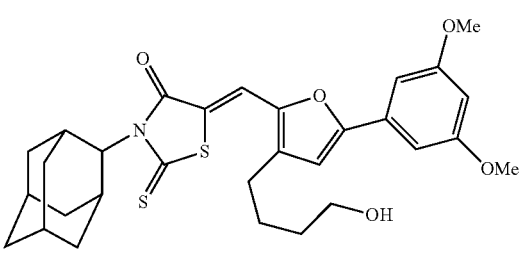 [SMILES: COc1cc(OC)cc(-c2cc(CCCCO)c(/C=C3\SC(=S)N(C4C5CC6CC(C5)CC4C6)C3=O)o2)c1] | C30H35NO5S2<br>Exact Mass: 553.1957<br>Molecular Weight: 553.7326 | A | A |
| 115 | 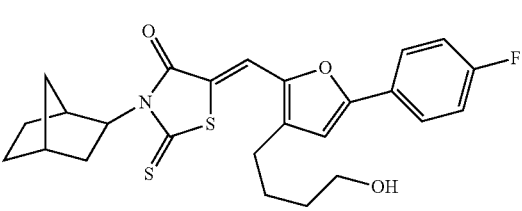 [SMILES: O=C1/C(=C/c2oc(-c3ccc(F)cc3)cc2CCCCO)SC(=S)N1C1CC2CCC1C2] | C25H26FNO3S2<br>Exact Mass: 471.1338<br>Molecular Weight: 471.6072 | A | A |
| 116 | 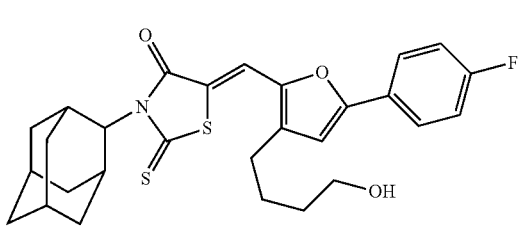 [SMILES: O=C1/C(=C/c2oc(-c3ccc(F)cc3)cc2CCCCO)SC(=S)N1C1C2CC3CC(C2)CC1C3] | C28H30FNO3S2<br>Exact Mass: 511.1651<br>Molecular Weight: 511.6711 | A | A |
| 117 | 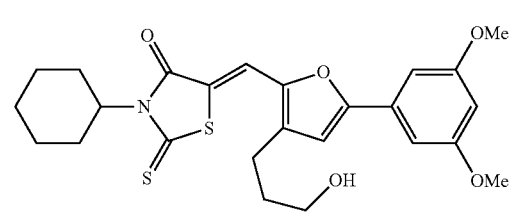 [SMILES: COc1cc(OC)cc(-c2cc(CCCO)c(/C=C3\SC(=S)N(C4CCCCC4)C3=O)o2)c1] | C25H29NO5S2<br>Exact Mass: 487.1487<br>Molecular Weight: 487.6315 | NA | C |
| 118 | 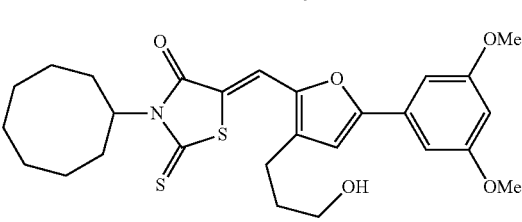 [SMILES: COc1cc(OC)cc(-c2cc(CCCO)c(/C=C3\SC(=S)N(C4CCCCCCC4)C3=O)o2)c1] | C27H33NO5S2<br>Exact Mass: 515.1800<br>Molecular Weight: 515.6846 | NA | C |

TABLE 1-continued
| Compound No | Structure | MW | EC$_{50}$ | Virus Yield |
|---|---|---|---|---|
| 119 | 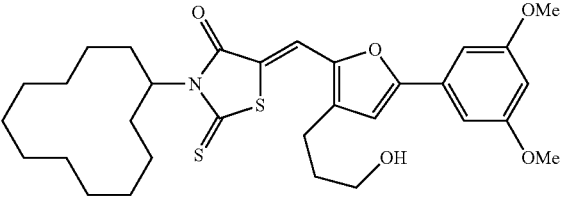 [SMILES: COc1cc(OC)cc(-c2cc(CCCO)c(/C=C3\SC(=S)N(C4CCCCCCCCCCC4)C3=O)o2)c1] | C31H41NO5S2<br>Exact Mass: 571.2426<br>Molecular Weight: 571.7909 | NA | C |
Type-6 Modification
of side chain in C-ring
(furan) with amine moiety
| | | | | |
|---|---|---|---|---|
| 120 | 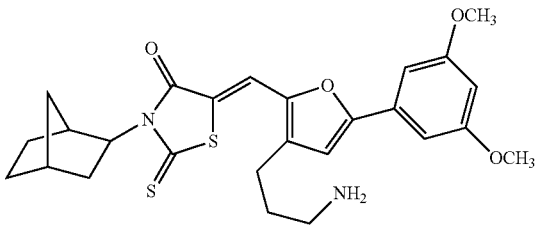 [SMILES: COc1cc(OC)cc(-c2cc(CCCN)c(/C=C3\SC(=S)N(C4CC5CCC4C5)C3=O)o2)c1] | C26H30N2O4S2<br>Exact Mass: 498.1647<br>Molecular Weight: 498.6574 | A | A |
| 121 | 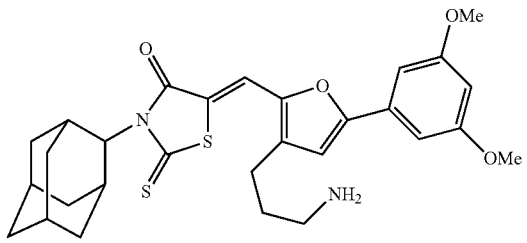 | C29H34N2O4S2<br>Exact Mass: 538.1960<br>Molecular Weight: 538.7213 | A | A |
| 122 | 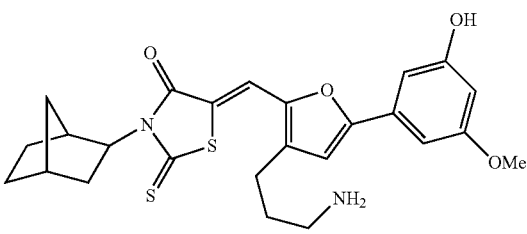 | C25H28N2O4S2<br>Exact Mass: 484.1490<br>Molecular Weight: 484.6308 | A | A |
| 123 | 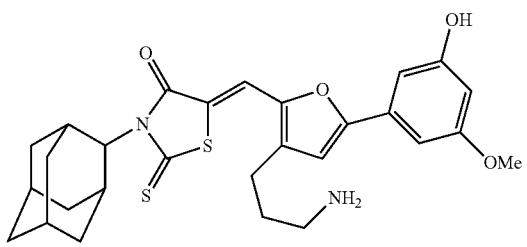 [SMILES: COc1cc(O)cc(-c2cc(CCCN)c(/C=C3\SC(=S)N(C4C5CC6CC(C5)CC4C6)C3=O)o2)c1] | C28H32N2O4S2<br>Exact Mass: 524.1803<br>Molecular Weight: 524.6947 | A | A |

TABLE 1-continued

| Compound No | Structure | MW | EC$_{50}$ | Virus Yield |
|---|---|---|---|---|
| 124 | 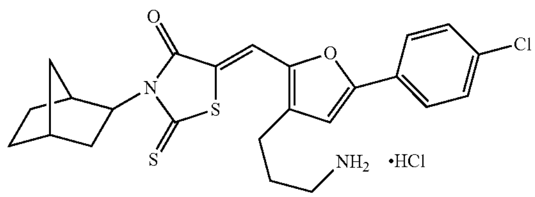 [SMILES: NCCCc1cc(-c2ccc(Cl)cc2)oc1/C=C1\SC(=S)N(C2CC3CCC2C3)C1=O ; Cl] | C24H26Cl2N2O2S2<br>Exact Mass: 508.0813<br>Molecular Weight: 509.5114 | A | A |
| 125 | 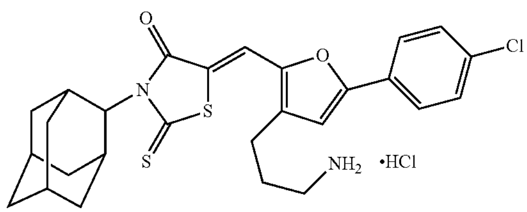 [SMILES: NCCCc1cc(-c2ccc(Cl)cc2)oc1/C=C1\SC(=S)N(C2C3CC4CC(C3)CC2C4)C1=O ; Cl] | C27H30Cl2N2O2S2<br>Exact Mass: 548.1126<br>Molecular Weight: 549.5753 | A | A |
| 126 | 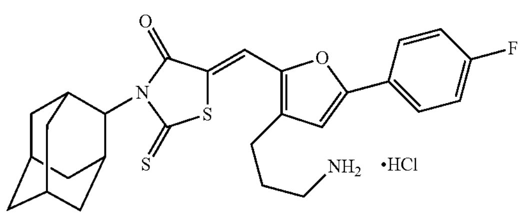 [SMILES: NCCCc1cc(-c2ccc(F)cc2)oc1/C=C1\SC(=S)N(C2C3CC4CC(C3)CC2C4)C1=O ; Cl] | C27H30ClFN2O2S2<br>Exact Mass: 532.1421<br>Molecular Weight: 533.1207 | A | A |
| 127 | 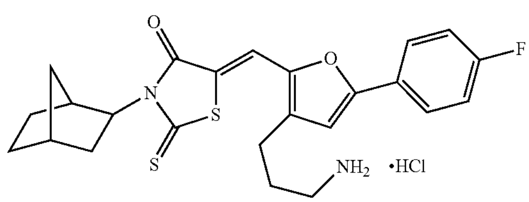 [SMILES: NCCCc1cc(-c2ccc(F)cc2)oc1/C=C1\SC(=S)N(C2CC3CCC2C3)C1=O ; Cl] | C24H26ClFN2O2S2<br>Exact Mass: 492.1108<br>Molecular Weight: 493.0568 | A | A |
| 128 | 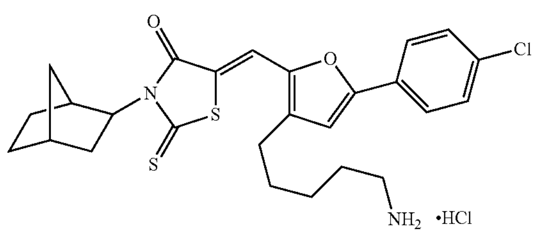 [SMILES: NCCCCCc1cc(-c2ccc(Cl)cc2)oc1/C=C1\SC(=S)N(C2CC3CCC2C3)C1=O ; Cl] | C26H30Cl2N2O2S2<br>Exact Mass: 536.1126<br>Molecular Weight: 537.5646 | NA | A |

Type-7 Modification
of side chain in C-ring
(furan) with acid moiety

TABLE 1-continued
| Compound No | Structure | MW | EC$_{50}$ | Virus Yield |
|---|---|---|---|---|
| 129 | 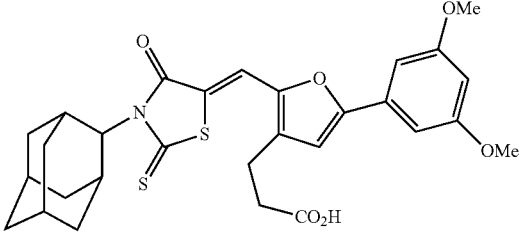 [SMILES: COc1cc(OC)cc(-c2cc(CCC(=O)O)c(/C=C3\SC(=S)N(C4C5CC6CC(C5)CC4C6)C3=O)o2)c1] | C29H31NO6S2<br>Exact Mass: 553.1593<br>Molecular Weight: 553.6895 | A | B |
| 130 | 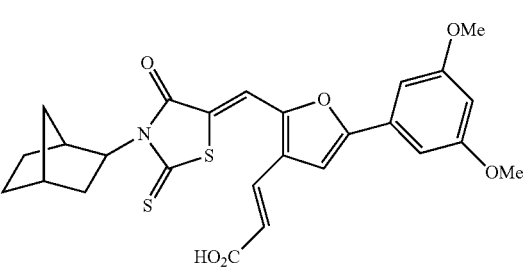 [SMILES: COc1cc(OC)cc(-c2cc(/C=C/C(=O)O)c(/C=C3\SC(=S)N(C4CC5CCC4C5)C3=O)o2)c1] | C26H25NO6S2<br>Exact Mass: 511.1123<br>Molecular Weight: 511.6098 | A | B |
| 131 | 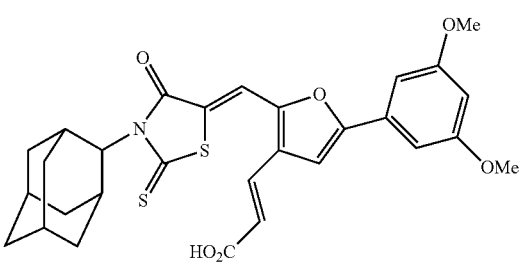 [SMILES: COc1cc(OC)cc(-c2cc(/C=C/C(=O)O)c(/C=C3\SC(=S)N(C4C5CC6CC(C5)CC4C6)C3=O)o2)c1] | C29H29NO6S2<br>Exact Mass: 551.1436<br>Molecular Weight: 551.67376 | A | A |
| 132 | 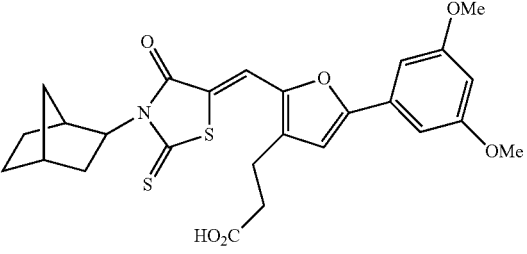 [SMILES: COc1cc(OC)cc(-c2cc(CCC(=O)O)c(/C=C3\SC(=S)N(C4CC5CCC4C5)C3=O)o2)c1] | C26H27NO6S2<br>Exact Mass: 513.1280<br>Molecular Weight: 513.6257 | A | B |
| 133 | 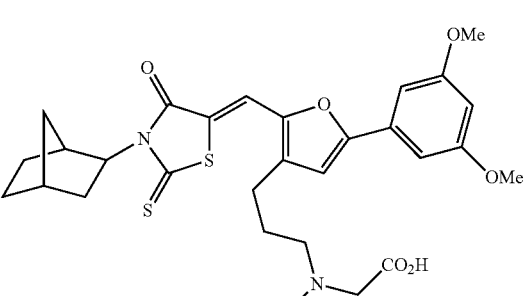 | C30H34N2O8S2<br>Exact Mass: 614.1757<br>Molecular Weight: 614.7296 | B | C |

TABLE 1-continued

| Compound No | Structure | MW | EC$_{50}$ | Virus Yield |
|---|---|---|---|---|
| 134 | 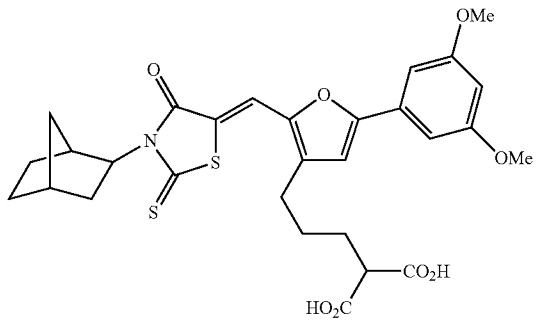 | C29H31NO8S2<br>Exact Mass: 585.1491<br>Molecular Weight: 585.6883 | A | C |
| 135 | 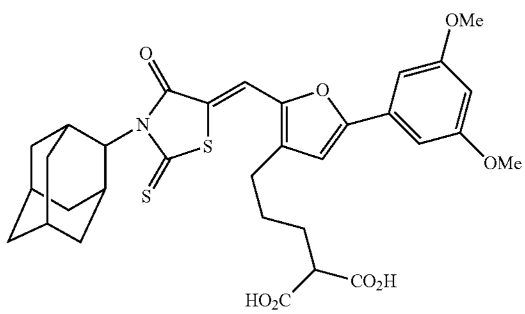 [SMILES: COc1cc(OC)cc(-c2cc(CCCC(C(=O)O)C(=O)O)c(/C=C3\SC(=S)N(C4C5CC6CC(C5)CC4C6)C3=O)o2)c1] | C32H35NO8S2<br>Exact Mass: 625.1804<br>Molecular Weight: 625.7522 | B | C |
| 136 | 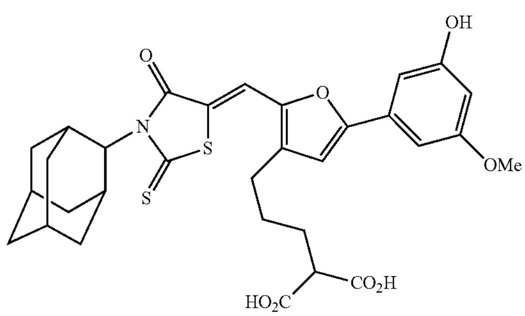 [SMILES: COc1cc(O)cc(-c2cc(CCCC(C(=O)O)C(=O)O)c(/C=C3\SC(=S)N(C4C5CC6CC(C5)CC4C6)C3=O)o2)c1] | C31H33NO8S2<br>Exact Mass: 611.1648<br>Molecular Weight: 611.7256 | B | C |
| 137 | 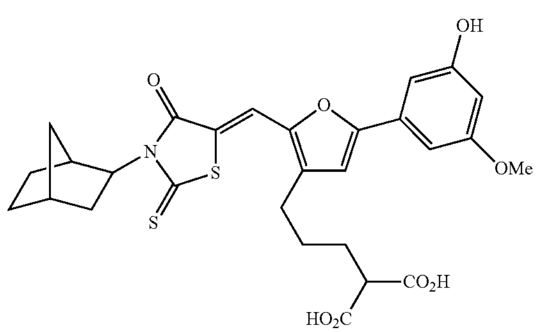 [SMILES: COc1cc(O)cc(-c2cc(CCCC(C(=O)O)C(=O)O)c(/C=C3\SC(=S)N(C4CC5CCC4C5)C3=O)o2)c1] | C28H29NO8S2<br>Exact Mass: 571.1335<br>Molecular Weight: 571.6618 | NA | C |

TABLE 1-continued

Type-8 Modification of side chain in C-ring (furan) with amino acid moiety

| Compound No | Structure | MW | EC₅₀ | Virus Yield |
|---|---|---|---|---|
| 138 | 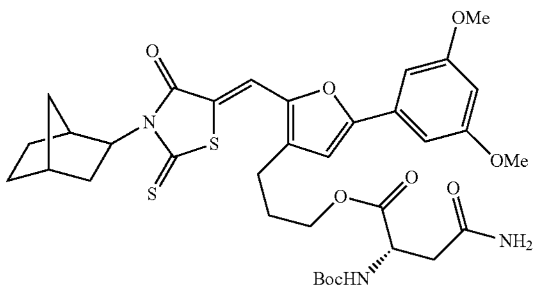 [SMILES: COc1cc(OC)cc(-c2cc(CCCOC(=O)[C@H](CC(N)=O)NC(=O)OC(C)(C)C)c(/C=C3\SC(=S)N(C4CC5CCC4C5)C3=O)o2)c1] | C35H43N3O9S2<br>Exact Mass: 713.2441<br>Molecular Weight: 713.8606 | A | A |
| 139 | 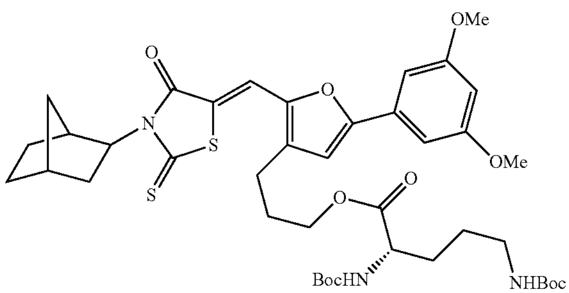 [SMILES: COc1cc(OC)cc(-c2cc(CCCOC(=O)[C@H](CCCNC(=O)OC(C)(C)C)NC(=O)OC(C)(C)C)c(/C=C3\SC(=S)N(C4CC5CCC4C5)C3=O)o2)c1] | C41H55N3O10S2<br>Exact Mass: 813.3329<br>Molecular Weight: 814.0195 | A | C |
| 140 | 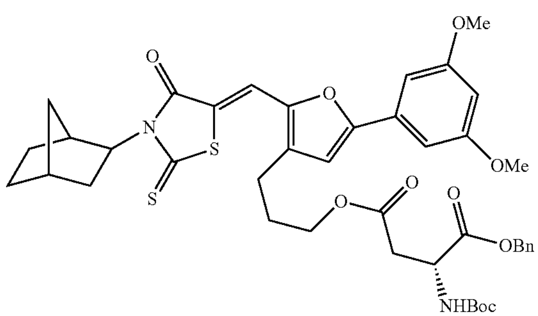 [SMILES: COc1cc(OC)cc(-c2cc(CCCOC(=O)C[C@@H](NC(=O)OC(C)(C)C)C(=O)OCc3ccccc3)c(/C=C3\SC(=S)N(C4CC5CCC4C5)C3=O)o2)c1] | C42H48N2O10S2<br>Exact Mass: 804.2750<br>Molecular Weight: 804.9679 | NA | B |
| 141 | 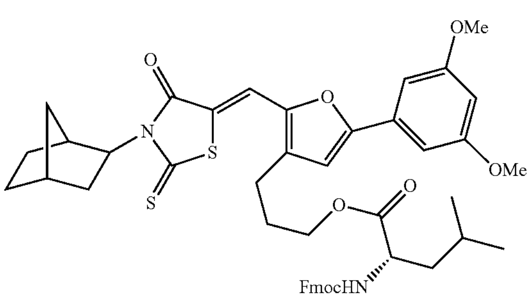 | C47H50N2O8S2<br>Exact Mass: 834.3009<br>Molecular Weight: 835.0385 | C | C |

TABLE 1-continued

| Compound No | Structure | MW | EC$_{50}$ | Virus Yield |
|---|---|---|---|---|
| 142 | 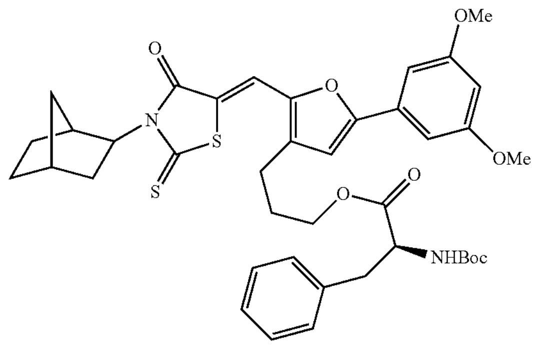 [SMILES: COc1cc(OC)cc(-c2cc(CCCOC(=O)[C@H](Cc3ccccc3)NC(=O)OC(C)(C)C)c(/C=C3\SC(=S)N(C4CC5CCC4C5)C3=O)o2)c1] | C40H46N2O8S2<br>Exact Mass: 746.2696<br>Molecular Weight: 746.9318 | A | C |
| 143 | 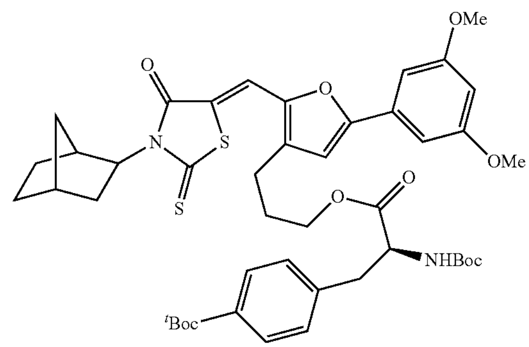 | C44H54N2O9S2<br>Exact Mass: 818.3271<br>Molecular Weight: 819.0376 | A | C |
| 144 | 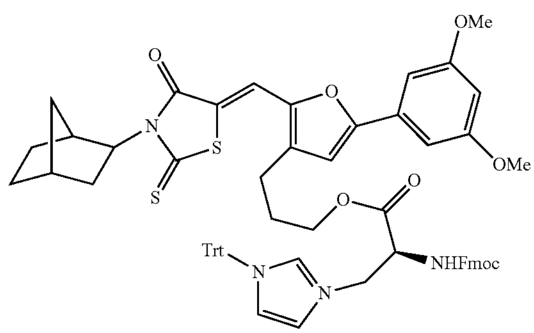 | C66H60N4O8S2<br>Exact Mass: 1100.3853<br>Molecular Weight: 1101.3346 | C | C |
| 145 | 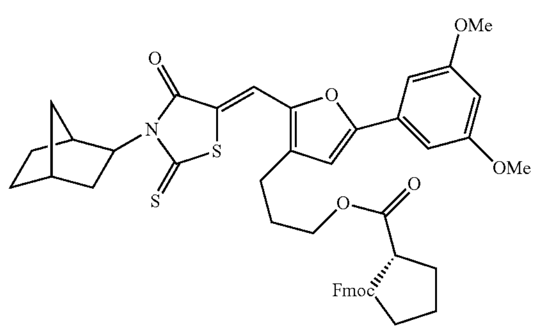 | C46H46N2O8S2<br>Exact Mass: 818.2696<br>Molecular Weight: 818.9960 | A | B |

TABLE 1-continued

| Compound No | Structure | MW | EC$_{50}$ | Virus Yield |
|---|---|---|---|---|
| 146 | 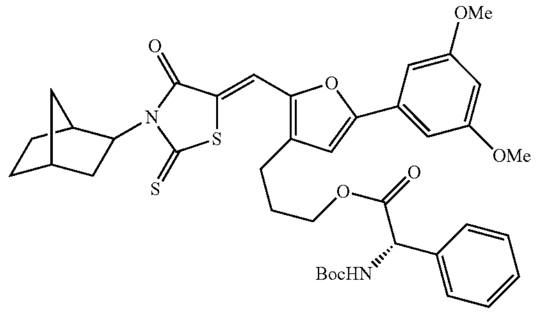 [SMILES: COc1cc(OC)cc(-c2cc(CCCOC(=O)[C@@H](NC(=O)OC(C)(C)C)c3ccccc3)c(/C=C3\SC(=S)N(C4CC5CCC4C5)C3=O)o2)c1] | C39H44N2O8S2<br>Exact Mass: 732.2539<br>Molecular Weight: 732.9053 | A | C |
| 147 | 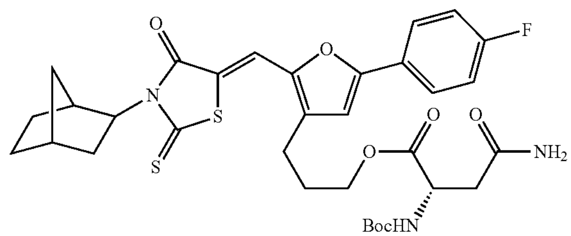 | C33H38FN3O7S2<br>Exact Mass: 671.2135<br>Molecular Weight: 671.7991 | A | B |
| 148 | 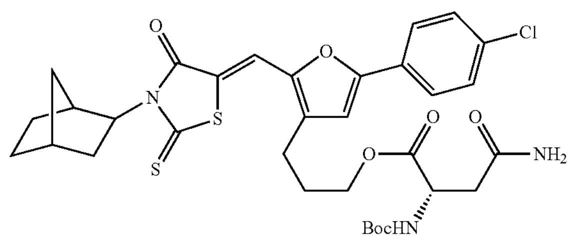 [SMILES: CC(C)(C)OC(=O)N[C@@H](CC(N)=O)C(=O)OCCCc1cc(-c2ccc(F)cc2)oc1/C=C1\SC(=S)N(C2CC3CCC2C3)C1=O] | C33H38ClN3O7S2<br>Exact Mass: 687.1840<br>Molecular Weight: 688.2537 | A | A |
| 149 | 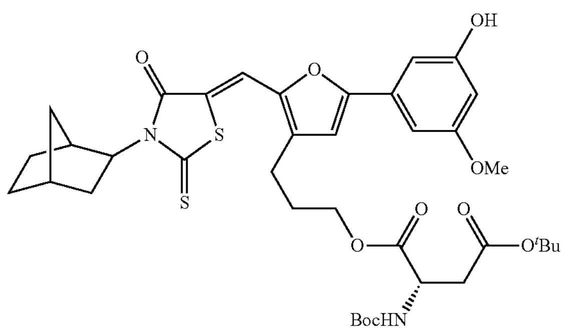 [SMILES: COc1cc(O)cc(-c2cc(CCCOC(=O)[C@H](CC(=O)OC(C)(C)C)NC(=O)OC(C)(C)C)c(/C=C3\SC(=S)N(C4CC5CCC4C5)C3=O)o2)c1] | C38H48N2O10S2<br>Exact Mass: 756.2750<br>Molecular Weight: 756.9251 | A | A |
| 150 | 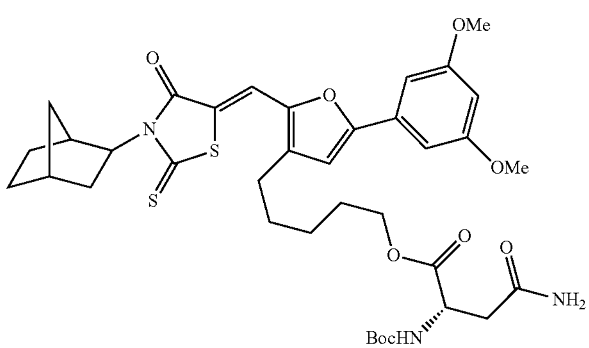 [SMILES: COc1cc(OC)cc(-c2cc(CCCCCOC(=O)[C@H](CC(N)=O)NC(=O)OC(C)(C)C)c(/C=C3\SC(=S)N(C4CC5CCC4C5)C3=O)o2)c1] | C37H47N3O9S2<br>Exact Mass: 741.2754<br>Molecular Weight: 741.9138 | A | A |

TABLE 1-continued

| Compound No | Structure | MW | EC$_{50}$ | Virus Yield |
|---|---|---|---|---|
| 151 | 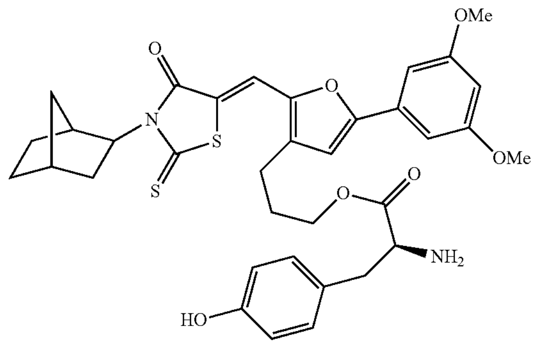 [SMILES: COc1cc(OC)cc(-c2cc(CCCOC(=O)[C@@H](N)Cc3ccc(O)cc3)c(/C=C3\SC(=S)N(C4CC5CCC4C5)C3=O)o2)c1] | C35H38N2O7S2<br>Exact Mass: 662.2120<br>Molecular Weight: 662.8154 | A | A |
| 152 | 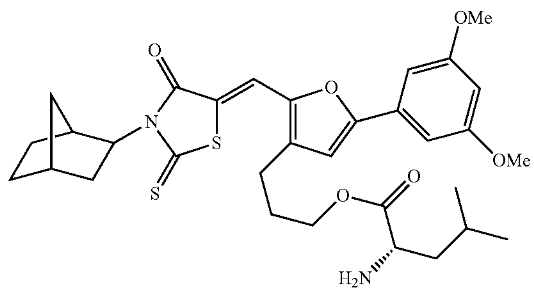 [SMILES: COc1cc(OC)cc(-c2cc(CCCOC(=O)[C@@H](N)CC(C)C)c(/C=C3\SC(=S)N(C4CC5CCC4C5)C3=O)o2)c1] | C32H40N2O6S2<br>Exact Mass: 612.2328<br>Molecular Weight: 612.7998 | NA | A |
| 153 | 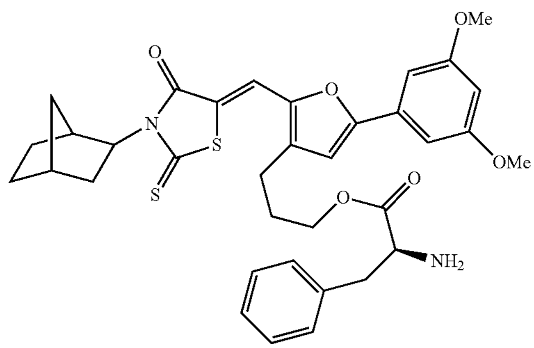 [SMILES: COc1cc(OC)cc(-c2cc(CCCOC(=O)[C@@H](N)Cc3ccccc3)c(/C=C3\SC(=S)N(C4CC5CCC4C5)C3=O)o2)c1] | C35H38N2O6S2<br>Exact Mass: 646.2171<br>Molecular Weight: 646.8160 | A | B |
| 154 | 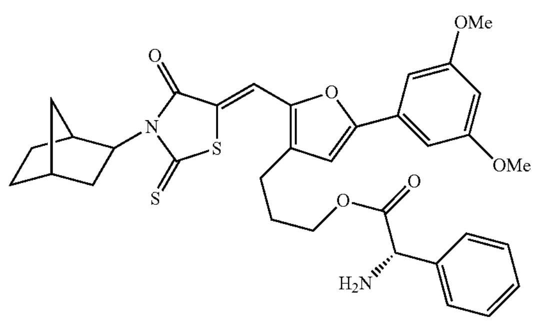 [SMILES: COc1cc(OC)cc(-c2cc(CCCOC(=O)[C@@H](N)c3ccccc3)c(/C=C3\SC(=S)N(C4CC5CCC4C5)C3=O)o2)c1] | C34H36N2O6S2<br>Exact Mass: 632.2015<br>Molecular Weight: 632.7894 | A | A |
| 155 | 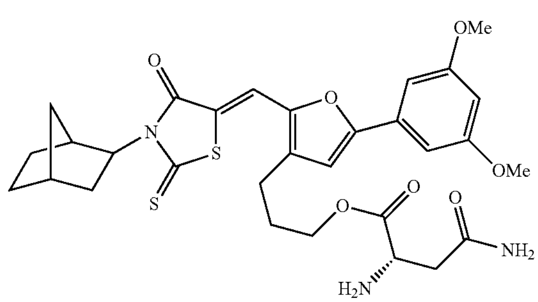 [SMILES: COc1cc(OC)cc(-c2cc(CCCOC(=O)[C@@H](N)CC(N)=O)c(/C=C3\SC(=S)N(C4CC5CCC4C5)C3=O)o2)c1] | C30H35N3O7S2<br>Exact Mass: 613.1916<br>Molecular Weight: 613.7448 | NA | C |

TABLE 1-continued

| Compound No | Structure | MW | EC$_{50}$ | Virus Yield |
|---|---|---|---|---|
| 156 | 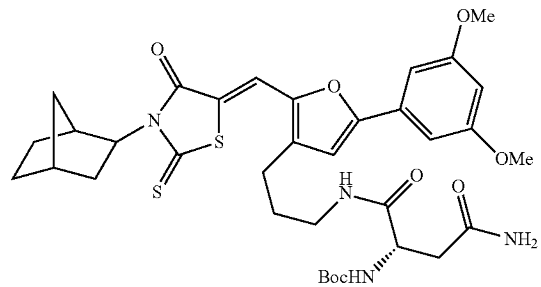 [SMILES: COc1cc(OC)cc(-c2cc(CCCNC(=O)[C@H](CC(N)=O)NC(=O)OC(C)(C)C)c(/C=C3\SC(=S)N(C4CC5CCC4C5)C3=O)o2)c1] | C35H44N4O8S2<br>Exact Mass: 712.2601<br>Molecular Weight: 712.8759 | A | B |
| 157 | 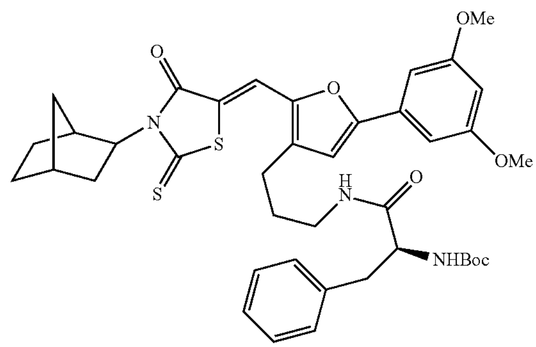 [SMILES: COc1cc(OC)cc(-c2cc(CCCNC(=O)[C@H](Cc3ccccc3)NC(=O)OC(C)(C)C)c(/C=C3\SC(=S)N(C4CC5CCC4C5)C3=O)o2)c1] | C40H47N3O7S2<br>Exact Mass: 745.2855<br>Molecular Weight: 745.9471 | A | C |
| 158 | 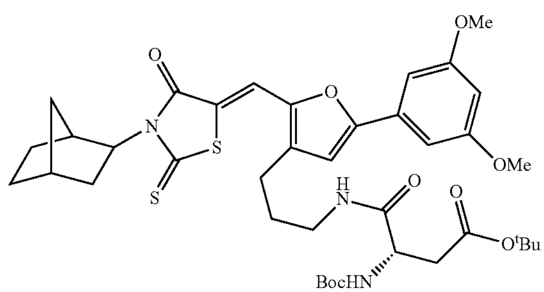 [SMILES: COc1cc(OC)cc(-c2cc(CCCNC(=O)[C@H](CC(=O)OC(C)(C)C)NC(=O)OC(C)(C)C)c(/C=C3\SC(=S)N(C4CC5CCC4C5)C3=O)o2)c1] | C39H541N3O9S2<br>Exact Mass: 769.3067<br>Molecular Weight: 769.9669 | A | C |
| 159 | 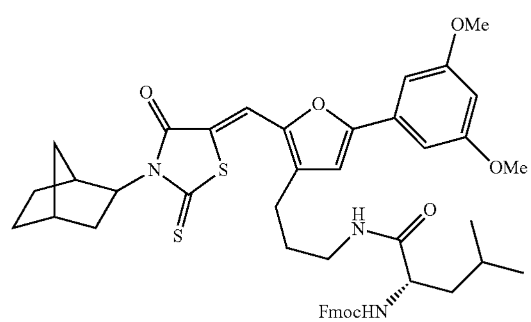 | C47H51N3O7S2<br>Exact Mass: 833.3168<br>Molecular Weight: 834.0537 | A | C |

TABLE 1-continued

| Compound No | Structure | MW | EC$_{50}$ | Virus Yield |
|---|---|---|---|---|
| 160 | 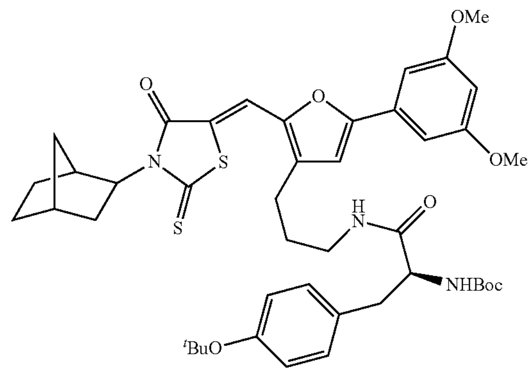 [SMILES: COc1cc(OC)cc(-c2cc(CCCNC(=O)[C@H](Cc3ccc(OC(C)(C)C)cc3)NC(=O)OC(C)(C)C)c(/C=C3\SC(=S)N(C4CC5CCC4C5)C3=O)o2)c1] | C44H55N3O8S2<br>Exact Mass: 817.3431<br>Molecular Weight: 818.0528 | A | C |
| 161 | 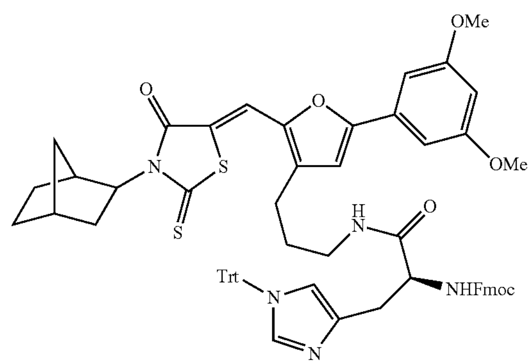 | C66H61N5O7S2<br>Exact Mass: 1099.4012<br>Molecular Weight: 1100.3498 | A | C |
| 162 | 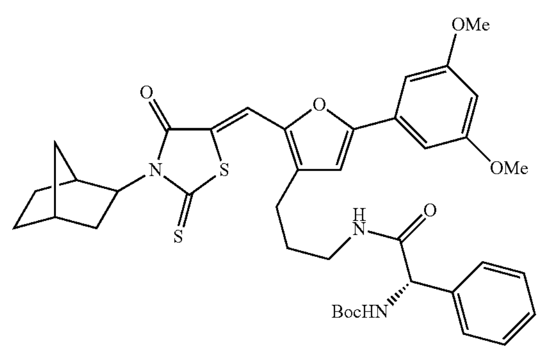 [SMILES: COc1cc(OC)cc(-c2cc(CCCNC(=O)[C@@H](NC(=O)OC(C)(C)C)c3ccccc3)c(/C=C3\SC(=S)N(C4CC5CCC4C5)C3=O)o2)c1] | C39H45N3O7S2<br>Exact Mass: 731.2699<br>Molecular Weight: 731.9205 | A | C |
| 163 | 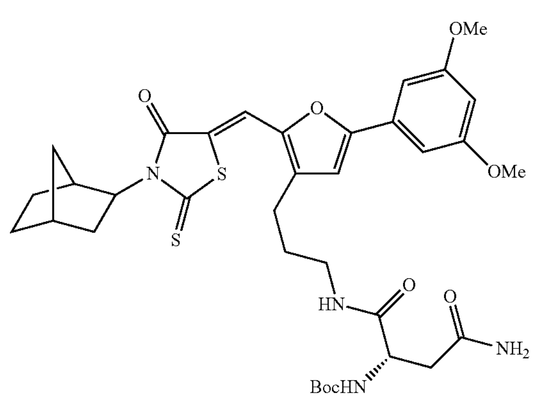 [SMILES: COc1cc(OC)cc(-c2cc(CCCNC(=O)[C@H](CC(N)=O)NC(=O)OC(C)(C)C)c(/C=C3\SC(=S)N(C4CC5CCC4C5)C3=O)o2)c1] | C34H42N4O8S2<br>Exact Mass: 698.2444<br>Molecular Weight: 698.8493 | A | B |

TABLE 1-continued

| Compound No | Structure | MW | EC$_{50}$ | Virus Yield |
|---|---|---|---|---|
| 164 | 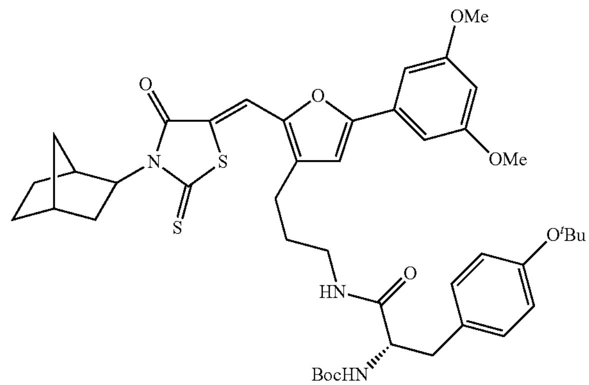 [SMILES: COc1cc(OC)cc(-c2cc(CCCNC(=O)[C@H](Cc3ccc(OC(C)(C)C)cc3)NC(=O)OC(C)(C)C)c(/C=C3\SC(=S)N(C4CC5CCC4C5)C3=O)o2)c1] | C43H53N3O8S2<br>Exact Mass: 803.3274<br>Molecular Weight: 804.0262 | A | B |
| 165 | 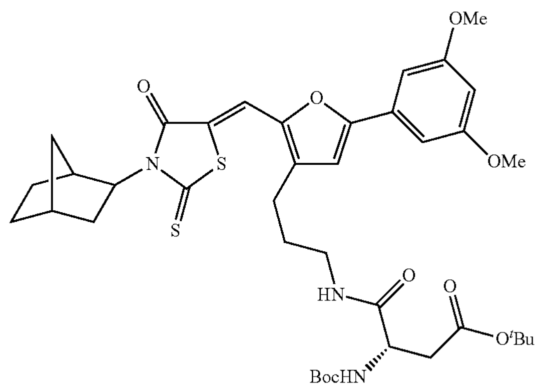 [SMILES: COc1cc(OC)cc(-c2cc(CCCNC(=O)[C@H](CC(=O)OC(C)(C)C)NC(=O)OC(C)(C)C)c(/C=C3\SC(=S)N(C4CC5CCC4C5)C3=O)o2)c1] | C38H49N3O9S2<br>Exact Mass: 755.2910<br>Molecular Weight: 755.9404 | A | A |
| 166 | 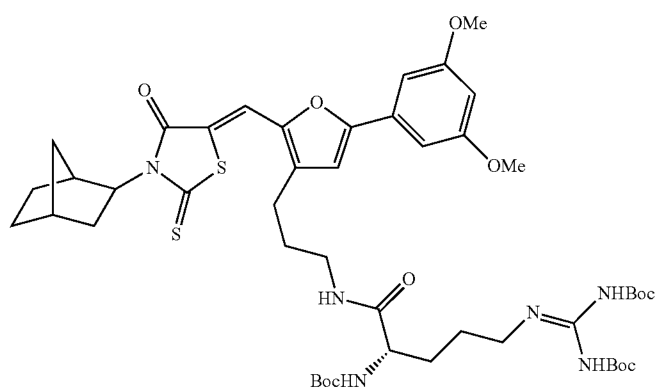 [SMILES: COc1cc(OC)cc(-c2cc(CCCNC(=O)[C@H](CCCN=C(NC(=O)OC(C)(C)C)NC(=O)OC(C)(C)C)NC(=O)OC(C)(C)C)c(/C=C3\SC(=S)N(C4CC5CCC4C5)C3=O)o2)c1] | C46H64N6O11S2<br>Exact Mass: 940.4074<br>Molecular Weight: 941.1640 | A | C |
| 167 | 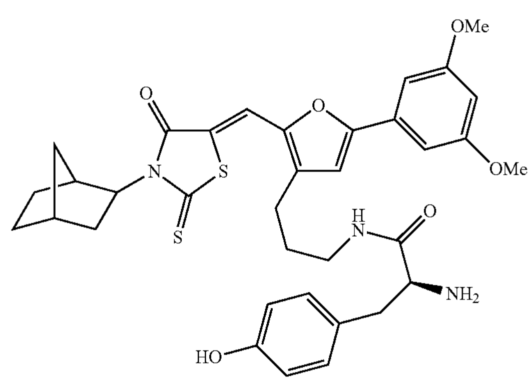 [SMILES: COc1cc(OC)cc(-c2cc(CCCNC(=O)[C@@H](N)Cc3ccc(O)cc3)c(/C=C3\SC(=S)N(C4CC5CCC4C5)C3=O)o2)c1] | C35H39N3O6S2<br>Exact Mass: 661.2280<br>Molecular Weight: 661.8307 | A | A |

TABLE 1-continued

| Compound No | Structure | MW | EC$_{50}$ | Virus Yield |
|---|---|---|---|---|
| 168 | 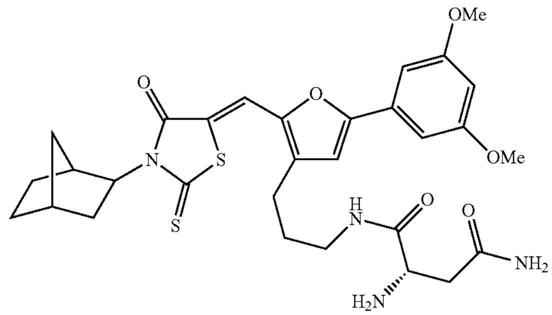 [SMILES: COc1cc(OC)cc(-c2cc(CCCNC(=O)[C@@H](N)CC(N)=O)c(/C=C3\SC(=S)N(C4CC5CCC4C5)C3=O)o2)c1] | C30H36N4O6S2<br>Exact Mass: 612.2076<br>Molecular Weight: 612.7600 | A | B |
| 169 | 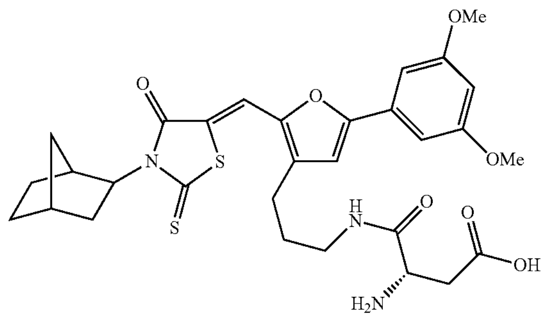 [SMILES: COc1cc(OC)cc(-c2cc(CCCNC(=O)[C@@H](N)CC(=O)O)c(/C=C3\SC(=S)N(C4CC5CCC4C5)C3=O)o2)c1] | C30H35N3O7S2<br>Exact Mass: 613.1916<br>Molecular Weight: 613.7448 | A | C |
| 170 | 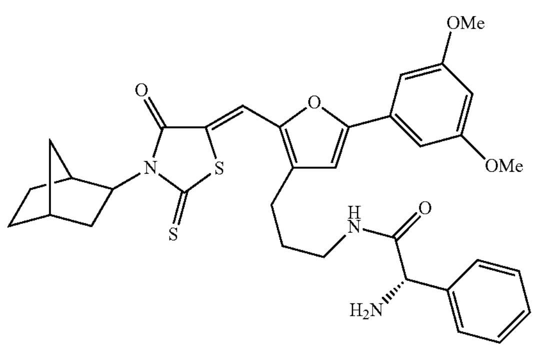 [SMILES: COc1cc(OC)cc(-c2cc(CCCNC(=O)[C@@H](N)c3ccccc3)c(/C=C3\SC(=S)N(C4CC5CCC4C5)C3=O)o2)c1] | C34H37N3O5S2<br>Exact Mass: 631.2175<br>Molecular Weight: 631.8047 | A | A |
| 171 | 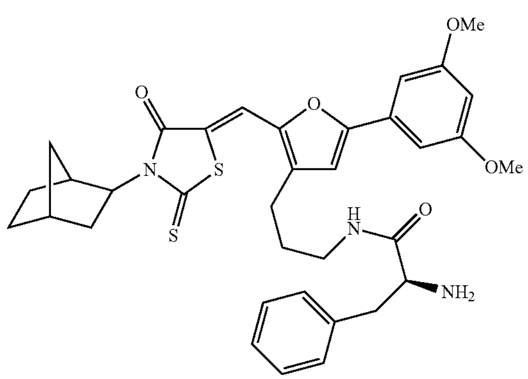 [SMILES: COc1cc(OC)cc(-c2cc(CCCNC(=O)[C@@H](N)Cc3ccccc3)c(/C=C3\SC(=S)N(C4CC5CCC4C5)C3=O)o2)c1] | C35H39N3O5S2<br>Exact Mass: 645.2331<br>Molecular Weight: 645.8313 | A | A |

TABLE 1-continued

| Compound No | Structure | MW | EC$_{50}$ | Virus Yield |
|---|---|---|---|---|
| 172 | 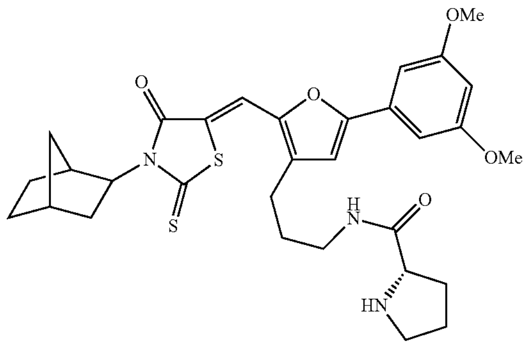 [SMILES: COc1cc(OC)cc(-c2cc(CCCNC(=O)[C@@H]3CCCN3)c(/C=C3\SC(=S)N(C4CC5CCC4C5)C3=O)o2)c1] | C31H37N3O5S2<br>Exact Mass: 595.2175<br>Molecular Weight: 595.7726 | A | C |
| 173 | 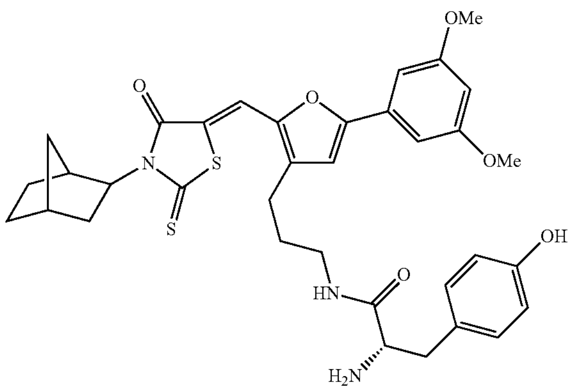 [SMILES: COc1cc(OC)cc(-c2cc(CCCNC(=O)[C@@H](N)Cc3ccc(O)cc3)c(/C=C3\SC(=S)N(C4CC5CCC4C5)C3=O)o2)c1] | C34H37N3O6S2<br>Exact Mass: 647.2124<br>Molecular Weight: 647.8041 | A | A |
| 174 | 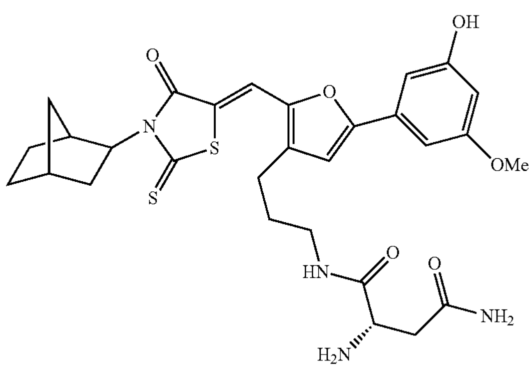 [SMILES: COc1cc(O)cc(-c2cc(CCCNC(=O)[C@@H](N)CC(N)=O)c(/C=C3\SC(=S)N(C4CC5CCC4C5)C3=O)o2)c1] | C29H34N4O6S2<br>Exact Mass: 598.1920<br>Molecular Weight: 598.7335 | A | A |
| 175 | 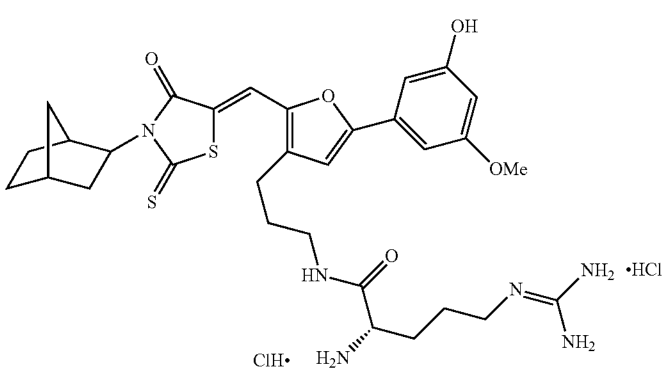 [SMILES: COc1cc(O)cc(-c2cc(CCCNC(=O)[C@@H](N)CCCN=C(N)N)c(/C=C3\SC(=S)N(C4CC5CCC4C5)C3=O)o2)c1 ; Cl] | C31H42Cl2N6O5S2<br>Exact Mass: 712.2035<br>Molecular Weight: 713.7384 | A | B |

TABLE 1-continued
| Compound No | Structure | MW | EC$_{50}$ | Virus Yield |
|---|---|---|---|---|
| | 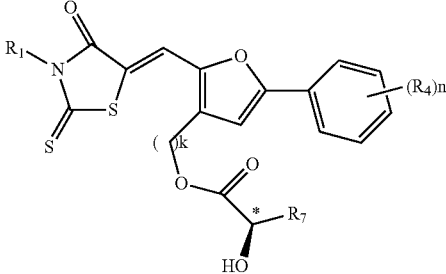<br>Type-9 Modification of side chain in C-ring (furan) with α-hydroxy acid moiety | | | |
| 176 | 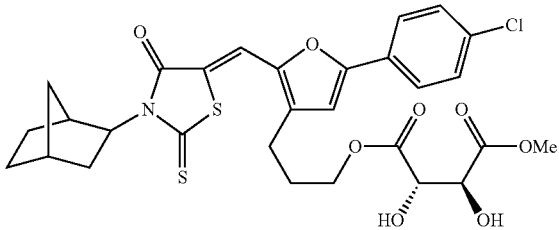 [SMILES: COC(=O)[C@@H](O)[C@H](O)C(=O)OCCCc1cc(-c2ccc(Cl)cc2)oc1/C=C1\SC(=S)N(C2CC3CCC2C3)C1=O] | C29H30ClNO8S2<br>Exact Mass: 619.1101<br>Molecular Weight: 620.1334 | NA | A |
| 177 | 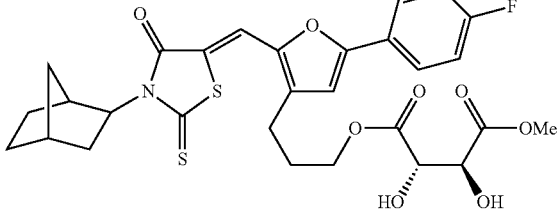 | C29H30FNO8S2<br>Exact Mass: 603.1397<br>Molecular Weight: 603.6788 | A | A |
| 178 | 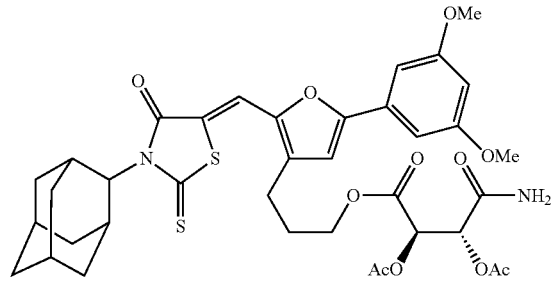 [SMILES: COc1cc(OC)cc(-c2cc(CCCOC(=O)[C@H](OC(C)=O)[C@@H](OC(C)=O)C(N)=O)c(/C=C3\SC(=S)N(C4C5CC6CC(C5)CC4C6)C3=O)o2)c1] | C37H42N2O11S2<br>Exact Mass: 754.2230<br>Molecular Weight: 754.8662 | NA | A |
| | 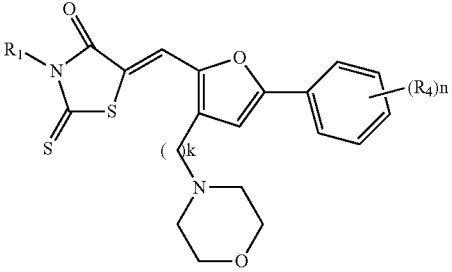 | | | |

TABLE 1-continued

| Compound No | Structure | MW | EC$_{50}$ | Virus Yield |
|---|---|---|---|---|
| 179 | 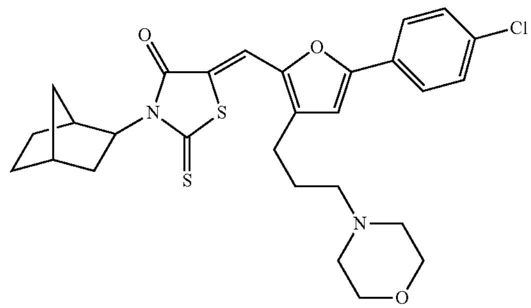 [SMILES: O=C1/C(=C/c2oc(-c3ccc(Cl)cc3)cc2CCCN2CCOCC2)SC(=S)N1C1CC2CCC1C2] | C28H31ClN2O3S2<br>Exact Mass: 542.1465<br>Molecular Weight: 543.1403 | A | A |
| 180 | 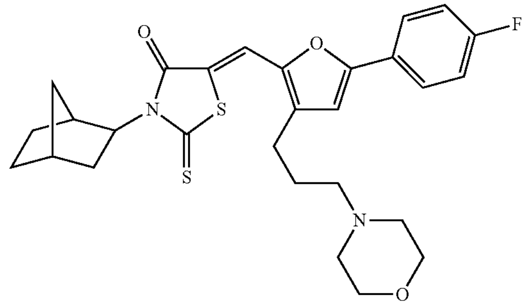 [SMILES: O=C1/C(=C/c2oc(-c3ccc(F)cc3)cc2CCCN2CCOCC2)SC(=S)N1C1CC2CCC1C2] | C28H31FN2O3S2<br>Exact Mass: 526.1760<br>Molecular Weight: 526.6857 | A | A |
| 181 | 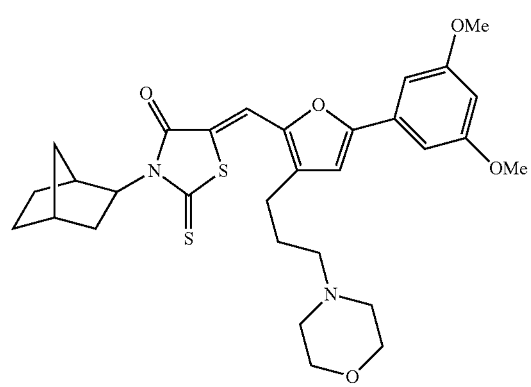 [SMILES: COc1cc(OC)cc(-c2cc(CCCN3CCOCC3)c(/C=C3\SC(=S)N(C4CC5CCC4C5)C3=O)o2)c1] | C30H36N2O5S2<br>Exact Mass: 568.2066<br>Molecular Weight: 568.7472 | A | A |
| 182 | 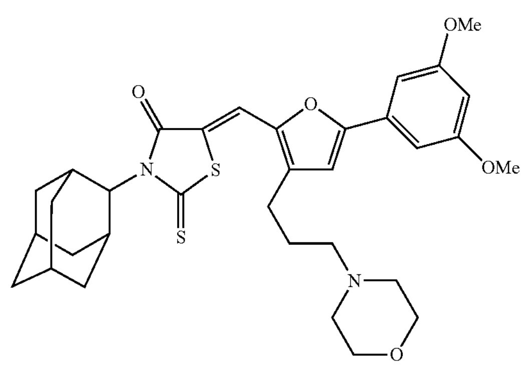 [SMILES: COc1cc(OC)cc(-c2cc(CCCN3CCOCC3)c(/C=C3\SC(=S)N(C4C5CC6CC(C5)CC4C6)C3=O)o2)c1] | C33H40N2O5S2<br>Exact Mass: 608.2379<br>Molecular Weight: 608.8111 | A | A |

TABLE 1-continued

| Compound No | Structure | MW | EC$_{50}$ | Virus Yield |
|---|---|---|---|---|
| 183 | 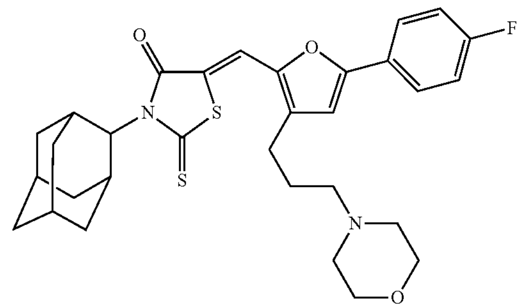 [SMILES: O=C1/C(=C/c2oc(-c3ccc(F)cc3)cc2CCCN2CCOCC2)SC(=S)N1C1C2CC3CC(C2)CC1C3] | C31H35FN2O3S2<br>Exact Mass: 566.2073<br>Molecular Weight: 566.7496 | A | A |
| 184 | 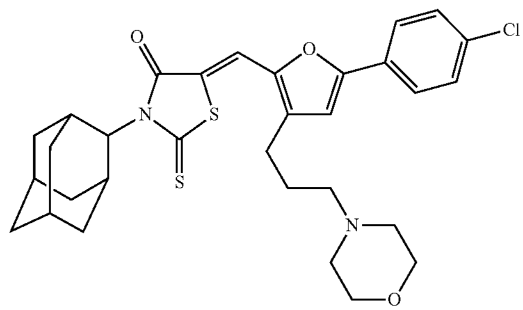 [SMILES: O=C1/C(=C/c2oc(-c3ccc(Cl)cc3)cc2CCCN2CCOCC2)SC(=S)N1C1C2CC3CC(C2)CC1C3] | C31H35ClN2O3S2<br>Exact Mass: 582.1778<br>Molecular Weight: 583.2042 | A | A |
| 185 | 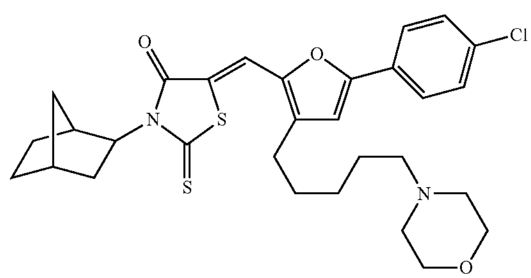 [SMILES: O=C1/C(=C/c2oc(-c3ccc(Cl)cc3)cc2CCCCCN2CCOCC2)SC(=S)N1C1CC2CCC1C2] | C30H35ClN2O3S2<br>Exact Mass: 570.1778<br>Molecular Weight: 571.1935 | NA | A |

Type-11 Modification
of side chain in
C-ring (furan) with
piperazine moiety

TABLE 1-continued

| Compound No | Structure | MW | EC$_{50}$ | Virus Yield |
|---|---|---|---|---|
| 186 | 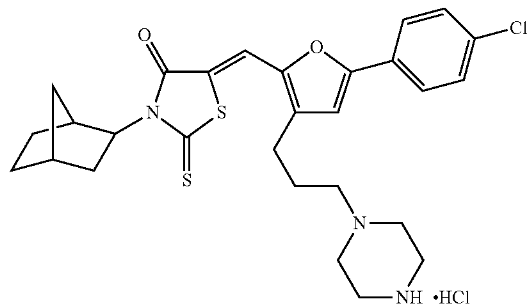 [SMILES: O=C1/C(=C/c2oc(-c3ccc(Cl)cc3)cc2CCCN2CCNCC2)SC(=S)N1C1CC2CCC1C2 ; Cl] | C28H33Cl2N3O2S2<br>Exact Mass: 577.1391<br>Molecular Weight: 578.6165 | A | A |
| 187 | 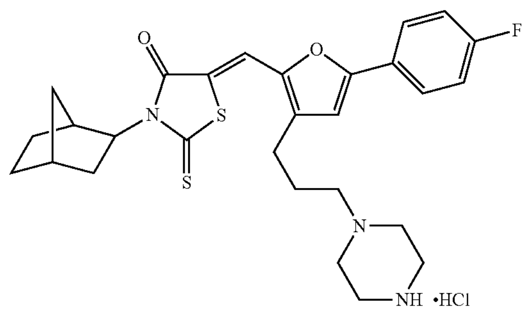 [SMILES: O=C1/C(=C/c2oc(-c3ccc(F)cc3)cc2CCCN2CCNCC2)SC(=S)N1C1CC2CCC1C2 ; Cl] | C28H33ClFN3O2S2<br>Exact Mass: 561.1687<br>Molecular Weight: 562.1619 | A | A |
| 188 | 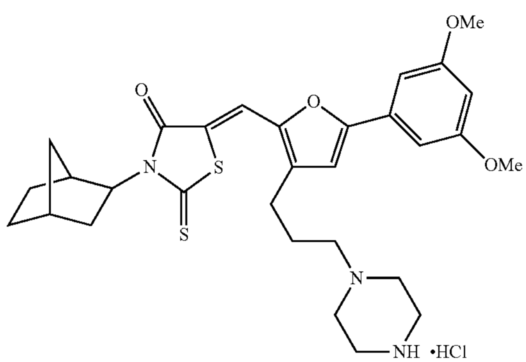 [SMILES: COc1cc(OC)cc(-c2cc(CCCN3CCNCC3)c(/C=C3\SC(=S)N(C4CC5CCC4C5)C3=O)o2)c1 ; Cl] | C30H38ClN3O4S2<br>Exact Mass: 603.1992<br>Molecular Weight: 604.2234 | A | A |
| 189 | 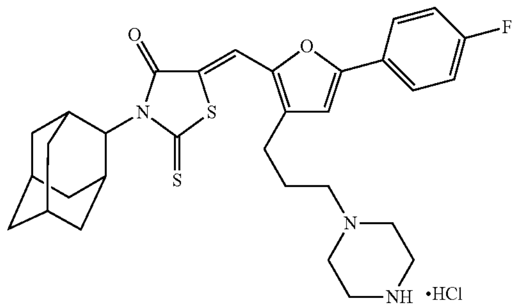 [SMILES: O=C1/C(=C/c2oc(-c3ccc(F)cc3)cc2CCCN2CCNCC2)SC(=S)N1C1C2CC3CC(C2)CC1C3 ; Cl] | C31H37ClFN3O2S2<br>Exact Mass: 601.2000<br>Molecular Weight: 602.2258 | A | A |

TABLE 1-continued

| Compound No | Structure | MW | EC$_{50}$ | Virus Yield |
|---|---|---|---|---|
| 190 | 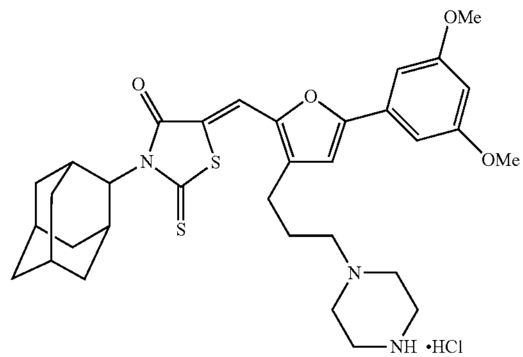 [SMILES: COc1cc(OC)cc(-c2cc(CCCN3CCNCC3)c(/C=C3\SC(=S)N(C4C5CC6CC(C5)CC4C6)C3=O)o2)c1 ; Cl] | C33H42ClN3O4S2<br>Exact Mass: 643.2305<br>Molecular Weight: 644.2873 | A | A |
| 191 | 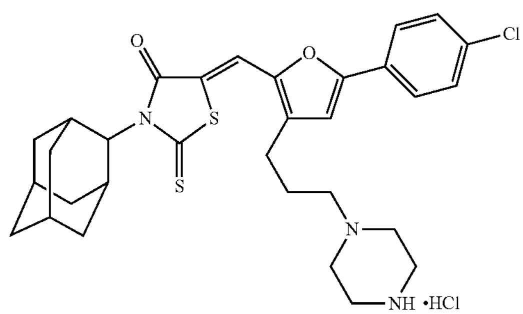 [SMILES: O=C1/C(=C/c2oc(-c3ccc(Cl)cc3)cc2CCCN2CCNCC2)SC(=S)N1C1C2CC3CC(C2)CC1C3 ; Cl] | C31H37Cl2N3O2S2<br>Exact Mass: 617.1704<br>Molecular Weight: 618.6804 | A | A |
| 192 | 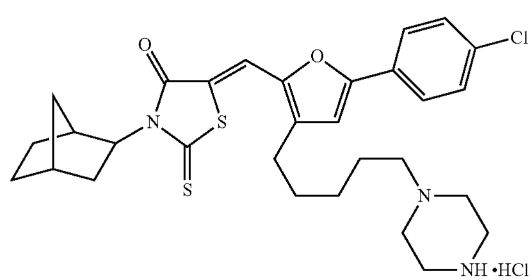 [SMILES: O=C1/C(=C/c2oc(-c3ccc(Cl)cc3)cc2CCCCCN2CCNCC2)SC(=S)N1C1CC2CCC1C2 ; Cl] | C30H37Cl2N3O2S2<br>Exact Mass: 605.1704<br>Molecular Weight: 606.6697 | A | A |

Type-12 Modification
of side chain in
C-ring (furan) with
guanidine moiety

TABLE 1-continued
| Compound No | Structure | MW | EC$_{50}$ | Virus Yield |
|---|---|---|---|---|
| 193 | 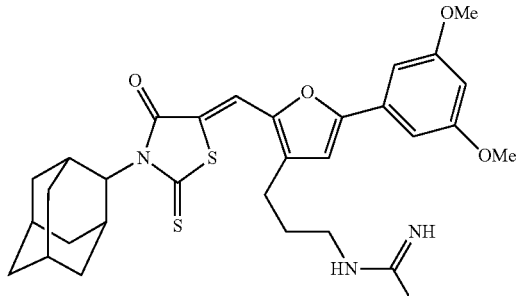 | C35H44N4O6S2<br>Exact Mass: 680.2702<br>Molecular Weight: 680.8771 | NA | C |
| 194 | 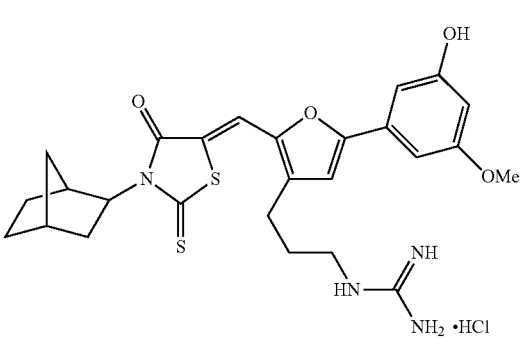 [SMILES: COc1cc(O)cc(-c2cc(CCCNC(=N)N)c(/C=C3\SC(=S)N(C4CC5CCC4C5)C3=O)o2)c1 ; Cl] | C26H31ClN4O4S2<br>Exact Mass: 562.1475<br>Molecular Weight: 563.1317 | A | A |
| 195 | 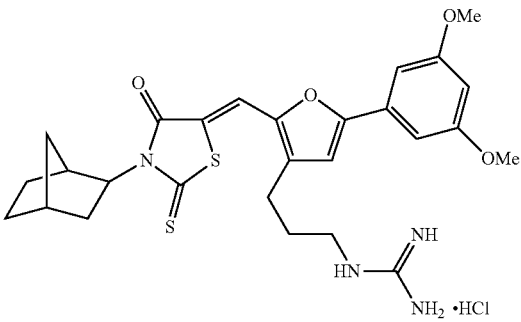 [SMILES: COc1cc(OC)cc(-c2cc(CCCNC(=N)N)c(/C=C3\SC(=S)N(C4CC5CCC4C5)C3=O)o2)c1 ; Cl] | C27H33ClN4O4S2<br>Exact Mass: 576.1632<br>Molecular Weight: 577.1583 | A | B |
| 196 | 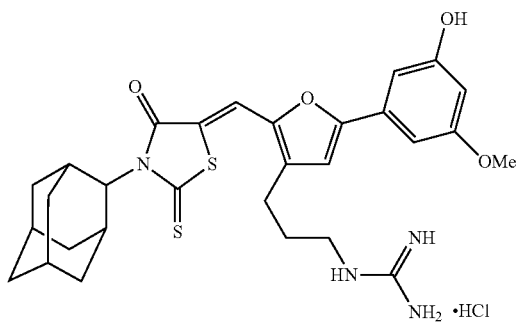 [SMILES: COc1cc(O)cc(-c2cc(CCCNC(=N)N)c(/C=C3\SC(=S)N(C4C5CC6CC(C5)CC4C6)C3=O)o2)c1 ; Cl] | C30H37ClN4O4S2<br>Exact Mass: 616.1945<br>Molecular Weight: 617.2222 | A | A |
| 197 | 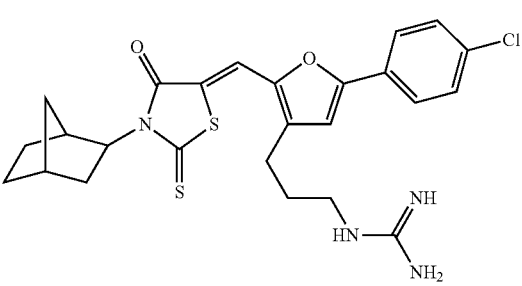 [SMILES: N=C(N)NCCCc1cc(-c2ccc(Cl)cc2)oc1/C=C1\SC(=S)N(C2CC3CCC2C3)C1=O] | C25H27ClN4O2S2<br>Exact Mass: 514.1264<br>Molecular Weight: 515.0905 | A | B |

TABLE 1-continued
| Compound No | Structure | MW | EC$_{50}$ | Virus Yield |
|---|---|---|---|---|
| | 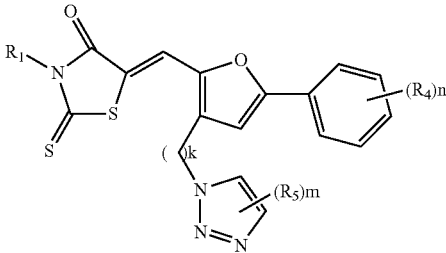 Type-13 Modification of side chain in C-ring (furan) with heterocyclic moiety | | | |
| 198 | 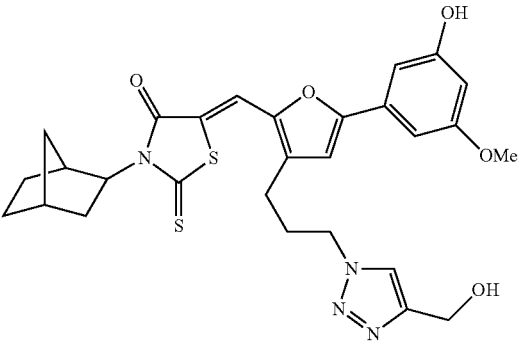 [SMILES: COc1cc(O)cc(-c2cc(CCCn3cc(CO)nn3)c(/C=C3\SC(=S)N(C4CC5CCC4C5)C3=O)o2)c1] | C29H32N4O5S2<br>Exact Mass: 580.1814<br>Molecular Weight: 580.7182 | A | B |
| 199 | 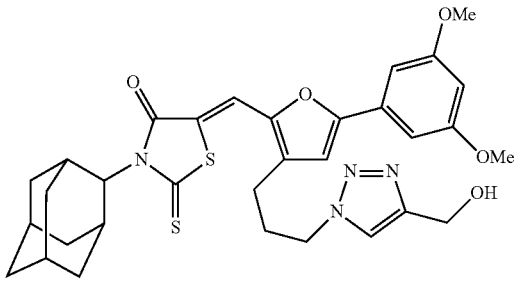 [SMILES: COc1cc(OC)cc(-c2cc(CCCn3cc(CO)nn3)c(/C=C3\SC(=S)N(C4C5CC6CC(C5)CC4C6)C3=O)o2)c1] | C32H36N4O5S2<br>Exact Mass: 620.2127<br>Molecular Weight: 620.7820 | A | A |
| 200 | 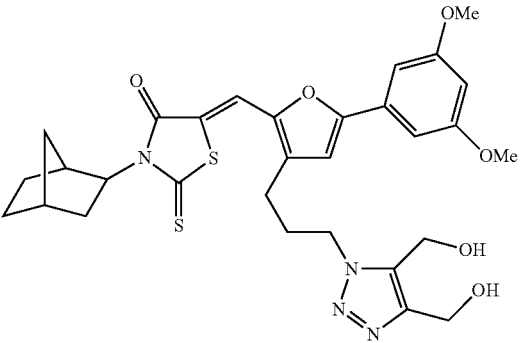 [SMILES: COc1cc(OC)cc(-c2cc(CCCn3nnc(CO)c3CO)c(/C=C3\SC(=S)N(C4CC5CCC4C5)C3=O)o2)c1] | C30H34N4O6S2<br>Exact Mass: 610.1920<br>Molecular Weight: 610.7442 | A | A |

TABLE 1-continued
| Compound No | Structure | MW | EC$_{50}$ | Virus Yield |
|---|---|---|---|---|
| 201 | 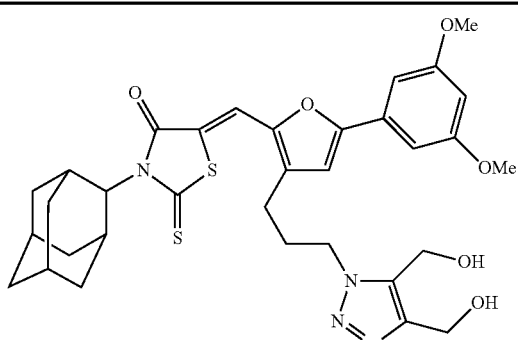 | C33H38N4O6S2<br>Exact Mass: 650.2233<br>Molecular Weight: 650.8080 | A | A |
| | Type-14 Modification of side chain in C-ring (furan) with ether moiety | | | |
| 202 | 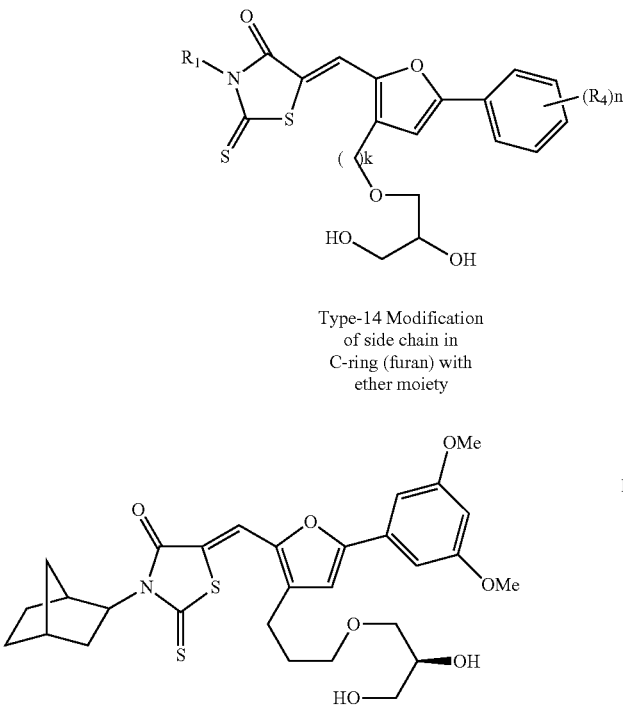 | C29H35NO7S2<br>Exact Mass: 573.1855<br>Molecular Weight: 573.7207 | A | A |
| 203 | 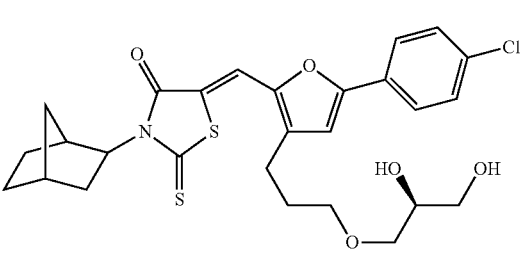 [SMILES: O=C1/C(=C/c2oc(-c3ccc(Cl)cc3)cc2CCCOC[C@@H](O)CO)SC(=S)N1C1CC2CCC1C2] | C27H30ClNO5S2<br>Exact Mass: 547.1254<br>Molecular Weight: 548.1138 | A | C |
| 204 | 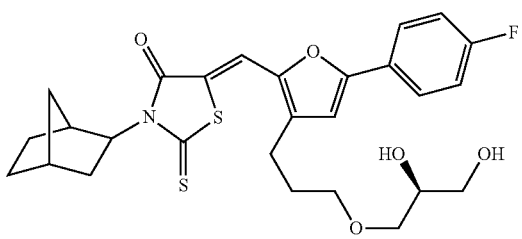 [SMILES: O=C1/C(=C/c2oc(-c3ccc(F)cc3)cc2CCCOC[C@@H](O)CO)SC(=S)N1C1CC2CCC1C2] | C27H30FNO5S2<br>Exact Mass: 531.1549<br>Molecular Weight: 531.6592 | A | C |

TABLE 1-continued

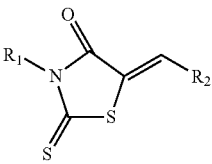

Type-15
Missing C-ring

| Compound No | Structure | MW | EC$_{50}$ | Virus Yield |
|---|---|---|---|---|
| 205 | 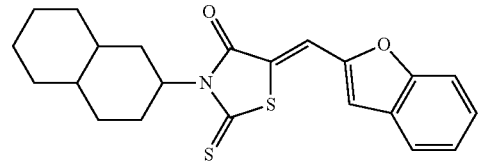 [SMILES: O=C1/C(=C/c2cc3ccccc3o2)SC(=S)N1C1CCC2CCCCC2C1] | C22H23NO2S2<br>Exact Mass: 397.1170<br>Molecular Weight: 397.5535 | NA | A |
| 206 | 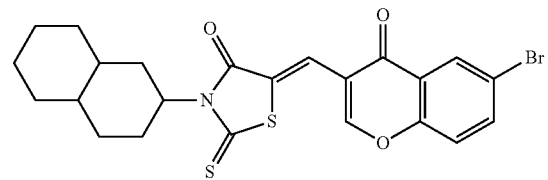 | C23H22BrNO3S2<br>Exact Mass: 503.0224<br>Molecular Weight: 504.4597 | A | NA |
| 207 | 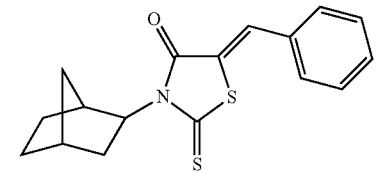 [SMILES: O=C1/C(=C/c2ccccc2)SC(=S)N1C1CC2CCC1C2] | C17H17NOS2<br>Exact Mass: 315.0752<br>Molecular Weight: 315.4530 | C | NA |
| 208 | 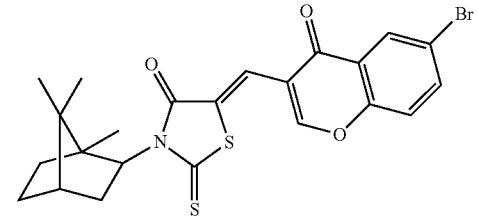 [SMILES: CC1(C)C2CCC1(C)C(N1C(=O)/C(=C/c3coc4ccc(Br)cc4c3=O)SC1=S)C2] | C23H22BrNO3S2<br>Exact Mass: 503.0224<br>Molecular Weight: 504.4597 | NA | A |
| 209 | 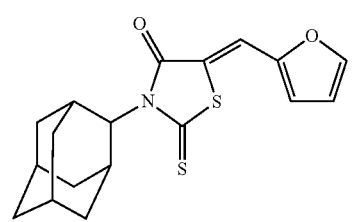 [SMILES: O=C1/C(=C/c2ccco2)SC(=S)N1C1C2CC3CC(C2)CC1C3] | Chemical Formula:<br>C18H19NO2S2<br>Exact Mass: 345.0857<br>Molecular Weight: 345.4790 | C | NA |
| 210 | 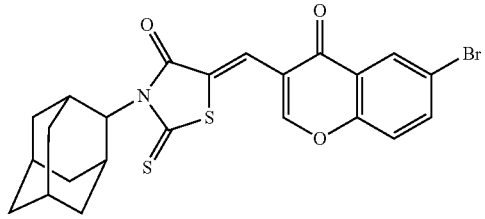 [SMILES: O=C1/C(=C/c2coc3ccc(Br)cc3c2=O)SC(=S)N1C1C2CC3CC(C2)CC1C3] | C23H20BrNO3S2<br>Exact Mass: 501.0068<br>Molecular Weight: 502.4438 | A | NA |

TABLE 1-continued

| Compound No | Structure | MW | EC$_{50}$ | Virus Yield |
|---|---|---|---|---|
| 211 | 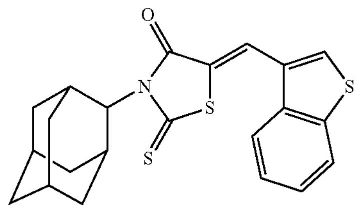 [SMILES: O=C1/C(=C/c2csc3ccccc23)SC(=S)N1C1C2CC3CC(C2)CC1C3] | C22H21NOS3<br>Exact Mass: 411.0785<br>Molecular Weight: 411.6032 | A | NA |
| 212 | 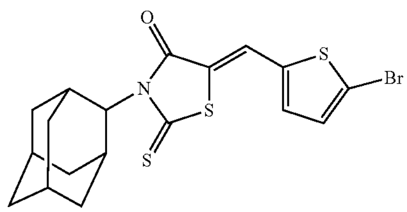 [SMILES: O=C1/C(=C/c2ccc(Br)s2)SC(=S)N1C1C2CC3CC(C2)CC1C3] | C18H18BrNOS3<br>Exact Mass: 438.9734<br>Molecular Weight: 440.4406 | A | NA |
| 213 | 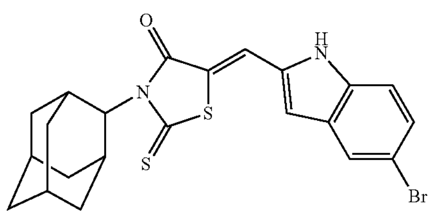 [SMILES: O=C1/C(=C/c2cc3cc(Br)ccc3[nH]2)SC(=S)N1C1C2CC3CC(C2)CC1C3] | C22H21BrN2OS2<br>Exact Mass: 472.0279<br>Molecular Weight: 473.4489 | A | NA |
| 214 | 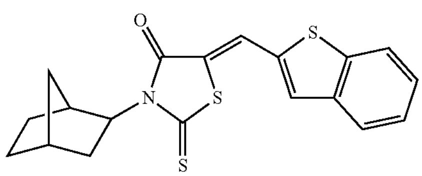 [SMILES: O=C1/C(=C/c2cc3ccccc3s2)SC(=S)N1C1CC2CCC1C2] | C19H17NOS3<br>Exact Mass: 371.0472<br>Molecular Weight: 371.5394 | A | NA |
| 215 | 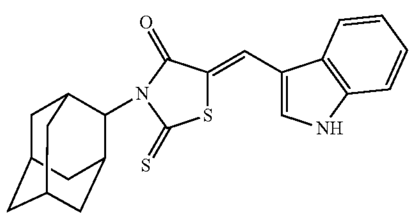 [SMILES: O=C1/C(=C/c2c[nH]c3ccccc23)SC(=S)N1C1C2CC3CC(C2)CC1C3] | C22H22N2OS2<br>Exact Mass: 394.1174<br>Molecular Weight: 394.5529 | A | NA |
| 216 | 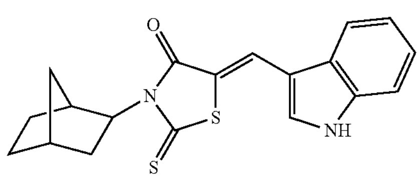 [SMILES: O=C1/C(=C/c2c[nH]c3ccccc23)SC(=S)N1C1CC2CCC1C2] | C19H18N2OS2<br>Exact Mass: 354.0861<br>Molecular Weight: 354.4890 | A | NA |
| 217 | 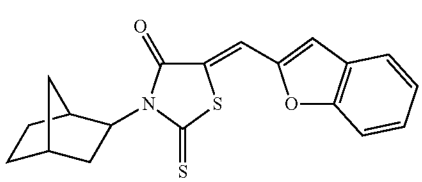 [SMILES: O=C1/C(=C/c2cc3ccccc3o2)SC(=S)N1C1CC2CCC1C2] | Chemical Formula:<br>C19H17NO2S2<br>Exact Mass: 355.0701<br>Molecular Weight: 355.4738 | A | NA |

TABLE 1-continued

| Compound No | Structure | MW | EC$_{50}$ | Virus Yield |
|---|---|---|---|---|
| 218 | | C22H21NO2S2<br>Exact Mass: 395.1014<br>Molecular Weight: 395.5376 | A | NA |
| 219 | | Chemical Formula:<br>C15H17NO2S2<br>Exact Mass: 307.0701<br>Molecular Weight: 307.4310 | C | NA |
| 220 | | Chemical Formula:<br>C14H15NO2S2<br>Exact Mass: 293.0544<br>Molecular Weight: 293.4044 | C | NA |

Type-16 Modification
of aliphatic chain
as D-ring

| Compound No | Structure | MW | EC$_{50}$ | Virus Yield |
|---|---|---|---|---|
| 221 | 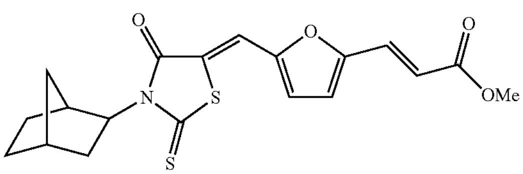 [SMILES: COC(=O)/C=C/c1ccc(/C=C2\SC(=S)N(C3CC4CCC3C4)C2=O)o1] | C19H19NO4S2<br>Exact Mass: 389.0755<br>Molecular Weight: 389.4885 | A | NA |
| 222 | 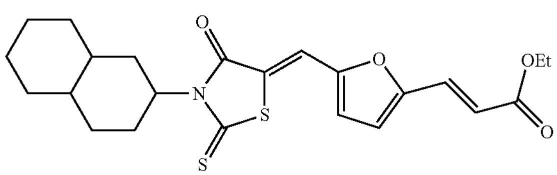 [SMILES: CCOC(=O)/C=C/c1ccc(/C=C2\SC(=S)N(C3CCC4CCCCC4C3)C2=O)o1] | C23H27NO4S2<br>Exact Mass: 445.1381<br>Molecular Weight: 445.5948 | NA | A |
| 223 | 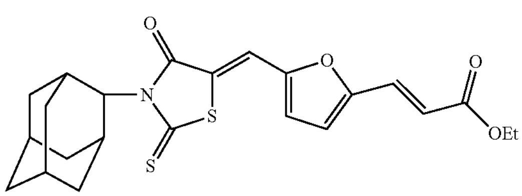 [SMILES: CCOC(=O)/C=C/c1ccc(/C=C2\SC(=S)N(C3C4CC5CC(C4)CC3C5)C2=O)o1] | C23H25NO4S2<br>Exact Mass: 443.1225<br>Molecular Weight: 443.5789 | A | NA |
| 224 | 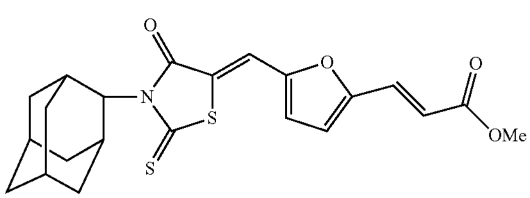 [SMILES: COC(=O)/C=C/c1ccc(/C=C2\SC(=S)N(C3C4CC5CC(C4)CC3C5)C2=O)o1] | C22H23NO4S2<br>Exact Mass: 429.1068<br>Molecular Weight: 429.5523 | A | NA |

TABLE 1-continued

| Compound No | Structure | MW | EC$_{50}$ | Virus Yield |
|---|---|---|---|---|
| 225 | 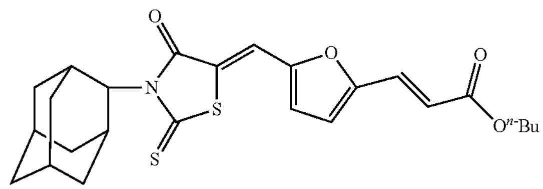 | C25H29NO4S2 Exact Mass: 471.1538 Molecular Weight: 471.6321 | A | NA |

**NA means that the measurement was not available.

Table 2 lists compounds according to embodiments of the present invention. The EC$_{50}$ classifications are based on assays for inhibiting HIV pseudovirus transducing.

| Compound No | Structure | MW | HIV EC$_{50}$ |
|---|---|---|---|
| Type-1 Basic Skeleton | 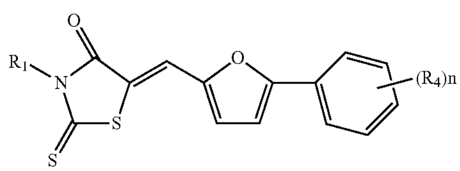 | | |
| 17 | 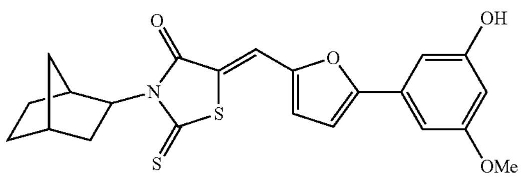 [SMILES: COc1cc(O)cc(-c2ccc(/C=C3\SC(=S)N(C4CC5CCC4C5)C3=O)o2)c1] | C22H21NO4S2 Exact Mass: 427.0912 Molecular Weight: 427.5364 | A |
| 19 | 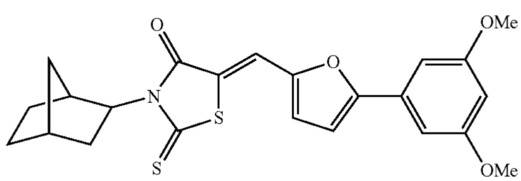 [SMILES: COc1cc(OC)cc(-c2ccc(/C=C3\SC(=S)N(C4CC5CCC4C5)C3=O)o2)c1] | C23H23NO4S2 Exact Mass: 441.1068 Molecular Weight: 441.5630 | A |
| 20 | 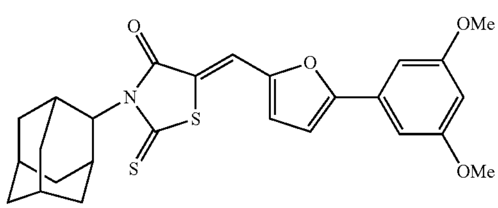 [SMILES: COc1cc(OC)cc(-c2ccc(/C=C3\SC(=S)N(C4C5CC6CC(C5)CC4C6)C3=O)o2)c1] | C26H27NO4S2 Exact Mass: 481.1381 Molecular Weight: 481.6269 | A |
| 21 | 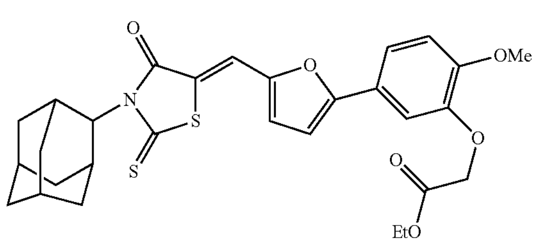 | C29H31NO6S2 Exact Mass: 553.1593 Molecular Weight: 553.6895 | A |

-continued

| Compound No | Structure | MW | HIV EC$_{50}$ |
|---|---|---|---|
| 22 | 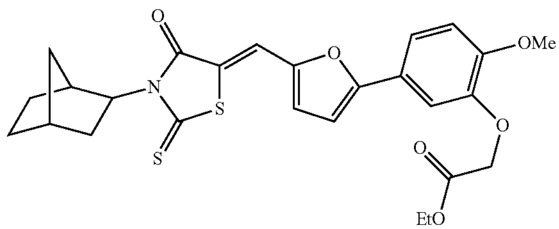 [SMILES: CCOC(=O)COc1cc(-c2ccc(/C=C3\SC(=S)N(C4CC5CCC4C5)C3=O)o2)ccc1OC] | C26H27NO6S2<br>Exact Mass:<br>513.1280<br>Molecular Weight:<br>513.6257 | A |
| 23 | 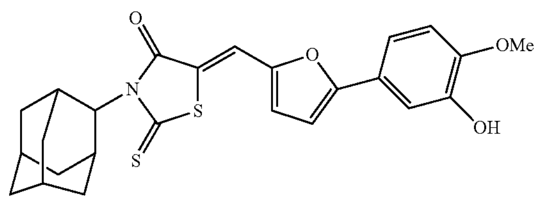 [SMILES: COc1ccc(-c2ccc(/C=C3\SC(=S)N(C4C5CC6CC(C5)CC4C6)C3=O)o2)cc1O] | C25H25NO4S2<br>Exact Mass:<br>467.1225<br>Molecular Weight:<br>467.6003 | A |
| 29 | 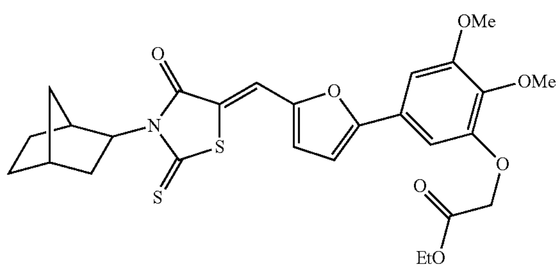 [SMILES: CCOC(=O)COc1cc(-c2ccc(/C=C3\SC(=S)N(C4CC5CCC4C5)C3=O)o2)cc(OC)c1OC] | C27H29NO7S2<br>Exact Mass:<br>543.1385<br>Molecular Weight:<br>543.6517 | A |
| 30 | 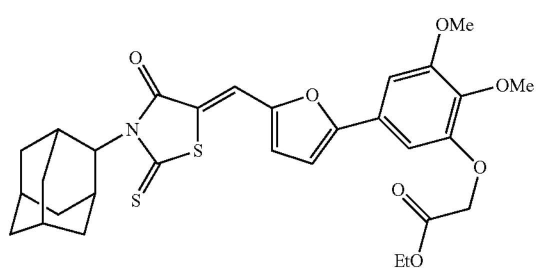 [SMILES: CCOC(=O)COc1cc(-c2ccc(/C=C3\SC(=S)N(C4C5CC6CC(C5)CC4C6)C3=O)o2)cc(OC)c1OC] | C30H33NO7S2<br>Exact Mass:<br>583.1698<br>Molecular Weight:<br>583.7155 | A |
| 31 | 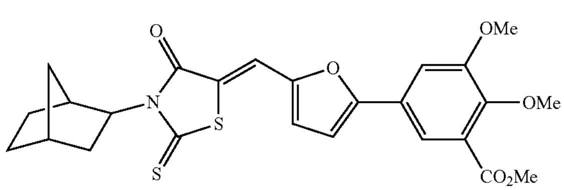 [SMILES: COC(=O)c1cc(-c2ccc(/C=C3\SC(=S)N(C4CC5CCC4C5)C3=O)o2)cc(OC)c1OC] | C25H25NO6S2<br>Exact Mass:<br>499.1123<br>Molecular Weight:<br>499.5991 | A |
| 32 | 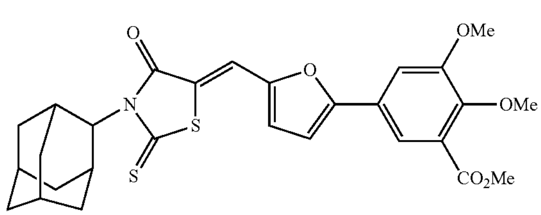 [SMILES: COC(=O)c1cc(-c2ccc(/C=C3\SC(=S)N(C4C5CC6CC(C5)CC4C6)C3=O)o2)cc(OC)c1OC] | C28H29NO6S2<br>Exact Mass:<br>539.1436<br>Molecular Weight:<br>539.6630 | A |

-continued

| Compound No | Structure | MW | HIV EC$_{50}$ |
|---|---|---|---|
| 33 | 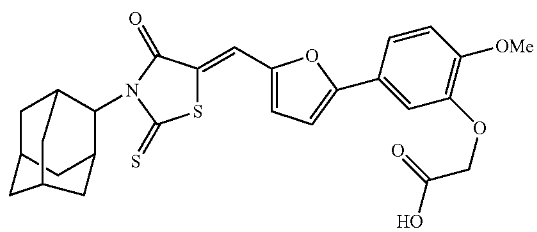 [SMILES: COc1ccc(-c2ccc(/C=C3\SC(=S)N(C4C5CC6CC(C5)CC4C6)C3=O)o2)cc1OCC(=O)O] | C27H27NO6S2 Exact Mass: 525.1280 Molecular Weight: 525.6364 | A |
| 37 | 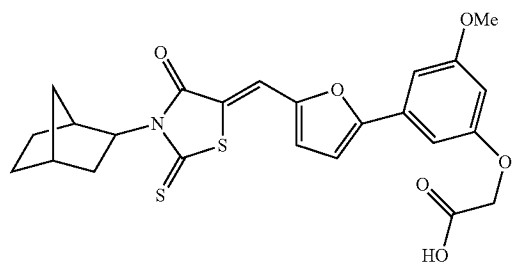 [SMILES: COc1cc(OCC(=O)O)cc(-c2ccc(/C=C3\SC(=S)N(C4CC5CCC4C5)C3=O)o2)c1] | C24H23NO6S2 Exact Mass: 485.0967 Molecular Weight: 485.5725 | A |
| Type-4 Modification of D-ring with amino acid | 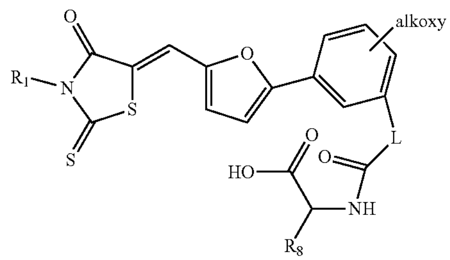 | | |
| 83 | 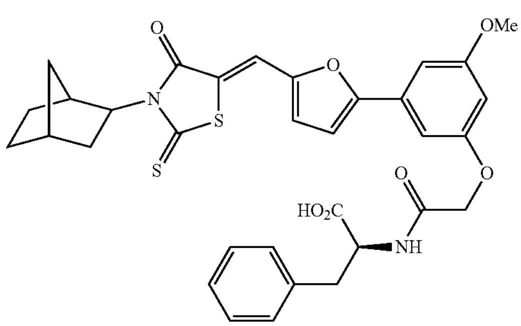 [SMILES: COc1cc(OCC(=O)N[C@@H](Cc2ccccc2)C(=O)O)cc(-c2ccc(/C=C3\SC(=S)N(C4CC5CCC4C5)C3=O)o2)c1] | C33H32N2O7S2 Exact Mass: 632.1651 Molecular Weight: 632.7464 | A |
| 84 | 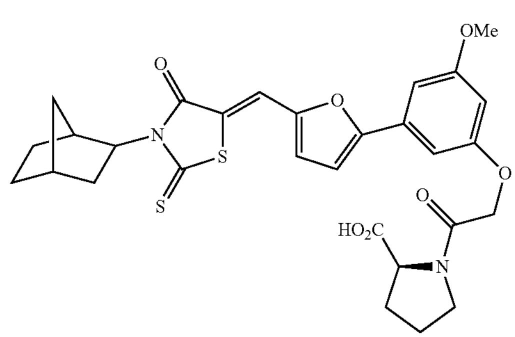 [SMILES: COc1cc(OCC(=O)N2CCC[C@H]2C(=O)O)cc(-c2ccc(/C=C3\SC(=S)N(C4CC5CCC4C5)C3=O)o2)c1] | C29H30N2O7S2 Exact Mass: 582.1494 Molecular Weight: 582.6877 | A |

-continued

| Compound No | Structure | MW | HIV EC$_{50}$ |
|---|---|---|---|
| 86 | 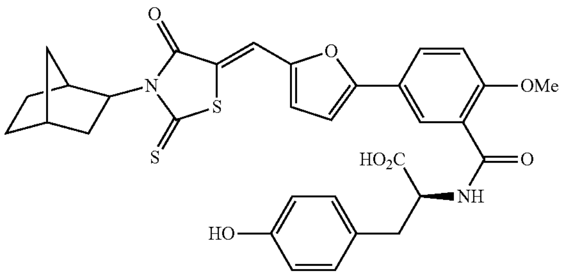 [SMILES: COc1ccc(-c2ccc(/C=C3\SC(=S)N(C4CC5CCC4C5)C3=O)o2)cc1C(=O)N[C@@H](Cc1ccc(O)cc1)C(=O)O] | C32H30N2O7S2<br>Exact Mass:<br>618.1494<br>Molecular Weight:<br>618.7198 | A |
| Type-5 Modification of side chain in C-ring (furan) with alcohol moiety | 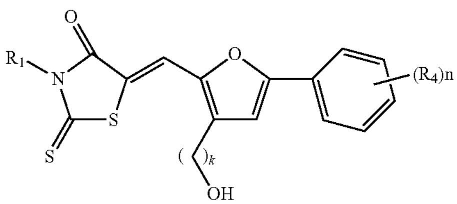 | | |
| 92 | 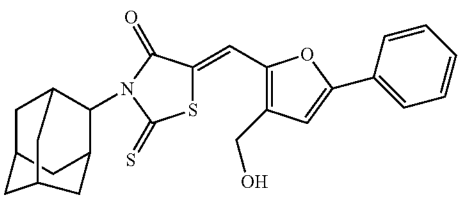 [SMILES: O=C1/C(=C/c2oc(-c3ccccc3)cc2CO)SC(=S)N1C1C2CC3CC(C2)CC1C3] | C25H25NO3S2<br>Exact Mass:<br>451.1276<br>Molecular Weight:<br>451.6009 | B |
| 95 | 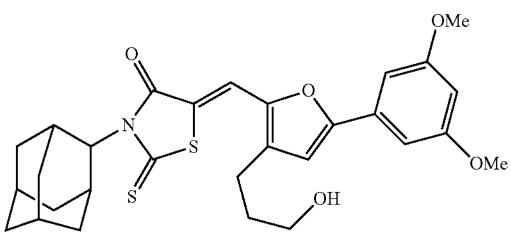 [SMILES: COc1cc(OC)cc(-c2cc(CCCO)c(/C=C3\SC(=S)N(C4C5CC6CC(C5)CC4C6)C3=O)o2)c1] | C29H33NO5S2<br>Exact Mass:<br>539.1800<br>Molecular Weight:<br>539.7060 | A |
| 99 | 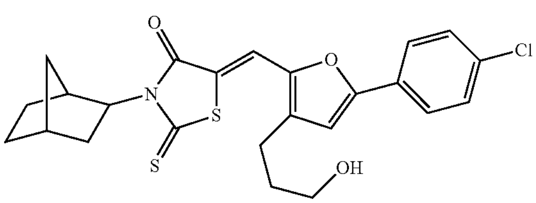 [SMILES: O=C1/C(=C/c2oc(-c3ccc(Cl)cc3)cc2CCCO)SC(=S)N1C1CC2CCC1C2] | C24H24ClNO3S2<br>Exact Mass:<br>473.0886<br>Mol. Wt.:<br>474.0353 | A |
| 101 | 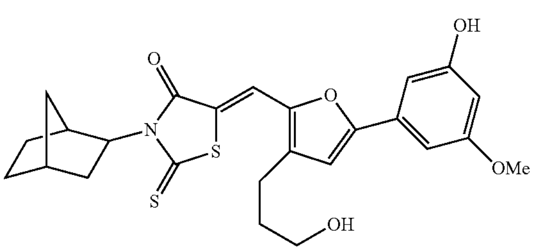 [SMILES: COc1cc(O)cc(-c2cc(CCCO)c(/C=C3\SC(=S)N(C4CC5CCC4C5)C3=O)o2)c1] | C25H27NO5S2<br>Exact Mass:<br>485.1331<br>Molecular Weight:<br>485.6156 | A |

| Compound No | Structure | MW | HIV EC$_{50}$ |
|---|---|---|---|
| 102 | 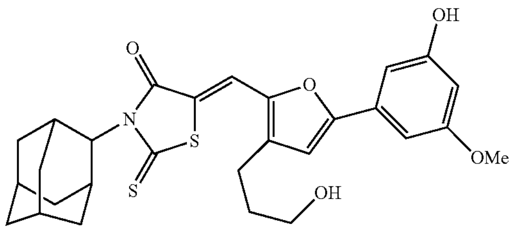 [SMILES: COc1cc(O)cc(-c2cc(CCCO)c(/C=C3\SC(=S)N(C4C5CC6CC(C5)CC4C6)C3=O)o2)c1] | C28H31NO5S2<br>Exact Mass:<br>525.1644<br>Molecular Weight:<br>525.6794 | A |
| 103 | 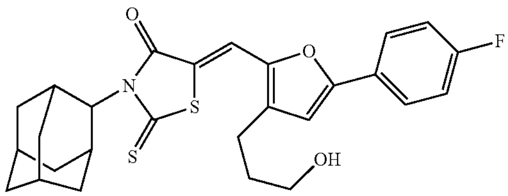 [SMILES: O=C1/C(=C/c2oc(-c3ccc(F)cc3)cc2CCCO)SC(=S)N1C1C2CC3CC(C2)CC1C3] | C27H28FNO3S2<br>Exact Mass:<br>497.1495<br>Molecular Weight:<br>497.6445 | A |
| 104 | 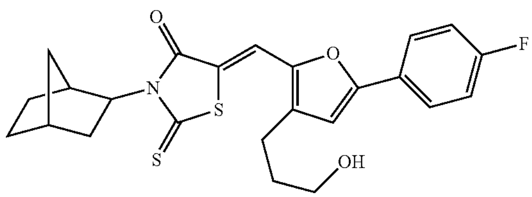 [SMILES: O=C1/C(=C/c2oc(-c3ccc(F)cc3)cc2CCCO)SC(=S)N1C1CC2CCC1C2] | C24H24FNO3S2<br>Exact Mass:<br>457.1182<br>Molecular Weight:<br>457.5807 | A |
| 113 | 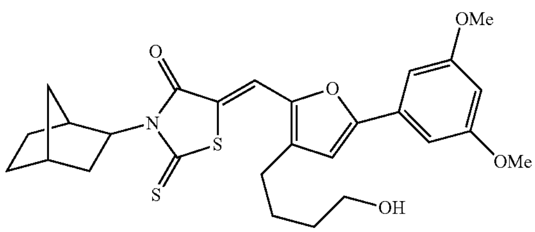 [SMILES: COc1cc(OC)cc(-c2cc(CCCCO)c(/C=C3\SC(=S)N(C4CC5CCC4C5)C3=O)o2)c1] | C27H31NO5S2<br>Exact Mass:<br>513.1644<br>Molecular Weight:<br>513.6687 | A |
| 114 | 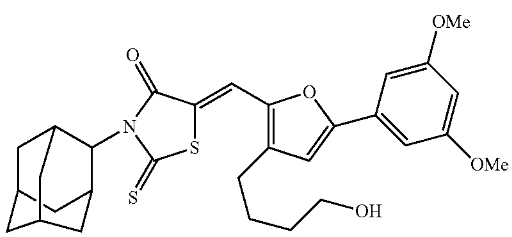 [SMILES: COc1cc(OC)cc(-c2cc(CCCCO)c(/C=C3\SC(=S)N(C4C5CC6CC(C5)CC4C6)C3=O)o2)c1] | C30H35NO5S2<br>Exact Mass:<br>553.1957<br>Molecular Weight:<br>553.7326 | A |
| Type-6 Modification of side chain C-ring (furan) with amine moiety | 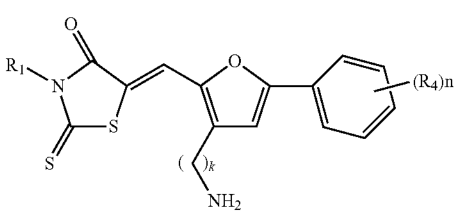 | | |
| 120 | 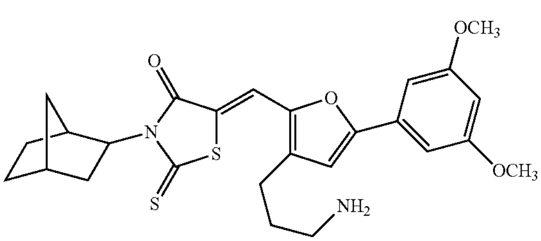 [SMILES: COc1cc(OC)cc(-c2cc(CCCN)c(/C=C3\SC(=S)N(C4CC5CCC4C5)C3=O)o2)c1] | C26H30N2O4S2<br>Exact Mass:<br>498.1647<br>Molecular Weight:<br>498.6574 | A |

-continued

| Compound No | Structure | MW | HIV EC$_{50}$ |
|---|---|---|---|
| 121 | 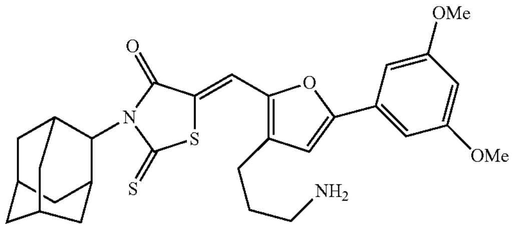 | C29H34N2O4S2<br>Exact Mass:<br>538.1960<br>Molecular Weight:<br>538.7213 | A |
| 122 | 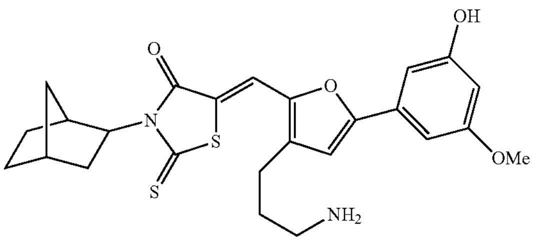 [SMILES: COc1cc(O)cc(-c2cc(CCCN)c(/C=C3\SC(=S)N(C4CC5CCC4C5)C3=O)o2)c1] | C25H28N2O4S2<br>Exact Mass:<br>484.1490<br>Molecular Weight:<br>484.6308 | A |
| 123 | 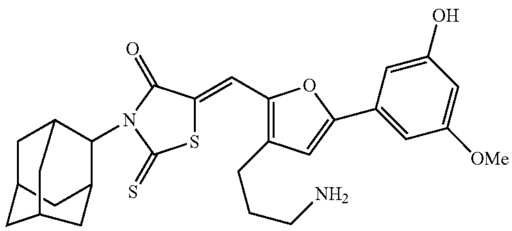 | C28H32N2O4S2<br>Exact Mass:<br>524.1803<br>Molecular Weight:<br>524.6947 | A |
| 124 | 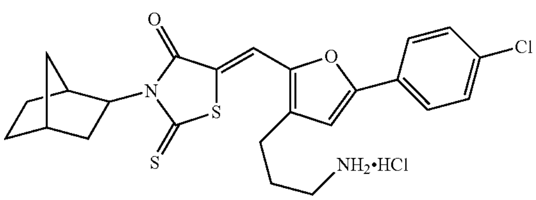 | C24H26Cl2N2O2S2<br>Exact Mass:<br>508.0813<br>Molecular Weight:<br>509.5114 | A |
| 125 | 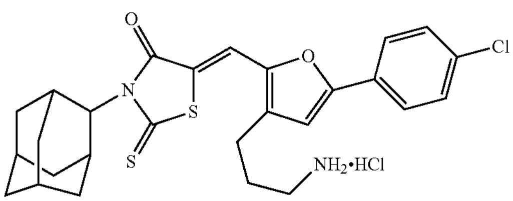 | C27H30Cl2N2O2S2<br>Exact Mass:<br>548.1126<br>Molecular Weight:<br>549.5753 | A |
| Type-7 Modification of side chain in C-ring (furan) with acid moiety | 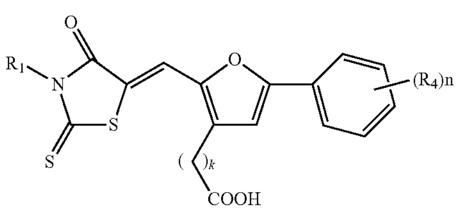 | | |
| 129 | 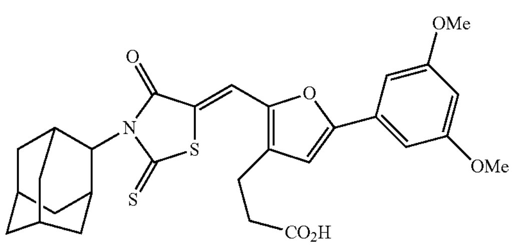 [SMILES: COc1cc(OC)cc(-c2cc(CCC(=O)O)c(/C=C3\SC(=S)N(C4C5CC6CC(C5)CC4C6)C3=O)o2)c1] | C29H31NO6S2<br>Exact Mass:<br>553.1593<br>Molecular Weight:<br>553.6895 | A |

-continued

| Compound No | Structure | MW | HIV EC$_{50}$ |
|---|---|---|---|
| 130 | 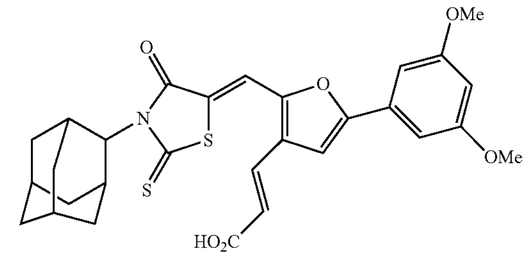 [SMILES: COc1cc(OC)cc(-c2cc(/C=C/C(=O)O)c(/C=C3\SC(=S)N(C4C5CC6CC(C5)CC4C6)C3=O)o2)c1] | C29H29NO6S2<br>Exact Mass:<br>551.1436<br>Molecular Weight:<br>551.67376 | A |
| 137 | 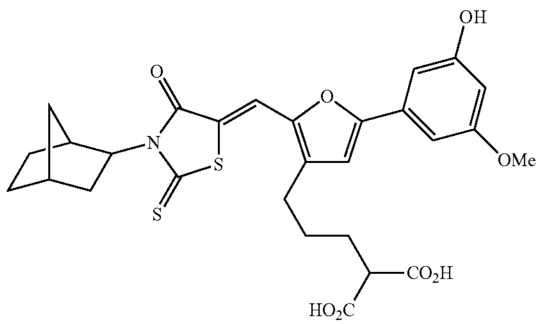 [SMILES: COc1cc(O)cc(-c2cc(CCCC(C(=O)O)C(=O)O)c(/C=C3\SC(=S)N(C4CC5CCC4C5)C3=O)o2)c1] | C28H29NO8S2<br>Exact Mass:<br>571.1335<br>Molecular Weight:<br>571.6618 | A |
| Type-8 Modification of side chain in C-ring (furan) with amino acid moiety | 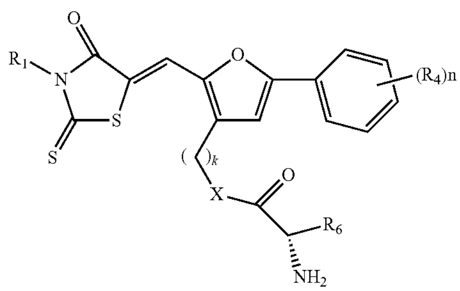 | | |
| 138 | 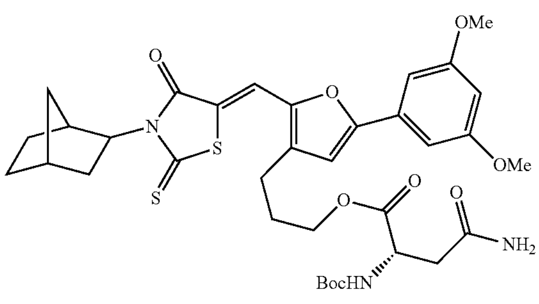 [SMILES: COc1cc(OC)cc(-c2cc(CCCOC(=O)[C@H](CC(N)=O)NC(=O)OC(C)(C)C)c(/C=C3\SC(=S)N(C4CC5CCC4C5)C3=O)o2)c1] | C35H43N3O9S2<br>Exact Mass:<br>713.2441<br>Molecular Weight:<br>713.8606 | A |
| 151 | 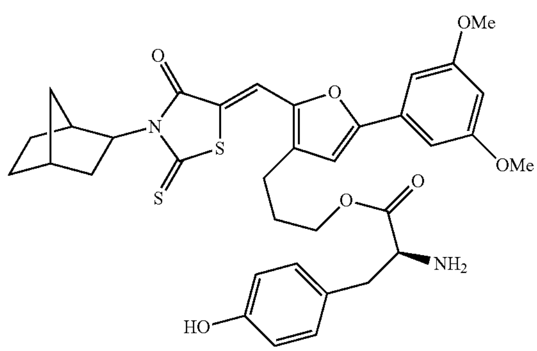 [SMILES: COc1cc(OC)cc(-c2cc(CCCOC(=O)[C@@H](N)Cc3ccc(O)cc3)c(/C=C3\SC(=S)N(C4CC5CCC4C5)C3=O)o2)c1] | C35H38N2O7S2<br>Exact Mass:<br>662.2120<br>Molecular Weight:<br>662.8154 | A |

| Compound No | Structure | MW | HIV EC$_{50}$ |
|---|---|---|---|
| 156 | 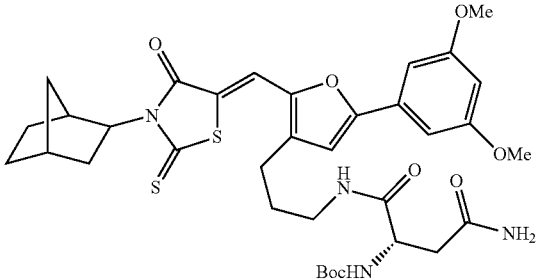 [SMILES: COc1cc(OC)cc(-c2cc(CCCNC(=O)[C@H](CC(N)=O)NC(=O)OC(C)(C)C)c(/C=C3\SC(=S)N(C4CC5CCC4C5)C3=O)o2)c1] | C35H44N4O8S2<br>Exact Mass:<br>712.2601<br>Molecular Weight:<br>712.8759 | A |
| 157 | 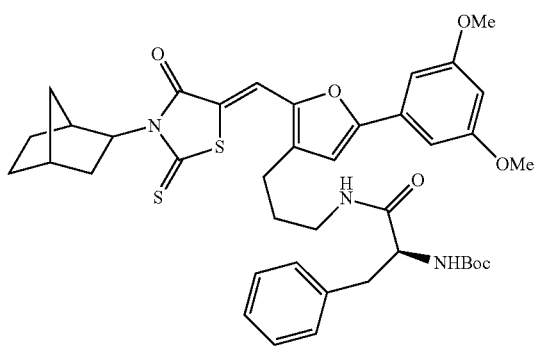 [SMILES: COc1cc(OC)cc(-c2cc(CCCNC(=O)[C@H](Cc3ccccc3)NC(=O)OC(C)(C)C)c(/C=C3\SC(=S)N(C4CC5CCC4C5)C3=O)o2)c1] | C40H47N3O7S2<br>Exact Mass:<br>745.2855<br>Molecular Weight:<br>745.9471 | A |
| 163 | 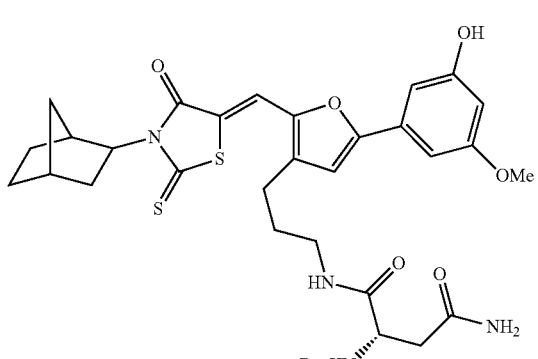 | C34H42N4O8S2<br>Exact Mass:<br>698.2444<br>Molecular Weight:<br>698.8493 | A |
| 167 | 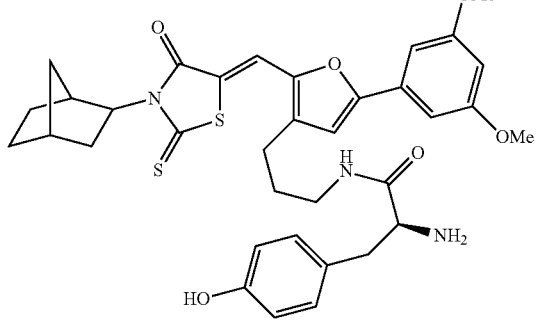 | C35H39N3O6S2<br>Exact Mass:<br>661.2280<br>Molecular Weight:<br>661.8307 | A |

| Compound No | Structure | MW | HIV EC$_{50}$ |
|---|---|---|---|
| 168 | 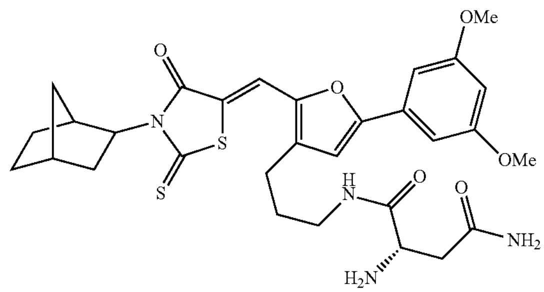 [SMILES: COc1cc(OC)cc(-c2cc(CCCNC(=O)[C@@H](N)CC(N)=O)c(/C=C3\SC(=S)N(C4CC5CCC4C5)C3=O)o2)c1] | C30H36N4O6S2<br>Exact Mass:<br>612.2076<br>Molecular Weight:<br>612.7600 | A |
| 170 | 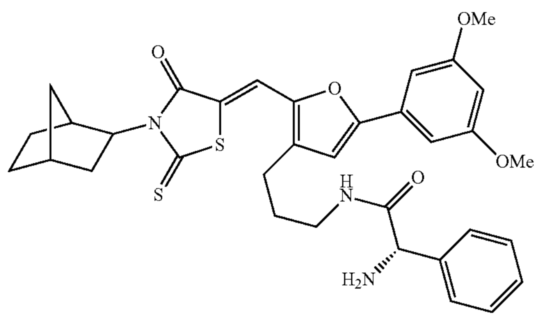 [SMILES: COc1cc(OC)cc(-c2cc(CCCNC(=O)[C@@H](N)c3ccccc3)c(/C=C3\SC(=S)N(C4CC5CCC4C5)C3=O)o2)c1] | C34H37N3O5S2<br>Exact Mass:<br>631.2175<br>Molecular Weight:<br>631.8047 | A |
| 171 | 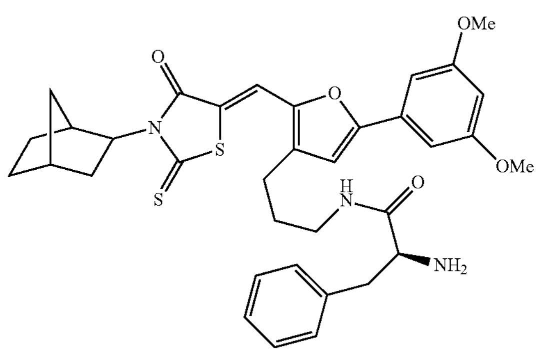 [SMILES: COc1cc(OC)cc(-c2cc(CCCNC(=O)[C@@H](N)Cc3ccccc3)c(/C=C3\SC(=S)N(C4CC5CCC4C5)C3=O)o2)c1] | C35H39N3O5S2<br>Exact Mass:<br>645.2331<br>Molecular Weight:<br>645.8313 | A |
| 173 | 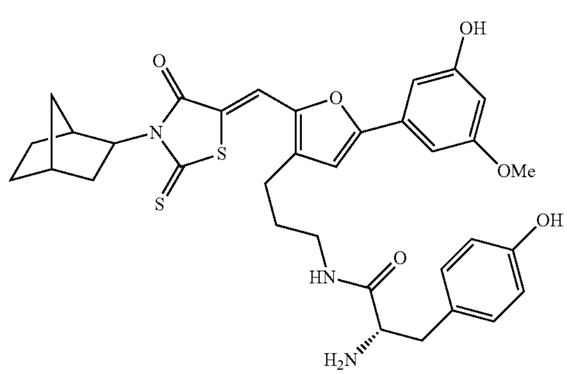 [SMILES: COc1cc(O)cc(-c2cc(CCCNC(=O)[C@@H](N)Cc3ccc(O)cc3)c(/C=C3\SC(=S)N(C4CC5CCC4C5)C3=O)o2)c1] | C34H37N3O6S2<br>Exact Mass:<br>647.2124<br>Molecular Weight:<br>647.8401 | A |

| Compound No | Structure | MW | HIV EC$_{50}$ |
|---|---|---|---|
| 174 | 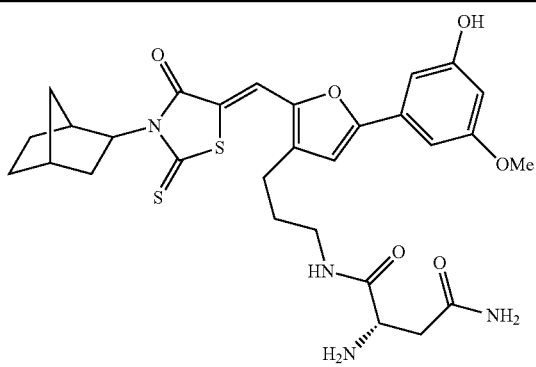 | C29H34N4O6S2<br>Exact Mass:<br>598.1920<br>Molecular Weight:<br>598.7335 | A |
| Type-11<br>Modification<br>of side chain<br>in<br>C-ring<br>(furan) with<br>piperazine<br>moiety | 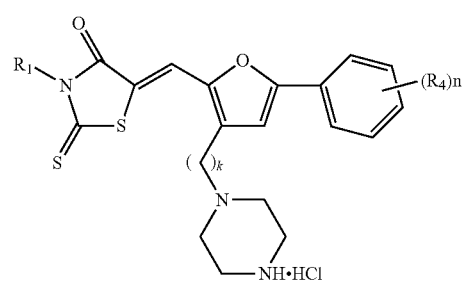 | | |
| 186 | 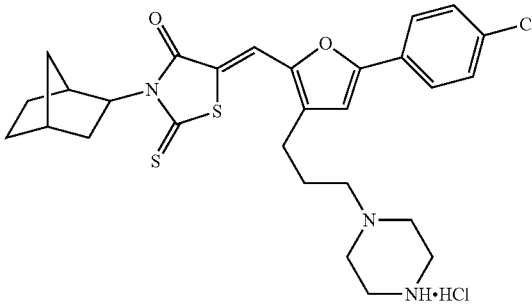 | C28H33Cl2N3O2S2<br>Exact Mass:<br>577.1391<br>Molecular Weight:<br>578.6165 | A |
| Type-12<br>Modification<br>of side chain<br>in<br>C-ring<br>(furan) with<br>guanidine<br>moiety | 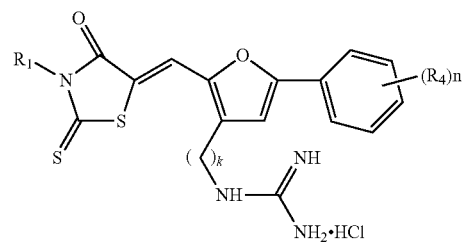 | | |
| 194 | 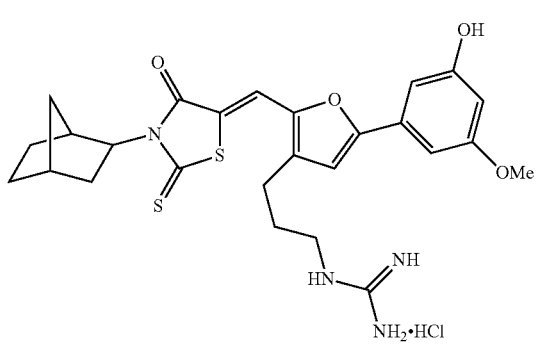 | C26H31ClN4O4S2<br>Exact Mass:<br>562.1475<br>Molecular Weight:<br>563.1317 | A |

-continued
| Compound No | Structure | MW | HIV EC$_{50}$ |
|---|---|---|---|
| 195 | 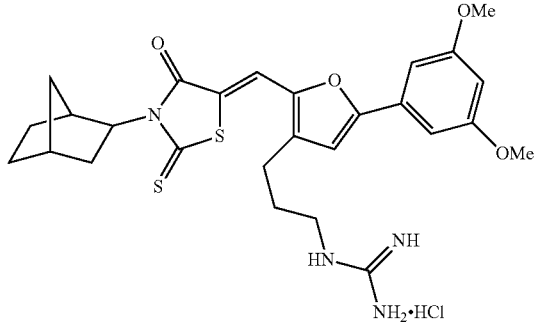 | C27H33ClN4O4S2<br>Exact Mass:<br>576.1632<br>Molecular Weight:<br>577.1583 | A |
| Type-13 Modification of side chain in C-ring (furan) with heterocyclic moiety | 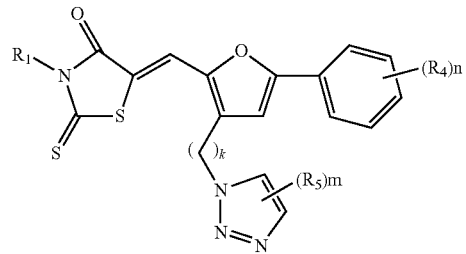 | | |
| 198 | 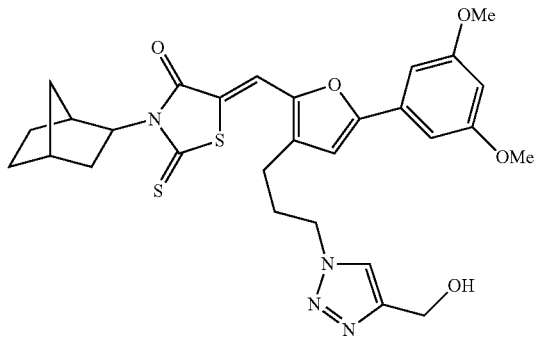 [SMILES: COc1cc(OC)cc(-c2cc(CCCn3cc(CO)nn3)c(/C=C3\SC(=S)N(C4CC5CCC4C5)C3=O)o2)c1] | C29H32N4O5S2<br>Exact Mass:<br>580.1814<br>Molecular Weight:<br>580.7182 | A |
| 200 | 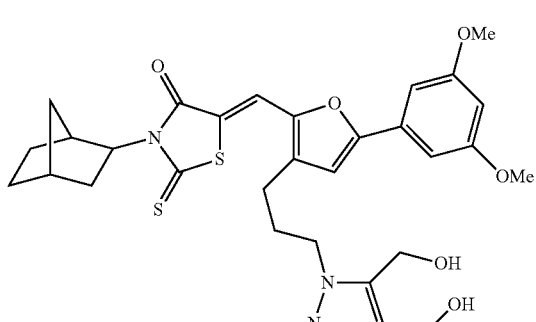 | C30H34N4O6S2<br>Exact Mass:<br>610.1920<br>Molecular Weight:<br>610.7442 | A |

| Compound No | Structure | MW | HIV EC$_{50}$ |
|---|---|---|---|
| 201 | 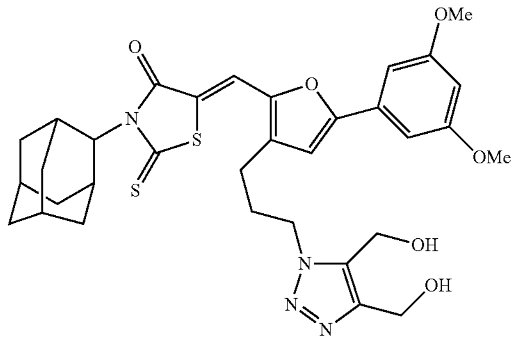 [SMILES: COc1cc(OC)cc(-c2cc(CCCn3nnc(CO)c3CO)c(/C=C3\SC(=S)N(C4C5CC6CC(C5)CC4C6)C3=O)o2)c1] | C33H38N4O6S2 Exact Mass: 650.2233 Molecular Weight: 650.8080 | A |

Table 3 lists additional compounds according to embodiments of the present invention. The EC50 and virus yield classifications are based on assays for inhibiting influenza virus infection.

| Compound No. | Structure | MW | EC50 (nM) | 24 hr titer |
|---|---|---|---|---|
| Formula (III)(a) | R$_4$ is an optionally substituted aryl, heteraryl, cycloalkyl or heterocyclic ring | | | |
| 226 | 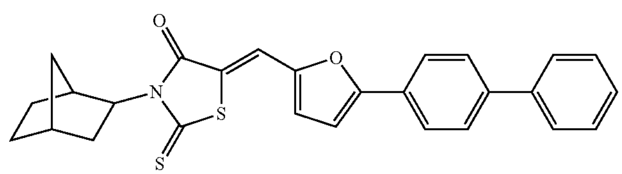 [SMILES: O=C1/C(=C/c2ccc(-c3ccc(-c4ccccc4)cc3)o2)SC(=S)N1C1CC2CCC1C2] | C27H23NO2S2 Exact Mass: 457.1170 Molecular Weight: 457.6070 | A | A |
| 227 | 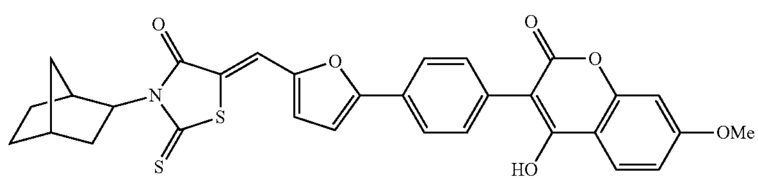 [SMILES: COc1ccc2c(O)c(-c3ccc(-c4ccc(/C=C5\SC(=S)N(C6CC7CCC6C7)C5=O)o4)cc3)c(=O)oc2c1] | C31H25NO6S2 Exact Mass: 571.1123 Molecular Weight: 571.6633 | A | B |
| Formula (III)(b)(1)-(III)(b)(12) | R$_2$ = A—B; W = S or an optionally substituted NH | | | |
| 228 | 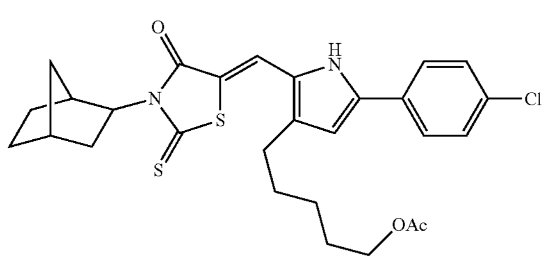 [SMILES: CC(=O)OCCCCCc1cc(-c2ccc(Cl)cc2)[nH]c1/C=C1\SC(=S)N(C2CC3CCC2C3)C1=O] | C28H31ClN2O3S2 Exact Mass: 542.1465 Molecular Weight: 543.1403 | NA | C |
| 229 | 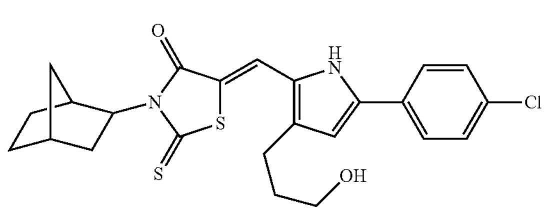 | C24H25ClN2O2S2 Exact Mass: 472.1046 Molecular Weight: 473.0505 | A | C |

-continued

| Compound No. | Structure | MW | EC50 (nM) | 24 hr titer |
|---|---|---|---|---|
| 230 | 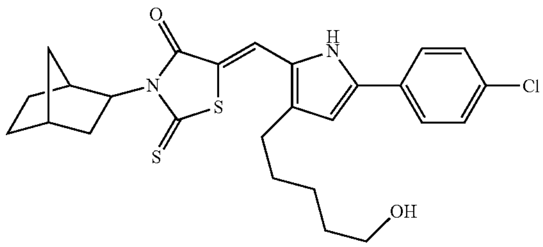 | C26H29ClN2O2S2<br>Exact Mass: 500.1359<br>Molecular Weight: 501.1037 | A | C |
| 231 | 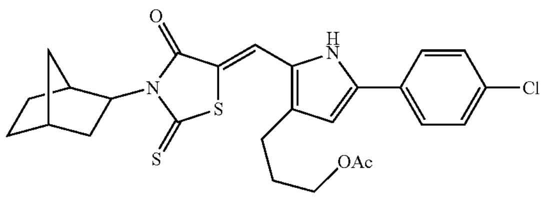 [SMILES: O=C1/C(=C/c2[nH]c(-c3ccc(Cl)cc3)cc2CCCO)SC(=S)N1C1CC2CCC1C2] | C26H27ClN2O3S2<br>Exact Mass: 514.1152<br>Molecular Weight: 515.0872 | A | C |
| 232 | 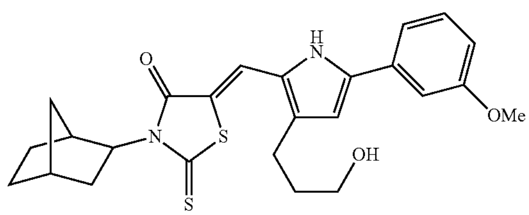 [SMILES: COc1cccc(-c2cc(CCCO)c(/C=C3\SC(=S)N(C4CC5CCC4C5)C3=O)[nH]2)c1] | C25H28N2O3S2<br>Exact Mass: 468.1541<br>Mol. Wt.: 468.6314 | A | C |
| 233 | 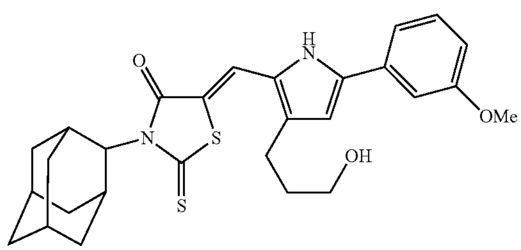 [SMILES: COc1cccc(-c2cc(CCCO)c(/C=C3\SC(=S)N(C4C5CC6CC(C5)CC4C6)C3=O)[nH]2)c1] | C28H32N2O3S2<br>Exact Mass: 508.1854<br>Mol. Wt.: 508.6953 | A | C |
| 234 | 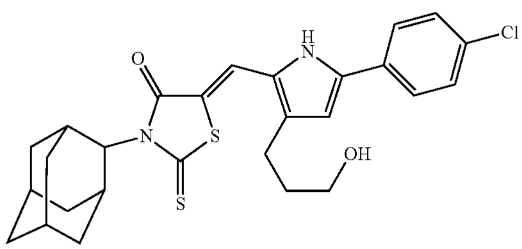 [SMILES: O=C1/C(=C/c2[nH]c(-c3ccc(Cl)cc3)cc2CCCO)SC(=S)N1C1C2CC3CC(C2)CC1C3] | C27H29ClN2O2S2<br>Exact Mass: 512.1359<br>Mol. Wt.: 513.1144 | A | A |
| 235 | 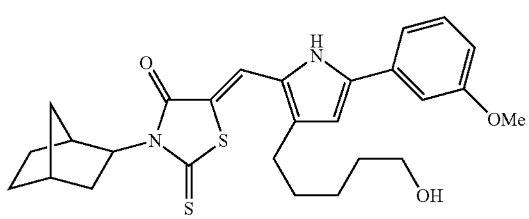 [SMILES: COc1cccc(-c2cc(CCCCCO)c(/C=C3\SC(=S)N(C4CC5CCC4C5)C3=O)[nH]2)c1] | C27H32N2O3S2<br>Exact Mass: 496.1854<br>Mol. Wt.: 496.6846 | A | C |

-continued

| Compound No. | Structure | MW | EC50 (nM) | 24 hr titer |
|---|---|---|---|---|
| 236 | 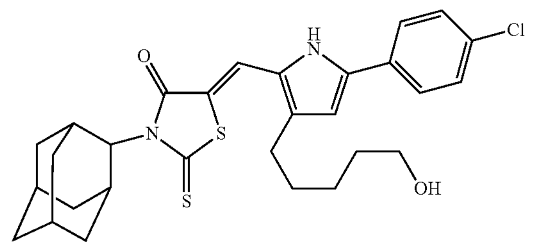 | C29H33ClN2O2S2<br>Exact Mass: 540.1672<br>Mol. Wt.: 541.1675 | A | B |
| 237 | 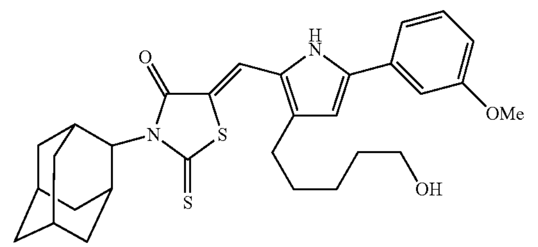 [SMILES: COc1cccc(-c2cc(CCCCCO)c(/C=C3\SC(=S)N(C4C5CC6CC(C5)CC4C6)C3=O)[nH]2)c1] | C30H36N2O3S2<br>Exact Mass: 536.2167<br>Mol. Wt.: 536.7484 | A | C |
| 238 | 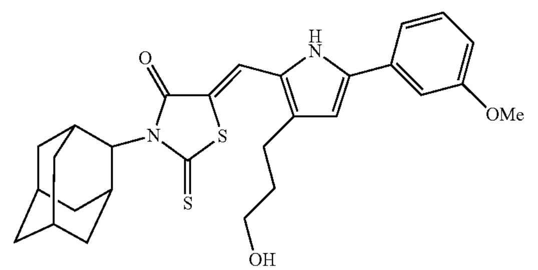 [SMILES: COc1cccc(-c2cc(CCCO)c(/C=C3\SC(=S)N(C4C5CC6CC(C5)CC4C6)C3=O)[nH]2)c1] | C28H32N2O3S2<br>Exact Mass: 508.1854<br>Mol. Wt.: 508.6953 | C | C |
| 239 | 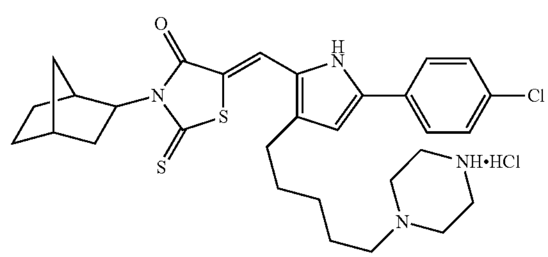 | C30H38Cl2N4OS2<br>Exact Mass: 604.1864<br>Molecular Weight: 605.6849 | A | C |
| 240 | 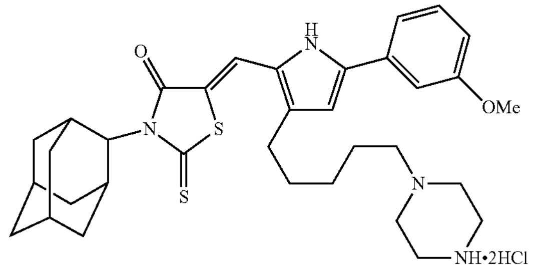 | C34H46Cl2N4O2S2<br>Exact Mass: 676.2439<br>Mol. Wt.: 677.7906 | A | A |

-continued

| Compound No. | Structure | MW | EC50 (nM) | 24 hr titer |
|---|---|---|---|---|
| 241 | 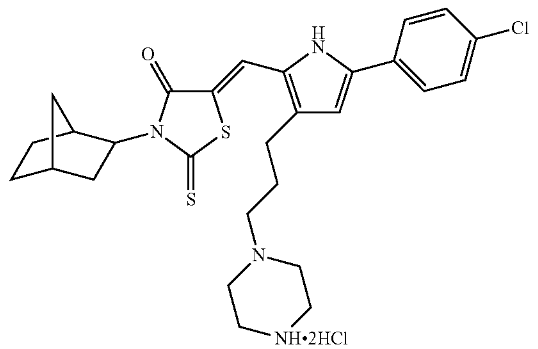 | C28H35Cl3N4OS2<br>Exact Mass: 612.1318<br>Molecular Weight: 614.0927 | A | C |
| 242 | 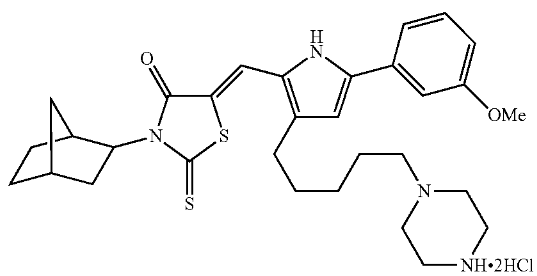 | C31H42Cl2N4O2S2<br>Exact Mass: 636.2126<br>Mol. Wt.: 637.7268 | A | B |
| 243 | 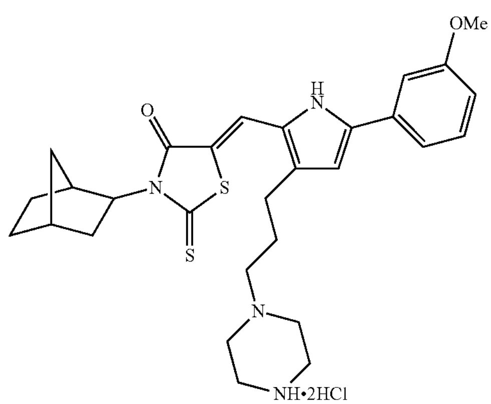 | C29H38Cl2N4O2S2<br>Exact Mass: 608.1813<br>Mol. Wt.: 609.6736 | A | C |
| 244 | 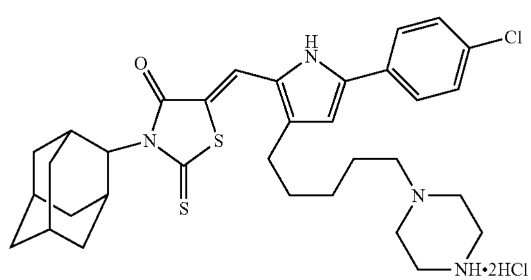 | C33H43Cl3N4O2S2<br>Exact Mass: 680.1944<br>Mol. Wt.: 682.2097 | A | A |

-continued
| Compound No. | Structure | MW | EC50 (nM) | 24 hr titer |
|---|---|---|---|---|
| 245 | 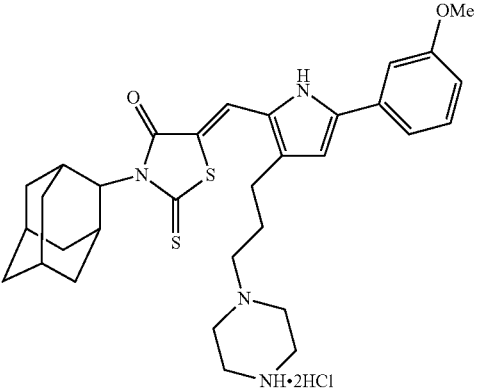 | C32H42Cl2N4O2S2<br>Exact Mass: 648.2126<br>Mol. Wt.: 649.7375 | A | C |
| 246 | 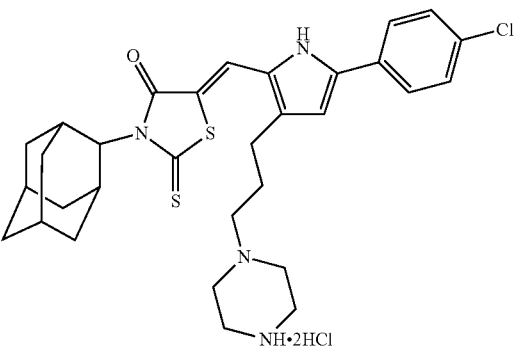 | C31H39Cl3N4OS2<br>Exact Mass: 652.1631<br>Mol. Wt.: 654.1566 | A | C |
| 247 | 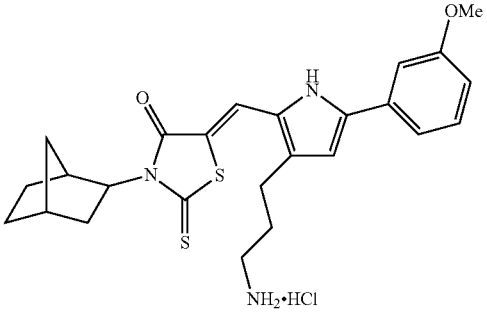 | C25H30ClN3O2S2<br>Exact Mass: 503.1468<br>Mol. Wt.: 504.1076 | A | C |
| 248 | 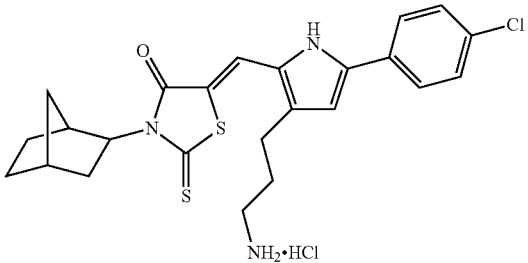 | C24H27Cl2N3OS2<br>Exact Mass: 507.0973<br>Mol. Wt.: 508.5267 | A | B |
| 249 | 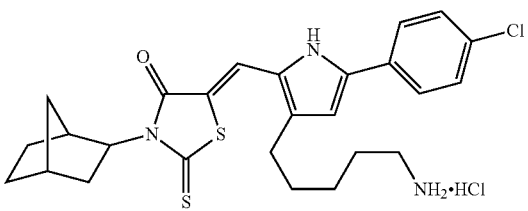 | C26H31Cl2N3OS2<br>Exact Mass: 535.1286<br>Mol. Wt.: 536.5798 | A | B |

-continued

| Compound No. | Structure | MW | EC50 (nM) | 24 hr titer |
|---|---|---|---|---|
| 250 | 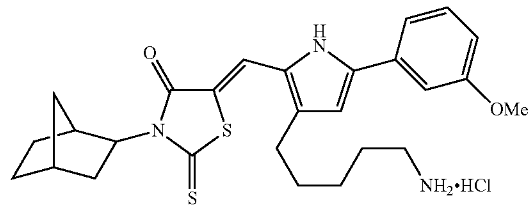 | C27H34ClN3O2S2<br>Exact Mass: 531.1781<br>Mol. Wt.: 532.1608 | A | C |
| 251 | 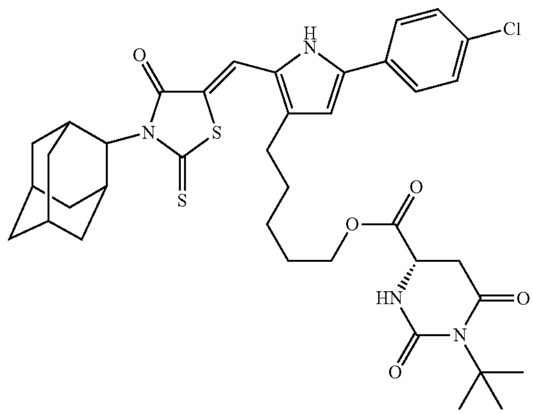 [SMILES: CC(C)(C)N1C(=O)C[C@@H](C(=O)OCCCCCc2cc(-c3ccc(Cl)cc3)[nH]c2/C=C2\SC(=S)N(C3C4CC5CC(C4)CC3C5)C2=O)NC1=O] | C38H45ClN4O5S2<br>Exact Mass: 736.252<br>Mol. Wt.: 737.3707 | A | C |
| 252 | 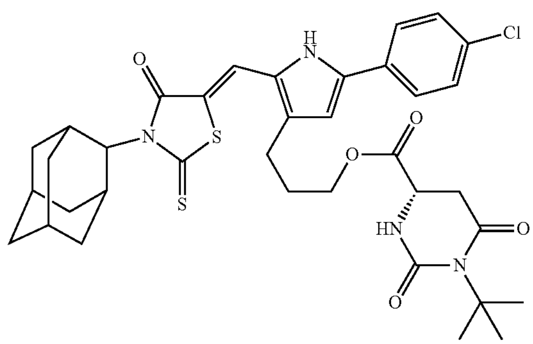 [SMILES: CC(C)(C)N1C(=O)C[C@@H](C(=O)OCCCc2cc(-c3ccc(Cl)cc3)[nH]c2/C=C2\SC(=S)N(C3C4CC5CC(C4)CC3C5)C2=O)NC1=O] | C36H41ClN4O5S2<br>Exact Mass: 708.2207<br>Mol. Wt.: 709.3175 | A | C |
| 253 | 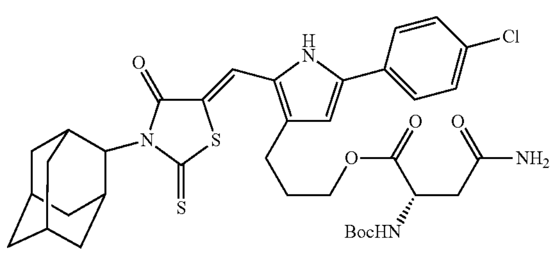 [SMILES: CC(C)(C)OC(=O)N[C@@H](CC(N)=O)C(=O)OCCCc1cc(-c2ccc(Cl)cc2)[nH]c1/C=C1\SC(=S)N(C2C3CC4CC(C3)CC2C4)C1=O] | C36H43ClN4O6S2<br>Exact Mass: 726.2313<br>Mol. Wt.: 727.3328 | A | B |
| 254 | 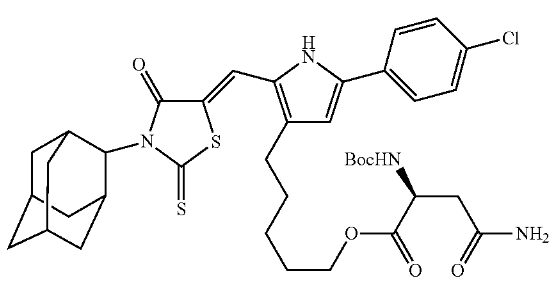 [SMILES: CC(C)(C)OC(=O)N[C@@H](CC(N)=O)C(=O)OCCCCCc1cc(-c2ccc(Cl)cc2)[nH]c1/C=C1\SC(=S)N(C2C3CC4CC(C3)CC2C4)C1=O] | C38H47ClN4O6S2<br>Exact Mass: 754.2626<br>Mol. Wt.: 755.386 | A | C |

-continued

| Compound No. | Structure | MW | EC50 (nM) | 24 hr titer |
|---|---|---|---|---|
| 255 | 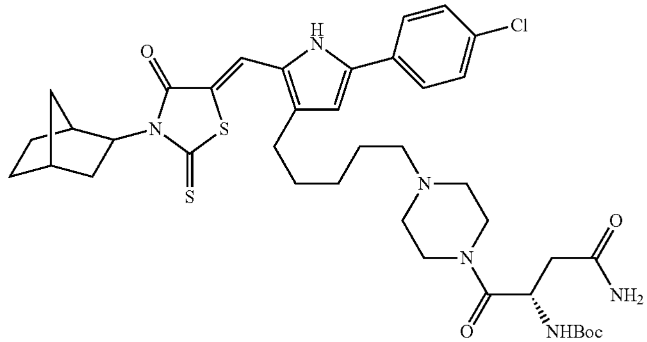 [SMILES: CC(C)(C)OC(=O)N[C@@H](CC(N)=O)C(=O)N1CCN(CCCCCc2cc(-c3ccc(Cl)cc3)[nH]c2/C=C2\SC(=S)N(C3CC4CCC3C4)C2=O)CC1] | C39H51ClN6O5S2<br>Exact Mass: 782.3051<br>Mol. Wt.: 783.4424 | A | C |
| 256 | 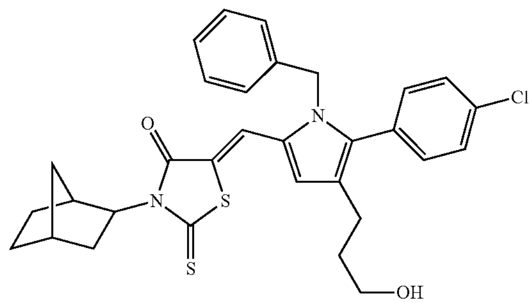 [SMILES: O=C1/C(=C/c2cc(CCCO)c(-c3ccc(Cl)cc3)n2Cc2ccccc2)SC(=S)N1C1CC2CCC1C2] | C31H31ClN2O2S2<br>Exact Mass: 562.1515<br>Molecular Weight: 563.1730 | A | C |
| 257 | 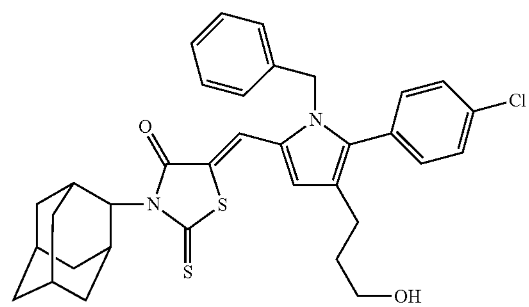 [SMILES: O=C1/C(=C/c2cc(CCCO)c(-c3ccc(Cl)cc3)n2Cc2ccccc2)SC(=S)N1C1C2CC3CC(C2)CC1C3] | C34H35ClN2O2S2<br>Exact Mass: 602.1828<br>Molecular Weight: 603.2369 | A | C |
| 258 | 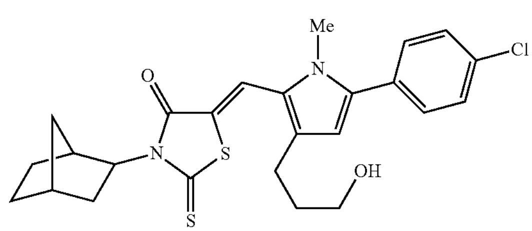 [SMILES: Cn1c(-c2ccc(Cl)cc2)cc(CCCO)c1/C=C1\SC(=S)N(C2CC3CCC2C3)C1=O] | C25H27ClN2O2S2<br>Exact Mass: 486.1202<br>Mol. Wt.: 487.0771 | D | C |
| 259 | 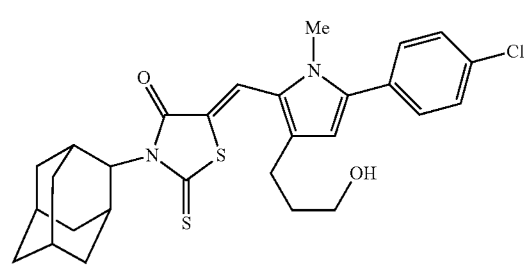 [SMILES: Cn1c(-c2ccc(Cl)cc2)cc(CCCO)c1/C=C1\SC(=S)N(C2C3CC4CC(C3)CC2C4)C1=O] | C28H31ClN2O2S2<br>Exact Mass: 526.1515<br>Mol. Wt.: 527.1409 | D | C |

| Compound No. | Structure | MW | EC50 (nM) | 24 hr titer |
|---|---|---|---|---|
| 260 | 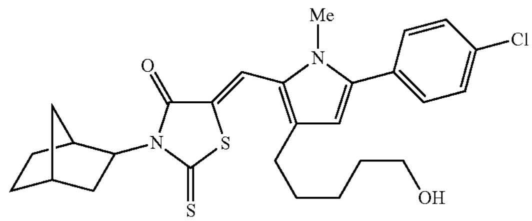 [SMILES: Cn1c(-c2ccc(Cl)cc2)cc(CCCCCO)c1/C=C1\SC(=S)N(C2CC3CCC2C3)C1=O] | C27H31ClN2O2S2<br>Exact Mass: 514.1515<br>Mol. Wt.: 515.1302 | A | C |
| 261 | 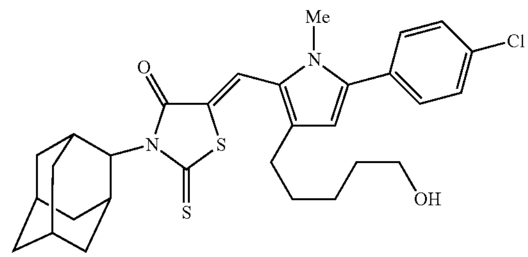 [SMILES: Cn1c(-c2ccc(Cl)cc2)cc(CCCCCO)c1/C=C1\SC(=S)N(C2C3CC4CC(C3)CC2C4)C1=O] | C30H35ClN2O2S2<br>Exact Mass: 554.1828<br>Mol. Wt.: 555.1941 | A | B |
| 262 | 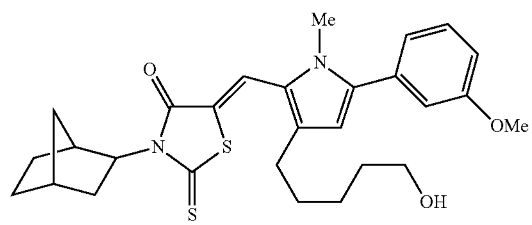 [SMILES: COc1cccc(-c2cc(CCCCCO)c(/C=C3\SC(=S)N(C4CC5CCC4C5)C3=O)n2C)c1] | C28H34N2O3S2<br>Exact Mass: 510.2011<br>Mol. Wt.: 510.7112 | D | C |
| 263 | 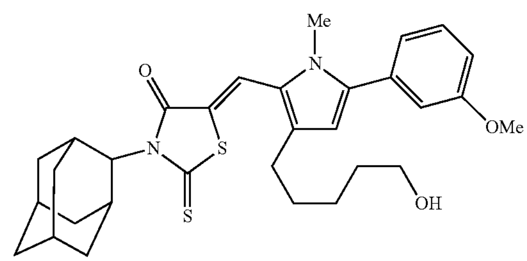 [SMILES: COc1cccc(-c2cc(CCCCCO)c(/C=C3\SC(=S)N(C4C5CC6CC(C5)CC4C6)C3=O)n2C)c1] | C31H38N2O3S2<br>Exact Mass: 550.2324<br>Mol. Wt.: 550.775 | C | C |
| 264 | 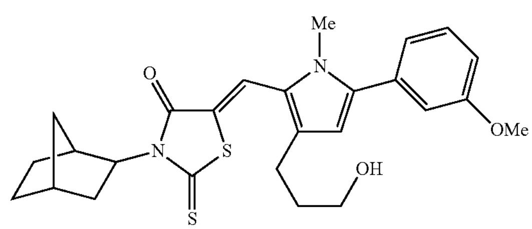 [SMILES: COc1cccc(-c2cc(CCCO)c(/C=C3\SC(=S)N(C4CC5CCC4C5)C3=O)n2C)c1] | C26H30N2O3S2<br>Exact Mass: 482.1698<br>Mol. Wt.: 482.658 | C | C |
| 265 | 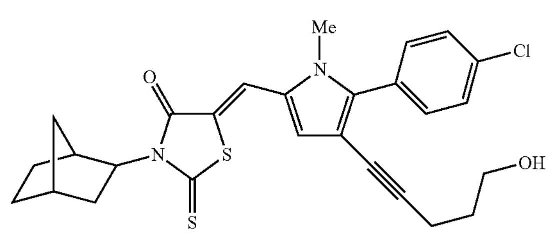 [SMILES: Cn1c(/C=C2\SC(=S)N(C3CC4CCC3C4)C2=O)cc(C#CCCCO)c1-c1ccc(Cl)cc1] | C27H27ClN2O2S2<br>Exact Mass: 510.1202<br>Mol. Wt.: 511.0985 | A | C |

-continued

| Compound No. | Structure | MW | EC50 (nM) | 24 hr titer |
|---|---|---|---|---|
| 266 | 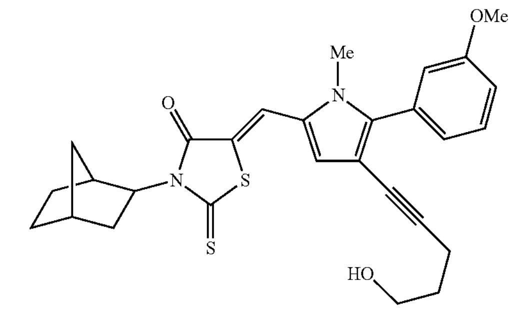 [SMILES: COc1cccc(-c2c(C#CCCCO)cc(/C=C3\SC(=S)N(C4CC5CCC4C5)C3=O)n2C)c1] | C28H30N2O3S2<br>Exact Mass: 506.1698<br>Mol. Wt.: 506.6794 | A | C |
| 267 | 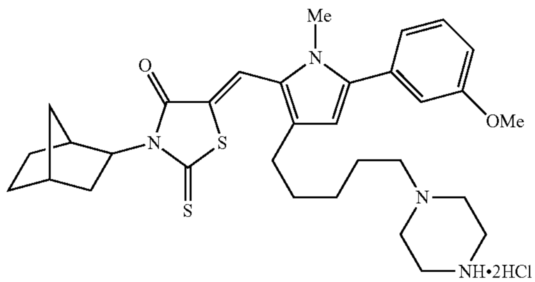 | C32H44Cl2N4O2S2<br>Exact Mass: 650.2283<br>Mol. Wt.: 651.7534 | A | C |
| 268 | 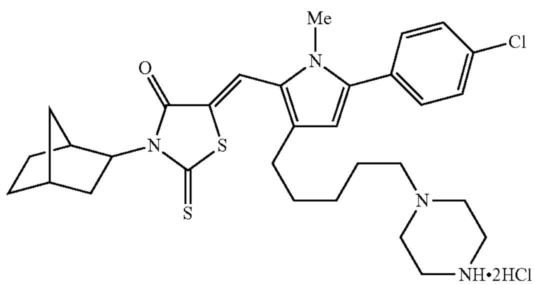 | C31H41Cl3N4OS2<br>Exact Mass: 654.1787<br>Mol. Wt.: 656.1724 | A | B |
| 269 | 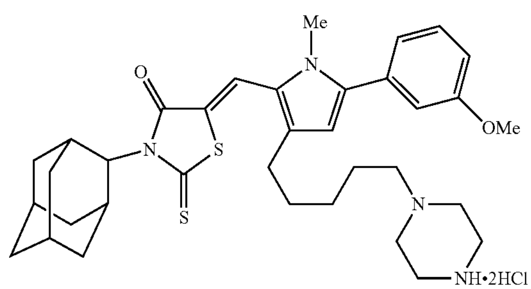 | C35H48Cl2N4O2S2<br>Exact Mass: 690.2596<br>Mol. Wt.: 691.8172 | B | C |
| 270 | 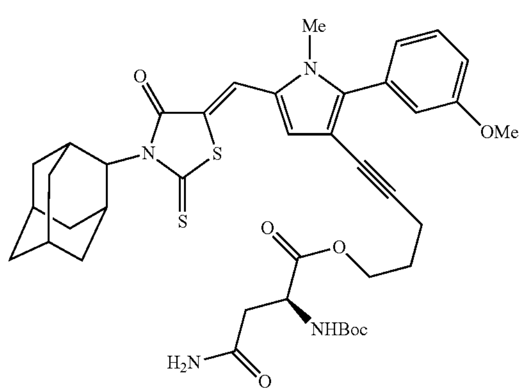 [SMILES: COc1cccc(-c2c(C#CCCCOC(=O)[C@H](CC(N)=O)NC(=O)OC(C)(C)C)cc(/C=C3\SC(=S)N(C4C5CC6CC(C5)CC4C6)C3=O)n2C)c1] | C40H48N4O7S2<br>Exact Mass: 760.2964<br>Mol. Wt.: 760.9617 | A | C |

| Compound No. | Structure | MW | EC50 (nM) | 24 hr titer |
|---|---|---|---|---|
| 271 | 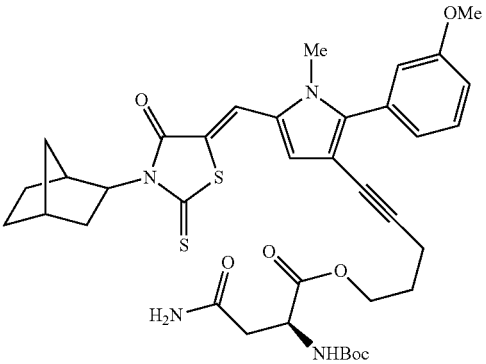 [SMILES: COc1cccc(-c2c(C#CCCCOC(=O)[C@H](CC(N)=O)NC(=O)OC(C)(C)C)cc(/C=C3\SC(=S)N(C4CC5CCC4C5)C3=O)n2C)c1] | C37H44N4O7S2<br>Exact Mass: 720.2651<br>Mol. Wt.: 720.8979 | A | C |
| 272 | 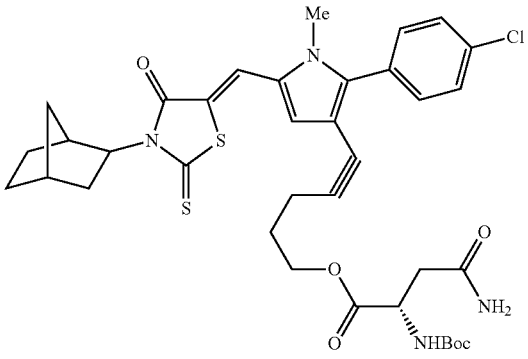 [SMILES: Cn1c(/C=C2\SC(=S)N(C3CC4CCC3C4)C2=O)cc(C#CCCCOC(=O)[C@H](CC(N)=O)NC(=O)OC(C)(C)C)c1-c1ccc(Cl)cc1] | C36H41ClN4O6S2<br>Exact Mass: 724.2156<br>Mol. Wt.: 725.3169 | A | C |
| 273 | 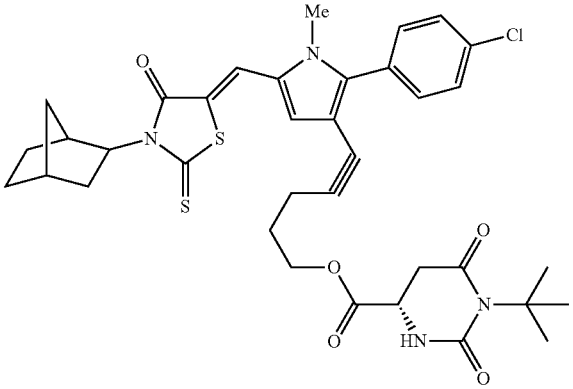 [SMILES: Cn1c(/C=C2\SC(=S)N(C3CC4CCC3C4)C2=O)cc(C#CCCCOC(=O)[C@@H]2CC(=O)N(C(C)(C)C)C(=O)N2)c1-c1ccc(Cl)cc1] | C36H39ClN4O5S2<br>Exact Mass: 706.205<br>Mol. Wt.: 707.3017 | B | C |
| 274 | 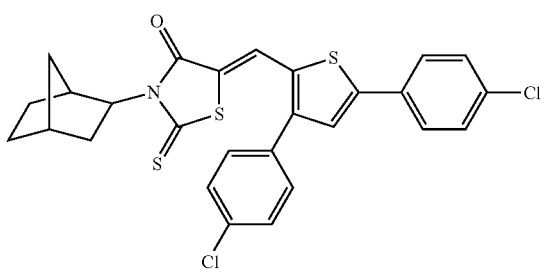 [SMILES: O=C1/C(=C/c2sc(-c3ccc(Cl)cc3)cc2-c2ccc(Cl)cc2)SC(=S)N1C1CC2CCC1C2] | C27H21Cl2NOS3<br>Exact Mass: 541.0162<br>Molecular Weight: 542.5627 | A | C |

| Compound No. | Structure | MW | EC50 (nM) | 24 hr titer |
|---|---|---|---|---|
| 275 | 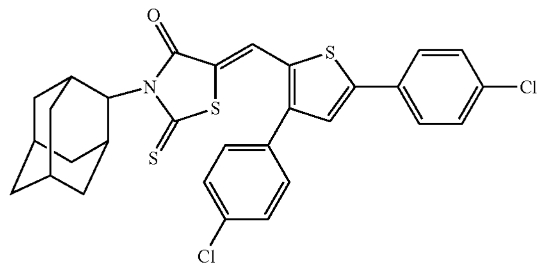 [SMILES: O=C1/C(=C/c2sc(-c3ccc(Cl)cc3)cc2-c2ccc(Cl)cc2)SC(=S)N1C1C2CC3CC(C2)CC1C3] | C30H25Cl2NOS3<br>Exact Mass: 581.0475<br>Molecular Weight: 582.6266 | A | C |
| 276 | 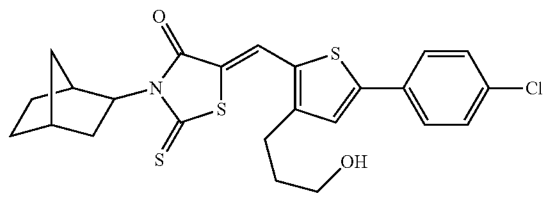 [SMILES: O=C1/C(=C/c2sc(-c3ccc(Cl)cc3)cc2CCCO)SC(=S)N1C1CC2CCC1C2] | C24H24ClNO2S3<br>Exact Mass: 489.0658<br>Molecular Weight: 490.1009 | A | C |
| 277 | 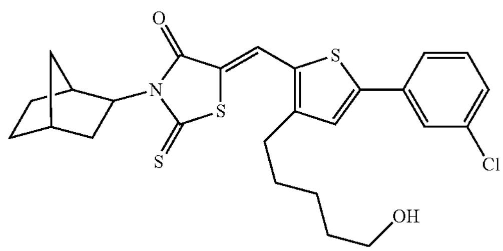 [SMILES: O=C1/C(=C/c2sc(-c3cccc(Cl)c3)cc2CCCCCO)SC(=S)N1C1CC2CCC1C2] | C26H28ClNO2S3<br>Exact Mass: 517.0971<br>Mol. Wt.: 518.154 | A | A |
| 278 | 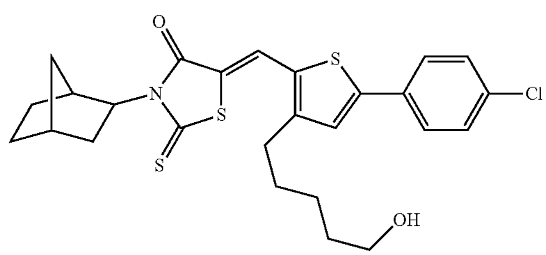 [SMILES: O=C1/C(=C/c2sc(-c3ccc(Cl)cc3)cc2CCCCCO)SC(=S)N1C1CC2CCC1C2] | C26H28ClNO2S3<br>Exact Mass: 517.0971<br>Molecular Weight: 518.1540 | A | C |
| 279 | 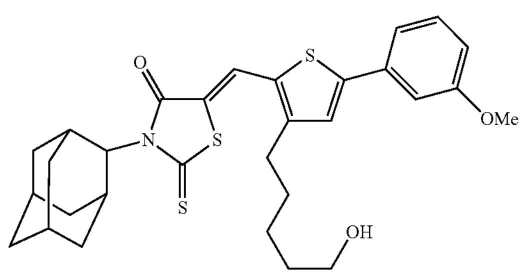 [SMILES: COc1cccc(-c2cc(CCCCCO)c(/C=C3\SC(=S)N(C4C5CC6CC(C5)CC4C6)C3=O)s2)c1] | C30H35NO3S3<br>Exact Mass: 553.1779<br>Mol. Wt.: 553.7988 | A | B |
| 280 | 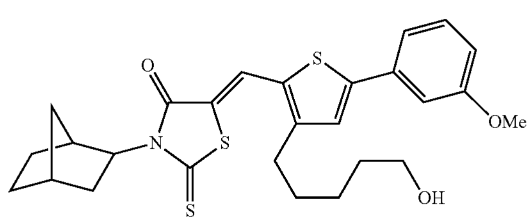 [SMILES: COc1cccc(-c2cc(CCCCCO)c(/C=C3\SC(=S)N(C4CC5CCC4C5)C3=O)s2)c1] | C27H31NO3S3<br>Exact Mass: 513.1466<br>Mol. Wt.: 513.7349 | A | B |

| Compound No. | Structure | MW | EC50 (nM) | 24 hr titer |
|---|---|---|---|---|
| 281 | 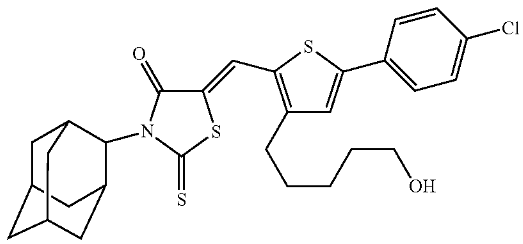 [SMILES: O=C1/C(=C/c2sc(-c3ccc(Cl)cc3)cc2CCCCCO)SC(=S)N1C1C2CC3CC(C2)CC1C3] | C29H32ClNO2S3<br>Exact Mass: 557.1284<br>Mol. Wt.: 558.2179 | A | C |
| 282 | 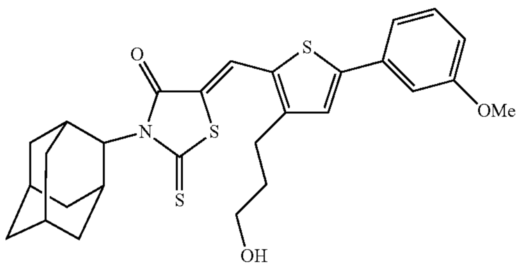 | C28H31NO3S3<br>Exact Mass: 525.1466<br>Mol. Wt.: 525.7456 | A | C |
| 283 | 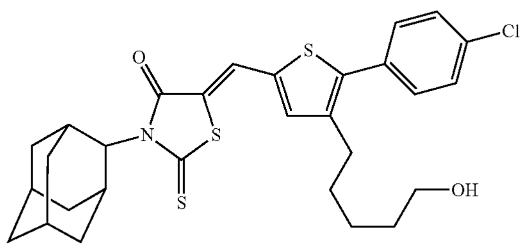 [SMILES: O=C1/C(=C/c2cc(CCCCCO)c(-c3ccc(Cl)cc3)s2)SC(=S)N1C1C2CC3CC(C2)CC1C3] | C29H32ClNO2S3<br>Exact Mass: 557.1284<br>Molecular Weight: 558.2179 | A | A |
| 284 | 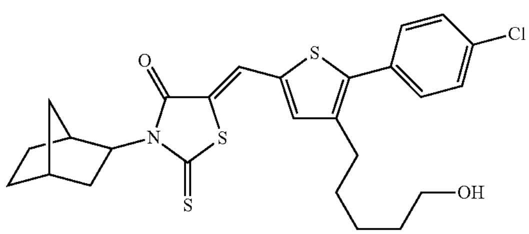 [SMILES: O=C1/C(=C/c2cc(CCCCCO)c(-c3ccc(Cl)cc3)s2)SC(=S)N1C1CC2CCC1C2] | C26H28ClNO2S3<br>Exact Mass: 517.0971<br>Molecular Weight: 518.1540 | A | A |
| 285 | 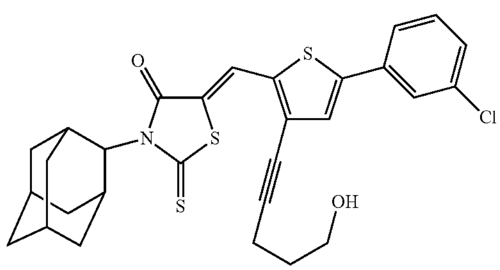 [SMILES: O=C1/C(=C/c2sc(-c3cccc(Cl)c3)cc2C#CCCCO)SC(=S)N1C1C2CC3CC(C2)CC1C3] | C29H28ClNO2S3<br>Exact Mass: 553.0971<br>Molecular Weight: 554.1861 | A | C |
| 286 | 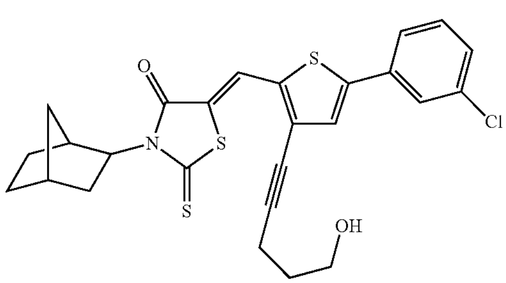 [SMILES: O=C1/C(=C/c2sc(-c3cccc(Cl)c3)cc2C#CCCCO)SC(=S)N1C1CC2CCC1C2] | C26H24ClNO2S3<br>Exact Mass: 513.0658<br>Molecular Weight: 514.1223 | A | A |

-continued

| Compound No. | Structure | MW | EC50 (nM) | 24 hr titer |
|---|---|---|---|---|
| 287 | 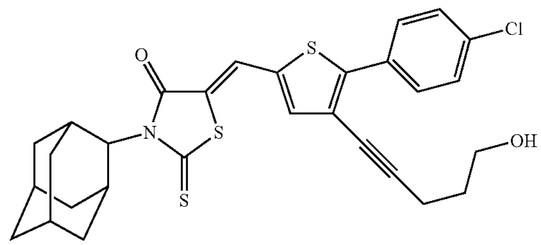 [SMILES: O=C1/C(=C/c2cc(C#CCCCO)c(-c3ccc(Cl)cc3)s2)SC(=S)N1C1C2CC3CC(C2)CC1C3] | C29H28ClNO2S3<br>Exact Mass: 553.0971<br>Mol. Wt.: 554.1861 | A | A |
| 288 | 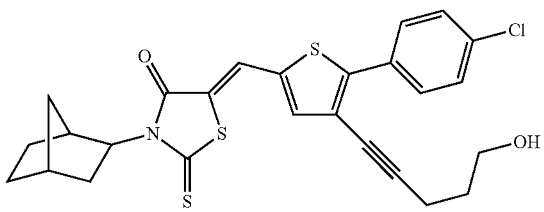 [SMILES: O=C1/C(=C/c2cc(C#CCCCO)c(-c3ccc(Cl)cc3)s2)SC(=S)N1C1CC2CCC1C2] | C26H24ClNO2S3<br>Exact Mass: 513.0658<br>Mol. Wt.: 514.1223 | A | A |
| 289 | 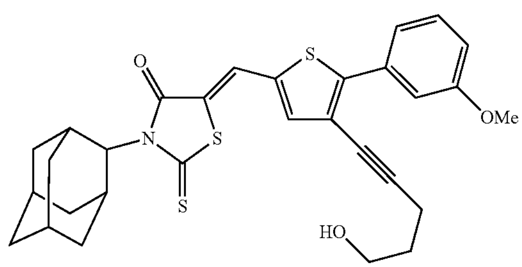 [SMILES: COc1cccc(-c2sc(/C=C3\SC(=S)N(C4C5CC6CC(C5)CC4C6)C3=O)cc2C#CCCCO)c1] | C30H31NO3S3<br>Exact Mass: 549.1466<br>Mol. Wt.: 549.767 | A | B |
| 290 | 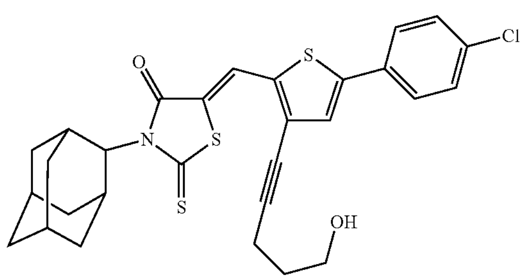 [SMILES: O=C1/C(=C/c2sc(-c3ccc(Cl)cc3)cc2C#CCCCO)SC(=S)N1C1C2CC3CC(C2)CC1C3] | C29H28ClNO2S3<br>Exact Mass: 553.0971<br>Mol. Wt.: 554.1861 | A | B |
| 291 | 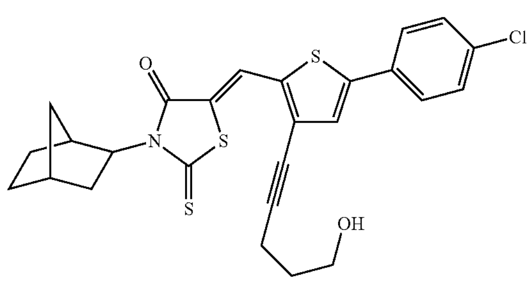 [SMILES: O=C1/C(=C/c2sc(-c3ccc(Cl)cc3)cc2C#CCCCO)SC(=S)N1C1CC2CCC1C2] | C26H24ClNO2S3<br>Exact Mass: 513.0658<br>Mol. Wt.: 514.1223 | A | A |
| 292 | 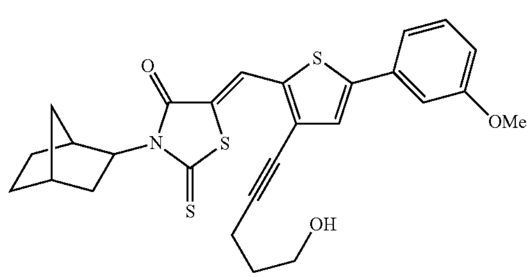 [SMILES: COc1cccc(-c2cc(C#CCCCO)c(/C=C3\SC(=S)N(C4CC5CCC4C5)C3=O)s2)c1] | C27H27NO3S3<br>Exact Mass: 509.1153<br>Mol. Wt.: 509.7032 | A | B |

| Compound No. | Structure | MW | EC50 (nM) | 24 hr titer |
|---|---|---|---|---|
| 293 | 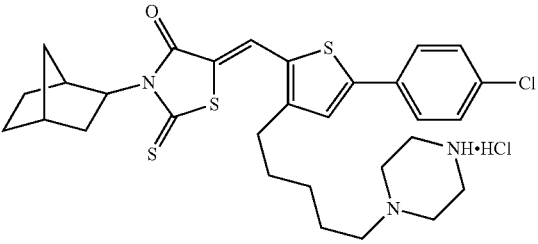 | C30H37Cl2N3OS3<br>Exact Mass: 621.1476<br>Molecular Weight: 622.7353 | NA | C |
| 294 | 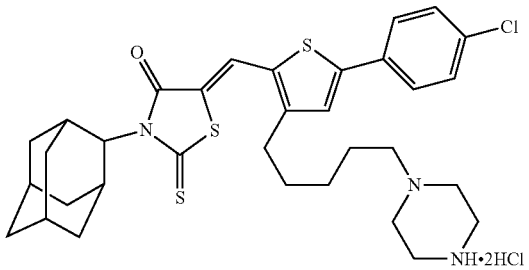 | C33H42Cl3N3OS3<br>Exact Mass: 697.1556<br>Mol. Wt.: 699.2601 | A | A |
| 295 | 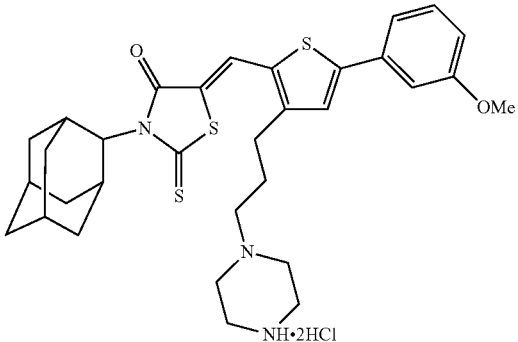 | C32H41Cl2N3O2S3<br>Exact Mass: 665.1738<br>Mol. Wt.: 666.7878 | A | A |
| 296 | 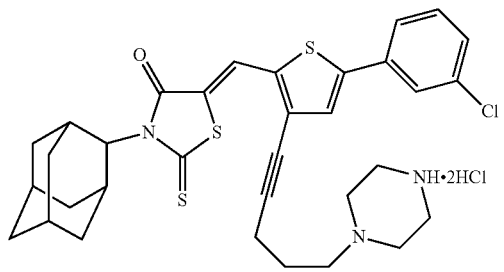 | C33H38Cl3N3OS3<br>Exact Mass: 693.1243<br>Molecular Weight: 695.2283 | A | A |
| 297 | 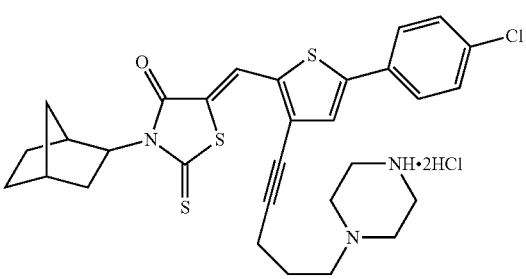 | C30H34Cl3N3OS3<br>Exact Mass: 653.0930<br>Molecular Weight: 655.1645 | A | A |

-continued
| Compound No. | Structure | MW | EC50 (nM) | 24 hr titer |
|---|---|---|---|---|
| 298 | 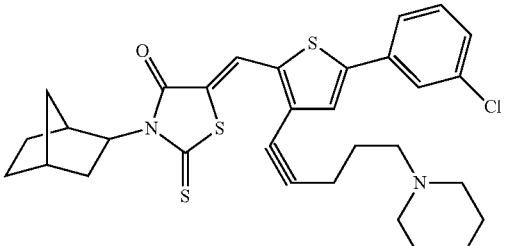 | C30H34Cl3N3OS3<br>Exact Mass: 653.093<br>Mol. Wt.: 655.1645 | A | A |
| 299 | 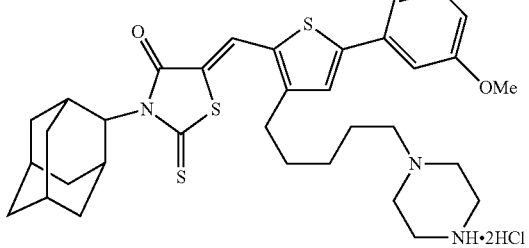 | C34H45Cl2N3O2S3<br>Exact Mass: 693.2051<br>Mol. Wt.: 694.841 | A | A |
| 300 | 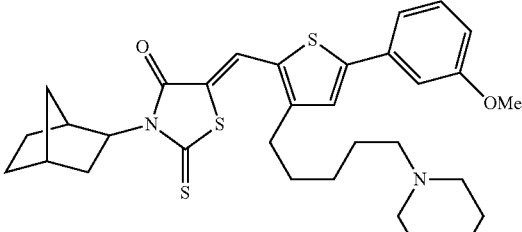 | C31H41Cl2N3O2S3<br>Exact Mass: 653.1738<br>Mol. Wt.: 654.7771 | A | A |
| 301 | 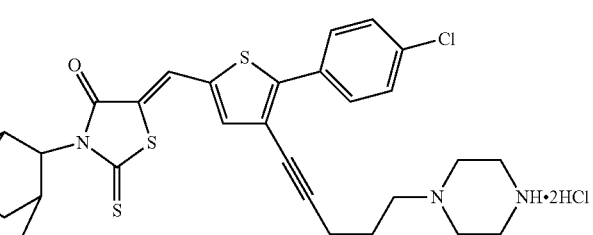 | C33H38Cl3N3OS3<br>Exact Mass: 693.1243<br>Mol. Wt.: 695.2283 | A | A |
| 302 | 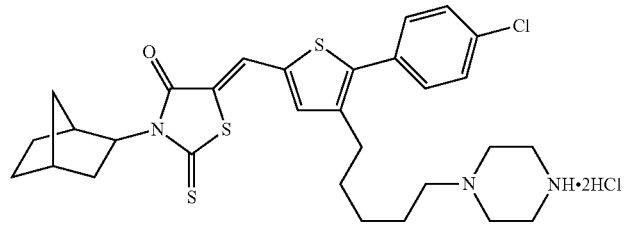 | C30H38Cl3N3OS3<br>Exact Mass: 657.1243<br>Molecular Weight: 659.1962 | A | A |
| 303 | 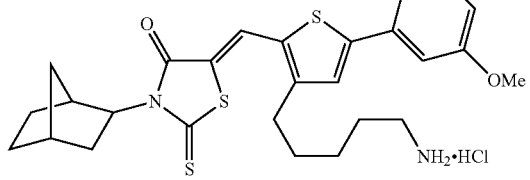 | C27H33ClN2O2S3<br>Exact Mass: 548.1393<br>Mol. Wt.: 549.2111 | A | A |

| Compound No. | Structure | MW | EC50 (nM) | 24 hr titer |
|---|---|---|---|---|
| 304 | 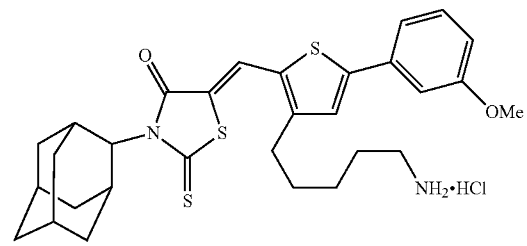 | C30H37ClN2O2S3<br>Exact Mass: 588.1706<br>Mol. Wt.: 589.275 | A | A |
| 305 | 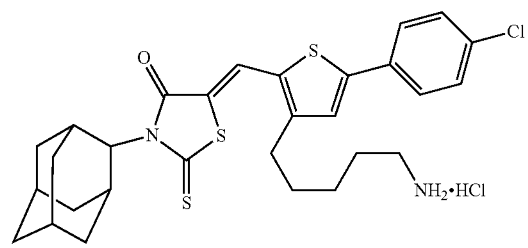 | C29H34Cl2N2OS3<br>Exact Mass: 592.121<br>Mol. Wt.: 593.6941 | A | A |
| 306 | 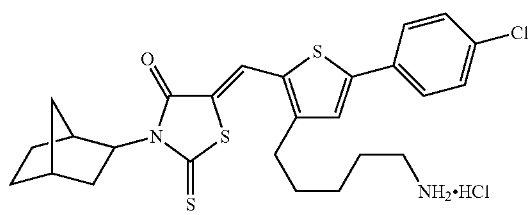 | C26H30Cl2N2OS3<br>Exact Mass: 552.0897<br>Mol. Wt.: 553.6302 | A | A |
| 307 | 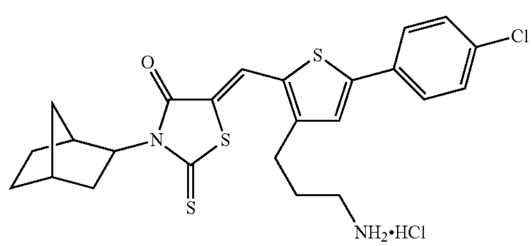 | C24H26Cl2N2OS3<br>Exact Mass: 524.0584<br>Mol. Wt.: 525.577 | A | A |
| 308 | 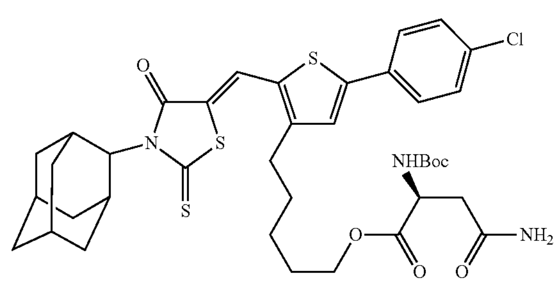 [SMILES: CC(C)(C)OC(=O)N[C@@H](CC(N)=O)C(=O)OCCCCCc1cc(-c2ccc(Cl)cc2)sc1/C=C1\SC(=S)N(C2C3CC4CC(C3)CC2C4)C1=O] | C38H46ClN3O6S3<br>Exact Mass: 771.2237<br>Mol. Wt.: 772.4363 | A | B |

-continued

| Compound No. | Structure | MW | EC50 (nM) | 24 hr titer |
|---|---|---|---|---|
| 309 | 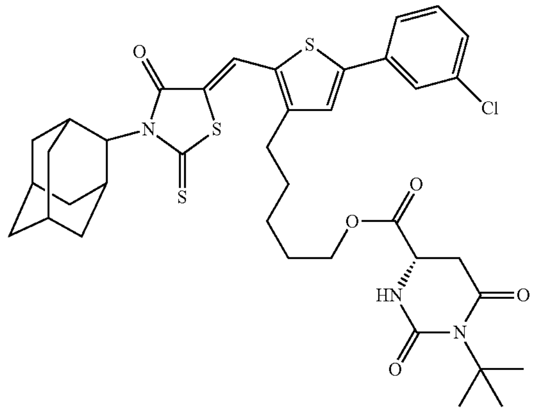 [SMILES: CC(C)(C)N1C(=O)C[C@@H](C(=O)OCCCCCc2cc(-c3cccc(Cl)c3)sc2/C=C2\SC(=S)N(C3C4CC5CC(C4)CC3C5)C2=O)NC1=O] | C38H44ClN3O5S3<br>Exact Mass: 753.2132<br>Mol. Wt.: 754.4211 | A | C |
| 310 | 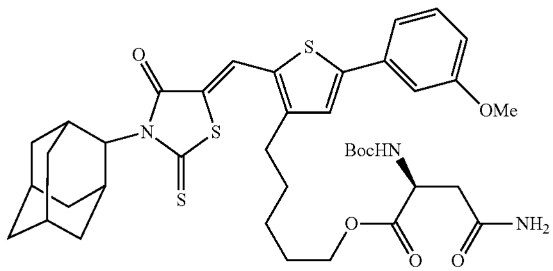 [SMILES: COc1cccc(-c2cc(CCCCCOC(=O)[C@H](CC(N)=O)NC(=O)OC(C)(C)C)c(/C=C3\SC(=S)N(C4C5CC6CC(C5)CC4C6)C3=O)s2)c1] | C39H49N3O7S3<br>Exact Mass: 767.2733<br>Mol. Wt.: 768.0173 | A | B |
| 311 | 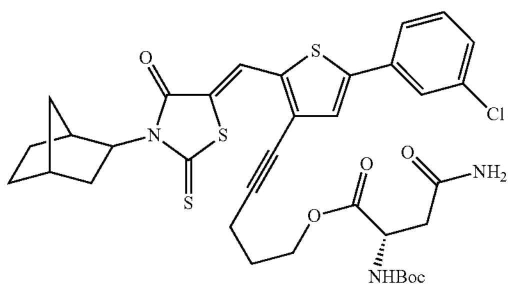 [SMILES: CC(C)(C)OC(=O)N[C@@H](CC(N)=O)C(=O)OCCCC#Cc1cc(-c2cccc(Cl)c2)sc1/C=C1\SC(=S)N(C2CC3CCC2C3)C1=O] | C35H38ClN3O6S3<br>Exact Mass: 727.1611<br>Mol. Wt.: 728.3407 | A | B |
| 312 | 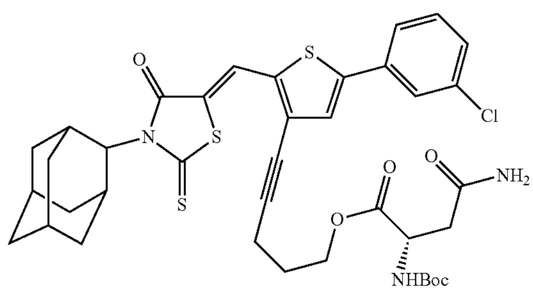 [SMILES: CC(C)(C)OC(=O)N[C@@H](CC(N)=O)C(=O)OCCCC#Cc1cc(-c2cccc(Cl)c2)sc1/C=C1\SC(=S)N(C2C3CC4CC(C3)CC2C4)C1=O] | Chemical Formula:<br>C38H42ClN3O6S3<br>Exact Mass: 767.1924<br>Molecular Weight:<br>768.4046 | A | B |
| 313 | 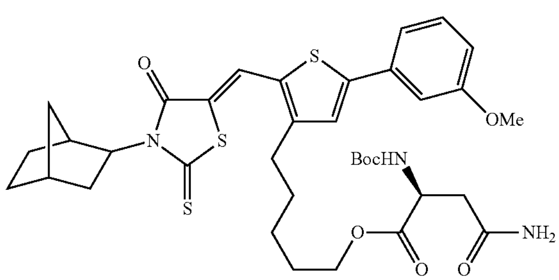 [SMILES: COc1cccc(-c2cc(CCCCCOC(=O)[C@H](CC(N)=O)NC(=O)OC(C)(C)C)c(/C=C3\SC(=S)N(C4CC5CCC4C5)C3=O)s2)c1] | C36H45N3O7S3<br>Exact Mass: 727.242<br>Mol. Wt.: 727.9534 | A | B |

| Compound No. | Structure | MW | EC50 (nM) | 24 hr titer |
|---|---|---|---|---|
| 314 | 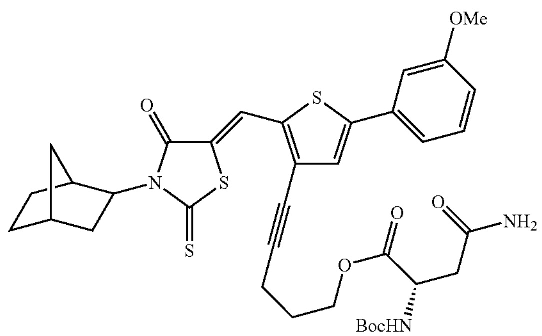 [SMILES: COc1cccc(-c2cc(C#CCCCOC(=O)[C@H](CC(N)=O)NC(=O)OC(C)(C)C)c(/C=C3\SC(=S)N(C4CC5CCC4C5)C3=O)s2)c1] | C36H41N3O7S3 Exact Mass: 723.2107 Mol. Wt.: 723.9216 | A | B |
| Formula (III) | R₂ is H, W is S | | | |
| 315 | 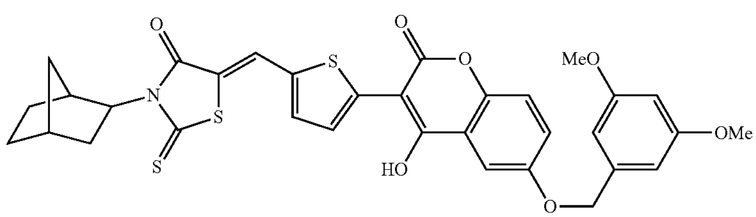 [SMILES: COc1cc(COc2ccc3oc(=O)c(-c4ccc(/C=C5\SC(=S)N(C6CC7CCC6C7)C5=O)s4)c(O)c3c2)cc(OC)c1] | C33H29NO7S3 Exact Mass: 647.1106 Molecular Weight: 647.7809 | A | C |
| 316 | 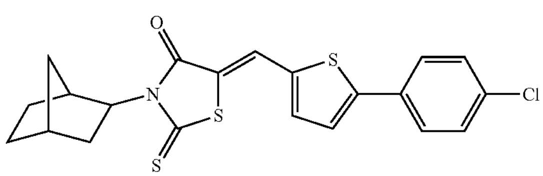 [SMILES: O=C1/C(=C/c2ccc(-c3ccc(Cl)cc3)s2)SC(=S)N1C1CC2CCC1C2] | C21H18ClNOS3 Exact Mass: 431.0239 Molecular Weight: 432.0217 | A | C |
| 317 | 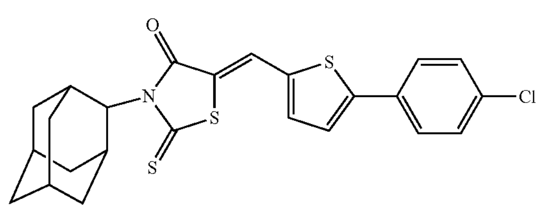 [SMILES: O=C1/C(=C/c2ccc(-c3ccc(Cl)cc3)s2)SC(=S)N1C1C2CC3CC(C2)CC1C3] | C24H22ClNOS3 Exact Mass: 471.0552 Molecular Weight: 472.0856 | A | C |
| Type-3 Coumarin as D-ring | 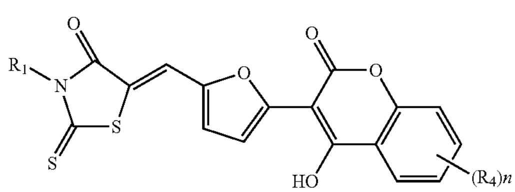 | | | |
| 318 | 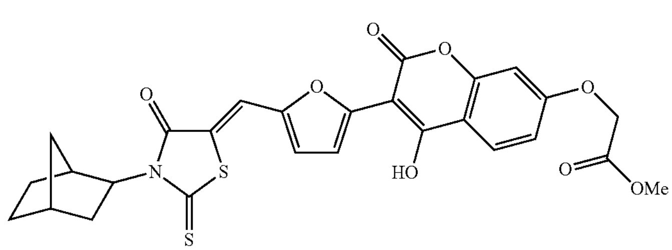 [SMILES: COC(=O)COc1ccc2c(O)c(-c3ccc(/C=C4\SC(=S)N(C5CC6CCC5C6)C4=O)o3)c(=O)oc2c1] | C27H23NO8S2 Exact Mass: 553.0865 Mol. Wt.: 553.6034 | A | B |

-continued

| Compound No. | Structure | MW | EC50 (nM) | 24 hr titer |
|---|---|---|---|---|
| 319 | 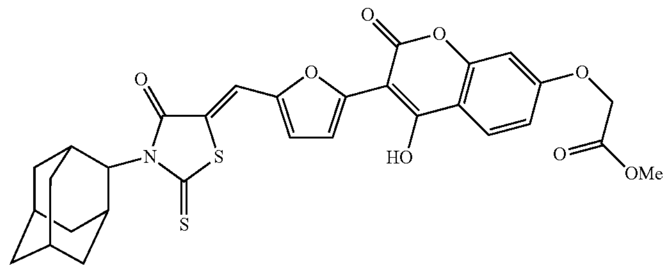 [SMILES: COC(=O)COc1ccc2c(O)c(-c3ccc(/C=C4\SC(=S)N(C5C6CC7CC(C6)CC5C7)C4=O)o3)c(=O)oc2c1] | C30H27NO8S2<br>Exact Mass: 593.1178<br>Mol. Wt.: 593.6673 | A | C |
| 320 | 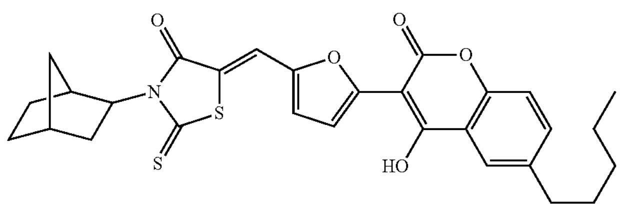 [SMILES: CCCCCc1ccc2oc(=O)c(-c3ccc(/C=C4\SC(=S)N(C5CC6CCC5C6)C4=O)o3)c(O)c2c1] | C29H29NO5S2<br>Exact Mass: 535.1487<br>Molecular Weight: 535.6743 | A | B |
| 321 | 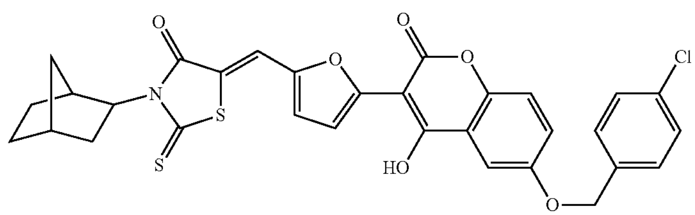 [SMILES: O=C1/C(=C/c2ccc(-c3c(O)c4cc(OCc5ccc(Cl)cc5)ccc4oc3=O)o2)SC(=S)N1C1CC2CCC1C2] | C31H24ClNO6S2<br>Exact Mass: 605.0734<br>Molecular Weight: 606.1084 | A | C |
| 322 | 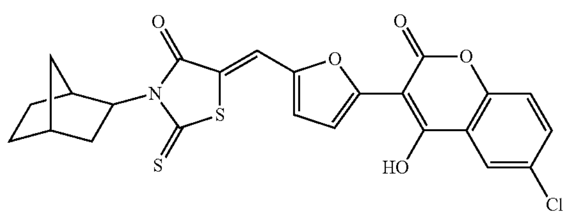 [SMILES: O=C1/C(=C/c2ccc(-c3c(O)c4cc(Cl)ccc4oc3=O)o2)SC(=S)N1C1CC2CCC1C2] | C24H18ClNO5S2<br>Exact Mass: 499.0315<br>Molecular Weight: 499.9864 | A | A |
| 323 | 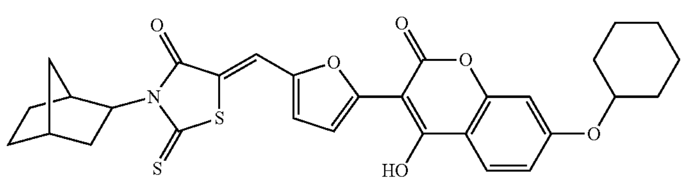 [SMILES: O=C1/C(=C/c2ccc(-c3c(O)c4ccc(OC5CCCCC5)cc4oc3=O)o2)SC(=S)N1C1CC2CCC1C2] | C30H29NO6S2<br>Exact Mass: 563.1436<br>Molecular Weight: 563.6844 | A | A |
| 324 | 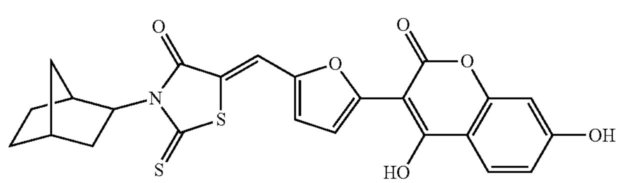 [SMILES: O=C1/C(=C/c2ccc(-c3c(O)c4ccc(O)cc4oc3=O)o2)SC(=S)N1C1CC2CCC1C2] | C24H19NO6S2<br>Exact Mass: 481.0654<br>Molecular Weight: 481.5408 | A | C |
| 325 | 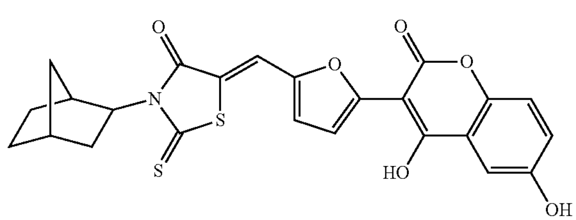 [SMILES: O=C1/C(=C/c2ccc(-c3c(O)c4cc(O)ccc4oc3=O)o2)SC(=S)N1C1CC2CCC1C2] | C24H19NO6S2<br>Exact Mass: 481.0654<br>Molecular Weight: 481.5408 | A | C |

| Compound No. | Structure | MW | EC50 (nM) | 24 hr titer |
|---|---|---|---|---|
| 326 | 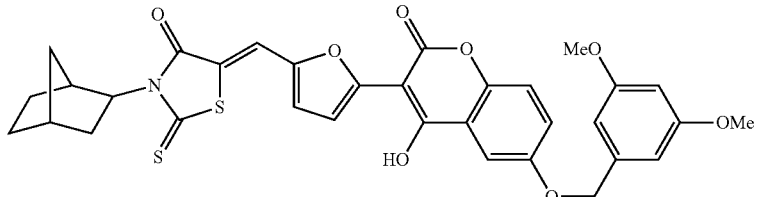 | C33H29NO8S2<br>Exact Mass: 631.1335<br>Molecular Weight: 631.7153 | A | A |
| Type-5 Modification of side chain in C-ring (furan) with alcohol moiety | 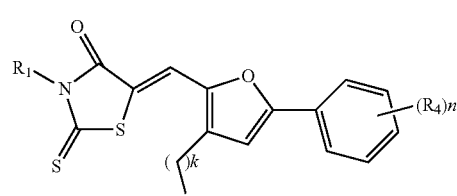 | | | |
| 327 | 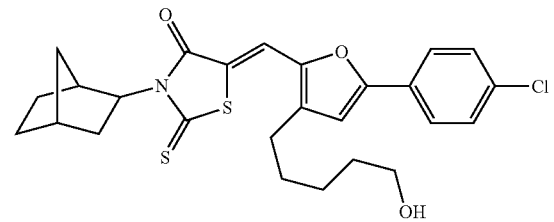 [SMILES: O=C1/C(=C/c2oc(-c3ccc(Cl)cc3)cc2CCCCCO)SC(=S)N1C1CC2CCC1C2] | C26H28ClNO3S2<br>Exact Mass: 501.1199<br>Molecular Weight: 502.0884 | NA | A |
| 328 | 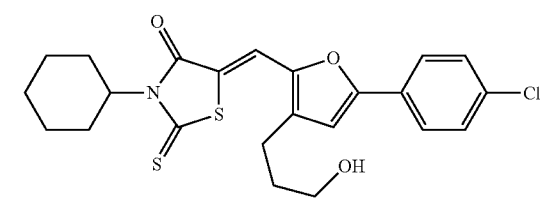 [SMILES: O=C1/C(=C/c2oc(-c3ccc(Cl)cc3)cc2CCCO)SC(=S)N1C1CCCCC1] | C23H24ClNO3S2<br>Exact Mass: 461.0886<br>Molecular Weight: 462.0246 | NA | C |
| 329 | 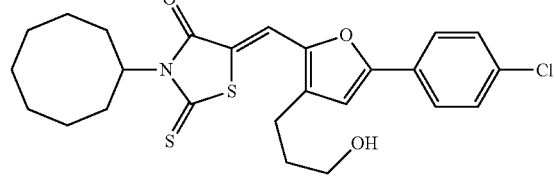 | C25H28ClNO3S2<br>Exact Mass: 489.1199<br>Molecular Weight: 490.0777 | NA | B |
| 330 | 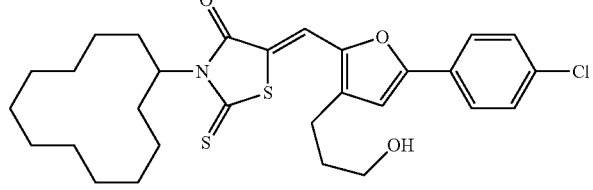 | C29H36ClNO3S2<br>Exact Mass: 545.1825<br>Molecular Weight: 546.1840 | NA | C |
| 331 | 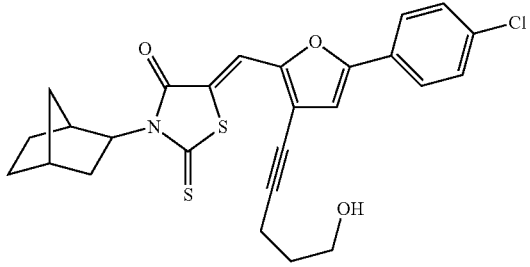 [SMILES: O=C1/C(=C/c2oc(-c3ccc(Cl)cc3)cc2C#CCCCO)SC(=S)N1C1CC2CCC1C2] | C26H24ClNO3S2<br>Exact Mass: 497.0886<br>Molecular Weight: 498.0567 | NA | C |

-continued

| Compound No. | Structure | MW | EC50 (nM) | 24 hr titer |
|---|---|---|---|---|
| 332 | 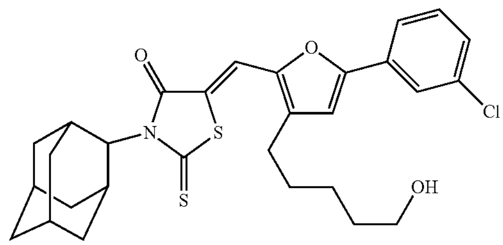 [SMILES: O=C1/C(=C/c2oc(-c3cccc(Cl)c3)cc2CCCCCO)SC(=S)N1C1C2CC3CC(C2)CC1C3] | C29H32ClNO2S3<br>Exact Mass: 557.1284<br>Mol. Wt.: 558.2179 | A | A |
| 333 | 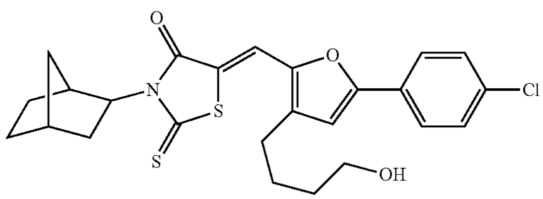 [SMILES: O=C1/C(=C/c2oc(-c3ccc(Cl)cc3)cc2CCCCO)SC(=S)N1C1CC2CCC1C2] | C25H26ClNO3S2<br>Exact Mass: 487.1043<br>Mol. Wt.: 488.0618 | A | A |
| 334 | 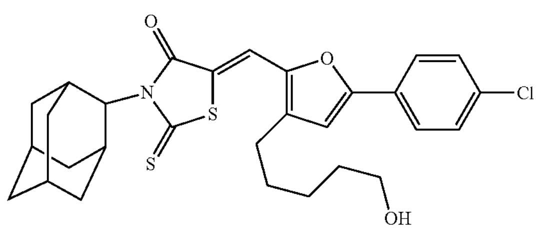 [SMILES: O=C1/C(=C/c2oc(-c3ccc(Cl)cc3)cc2CCCCCO)SC(=S)N1C1C2CC3CC(C2)CC1C3] | C29H32ClNO3S2<br>Exact Mass: 541.1512<br>Mol. Wt.: 542.1523 | A | A |
| 335 | 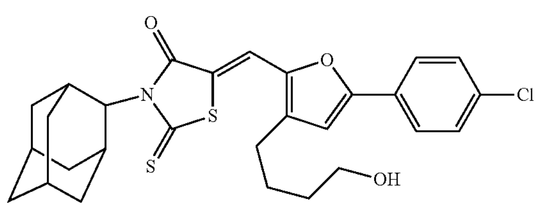 [SMILES: O=C1/C(=C/c2oc(-c3ccc(Cl)cc3)cc2CCCCO)SC(=S)N1C1C2CC3CC(C2)CC1C3] | C28H30ClNO3S2<br>Exact Mass: 527.1356<br>Mol. Wt.: 528.1257 | A | A |
| 336 | 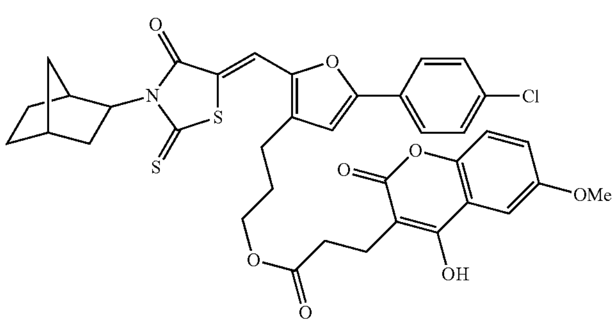 [SMILES: COc1ccc2oc(=O)c(CCC(=O)OCCCc3cc(-c4ccc(Cl)cc4)oc3/C=C3\SC(=S)N(C4CC5CCC4C5)C3=O)c(O)c2c1] | C37H34ClNO8S2<br>Exact Mass: 719.1414<br>Molecular Weight: 720.2508 | A | B |
| 337 | 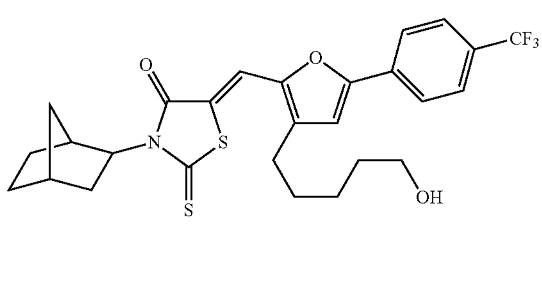 [SMILES: O=C1/C(=C/c2oc(-c3ccc(C(F)(F)F)cc3)cc2CCCCCO)SC(=S)N1C1CC2CCC1C2] | C27H28F3NO3S2<br>Exact Mass: 535.1463<br>Molecular Weight: 535.6413 | A | A |

-continued

| Compound No. | Structure | MW | EC50 (nM) | 24 hr titer |
|---|---|---|---|---|
| 338 | 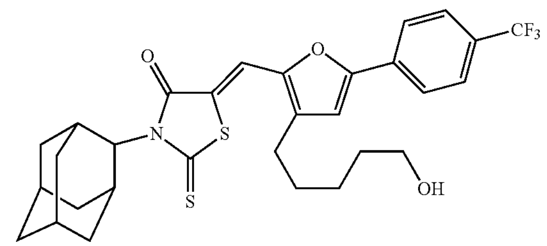 [SMILES: O=C1/C(=C/c2oc(-c3ccc(C(F)(F)F)cc3)cc2CCCCCO)SC(=S)N1C1C2CC3CC(C2)CC1C3] | C30H32F3NO3S2<br>Exact Mass: 575.1776<br>Molecular Weight: 575.7052 | A | A |
| 339 | 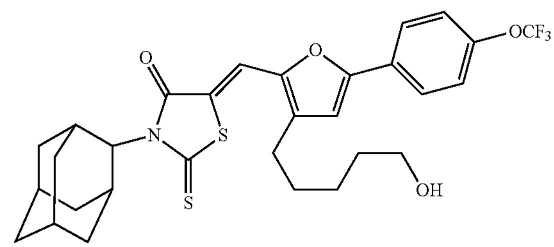 [SMILES: O=C1/C(=C/c2oc(-c3ccc(OC(F)(F)F)cc3)cc2CCCCCO)SC(=S)N1C1C2CC3CC(C2)CC1C3] | C30H32F3NO4S2<br>Exact Mass: 591.1725<br>Molecular Weight: 591.7046 | A | A |
| 340 | 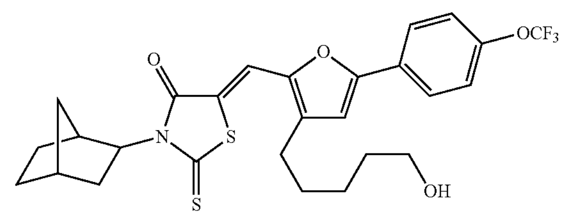 [SMILES: O=C1/C(=C/c2oc(-c3ccc(OC(F)(F)F)cc3)cc2CCCCCO)SC(=S)N1C1CC2CCC1C2] | C27H28F3NO4S2<br>Exact Mass: 551.1412<br>Molecular Weight: 551.6407 | A | A |
| 341 | 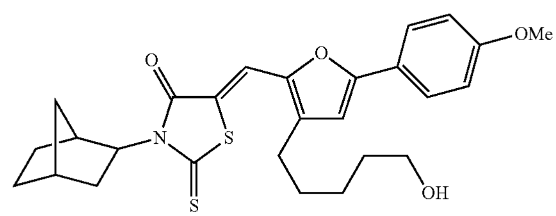 [SMILES: COc1ccc(-c2cc(CCCCCO)c(/C=C3\SC(=S)N(C4CC5CCC4C5)C3=O)o2)cc1] | C27H31NO4S2<br>Exact Mass: 497.1694<br>Mol. Wt.: 497.6693 | A | B |
| 342 | 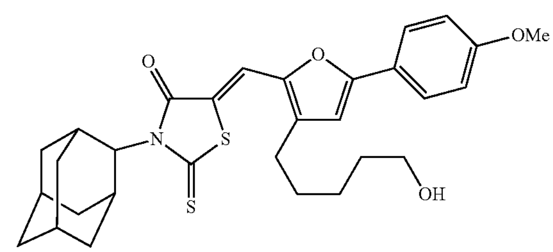 [SMILES: COc1ccc(-c2cc(CCCCCO)c(/C=C3\SC(=S)N(C4C5CC6CC(C5)CC4C6)C3=O)o2)cc1] | C30H35NO4S2<br>Exact Mass: 537.2007<br>Mol. Wt.: 537.7332 | A | B |
| 343 | 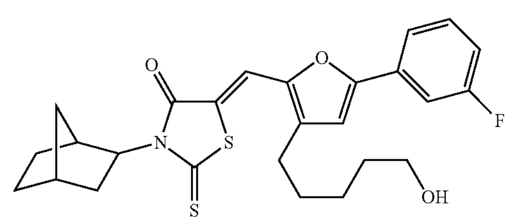 [SMILES: O=C1/C(=C/c2oc(-c3cccc(F)c3)cc2CCCCCO)SC(=S)N1C1CC2CCC1C2] | C26H28FNO3S2<br>Exact Mass: 485.1495<br>Mol. Wt.: 485.6338 | A | B |

-continued

| Compound No. | Structure | MW | EC50 (nM) | 24 hr titer |
|---|---|---|---|---|
| 344 | 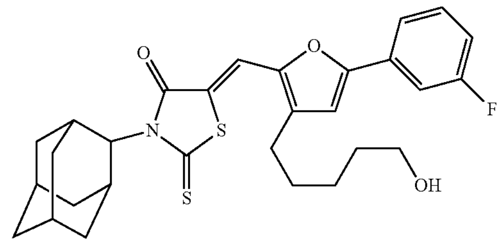 [SMILES: O=C1/C(=C/c2oc(-c3cccc(F)c3)cc2CCCCCO)SC(=S)N1C1C2CC3CC(C2)CC1C3] | C29H32FNO3S2<br>Exact Mass: 525.1808<br>Mol. Wt.: 525.6977 | A | A |
| 345 | 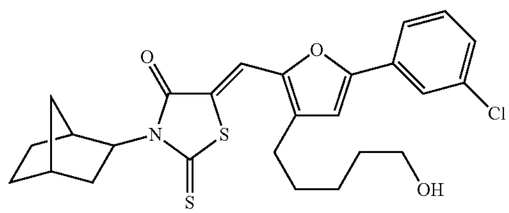 [SMILES: O=C1/C(=C/c2oc(-c3cccc(Cl)c3)cc2CCCCCO)SC(=S)N1C1CC2CCC1C2] | C26H28ClNO3S2<br>Exact Mass: 501.1199<br>Mol. Wt.: 502.0884 | A | A |
| 346 | 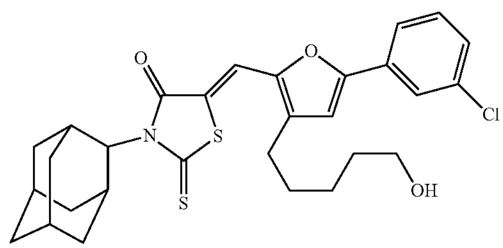 [SMILES: O=C1/C(=C/c2oc(-c3cccc(Cl)c3)cc2CCCCCO)SC(=S)N1C1C2CC3CC(C2)CC1C3] | C29H32ClNO3S2<br>Exact Mass: 541.1512<br>Mol. Wt.: 542.1523 | A | A |
| 347 | 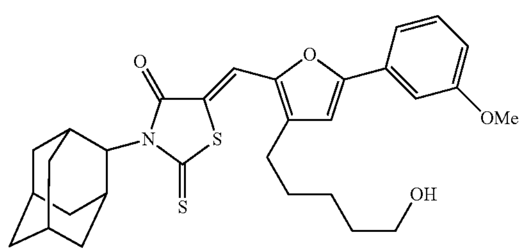 [SMILES: COc1cccc(-c2cc(CCCCCO)c(/C=C3\SC(=S)N(C4C5CC6CC(C5)CC4C6)C3=O)o2)c1] | C30H35NO4S2<br>Exact Mass: 537.2007<br>Molecular Weight: 537.7332 | A | A |
| 348 | 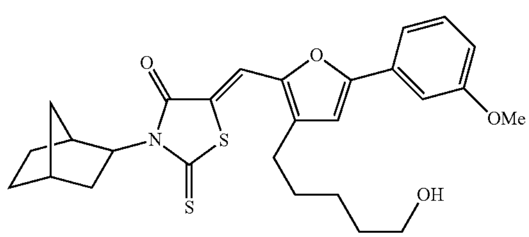 [SMILES: COc1cccc(-c2cc(CCCCCO)c(/C=C3\SC(=S)N(C4CC5CCC4C5)C3=O)o2)c1] | C27H31NO4S2<br>Exact Mass: 497.1694<br>Molecular Weight: 497.6693 | A | A |
| 349 | 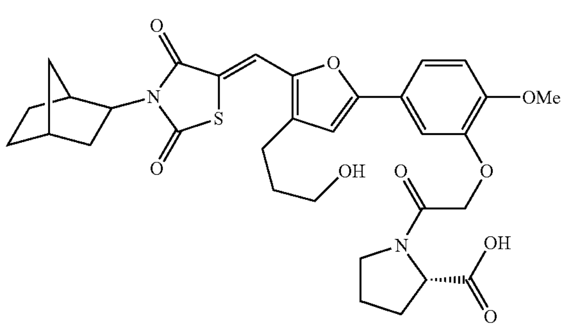 [SMILES: COc1ccc(-c2cc(CCCO)c(/C=C3\SC(=O)N(C4CC5CCC4C5)C3=O)o2)cc1OCC(=O)N1CCC[C@H]1C(=O)O] | C32H36N2O9S<br>Exact Mass: 624.2142<br>Molecular Weight: 624.7012 | A | C |

| Compound No. | Structure | MW | EC50 (nM) | 24 hr titer |
|---|---|---|---|---|
| 350 | 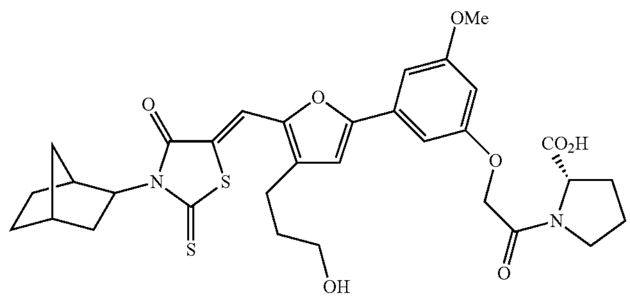 [SMILES: COc1cc(OCC(=O)N2CCC[C@H]2C(=O)O)cc(-c2cc(CCCO)c(/C=C3\SC(=S)N(C4CC5CCC4C5)C3=O)o2)c1] | C32H36N2O8S2<br>Exact Mass: 640.1913<br>Molecular Weight: 640.7668 | A | C |
| 351 | 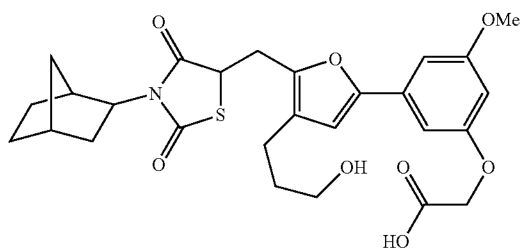 [SMILES: COc1cc(OCC(=O)O)cc(-c2cc(CCCO)c(CC3SC(=O)N(C4CC5CCC4C5)C3=O)o2)c1] | C27H29NO8S<br>Exact Mass: 527.1614<br>Molecular Weight: 527.5861 | C | C |
| 352 | 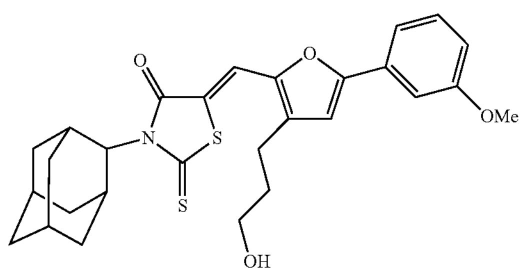 [SMILES: COc1cccc(-c2cc(CCCO)c(/C=C3\SC(=S)N(C4C5CC6CC(C5)CC4C6)C3=O)o2)c1] | C28H31NO4S2<br>Exact Mass: 509.1694<br>Mol. Wt.: 509.68 | A | A |
| 353 | 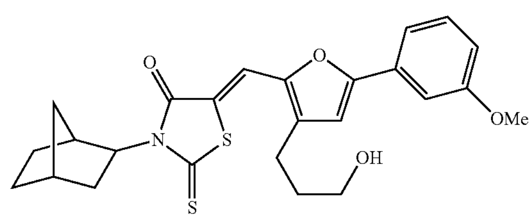 [SMILES: COc1cccc(-c2cc(CCCO)c(/C=C3\SC(=S)N(C4CC5CCC4C5)C3=O)o2)c1] | C25H27NO4S2<br>Exact Mass: 469.1381<br>Mol. Wt.: 469.6162 | A | C |
| Type-8 Modification of side chain in C-ring (furan) with amino acid moiety | 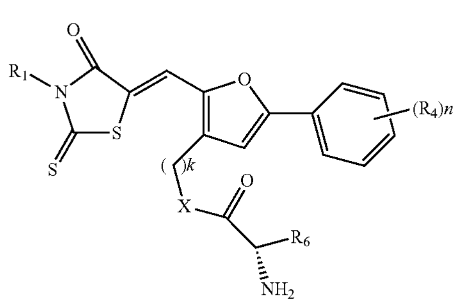 | | | |

| Compound No. | Structure | MW | EC50 (nM) | 24 hr titer |
|---|---|---|---|---|
| 354 | 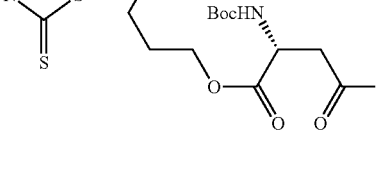 | C37H45N3O8S2<br>Exact Mass: 723.2648<br>Mol. Wt.: 723.8985 | A | A |
| Type-9 Modification of side chain in C-ring (furan) with α-hydroxy acid moiety | 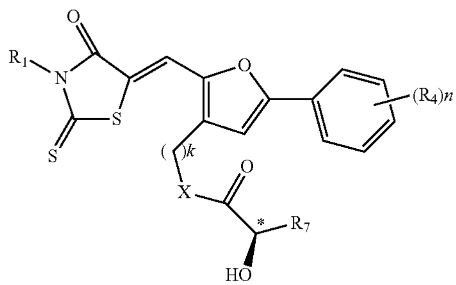 | | | |
| 355 | 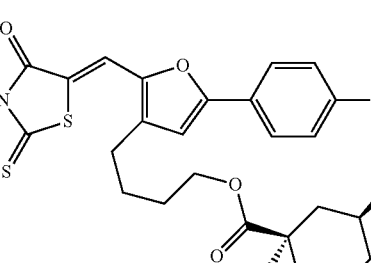 | C32H36ClNO8S2<br>Exact Mass: 661.1571<br>Molecular Weight: 662.2131 | NA | C |
| 356 | 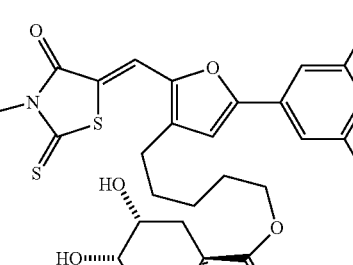 | C35H43NO10S2<br>Exact Mass: 701.2328<br>Molecular Weight: 701.8466 | A | C |
| 357 | 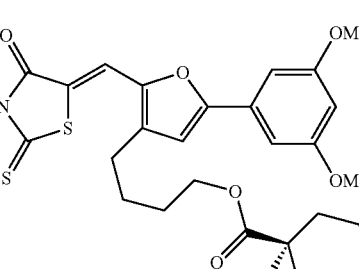 | C34H41NO10S2<br>Exact Mass: 687.2172<br>Molecular Weight: 687.8200 | A | B |

| Compound No. | Structure | MW | EC50 (nM) | 24 hr titer |
|---|---|---|---|---|
| Type-10 Modification of side chain in C-ring (furan) with morphiline moiety | 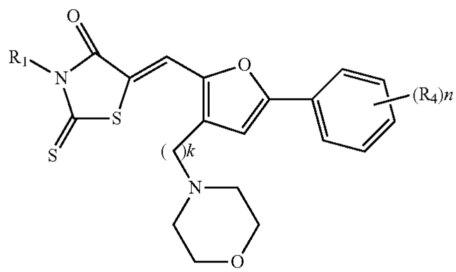 | | | |
| 358 | 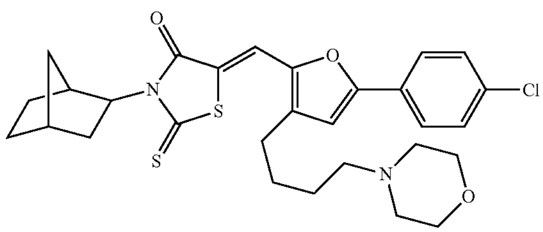 [SMILES: O=C1/C(=C/c2oc(-c3ccc(Cl)cc3)cc2CCCCN2CCOCC2)SC(=S)N1C1CC2CCC1C2] | C29H33ClN2O3S2<br>Exact Mass: 556.1621<br>Molecular Weight: 557.1669 | NA | A |
| 359 | 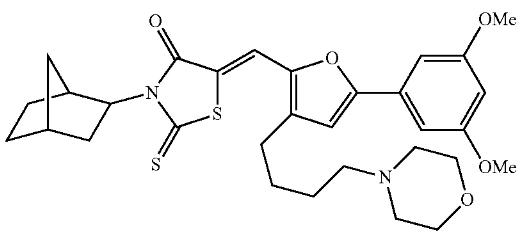 [SMILES: COc1cc(OC)cc(-c2cc(CCCCN3CCOCC3)c(/C=C3\SC(=S)N(C4CC5CCC4C5)C3=O)o2)c1] | C31H38N2O5S2<br>Exact Mass: 582.2222<br>Molecular Weight: 582.7738 | A | A |
| 360 | 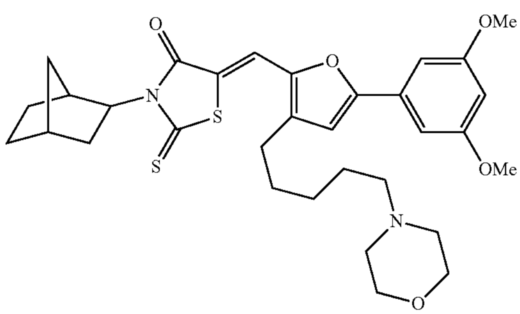 [SMILES: COc1cc(OC)cc(-c2cc(CCCCCN3CCOCC3)c(/C=C3\SC(=S)N(C4CC5CCC4C5)C3=O)o2)c1] | C32H40N2O5S2<br>Exact Mass: 596.2379<br>Molecular Weight: 596.8004 | A | A |
| Type-11 Modification of side chain in C-ring (furan) with piperazine moiety | 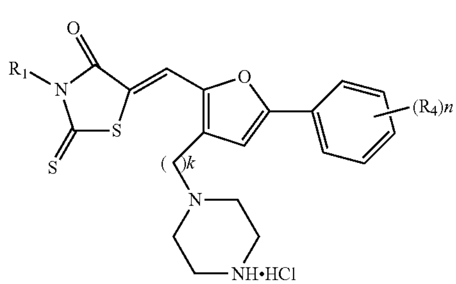 | | | |

-continued

| Compound No. | Structure | MW | EC50 (nM) | 24 hr titer |
|---|---|---|---|---|
| 361 | 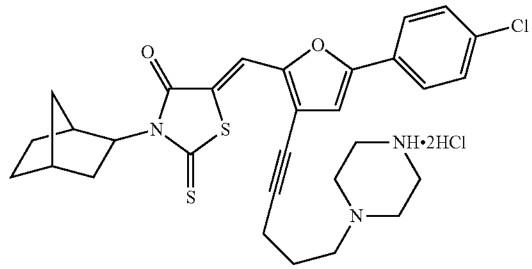 | C30H34Cl3N3O2S2<br>Exact Mass: 637.1158<br>Mol. Wt.: 639.0989 | A | A |
| 362 | 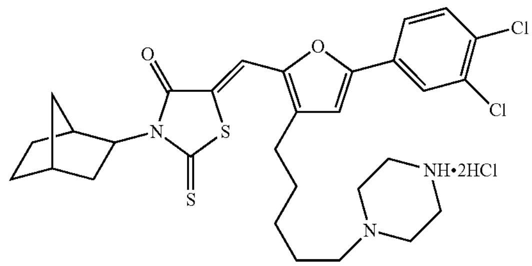 | C30H37Cl4N3O2S2<br>Exact Mass: 675.1081<br>Molecular Weight: 677.5757 | A | A |
| 363 | 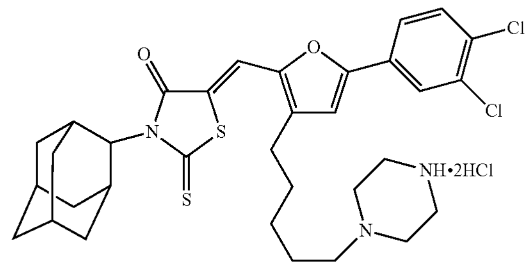 | C33H41Cl4N3O2S2<br>Exact Mass: 715.1394<br>Molecular Weight: 717.6395 | A | A |
| 364 | 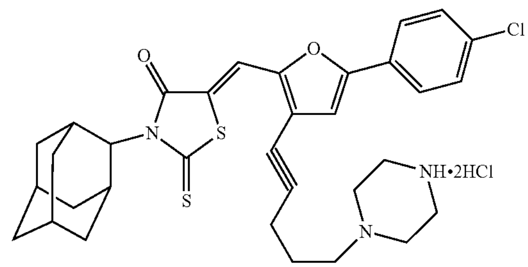 | C33H38Cl3N3OS3<br>Exact Mass: 693.1243<br>Mol. Wt.: 695.2283 | A | A |
| 365 | 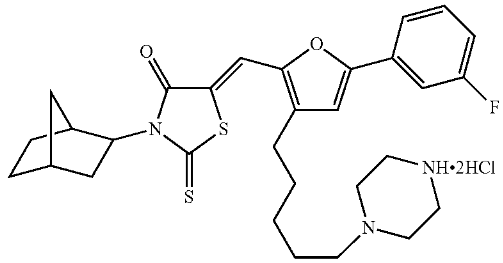 | C30H38Cl2FN3O2S2<br>Exact Mass: 625.1767<br>Mol. Wt.: 626.676 | A | A |

-continued

| Compound No. | Structure | MW | EC50 (nM) | 24 hr titer |
|---|---|---|---|---|
| 366 | 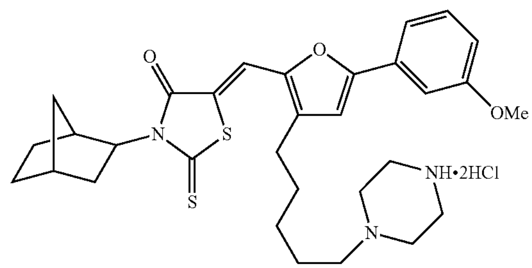 | C31H41Cl2N3O3S2<br>Exact Mass: 637.1966<br>Molecular Weight: 638.7115 | A | A |
| 367 | 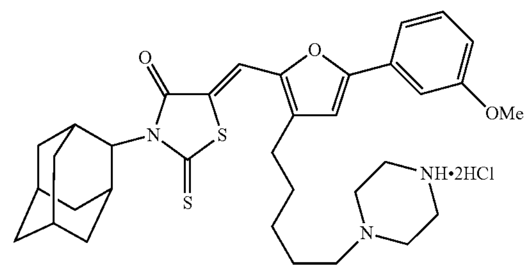 | C34H45Cl2N3O3S2<br>Exact Mass: 677.2279<br>Molecular Weight: 678.7754 | A | A |
| 368 | 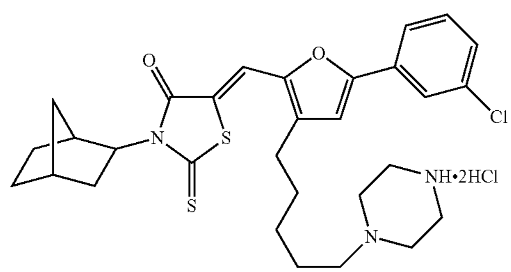 | C30H38Cl3N3O2S2<br>Exact Mass: 641.1471<br>Mol. Wt.: 643.1306 | A | A |
| 369 | 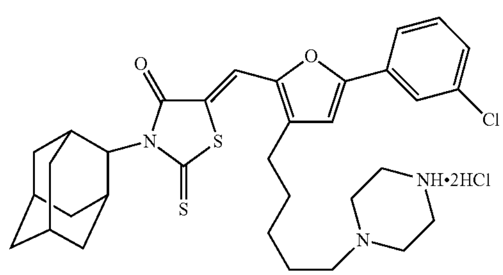 | C3H42Cl2FN3O2S2<br>Exact Mass: 665.208<br>Mol. Wt.: 666.7399 | A | A |
| 370 | 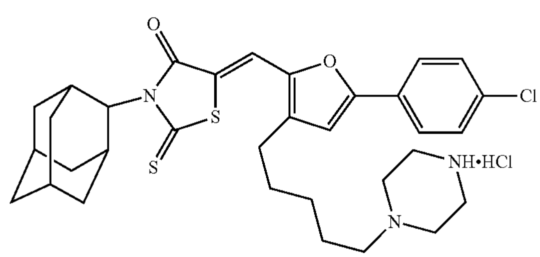 | C33H41Cl2N3O2S2<br>Exact Mass: 645.2017<br>Molecular Weight: 646.7335 | A | A |

| Compound No. | Structure | MW | EC50 (nM) | 24 hr titer |
|---|---|---|---|---|
| 371 | 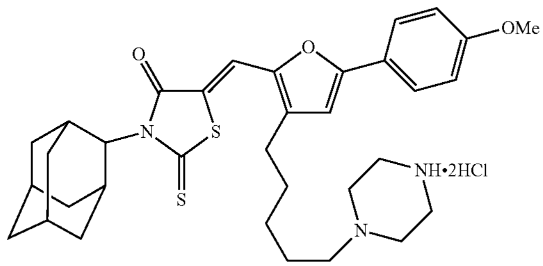 | C34H45Cl2N3O3S2<br>Exact Mass: 677.2279<br>Mol. Wt.: 678.7754 | A | A |
| 372 | 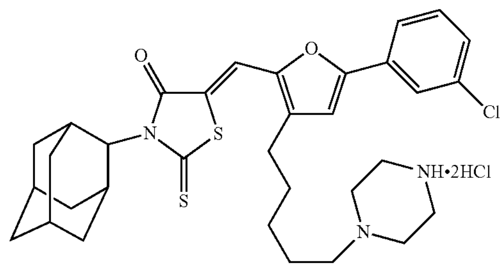 | C33H42Cl3N3O2S2<br>Exact Mass: 681.1784<br>Mol. Wt.: 683.1945 | A | A |
| 373 | 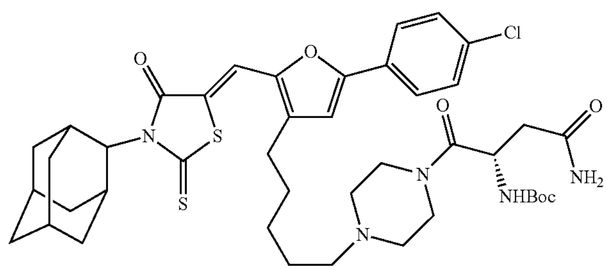 [SMILES: CC(C)(C)OC(=O)N[C@@H](CC(N)=O)C(=O)N1CCN(CCCCCc2cc(-c3ccc(Cl)cc3)oc2/C=C2\SC(=S)N(C3C4CC5CC(C4)CC3C5)C2=O)CC1] | C42H54ClN5O6S2<br>Exact Mass: 823.3204<br>Mol. Wt.: 824.4911 | A | A |
| 374 | 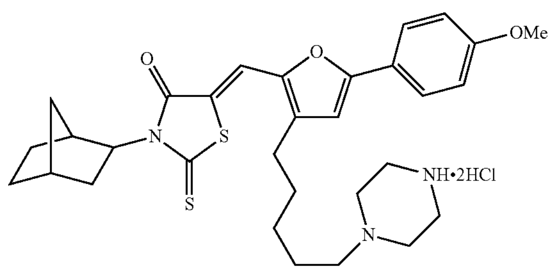 | C31H41Cl2N3O3S2<br>Exact Mass: 637.1966<br>Mol. Wt.: 638.7115 | A | A |
| 375 | 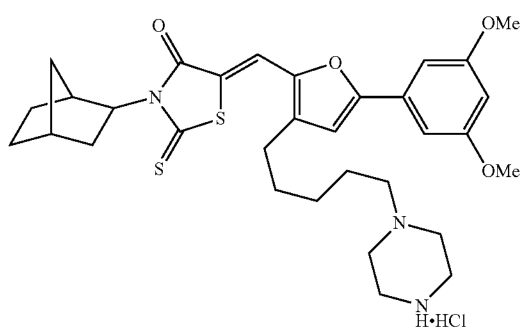 | C32H42ClN3O4S2<br>Exact Mass: 631.2305<br>Molecular Weight: 632.2766 | A | A |

| Compound No. | Structure | MW | EC50 (nM) | 24 hr titer |
|---|---|---|---|---|
| 376 | 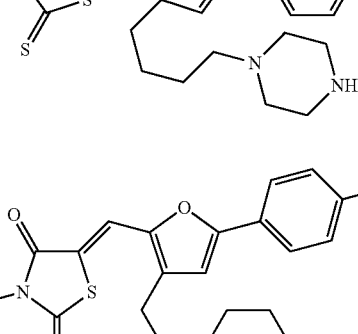 | C29H35Cl2N3O2S2<br>Exact Mass: 591.1548<br>Molecular Weight: 592.6431 | A | A |
| 377 | 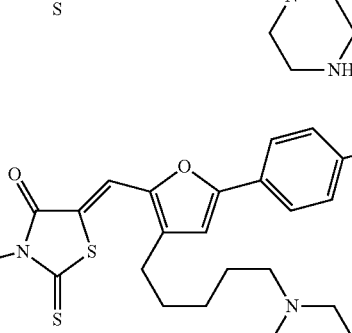 | C3H42Cl2FN3O2S2<br>Exact Mass: 665.2080<br>Molecular Weight: 666.7399 | A | A |
| 378 | 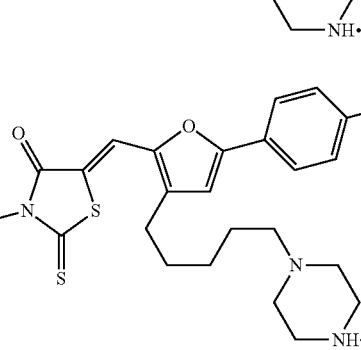 | C31H38Cl2F3N3O2S2<br>Exact Mass: 675.1735<br>Molecular Weight: 676.6835 | A | A |
| 379 | 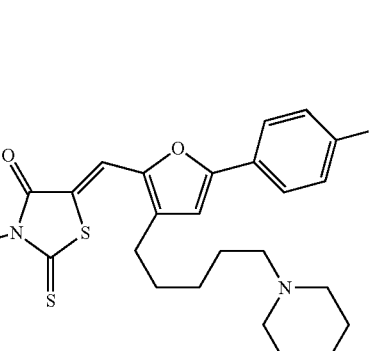 | C30H38Cl2FN3O2S2<br>Exact Mass: 625.1767<br>Molecular Weight: 626.6760 | A | A |
| 380 | 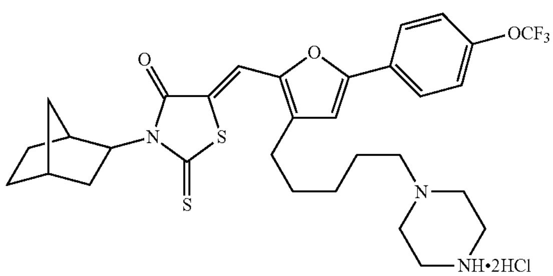 | C31H38Cl2F3N3O3S2<br>Exact Mass: 691.1684<br>Molecular Weight: 692.6829 | A | A |

-continued

| Compound No. | Structure | MW | EC50 (nM) | 24 hr titer |
|---|---|---|---|---|
| 381 | 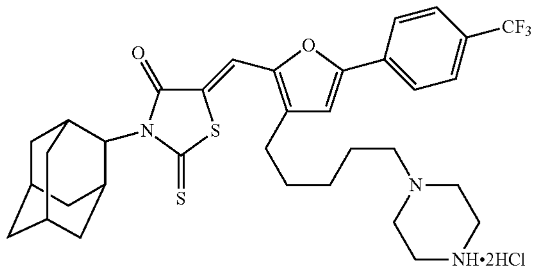 | C34H42Cl2F3N3O2S2<br>Exact Mass: 715.2048<br>Molecular Weight: 716.7474 | A | A |
| 382 | 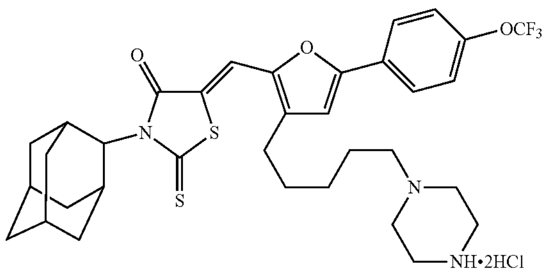 | C34H42Cl2F3N3O3S2<br>Exact Mass: 731.1997<br>Molecular Weight: 732.7468 | A | A |
| 383 | 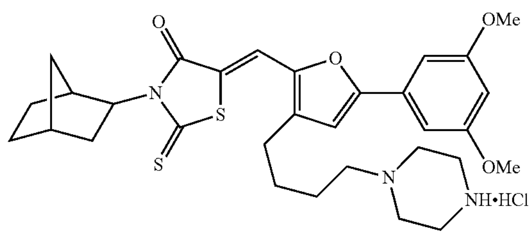 | C31H40ClN3O4S2<br>Exact Mass: 617.2149<br>Molecular Weight: 618.2500 | A | A |
| Type-12 Modification of side chain in C-ring (furan) with gunadine moiety | 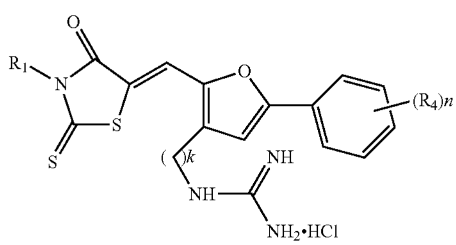 | | | |
| 384 | 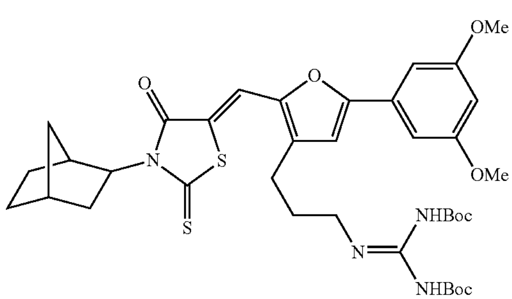 [SMILES: COc1cc(OC)cc(-c2cc(CCCN=C(NC(=O)OC(C)(C)C)NC(=O)OC(C)(C)C)c(/C=C3\SC(=S)N(C4CC5CCC4C5)C3=O)o2)c1] | C37H48N4O8S2<br>Exact Mass: 740.2914<br>Mol. Wt.: 740.9290 | NA | D |

| Compound No. | Structure | MW | EC50 (nM) | 24 hr titer |
|---|---|---|---|---|
| 385 | 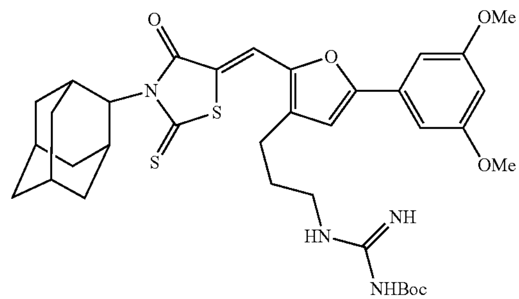 [SMILES: COc1cc(OC)cc(-c2cc(CCCNC(=N)NC(=O)OC(C)(C)C)c(/C=C3\SC(=S)N(C4C5CC6CC(C5)CC4C6)C3=O)o2)c1] | C35H44N4O6S2<br>Exact Mass: 680.2702<br>Mol. Wt.: 680.8771 | NA | C |

Assay Methods

The biological activities of compounds according to embodiments of the present invention can be tested or measured by any number of assays, including, but not limited to, the methods described below.

Plaque Assays in MDCK Cells

The following assays are used to screen compounds for antiviral activity. Madin-Darby canine kidney (MDCK) cells are cultured to monolayers in 6-well plates. 120 PFU of A/Udorn/72 (H3N2) virus is added to each well. Designated dosages of inhibitor compounds are added with the virus inoculum (0 hour) for determination of antiviral activities. Corresponding amounts of DMSO used to dissolve the compound is added in a separate well as the negative control.

The virus yield, at given time points, in the presence and absence of inhibitor compounds is determined in a plaque assay using MDCK cells and A/Udorn/72 ($H_3N_2$) virus following the protocol in Kati et al. (Kati, M. et al. "In Vitro Characterization of A-315675, a Highly Potent Inhibitor of A and B Strain Influenza Virus Neuramididases and Influenza Virus Replication" *Antimicrobial Agents and Chemotherapy*, April (2002) p. 1014-1021). MDCK cells are maintained in DMEM supplemented with 10% fetal calf serum, 20 mM HEPES buffer, and antibiotics. Cells are cultured in a flask at 37° C. and 5% $CO_2$. When monolayers of MDCK cells become 95% confluent in 6-well trays, the influenza virus inoculum in 0.1 mL DMEM is added to each well. After 1.0 hour absorption in 37° C., infected cells are washed with warm PBS once and the wells are overlaid with 0.6% agarose in DMEM supplemented with trypsin. After 48 hours of infection, the agar overlay is removed and the monolayers stained with 0.1% crystal violet in 10% formaldehyde. The virus yield is usually $1.0 \times 10^{7-8}$ plaque forming unit (PFU)/mL. The antiviral efficacy of inhibitor compounds can be evaluated for their reduction of the virus yield when they are added to the growth medium during virus infection.

Based on the virus yield assay, inhibitor compounds are divided in three groups: for inhibitor compounds that can reduce the virus yield to $<1.0 \times 10^5$ plaque forming unit (PFU)/mL at 1.0 µM, they are included in the group A; for inhibitor compounds that can reduce the virus yield to $>1.0 \times 10^5$ and $<1.0 \times 10^6$ plaque forming unit (PFU)/mL at 1.0 µM, they are included in the group B; for inhibitor compounds that can reduce the virus yield to $>1.0 \times 10^6$ and $\leq 1.0 \times 10^{-7}$ plaque forming unit (PFU)/mL at 1.0 µM, they are included in the group C.

The antiviral efficacy of the test compounds against the clinical isolates can also be assessed by counting the number of the plaques at each drug concentration. The 50% effective concentration of the drug, i.e., that which reduced plaque number by 50% ($EC_{50}$), was determined with visional inspection. Inhibitor compounds are divided in three groups: for inhibitor compounds that have an $EC_{50}$ value<100 nM, they are included in the group A; for inhibitor compounds that have an $EC_{50}$ value>100 nM and <250 nM, they are included in the group B; for inhibitor compounds that have an $EC_{50}$ value>250 nM and <1000 nM, they are included in the group C.

Pseudovirus Transducing Assay in MDCK Cells 293T cells are maintained with DMEM containing 10% FBS. Pseudo-influenza particles are prepared similar as described in (Luo et al., Vaccine. 2006 Jan. 23; 24(4):435-42). Briefly, a plasmid coding the HIV-1 genome, deleting the envelope protein gene and with a luciferase gene inserted, and two plasmids coding the influenza virus hemagglutinin (HA) gene and the influenza virus neuraminidase (NA) gene, respectively, are cotransfected into 293T cells. After 48 hr, the supernatant containing pseudoFlu particles is collected for transducing assay. In 96 well plates, MDCK cells are plated and incubated until confluent in DMEM supplemented with 10% fetal calf serum. The diluted pseudoFlu particles are incubated with various concentrations of inhibitor compounds for one hour in room temperature. Compound-treated pseudoFlu particles are added to transduce MDCK cells for six hours. Transduced cells are maintained for 48 hours in DMEM supplemented with 10% fetal calf serum. Cells are harvested and the luciferase activity is measured in each case. The 50% effective concentration of the drug, i.e., that which reduced luciferase activity by 50% ($EC_{50}$), is determined by comparisons with the control for which untreated pseudoFlu particles are added to transduce MDCK cells.

Inhibitor compounds are divided in three groups: for inhibitor compounds that have an $EC_{50}$ value<100 nM, they are included in the group A; for inhibitor compounds that have an $EC_{50}$ value>100 nM and <250 nM, they are included in the group B; for inhibitor compounds that have an $EC_{50}$ value>250 nM and $\leq$1000 nM, they are included in the group C.

HIV Pseudovirus Assay in X4 Cells

A plasmid coding the HIV-1 genome, deleting the envelope protein gene and with a luciferase gene inserted, and a plasmid coding the envelope protein gene were cotransfected into 293T cells. After 48 hr, the supernatant containing pseudoHIV particles was collected for transducing assay. In 96 well plates, X4 cells were plated and incubated till confluent. The pseudoHIV particles were incubated with various concentrations of inhibitor compounds for one hour in room temperature. The particles were then used for tranducing X4 cells. The transduced X4 cells were lysed after 48 hr and the luciferase activity was measured in a luminometer.

Inhibitor compounds are divided in two groups: for inhibitor compounds that have an $EC_{50}$ value<100 nM, they are included in the group A; for inhibitor compounds that have an $EC_{50}$ value>100 nM and <250 nM, they are included in the group B.

Methods of Use

Methods of Identifying Novel Antiviral Agents

One aspect of the uses of the compounds of the invention is a method of identifying novel antiviral agents. For example, a method for identifying an inhibitor for the HA or HIV grlycoprotein mediated membrane fusion according to an embodiment of the present invention, comprises:
  (a) synthesizing a compound of Formula (I), such as a compound disclosed above;
  (b) testing the compound by one or a number of antiviral assays as described supra;
  (c) designing a second compound that modifies the structure of the compound in order to incorporate one or more new functional chemical groups;
  (d) synthesizing the second compound;
  (e) determining the ability of the second compound to inhibit the HA or HIV glycoprotein mediated membrane fusion, and
  (f) identifying the second compound as the inhibitor for the HA or HIV grlycoprotein mediated membrane fusion based on the result of step (e).

These steps can be repeated to obtain the optimal compounds by fine tuning the interaction features between the compounds and virus particles bearing the HA or HIV glycoprotein.

Thus, a method according to an embodiment of the invention further comprises repeating steps (a) to (e) to obtain an optimal compound by fine tuning the interaction features between the compound and virus particles bearing the HA or HIV glycoprotein.

A particular method of the invention comprises synthesizing the designed compounds that incorporate functional chemical groups. Such a class of compounds can be synthesized using a variety of methods known in the art. For example, the synthesis methods described herein or the modification of these methods may prove to be useful to synthesize the designed compounds.

Yet another particular method of the invention comprises assaying the new compounds for its ability to inhibit the viral fusion process. The inhibition effect of the compound can be measured using any biological assays described supra.

Studies on the structure activity relationship of the rationally designed compounds will provide additional information for the design of new compounds with improved antiviral activity.

Method of Treating a Viral Infection

The compounds described herein can be used for a variety of purposes, including, but not limited to, treating or preventing a viral infection in a subject, inhibiting viral entry into a cell, inhibiting viral mediated membrane fusion, and destabilizing a viral fusion protein. The compounds described herein inhibit at least one (and, optionally, more than one) of the roles of HA, i.e., binding to sialic acid or acting as a membrane fusogen. For example, the compounds described herein can bind or otherwise inhibit the activity of hemagglutinin and/or can inhibit the docking and/or fusion of the virus with the host cell. Further, the compounds described herein can have good efficacy against mutated viruses.

Thus, another aspect of the present invention relates to the use of a compound according to an embodiment of the invention for making a medicament for treating or preventing a viral infection.

For example, described herein are methods for treating or preventing a viral infection in a subject, the method comprising administering to the subject an effective amount of one or more of the compounds or compositions described herein. As used herein the terms treating or preventing and treating and/or preventing include prevention; delay in onset; diminution, eradication, or delay in exacerbation of signs or symptoms after onset; and prevention of relapse.

Also described herein are methods of inhibiting viral entry into a cell, the method comprising administering to the cell an effective amount of one or more of the compounds or compositions described herein.

Also described herein are methods of inhibiting viral mediated membrane fusion, the method comprising administering to the cell an effective amount of one or more of the compounds or compositions described herein.

Also described herein are methods of destabilizing a viral fusion protein, the method comprising administering to a virally infected cell an effective amount of one or more of the compounds or compositions described herein. By destabilizing a fusion protein, the compounds or compositions described herein can prevent viral mediated membrane fusion and in turn prevent viral infection.

The compounds described herein can be administered to a subject before or after a viral, e.g., influenza, infection has taken place. As shown in the examples, the compounds described herein can both at least partially inhibit the binding of virions to target cells as well as at least partially inhibit viral replication after infection has occurred. Also, the effect of the compounds described herein on virions appears to be irreversible, and thus dilution of the compounds described herein bound to virions is not likely to lower the compounds efficacy against a viral infection. In addition, the compounds described herein can be administered in low concentrations (e.g., as low as 0.4 nM).

Other antiviral approaches have been employed to target other possible targets for viral inhibition. Other compositions used as antivirals or antiretrovirals are broadly classified by the phase of the virus or retrovirus life-cycle that the drug inhibits. For example, other compounds that have been used as viral inhibitors include, but are not limited to, a nucleoside or nucleotide reverse transcriptase inhibitor, a non-nucleoside reverse transcriptase inhibitor, a protease inhibitor, an integrase inhibitor, an RNA polymerase inhibitor, a DNA polymerase inhibitor, a kinase inhibitor, an enzyme inhibitor, an entry inhibitor, an assembly inhibitor, a maturation inhibitor, a M2 inhibitor, or a neuraminidase inhibitor. Nucleoside and nucleotide reverse transcriptase inhibitors (NRTI) inhibit reverse transcription by being incorporated into the newly synthesized viral DNA and preventing its further elongation. Non-nucleoside and nucleotide reverse transcriptase inhibitors (nNRTI) inhibit reverse transcriptase directly by binding to the enzyme and interfering with its function. Protease inhibitors (PIs) target viral assembly by inhibiting the activity of protease, an enzyme used by HIV to cleave nascent proteins for final assembly of new virons. Integrase inhibitors inhibit the enzyme integrase, which is responsible for integration of viral DNA into the DNA of the infected cell. There are several integrase inhibitors currently under clinical trial, and raltegravir became the first to receive FDA approval in October 2007. Entry inhibitors (or fusion inhibitors) interfere with binding, fusion, and entry of HIV-I to the host cell by blocking one of several targets. Maraviroc and enfuviritide are the two currently available agents in this class. Maturation inhibitors inhibit the last step in gag processing in which the viral capsid polyprotein is cleaved, thereby blocking the conversion of the polyprotein into the mature capsid protein (p24). Because these viral particles have a defective core, the virions released consist mainly of noninfectious particles. There are no drugs in this class currently available, though two are under investigation, bevirimat and Vivecon™.

In any of the methods described herein, the compounds described herein can be administered alone or in combination with one or more second compounds. For example, the compounds described herein can be administered in combination with one or more additional antiviral compounds. Antiviral compounds that can be used in combination with the compounds described herein include, but are not limited to, nucleoside or nucleotide reverse transcriptase inhibitors, non-nucleoside reverse transcriptase inhibitors, protease inhibitors, integrase inhibitors, RNA polymerase inhibitors, DNA polymerase inhibitors, kinase inhibitors, enzyme inhibitors, entry inhibitors, assembly inhibitors, maturation inhibitors, M2 inhibitors, and neuraminidase inhibitors. Examples of such additional antiviral compounds include, but are not limited to amantadine, rimantadine, oseltamivir (Tamilfu®, Roche Laboratories, Nutley, N.J.), zanamivir (Relenza®, GlaxoSmithKline, Philadelphia, Pa.), peramivir, raltegravir, Maraviros, enfuviritide, bevirimat, Vivecon™ (Myriad Genetics, Salt Lake City, Utah), Combivir® (zidovudine+lamivudine, AZT+3TC) (GlaxoSmithKline, Philadelphia, Pa.), Emtriva® (emtricitabine, FTC) (Gilead Sciences, Foster City, Calif.), Epivir® (lamivudine, 3TC) (GlaxoSmithKline, Philadelphia, Pa.), Epzicom® (Kivexa, abacavir+lamivudine, ABC+3TC) (GlaxoSmithKline, Philadelphia, Pa.), Retrovir® (zidovudine, AZT, ZDV) (GlaxoSmithKline, Philadelphia, Pa.), Trizivir® (abacavir+zidovudine+lamivudine, ABC+AZT+3TC) (GlaxoSmithKline, Philadelphia, Pa.), Truvada® (tenofovir DF+emtricitabine, TDF+FTC) (Gilead Sciences, Foster City, Calif.), Videx® & Videx EC® (didanosine, ddI) (Bristol-Myers Squibb, Princeton, N.J.), Viread® (tenofovir disoproxil fumarate, TDF) (Gilead Sciences, Foster City, Calif.), Zerit® (stavudine, d4T) (Bristol-Myers Squibb, Princeton, N.J.), Ziagen® (abacavir, ABC) (GlaxoSmithKline, Philadelphia, Pa.), Racivir™ (RCV) (Pharmasset, Princeton, N.J.), Amdoxovir™ (AMDX, DAPD) (RFS Pharma, Tucker, Ga.), apricitabine (SPD754, AVX754), elvucitabine (ACH-126,443, Beta-L-Fd4C), Immunitin® (HE2000, alpha-epibromide) (Hollis-Eden Pharmaceuticals, San Diego, Calif.), Proleukin® (aldesleukin, Interleukin-2, IL-2) (Chiron Corporation, Emeryville, Calif.), Remune® (HIV-I Immunogen, Salk vaccine) (Orchestra Therapeutics, Carlsbad, Calif.), BAY 50-4798, IRl03, Intelence™ (etravirine, TMC-125) (Tibotec Therapeutics, Irvine, Calif.), Rescriptor® (delavirdine, DLV) (Pfizer, New York, N.Y.), Sustiva® (Stocrin, efavirenz, EFV) (Bristol-Myers Squibb, Princeton, N.J.), Viramune® (nevirapine, NVP) (Boehringer Ingelheim, Ridgefield, Conn.), rilpivirine (TMC-278), Agenerase® (amprenavir, APV) (GlaxoSmithKline, Philadelphia, Pa.), Aptivus® (tipranavir, TPV) (Boehringer Ingelheim, Ridgefield, Conn.), Crixivan® (indinavir, IDV) (Merck, Whitehouse Station, N.J.), Invirase® (saquinavir, SQV) (Roche Laboratories, Nutley, N.J.), Kaletra® (Aluvia®, lopinavir/ritonavir, LPV/r) (Abbott Laboratories, Abbott Park, Ill.), Lexiva® (Telzir®, fosamprenavir, FPV) (GlaxoSmithKline, Philadelphia, Pa.), Norvir® (ritonavir, RTV) (Abbott Laboratories, Abbott Park, Ill.), Prezista® (darunavir, DRV) (Tibotec Therapeutics, Irvine, Calif.), Reyataz® (atazanavir, ATV) (Bristol-Myers Squibb, Princeton, N.J.), Viracept® (nelfinavir, NFV) (Pfizer, Inc., New York, N.Y.), Fuzeon® (enfuvirtide, ENF, T-20) (Roche Laboratories, Inc., Nutley, N.J.), Selzentry® (Celsentri®, maraviroc, UK-427,857) (Pfizer, Inc., New York, N.Y.), Vicriviroc® (SCH-417690, SCH-D) (Schering-Plough, Kenilworth, N.J.), PRO140 (Progenies Pharmaceuticals, Tarrytown, N.Y.), TNX-355 (Tanox, Inc., Houston, Tex.), Isentress® (raltegravir, MK-0518) (Merck, Whitehouse Station, N.J.), Elvitegravir™ (GS-9137) (Gilead Sciences, Foster City, Calif.), Bevirimat™ (PA-457) (Panacos Pharmaceuticals, Inc., Watertown, Mass.), and Droxia® or Hydrea® (hydroxyurea, HU) (Bristol-Myers Squibb, Princeton, N.J.).

The compounds described herein can provide inoculation against viruses prior to attack or the compounds described herein can be used to stop further replication of the invading virus once viral replication has begun. The present compounds, therefore, provide both a method for preventing viral replication in a host cell or host organism, as well as provide a method of treating a host organism (e.g., a subject that has been inoculated or otherwise exposed to an influenza strain, especially sub types of Influenza A or Influenza B, inter alia, A/Udorn/72, X-31, A/PR/8/34, A/NWS/G70C, A/Aich/68, and B/Lee/40).

Also described are methods for treating or preventing viral infection in cells comprising contacting the cells with an effective amount of one or more compounds described herein. The present disclosure further provides a method for treating or preventing a viral infection in a mammal comprising administering to a mammal an effective amount of one or more of the compounds described herein. The present disclosure yet further provides a method for treating or preventing a viral infection in a subject by inhibiting hemagglutinin and/or hemagglutinin having mutations wherein the mutations are based on conservative amino acid substitutions, comprising contacting hemagglutinin with an effective amount of one or more of the compounds described herein. The present disclosure still further provides a method for stopping virus replication in the presence of a host cell in vivo, in vitro, and ex vivo. For example, the present disclosure provides a method for treating or preventing Influenza A or Influenza B viral infection in a subject (e.g., a human) by administering to the subject an effective amount of one or more of the compounds described herein.

The present disclosure provides a method for treating or preventing a viral infection in a cell comprising providing to cells an effective amount of one or more of the compounds described herein or other compounds to destabilize the surface fusion protein on a virus. The present disclosure further provides a method for treating or preventing a viral infection in a mammal comprising administering to the mammal an effective amount of one or more of the compounds described herein or other compounds that destabilize the surface fusion protein on a virus. The present disclosure yet further provides a method for treating a subject by inhibiting a fusion protein and/or a fusion protein having mutations wherein the mutations are based on conservative amino acid substitutions, comprising contacting a fusion protein with an effective amount of one or more of the compounds described herein or other compounds that destabilize the fusion protein. The present disclosure still further provides a method for stopping virus replication in the presence of a host cell in vivo, in vitro, and ex vivo. The present disclosure also provides a method for treating or preventing a viral infection in a human by administering to the human an effective amount of one or more of the compounds described herein or other compounds that destabilize the surface fusion protein on the virion. The present disclosure further relates to the use of one or more of the compounds described herein or other compounds that destabilize the surface fusion protein on the virion for the making of a medicament for treating or preventing a viral infection (for example, an Influenza A or Influenza B viral infection) in a mammal (for example, a human). The present disclosure further relates to the use of the compounds described herein or other compounds that destabilize the surface fusion protein on the virion for the making of a medicament for inhibiting viral fusion protein in the presence of a potential host cell whether in vivo, in vitro, or ex vivo.

As used throughout, a subject is meant an individual. Thus, the subject can include mammals, including humans, primates, domesticated animals (e.g., cats, dogs, etc.), livestock (e.g., cattle, horses, pigs, sheep, goats, etc.), and laboratory animals (e.g., mouse, rabbit, rat, guinea pig, etc.), and birds.

Formulations

The present disclosure also relates to compositions or formulations which comprise the compounds according to the present disclosure. The compositions of the present disclosure comprise an effective amount (e.g., from about 0.001 mg to about 1000 mg, from about 0.01 mg to about 100 mg, and from about 0.1 mg to about 10 mg) of one or more viral inhibitors according to the present disclosure, and one or more excipients.

Excipients are used primarily to serve in delivering a safe, stable, and functional pharmaceutical composition, serving not only as part of the overall vehicle for delivery, but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The compounds of the present disclosure have improved cellular potency, pharmacokinetic properties, as well as improved oral bioavailability.

The term "effective amount" as used herein refers to an amount of one or more viral inhibitors, effective at dosages and for periods of time necessary to achieve the desired or therapeutic result. Effective dosages and schedules for administering the compositions may be determined empirically, and making such determination is within the skill in the art. The dosage ranges for the administration of the compositions are those large enough to produce the desired effect in which the symptoms of disorder are effected. The dosage should not be so large as to cause adverse side effects, such as unwanted cross-reactions, anaphylactic reactions, and the like. Generally, the dosage will vary with the age, condition, sex and extent of the disease in the subject, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. A typical daily dosage of the compounds described herein used alone might range from about 0.1 mg/kg to up to 10 mg/kg of body weight or more per day, depending on the factors mentioned above.

Following administration of one or more of the compounds described herein, for treating or preventing a viral invention in a subject, preventing viral infection in a subject, inhibiting viral entry into a cell, inhibiting viral mediated membrane fusion, or destabilizing a viral fusion protein, the efficacy of the compound can be assessed in various ways, some of which are known to the skilled practitioner.

The pharmaceutical compositions may be manufactured using any suitable means, e.g., by means of conventional mixing, dissolving, granulating, dragee-making, levigating, emulsifying, encapsulating, entrapping or lyophilizing processes.

Pharmaceutical compositions for use in accordance with the present disclosure thus may be formulated in a conventional manner using one or more physiologically or pharmaceutically acceptable carriers (vehicles, or diluents) comprising excipients and auxiliaries which facilitate processing of the active compounds into preparations which can be used pharmaceutically. Proper formulation is dependent upon the route of administration chosen.

Any suitable method of administering a pharmaceutical composition to a subject may be used in the methods of treatment as described herein, including injection, transmucosal, oral, inhalation, ocular, rectal, long acting implantation, liposomes, emulsion, or sustained release means.

For injection, the agents described herein may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art. For ocular administration, suspensions in an appropriate saline solution are used as is well known in the art.

For oral administration, the compounds can be formulated readily by combining the active compounds with pharmaceutically acceptable carriers well known in the art. Such carriers enable the compounds described herein to be formulated as tablets, pills, dragees, capsules, liquids, gels, syrups, slurries, suspensions and the like, for oral ingestion by a subject to be treated. Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients include fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds described herein are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, e.g., gelatin, for use in an inhaler or insufflator, may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing, and/or dispersing agents.

Pharmaceutical formulations for parenteral administration include aqueous solutions of the active compounds in water-soluble form. Additionally, suspensions of the active compounds may be prepared as appropriate oily injection suspensions.

Suitable lipophilic solvents or vehicles include fatty oils such as sesame oil, or synthetic fatty acid esters, such as ethyl oleate or triglycerides, or liposomes.

Aqueous injection suspensions may contain substances which increase the viscosity of the suspension, such as sodium carboxymethyl cellulose, sorbitol, or dextran.

Optionally, the suspension may also contain suitable stabilizers or agents which increase the solubility of the compounds to allow for the preparation of highly concentrated solutions.

Alternatively, the active ingredient may be in powder form for constitution with a suitable vehicle, such as sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

One type of pharmaceutical carrier for hydrophobic compounds described herein is a cosolvent system comprising benzyl alcohol, a nonpolar surfactant, a water-miscible organic polymer, and an aqueous phase.

The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD cosolvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied. For example, other low-toxicity nonpolar surfactants may be used instead of polysorbate 80; the fraction size of polyethylene glycol may be varied; other biocompatible polymers may replace polyethylene glycol, e.g., polyvinyl pyrrolidone; and other sugars or polysaccharides may be substituted for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed. Additionally, the compounds may be delivered using any suitable sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a prolonged period of time. Depending on the chemical nature and the biological stability of the therapeutic reagent, additional strategies for protein stabilization may be employed.

The pharmaceutical compositions may also comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the agents described herein may be provided as salts with pharmaceutically acceptable counterions. Salts tend to be more soluble in aqueous or other protonic solvents than are the corresponding free base forms.

Other aspects described herein include methods of treating a condition or a disease in a mammal comprising administering to said mammal a pharmaceutical composition described herein.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:
1. A compound having the formula of:

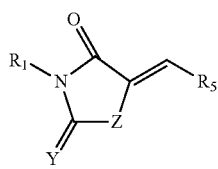

Formula (I)

or an optical isomer, enantiomer, diastereomer, racemate, or pharmaceutically acceptable salt thereof, wherein,
$R_1$ is an optionally substituted cycloalkyl having from 3 to 20 carbon atoms;
Z is S or NH;
Y is O or S;

$R_5$ is
a moiety having the formula of:

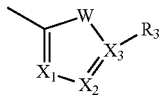

Formula 1a wherein,
W is selected from the group consisting of O, S, NH, and $CH_2$, wherein each of the NH and $CH_2$ is optionally substituted with an alkyl or aryl;
one of $X_1$ and $X_2$ is unsubstituted and is selected from the group consisting of CH, O, S and N,
the other one of $X_1$ and $X_2$ is C linked to a substituent $R_2$, and $R_2$ is A-B,
wherein,
A is an optionally substituted aryl, or an optionally substituted alkyl, alkenyl or alkynyl having 1 to 10 carbon atoms; and
B is selected from the group consisting of an alkoxy, a hydroxyl, an acid ester, a carboxyl, an amine, an amide, an ether, an amino acid derivative, an alpha-hydroxy acid, a guanidino, an optionally substituted aryl, an optionally substituted heteroaryl, an optionally substituted cycloalkyl, and an optionally substituted heterocyclic ring;
$X_3$ is selected from the group consisting of C and N; and
$R_3$ is selected from the group consisting of H, a halogen, an amino acid derivative, an acid ester, an optionally substituted aryl, an optionally substituted heteroaryl and an optionally substituted heterocyclic ring,
wherein the amino acid derivative is selected from the group consisting of

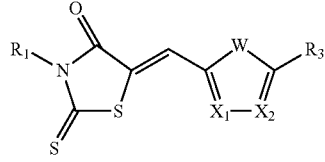

and wherein X is O, N or S, and each of $R_6$ and $R_8$ is independently a side chain of an amino acid.

2. The compound of claim 1, wherein the compound of Formula (I) has the formula of:

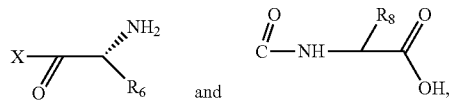

Formula (II)

wherein:
$R_3$ is selected from the group consisting of an optionally substituted aryl, an optionally substituted heteroaryl, and an optionally substituted heterocyclic ring.

3. The compound of claim 2, wherein $R_2$ has the formula of:

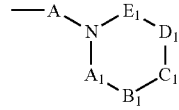

Formula 2a wherein each of A1, B1, C1, D1, E1 is independently selected from the group consisting of N, NH, S, O, CH and CH2, each of NH, CH and $CH_2$ is optionally independently substituted, and the $A_1B_1C_1D_1E_1N$ ring optionally contains one or more double bonds.

4. The compound of claim 3, wherein,
W is O, S or an optionally substituted NH;
one of $X_1$ and $X_2$ is the unsubstituted CH, and the other one of $X_1$ and $X_2$ is C—$R_2$;
A is an optionally substituted alkyl having 1 to 10 carbon atoms;
$X_3$ is C;
$R_1$ is an optionally substituted fused or bicyclic cycloalkyl ring; and
$R_3$ is an optionally substituted aryl or an optionally substituted heteroaryl.

5. The compound of claim 1, wherein $R_3$ has the formula of:

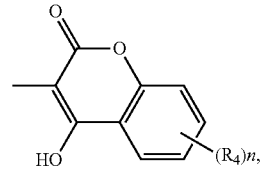

Formula 2b(1)

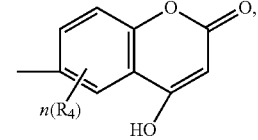

Formula 2b(2)

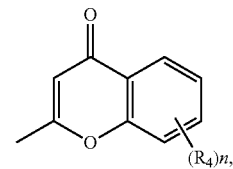

Formula 2b(3)

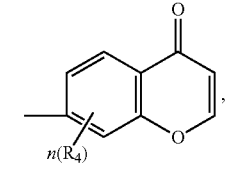

Formula 2b(4)

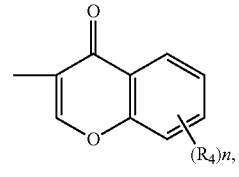

Formula 2b(5)

-continued

Formula 2b(6)
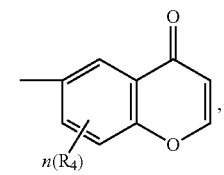

Formula 2b(7)
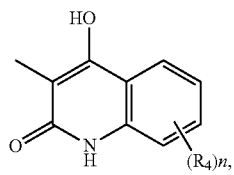

Formula 2b(8)
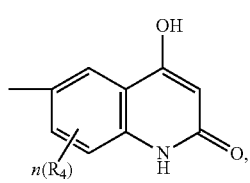

Formula 2b(9)
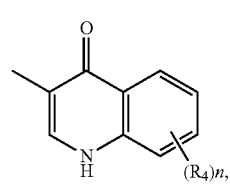

Formula 2b(10)
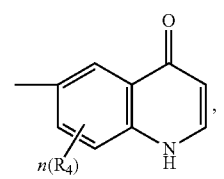

Formula 2b(11)
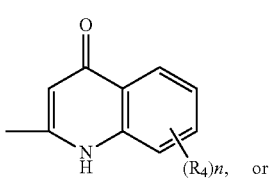

Formula 2b(12)
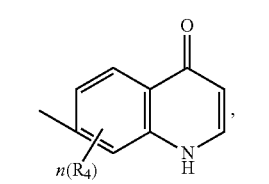

wherein, n is an integer of 0 to 3, and $R_4$ is independently selected from the group consisting of an alkoxy, a halogen, a hydroxy, an amide, a thio, a nitro, a cyano, an alkyl, an alcohol, an amine, an amino acid derivative, a carboxyl, an acid ester, an alpha-hydroxy acid, an ether, a guanidino, an optionally substituted aryl, an optionally substituted heteroaryl, an optionally substituted cycloalkyl, and an optionally substituted heterocyclic ring, wherein the amino acid derivative is selected from the group consisting of

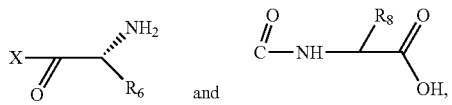

wherein X is O, N or S, and each of $R_6$ and $R_8$ is independently a side chain of an amino acid.

6. The compound of claim 5, wherein,

W is O, S or an optionally substituted NH;

$X_3$ is C;

Y is S;

Z is S; and $R_1$ is an optionally substituted fused or bicyclic cycloalkyl ring.

7. The compound of claim 1, wherein the compound of Formula (I) has the formula of:

Formula (III)
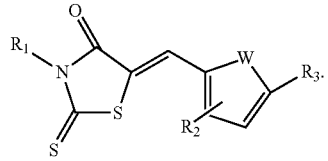

wherein W is O, S or an optionally substituted NH.

8. A compound having the formula of:

Formula III(a)(1)
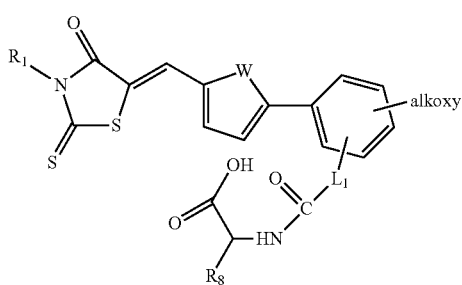

wherein, $R_1$ is an optionally substituted cycloalkyl having from 3 to 20 carbon atoms;

W is selected from the group consisting of O, S, and an optionally substituted NH;

$L_1$ is a direct bond or an optionally substituted linking unit, wherein the linking unit consists of 1 to 4 carbon atoms and up to 2 heteroatoms selected from the group consisting of O, N and S; and $R_8$ is a side chain of an amino acid.

9. The compound of claim 7, wherein the compound of Formula (III) has the formula of:

Formula (III)(b)(1)

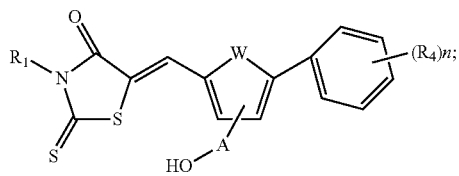

Formula (III)(b)(2)

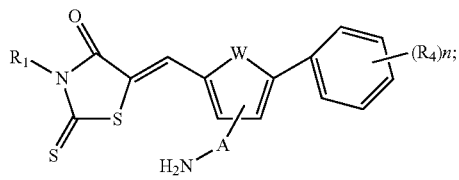

Formula (III)(b)(3)

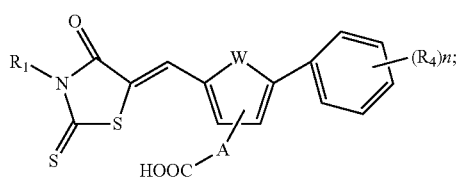

Formula (III)(b)(4)

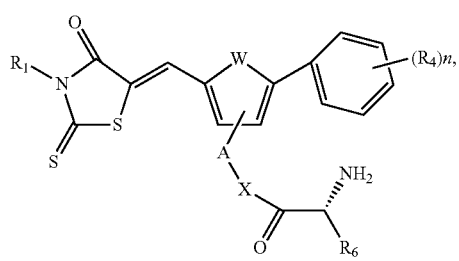

wherein X is O, N or S, and $R_6$ is a side chain of an amino acid;

Formula (III)(b)(5)

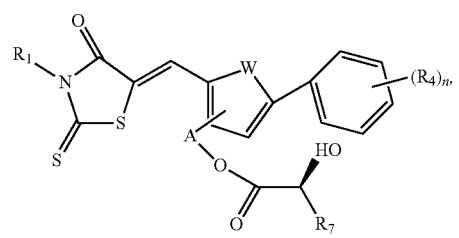

wherein $R_7$ is a side chain of an amino acid;

Formula (III)(b)(6)

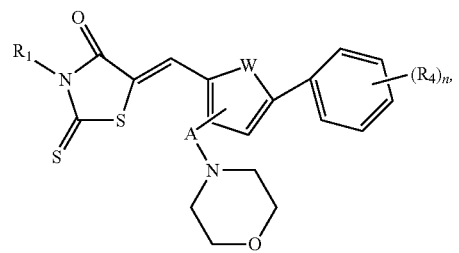

wherein the morpholine is optionally substituted;

Formula (III)(b)(7)

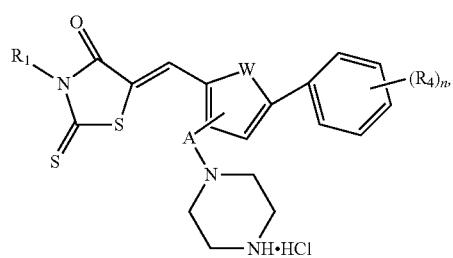

wherein the piperazine is optionally substituted;

Formula (III)(b)(8)

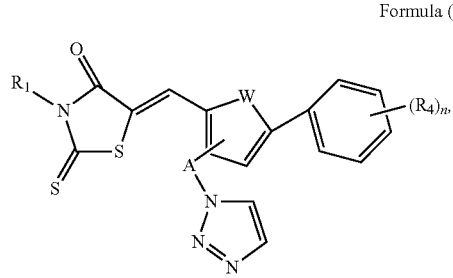

wherein the triazole is optionally substituted;

Formula (III)(b)(9)

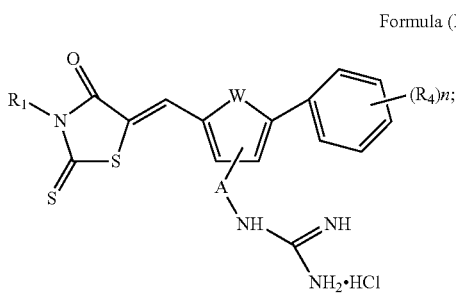

Formula (III)(b)(10)

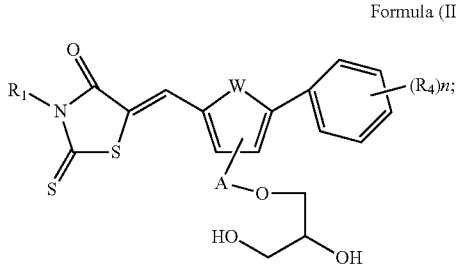

-continued

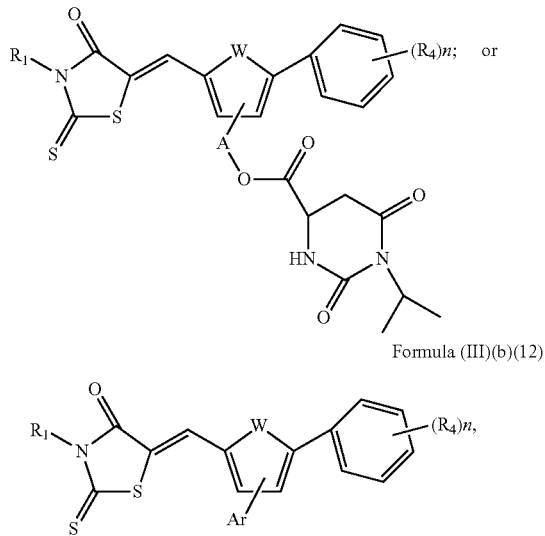

Formula (III)(b)(11)

Formula (III)(b)(12)

wherein the Ar is an optionally substituted aryl;
in each of Formula (III)(b)(1) to Formula (III)(b)(12), wherein,
n is an integer of 0 to 3; and
$R_4$ is independently selected from the group consisting of an alkoxy, a halogen, a hydroxy, an amide, a thio, a nitro, a cyano, an alkyl, an alcohol, an amine, an amino acid derivative, a carboxyl, an acid ester, an alpha-hydroxy acid, an ether, a guanidino, an optionally substituted aryl, an optionally substituted heteroaryl, an optionally substituted cycloalkyl, and an optionally substituted heterocyclic ring,
wherein the amino acid derivative is selected from the group consisting of

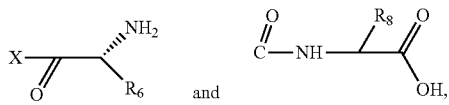

wherein X is O, N or S, and each of $R_6$ and $R_8$ is independently a side chain of an amino acid.

10. The compound of claim 1, wherein $R_1$ is selected from the group consisting of an optionally substituted 5-12 membered monocyclic ring, decalin, norbornane and adamantane.

11. A pharmaceutical composition comprising a pharmaceutically acceptable carrier and a compound of claim 1.

12. A method of treating a viral infection in a subject having a viral infection comprising administering to the subject a therapeutically effective amount of the pharmaceutical composition of claim 11, wherein the virus is selected from the group consisting of influenza and HIV.

13. The method of claim 12, further comprising administering to the subject one or more additional agents for treating the viral infection, wherein the additional agent is a nucleoside or nucleotide reverse transcriptase inhibitor, a non nucleoside reverse transcriptase inhibitor, a protease inhibitor, an integrase inhibitor, an RNA polymerase inhibitor, a DNA polymerase inhibitor, a kinase inhibitor, an enzyme inhibitor, an entry inhibitor, an assembly inhibitor, a maturation inhibitor, an M2 inhibitor, or a neuraminidase inhibitor.

14. The method of claim 13, wherein the additional agent is selected from the group consisting of amantadine, rimantadine, oseltamivir, zanamivir, peramivir, raltegravir, maraviros, enfuviritide, bevirimat, MP-9055, avacavir, zidovudine, emtricitabine, lamivudine, didanosine, tenofovir disoproxil fumarate, a combination of zidovudine and lamivudine, a combination of abacavir and lamivudine, a combination of abacavir and zidovudine and lamivudine, a combination of tenofovir disoproxil fumarate and emtricitabine, stavudine, racivir, amdoxovir, apricitabine, elvucitabine, alpha-epibromide, aldesleukin, HIV-1 Immunogen, BAY 50-4798, IR103, etravirine, delavirdine, efavirenz, nevirapine, rilpivirine, amprenavir, tipranavir, indinavir, saquinavir, a combination of lopinavir and ritonavir, fosamprenavir, ritonavir, darunavir, atazanavir, nelfinavir, enfuvirtude, maraviros, vicriviroc, PRO 140, TNX-355, raltegravir, elvitegravir, bevirimat and hydroxyurea.

15. A pharmaceutical composition comprising a pharmaceutically acceptable carrier and a compound of claim 8.

16. A method of treating a viral infection in a subject having a viral infection comprising administering to the subject a therapeutically effective amount of the pharmaceutical composition of claim 15, wherein the virus is selected from the group consisting of influenza and HIV.

* * * * *

UNITED STATES PATENT AND TRADEMARK OFFICE
CERTIFICATE OF CORRECTION

PATENT NO. : 8,933,075 B2  
APPLICATION NO. : 13/703383  
DATED : January 13, 2015  
INVENTOR(S) : Wang et al.

Page 1 of 1

It is certified that error appears in the above-identified patent and that said Letters Patent is hereby corrected as shown below:

In the Specification

Column 1, Lines 5-11 Please delete the entire paragraph under STATEMENT OF GOVERNMENT LICENSE RIGHTS and replace with the following paragraph:
STATEMENT OF GOVERNMENT LICENSE RIGHTS
This invention was made with government support under grant numbers AI057157 and AI080669 awarded by the National Institutes of Health. The government has certain rights in the invention.

Signed and Sealed this
Twenty-eighth Day of April, 2020

Andrei Iancu
*Director of the United States Patent and Trademark Office*